US011753648B2

(12) United States Patent
Nuccio et al.

(10) Patent No.: US 11,753,648 B2
(45) Date of Patent: Sep. 12, 2023

(54) INIR6 TRANSGENIC MAIZE

(71) Applicant: INARI AGRICULTURE TECHNOLOGY, INC., Cambridge, MA (US)

(72) Inventors: Michael Lee Nuccio, Salem, NH (US); Michael Andreas Kock, Rheinfelden (DE); Joshua L. Price, Cambridge, MA (US)

(73) Assignee: INARI AGRICULTURE TECHNOLOGY, INC., Cambridge, MA (US)

( * ) Notice: Subject to any disclaimer, the term of this patent is extended or adjusted under 35 U.S.C. 154(b) by 0 days.

(21) Appl. No.: 17/680,647

(22) Filed: Feb. 25, 2022

(65) Prior Publication Data

US 2022/0251584 A1   Aug. 11, 2022
US 2023/0021305 A9   Jan. 19, 2023

Related U.S. Application Data

(63) Continuation of application No. PCT/US2021/044198, filed on Aug. 2, 2021.

(60) Provisional application No. 63/203,137, filed on Jul. 9, 2021, provisional application No. 63/202,569, filed on Jun. 16, 2021, provisional application No. 63/201,029, filed on Apr. 9, 2021, provisional application No. 63/201,030, filed on Apr. 9, 2021, provisional application No. 63/199,949, filed on Feb. 4, 2021, provisional application No. 63/199,951, filed on Feb. 4, 2021, provisional application No. 63/199,930, filed on Feb. 3, 2021.

(51) Int. Cl.
*C12N 15/82* (2006.01)
*C12Q 1/6895* (2018.01)
*C12N 9/22* (2006.01)
*C12N 15/11* (2006.01)

(52) U.S. Cl.
CPC ............ *C12N 15/8201* (2013.01); *C12N 9/22* (2013.01); *C12N 15/11* (2013.01); *C12N 15/8213* (2013.01); *C12N 15/8286* (2013.01); *C12Q 1/6895* (2013.01); *C12N 2310/20* (2017.05); *C12Q 2600/13* (2013.01)

(58) Field of Classification Search
CPC ................................................. C12N 15/8201
See application file for complete search history.

(56) References Cited

U.S. PATENT DOCUMENTS

| | | | |
|---|---|---|---|
| 7,632,985 B2 | 12/2009 | Malven et al. | |
| 8,232,456 B2 | 7/2012 | Long et al. | |
| 8,450,561 B2 | 5/2013 | Beazley et al. | |
| 8,575,434 B2 * | 11/2013 | Diehn | A01H 5/10 |
| | | | 426/655 |
| 9,540,655 B2 | 1/2017 | Cui et al. | |
| 11,214,811 B1 | 1/2022 | Nuccio et al. | |
| 2003/0088081 A1 | 5/2003 | Maliga et al. | |
| 2010/0162428 A1 | 6/2010 | Brown et al. | |
| 2011/0191899 A1 | 8/2011 | Ainley et al. | |
| 2014/0196169 A1 | 7/2014 | D'Halluin et al. | |
| 2015/0059010 A1 | 2/2015 | Cigan et al. | |
| 2015/0082478 A1 | 3/2015 | Cigan et al. | |
| 2016/0333363 A1 | 11/2016 | Srivastava | |
| 2018/0163218 A1 | 6/2018 | Corbin et al. | |
| 2019/0136249 A1 | 5/2019 | Sakai et al. | |
| 2019/0352655 A1 | 11/2019 | Niu et al. | |
| 2020/0157554 A1 | 5/2020 | Cigan et al. | |

FOREIGN PATENT DOCUMENTS

CN   104830860 B   1/2018

OTHER PUBLICATIONS

Malzahn et al. 2019. Applicant of CRISPR-CAS12a temperature sensitivity for improved genome editing in rice, maize, and *Arabidopsis*. BMC Biology 17:9enomics. 1-7. (Year: 2019).*
Yau et al. 2013. Less is more: strategies to remove marker genes from transgenic plants. Biotechnology; 13-36. (Year: 2013).*
Srivastava et al. 2017. Dual-targeting by CRISPR/Cas9 for precise excision of transgenes from rice genome. Plant Cell Tiss Organ Cult 129: 153-160. (Year: 2017).*
International Searching Authority in connection with PCT/US21/43161, Notification of Transmittal of the International Search Report and the Written Opinion of the International Searching Authority, or the Declaration, 23 pages, dated Jan. 5, 2022.
International Searching Authority in connection with PCT/US21/43187 filed Jul. 26, 2021, "The International Search Report and the Written Opinion of the International Searching Authority, or the Declaration", 27 pages, dated Jan. 6, 2022.
International Searching Authority in connection with PCT/US21/43897 filed Jul. 30, 2021, "Invitation to Pay Additional Fees and, Where Applicable, Protest Fee", 3 pages, dated Oct. 27, 2021.
International Searching Authority in connection with PCT/US21/43945 filed Jul. 30, 2021, "Invitation to Pay Additional Fees and, Where Applicable, Protest Fee", 4 pages, dated Oct. 27, 2021.
International Searching Authority in connection with PCT/US21/43935 filed Jul. 30, 2021, "Invitation to Pay Additional Fees and, Where Applicable, Protest Fee", 3 pages, dated Oct. 26, 2021.
Baliga et al., "Investigation of direct repeats, spacers and proteins associated with clustered regularly interspaced short palindromic repeat (CRISPR) system of Vibrio parahaemolyticus", Molecular Genetics and Genomics, vol. 294, pp. 253-262, 2019.
Bortesi et al., "The CRISPR/Cas9 system for plant genome editing and beyond", Biotechnology Advances, vol. 33, pp. 41-52, Dec. 16, 2014.

(Continued)

*Primary Examiner* — Karen M Redden
(74) *Attorney, Agent, or Firm* — McKee, Voorhees & Sease, PLC

(57) ABSTRACT

Transgenic INIR6 maize plants comprising modifications of the DP-4114 maize locus which provide for facile excision of the modified DP-4114 transgenic locus or portions thereof, methods of making such plants, and use of such plants to facilitate breeding are disclosed.

4 Claims, 5 Drawing Sheets

Figure 1:
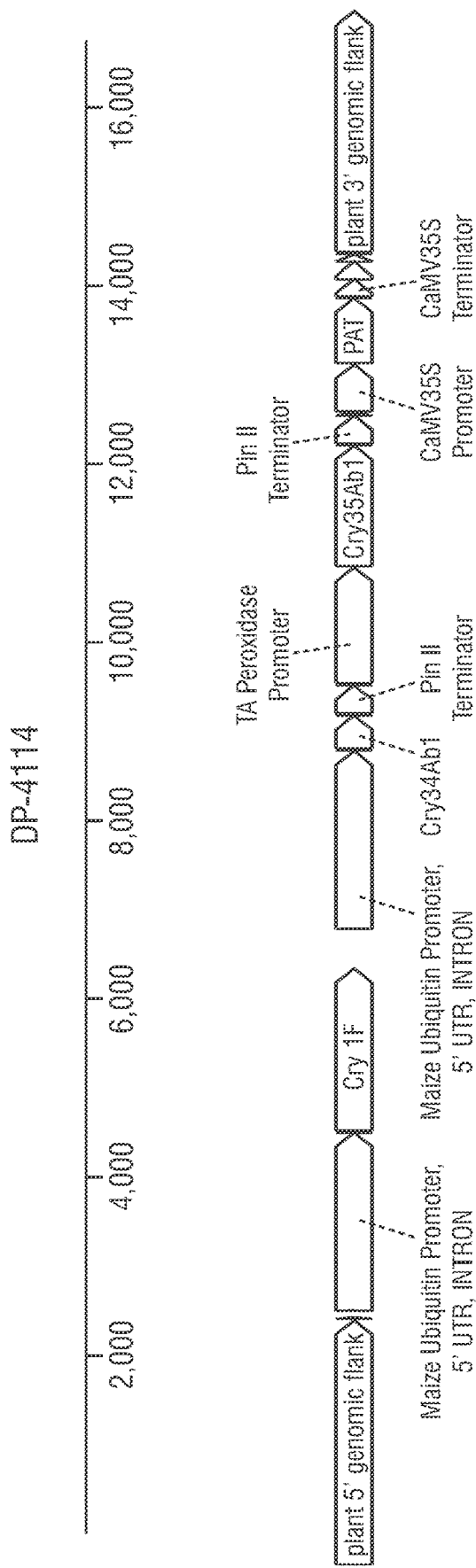

Specification includes a Sequence Listing.

(56) References Cited

OTHER PUBLICATIONS

Cho et al., "Nonallelic homologous recombination events responsible for copy number variation within an RNA silencing locus", Plant Direct, vol. 3, 16 pages, Aug. 5, 2019.
Du et al., "Construction of Marker-Free Genetically Modified Maize Using a Heat-Inducible Auto-Excision Vector", Genes, vol. 10, No. 374, pp. 1-17, 2019.
Finnigan et al., "mCAL: A New Approach for Versatile Multiplex Action of Cas9 Using One sgRNA and Loci Flanked by a Programmed Target Sequence", G3, vol. 6, pp. 2147-2156, Jul. 2016.
International Searching Authority in connection with PCT/US21/44198 filed Aug. 2, 2021, "The International Search Report and the Written Opinion of the International Searching Authority, or the Declaration", 20 pages, dated Jan. 19, 2022.
Kim et al., "CRISPR/Cpf1-mediated DNA-free plant genome editing", Nature Communications, vol. 8, No. 14406, pp. 1-20, Feb. 16, 2017.
Li et al., "Expanding the Scope of CRISPR/Cpf1-Mediated Genome Editing in Rice", Molecular Plant, vol. 11, pp. 995-998, Jul. 2018.
Luo et al., "Improperly Terminated, Unpolyadenylated mRNA of Sense Transgenes is Targeted by RDR6-Mediated RNA Silencing in *Arabidopsis*", The Plant Cell, vol. 19, pp. 943-958, Mar. 2007.
Malzahn et al., "Application of CRISPR-Cas12a temperature sensitivity for improved genome editing in rice, maize, and *Arabidopsis*", BMC Biology, vol. 17, No. 9, https://doi.org/10.1186/s12915-019-0629-5, pp. 1-14, 2019.
United States Patent and Trademark Office in connection with U.S. Appl. No. 17/302,739, filed May 11, 2021, "Non-Final Office Action", 29 pages, dated Aug. 3, 2021.
United States Patent and Trademark Office in connection with U.S. Appl. No. 17/248,936, filed Feb. 12, 2021, "Non-Final Office Action" 30 pages, dated Mar. 25, 2021.
United States Patent and Trademark Office in connection with U.S. Appl. No. 17/302,110, filed Apr. 23, 2021, "Non-Final Office Action", 22 pages, dated Jun. 29, 2021.
United States Patent and Trademark Office in connection with U.S. Appl. No. 17/302,121, filed Apr. 23, 2021, "Non-Final Office Action", 10 pages, dated Jul. 8, 2021.
Que et al., "Maize transformation technology development for commercial event generation", Frontiers in Plant Science, vol. 5, Article 379, pp. 1-19, 2014.
Srivastava, et al., "Dual-targeting by CRISPR/Cas9 for precise excision of transgenes from rice genome", Plant Cell Tissue and Organ Culture, vol. 129, pp. 153-160, 2017.
Srivastava et al., "Gene Stacking by recombinases", Plant Biotechnology Journal, vol. 14, pp. 471-482, 2016.
Stine, Harry H., "Request for Extension of Determination of Nonregulated Status to the Additional Regulated Article: Maize Line HCEM485", USDA Extension Petition (online), https://www.aphis.usda.gov/brs/aphisdocs/09_06301p_a3.pdf, pp. 1-3, Feb. 14, 2011.
U.S. Department of Agriculture, "Approval of AgrEvo Request (98-014-01p) Seeking Extension of Determination of Non-regulated Status for Glufosinate Resistant Soybean Transformation Event A5547-127", 6 pages Apr. 30, 1998.
U.S. Department of Agriculture, "Response to AgrEvo Petition 98-278-01p for Determination of Nonregulated Status for Canola Transformation Events MS8 and RF3 Genetically Engineered for Pollination Control and Tolerance to Glufosinate Herbicide", 4 pages Mar. 22, 1999.
U.S. Department of Agriculture, "Syngenta Petition 03-155-01p for Determination of Nonregulated Status for Lepitodopteran Resistant Cotton Event COT102", 3 pages May 2005.
U.S. Department of Agriculture, "Be Corn Crop Summary", USDA Report (online), https://www.ams.usda.gov/sites/defauiUfiles/media/BECornCropSummary.pdf, pp. 1-5, 2018.
Ward, Dennis P., "Petition for Determination of Nonregulated Status for Insect-Resistant MIR162 Maize", Syngenta, pp. 1-268, Aug. 31, 2007.
Xing et al., "Revealing frequent alternative polyadenylation and widespread low-level transcription read-through of novel plant transcription terminators", Plant Biotechnology Journal, vol. 8, pp. 772-782, 2010.
Young et al., "CRISPR-Cas9 Editing in Maize: Systematic Evaluation of Off-target Activity and Its Relevance in Crop Improvement", Scientific Reports, vol. 9, 11 pages, Apr. 15, 2019.
United States Patent and Trademark Office in connection with U.S. Appl. No. 17/248,936, filed Feb. 12, 2021, "Final Office Action", 46 pages, dated Jul. 27, 2021.

\* cited by examiner

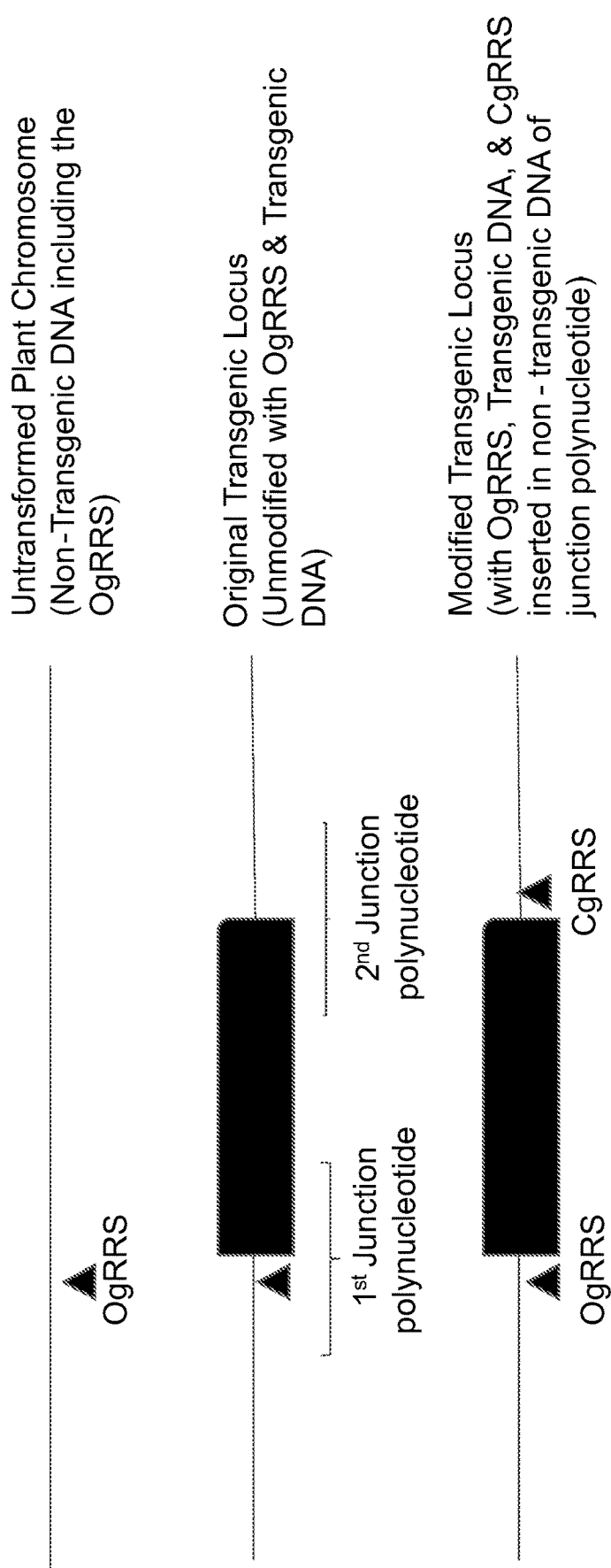

SEQUENCE LISTING

<160> NUMBER OF SEQ ID NOS: 35

<210> SEQ ID NO 1
<211> LENGTH: 16752
<212> TYPE: DNA
<213> ORGANISM: Artificial
<220> FEATURE:
<223> OTHER INFORMATION: synthetic

<400> SEQUENCE: 1

| | | | | | |
|---|---|---|---|---|---|
| gagcatatcc | agcaccagct | ggtaccaagg | tcgggtctct | gtgctagtgc | tattagctag | 60 |
| tgtaaggagc | gagtaggtca | gttaaggctg | gtgcgtcgtg | agggctgtct | tgtgtgtagc | 120 |
| tacagcagac | ggttcatcag | aaggattatt | cgtgcagtat | atacagtaca | actagacaat | 180 |
| gatgttgatg | attggtctag | agctagaggc | ctatagccct | atactactgt | gtattgtccg | 240 |
| ccgttttagt | tttttggtcc | catcccatca | atgcaaccgc | cttgttttgc | tccaattgtc | 300 |
| ccgttcctgc | gcctcgcttt | tgctctgtcg | catcgcatac | aaaaaaaaaa | acgccgcgcc | 360 |
| ggctttgaat | cgcgcccccc | aactgctcca | accaggcaac | ggacacggcc | accgtccgtg | 420 |
| tcgcgagcaa | aaaacaaaa | agaggaacgc | gtccaggacg | aagcagtcca | ctgccgctgt | 480 |
| ggccggcaaa | agatctggtt | gagcacatgg | agattggaga | aggttggttg | gttcttctgg | 540 |
| aaacgccaat | gaatggggc | actgacatgt | actcttaaca | tgtagtgcaa | tccagagatc | 600 |
| ggatatccag | acactggcag | cacgatcgcc | tcgcgccgta | gatcacgcac | gcaaattact | 660 |
| gaagaccatt | cacaaaaaaa | aaaaaacaca | caggggctag | cgtgccccac | accaaaccca | 720 |
| agtgctgcgt | tgcacgcagg | ggagcgaaaa | aaaacaataa | tgctcactgt | cacgtcgcgt | 780 |
| atccaacccc | gcggacgtct | cggctctcag | cagcagcaca | cggggcacct | cacgatgccg | 840 |
| ttctcgttgc | actccgtgca | ccgccggaac | ccgccgccgc | attcgtcgcc | ctcctcctcc | 900 |
| tcctccgcct | cgtcttcgtc | acccacgtac | accttgcagc | tgcccgagca | gacatcgcag | 960 |
| agcacgaacc | gcatgtcccc | gcaggcctcg | cacgcgccgg | cgtcgccgcc | gtgtgggccg | 1020 |
| gccgtcgacg | cagcgctctc | gcacccggcc | agcctcggcg | cgagctcccc | ggcctcgtgc | 1080 |
| agccgcttca | gctcctcggc | gttgccacg | agctccccgt | ccacgaagag | gctggggagg | 1140 |
| gcggcgggcg | tgccgccggc | ttggccgagc | ccgaggccga | aaggccgcg | gagctcgtcc | 1200 |
| cggaacccgc | ggtgcatgga | cacgtcgcgc | tcgtcgaggc | gcacgccgta | gcccttgagg | 1260 |
| atggcgcgcg | ccaggcagca | gtcctcgtgc | gtggcgcgca | cgccgcgcag | cgacgtgaag | 1320 |
| tagagcaccg | ccctccgcgg | cggcagcgcc | ttcccctccc | cgccgctcgt | cggggcggcg | 1380 |
| tcgggccgag | gcatcggcat | cggcagcggc | gtcaccttgg | cggacgccgc | gaggtcctgc | 1440 |
| gcaggcgccg | tggcgaccgg | gaacgagaag | gagtggcgcc | cgaacggcgc | gcccagcagc | 1500 |
| ggggagcggt | cctcgaggcc | ggccatgagc | gcccacgcgt | cgatgtcctc | gggctcgttg | 1560 |
| ggcggcgtca | tggtgggcgt | gcgcggcgcc | agcctcgtgg | gcgcgggctc | cggcgcccgc | 1620 |
| ggcagggcct | tgtccagctc | cagggacccg | agcgtggacg | acgtgagccg | caccacgtgg | 1680 |
| acgccgacgt | cgctggggca | ccgagccggg | aacgactggc | tgcgcggcag | cggtgacggg | 1740 |
| cagtaccgga | ggtcgtgacg | ggcctgcctt | gaggtggtgc | acccccatggc | accaatgtac | 1800 |
| acacacggcc | aaagcgccaa | gtgggctgca | gactgcctgc | caatgtgatc | aagcagccag | 1860 |
| gagcagagac | ggatctctgg | ggatcggggt | ttctggggtt | taggatctttt | atactactct | 1920 |
| gtcattgggg | atataaaact | aggagtgtgg | ttaattagga | ctcgtatagat | aagttttacca | 1980 |
| caagcgcgtg | aaatggtcta | cccgatgatg | tgattggcct | aaaaagaaca | agaagagtat | 2040 |

```
ttggagctac tgaacattct cttttcctga agataactaa ttttggaac attcagactt      2100
gggagtctgg acttttggag ggaagttcaa attgtggtct gcctctgcca tgtgttgttt      2160
tttagtcgga gagtggccct catttttttt gtcctgttta gctttatagt cgtagcagct      2220
agtagcgaaa tttaaccttg gattatggcc gtgttagtca aacaatcatt gatttatttc      2280
ctcccttttcg cgctgctttt cctgtacgca tctccgctgc ccttgattcg aggaccctgt     2340
tcacaacaca gggctctggc tttggagcct ctcgtttgta gcacttgcac gtagttaccc      2400
ggaccgaagc ttcaacacag atctgatagt ttaaacgctc ttcaactgga agagcggtta     2460
cccggaccga agcttcggcc ggggcccatc gatatccgcg gcatgcctg cagtgcagcg      2520
tgacccggtc gtgcccctct ctagagataa tgagcattgc atgtctaagt tataaaaaat    2580
taccacatat ttttttgtc acacttgttt gaagtgcagt ttatctatct ttatacatat     2640
atttaaactt tactctacga ataatataat ctatagtact acaataatat cagtgtttta    2700
gagaatcata taaatgaaca gttagacatg gtctaaagga caattgagta ttttgacaac    2760
aggactctac agttttatct tttagtgtg catgtgttct cctttttttt tgcaaatagc      2820
ttcacctata taatacttca tccattttat tagtacatcc atttagggtt tagggttaat    2880
ggttttata gactaatttt tttagtacat ctattttatt ctattttagc ctctaaatta     2940
agaaaactaa aactctattt tagtttttt atttaataat ttagatataa aatagaataa     3000
aataaagtga ctaaaaatta aacaaatacc ctttaagaaa ttaaaaaaac taaggaaaca     3060
tttttcttgt ttcgagtaga taatgccagc ctgttaaacg ccgtcgacga gtctaacgga     3120
caccaaccag cgaaccagca gcgtcgcgtc gggccaagcg aagcagacgg cacggcatct    3180
ctgtcgctgc ctctggaccc ctctcgagag ttccgctcca ccgttggact tgctccgctg    3240
tcggcatcca gaaattgcgt ggcggagcgg cagacgtgag ccggcacggc aggcggcctc    3300
ctcctcctct cacggcaccg gcagctacgg gggattcctt tcccaccgct ccttcgcttt    3360
cccttcctcg cccgccgtaa taaatagaca ccccctccac accctctttc cccaacctcg    3420
tgttgtcgg agcgcacaca cacacaacca gatctcccc aaatccaccc gtcggcacct      3480
ccgcttcaag gtacgccgct cgtcctcccc cccccccct ctctaccttc tctagatcgg     3540
cgttccggtc catggttagg gcccggtagt tctacttctg ttcatgtttg tgttagatcc    3600
gtgtttgtgt tagatccgtg ctgctagcgt tcgtacacgg atgcgacctg tacgtcagac    3660
acgttctgat tgctaacttg ccagtgtttc tctttgggga atcctgggat ggctctagcc    3720
gttccgcaga cgggatcgat ttcatgattt ttttgtttc gttgcatagg gtttggtttg    3780
cccttttcct ttatttcaat atatgccgtg cacttgtttg tcgggtcatc ttttcatgct    3840
ttttttgtc ttggttgtga tgatgtggtc tggttgggcg gtcgttctag atcggagtag     3900
aattctgttt caaactacct ggtggattta ttaattttgg atctgtatgt gtgtgccata    3960
catattcata gttacgaatt gaagatgatg gatggaaata tcgatctagg ataggtatac    4020
atgttgatgc gggttttact gatgcatata cagagatgct ttttgttcgc ttggttgtga    4080
tgatgtggtg tggttgggcg gtcgttcatt cgttctagat cggagtagaa tactgtttca    4140
aactacctgg tgtatttatt aattttggaa ctgtatgtgt gtgtcataca tcttcatagt    4200
tacgagttta agatggatgg aaatatcgat ctaggatagg tatacatgtt gatgtgggtt    4260
ttactgatgc atatacatga tggcatatgc agcatctatt catatgctct aaccttgagt    4320
acctatctat tataataaac aagtatgttt tataattatt ttgatcttga tatacttgga   4380
```

```
tgatggcata tgcagcagct atatgtggat ttttttagcc ctgccttcat acgctattta   4440
tttgcttggt actgtttctt ttgtcgatgc tcaccctgtt gtttggtgtt acttctgcag   4500
gtcgactcta gaggatccaa caatggagaa caacatacag aatcagtgcg tccnctacaa   4560
ctgcctcaac aatcctgaag tagagattct caacgaagag aggtcgactg gcagattgcc   4620
gttagacatc tccctgtccc ttacacgttt cctgttgtct gagtttgttc caggtgtggg   4680
agttgcgttt ggcctcttcg acctcatctg gggcttcatc actccatctg attggagcct   4740 cttctcttctc cagattgaac agttgattga acaaaggatt gagaccttgg aaaggaatcg   4800
ggccatcact acccttcgtg gcttagcaga cagctatgag atctacattg aagcactaag   4860
agagtgggaa gccaatccta caatgcccca actgagagaa gatgtgcgta tacgctttgc   4920
taacacagat gatgctttga tcacagccat caacaacttc cccttacca gcttcgagat   4980 ccctcttctc tcggtctatg ttcaagctgc taacctgcac ttgtcactac tgcgcgacgc   5040
tgtgtcgttt gggcaaggtt ggggactgga catagctact gtcaacaatc actacaacag   5100
actcatcaat ctgattcatc gatacacgaa acattgtttg gatacctaca atcagggatt   5160
ggagaacctg agaggtacta acactcgcca atgggccagg ttcaatcagt tcaggagaga   5220
ccttacactt actgtgttag acatagttgc tctctttccg aactacgatg ttcgtaccta   5280
tccgattcaa acgtcatccc aacttacaag ggagatctac accagttcag tcattgaaga   5340
ctctccagtt tctgcgaaca tacccaatgg tttcaacagg gctgagtttg gagtcagacc   5400
accccatctc atggacttca tgaactcttt gtttgtgact gcagagactg ttagatccca   5460
aactgtgtgg ggaggacact tagttagctc acgcaacacg gctggcaatc gtatcaactt   5520
tcctagttac ggggtcttca atcccggggg cgccatctgg attgcagatg aagatccacg   5580 tccttctctat cggaccttgt cagatcctgt cttcgtccga ggaggctttg gcaatcctca   5640
ctatgtactc ggtcttaggg gagtggcctt tcaacaaact ggtacgaatc acaccgcac   5700 attcaggaac tccgggacca ttgactctct agatgagata ccacctcaag acaacagcgg   5760
cgcaccttgg aatgactact cccatgtgct gaatcatgtt acctttgtgc gctggccagg   5820
tgagatctca ggttccgact catggagagc accaatgttc tcttggacgc atcgtagcgc   5880 taccccccaca acaccattg atccagagag aatcactcag attcccttgg tgaaggcaca   5940
cacacttcag tcaggaacta cagttgtaag agggccgggg ttcacgggag agacattct   6000 tcgacgcact agtggaggac cattcgcgta caccattgtc aacatcaatg ggcaacttcc   6060
ccaaaggtat cgtgccagga tacgctatgc ctctactacc aatctaagaa tctacgttac   6120
ggttgcaggt gaacggatct tgctggtca gttcaacaag acaatggata ccggtgatcc   6180
acttacattc caatctttct cctacgccac tatcaacacc gcgttcacct ttccaatgag   6240
ccagagcagt ttcacagtag gtgctgatac cttcagttca ggcaacgaag tgtacattga   6300
caggtttgag ttgattccag ttactgccac actcgagtaa ggatccgtcg acctgcagcc   6360
aagctttcgc gagctcgaga tccccgacat atgccccggt ttcgttgcga ctaacatgag   6420
ttcttggaca aatttgattg gacctgatga gatgatccaa cccgaggata tagcaaagct   6480
cgttcgtgca gcaatggaac ggccaaaccg tgcttttgtc cccaagaatg aggtgctatg   6540
catgaaggaa tctacccgtt gatgtccaac agtctcaggg ttaatgtcta tgtatcttaa   6600
ataatgttgt cggtattttg taatctcata tagattttca ctgtgcgacg caaaatatt   6660 aaataaaatat tattattatc tacgtttga ttgagatatc atcaatatta taataaaaat   6720
atccattaaa cacgatttga tacaaatgac agtcaataat ctgatttgaa tatttattaa   6780
```

```
ttgtaacgaa ttacataaag atcgaataga aaatactgca ctgcaaatga aaattaacac    6840
atactaataa atgcgtcaaa tatctttgcc aagatcaagc ggagtgaggg cctcatatcc    6900
ggtctcagtt acaagcacgg tatccccgaa gcgcgctcca ccaatgccct cgacatagat    6960
gccgggctcg acgctgagga cattgcctac cttgagcatg gtctcagcgc cggctttaag    7020
ctcaatccca tcccaatctg aatatcctat cccgcgccca gtccggtgta agaacgggtc    7080
tgtccatcca cctctgttgg gaattccggt ccgggtcacc tttgtccacc aagatggaac    7140
tgcggccagc ttgcatgcct gcagtgcagc gtgacccggt cgtgcccctc tctagagata    7200
atgagcattg catgtctaag ttataaaaaa ttaccacata ttttttttgt cacacttgtt    7260
tgaagtgcag tttatctatc tttatacata tatttaaact ttactctacg aataatataa    7320
tctatagtac tacaataata tcagtgtttt agagaatcat ataaatgaac agttagacat    7380
ggtctaaagg acaattgagt attttgacaa caggactcta cagttttatc ttttttagtgt    7440 gcatgtgttc tccttttttt ttgcaaatag cttcacctat ataatacttc atccatttta    7500
ttagtacatc catttagggt ttagggttaa tggtttttat agactaattt ttttagtaca    7560
tctattttat tctattttag cctctaaatt aagaaaacta aaactctatt ttagttttt    7620 tatttaataa tttagatata aaatagaata aaataaagtg actaaaaatt aaacaaatac    7680
cctttaagaa attaaaaaaa ctaaggaaac atttttcttg tttcgagtag ataatgccag    7740
cctgttaaac gccgtcgacg agtctaacgg acaccaacca gcgaaccagc agcgtcgcgt    7800
cgggccaagc gaagcagacg gcacggcatc tctgtcgctg cctctggacc cctctcgaga    7860
gttccgctcc accgttggac ttgctccgct gtcggcatcc agaaattgcg tggcggagcg    7920
gcagacgtga gccggcacgg caggcggcct cctcctcctc tcacggcacc ggcagctacg    7980
ggggattcct ttcccaccgc tccttcgctt tcccttcctc gcccgccgta ataaatagac    8040
accccctcca caccctcttt ccccaacctc gtgttgttcg gagcgcacac acacacaacc    8100
agatctcccc caaatccacc cgtcggcacc tccgcttcaa ggtacgccgc tcgtcctccc    8160 ccccccccc tctctacctt ctctagatcg gcgttccggt ccatggttag ggcccggtag    8220
ttctacttct gttcatgttt gtgttagatc cgtgtttgtg ttagatccgt gctgctagcg    8280
ttcgtacacg gatgcgacct gtacgtcaga cacgttctga ttgctaactt gccagtgttt    8340
ctctttgggg aatcctggga tggctctagc cgttccgcag acgggatcga tttcatgatt    8400
ttttttgttt cgttgcatag ggtttggttt gccccttttcc tttatttcaa tatatgccgt    8460
gcacttgttt gtcgggtcat cttttcatgc ttttttttgt cttggttgtg atgatgtggt    8520
ctggttgggc ggtcgttcta gatcggagta gaattctgtt tcaaactacc tggtggattt    8580
attaattttg gatctgtatg tgtgtgccat acatattcat agttacgaat tgaagatgat    8640
ggatggaaat atcgatctag gataggtata catgttgatg cgggttttac tgatgcatat    8700
acagagatgc ttttttgttcg cttggttgtg atgatgtggt gtggttgggc ggtcgttcat    8760
tcgttctaga tcggagtaga atactgtttc aaactacctg gtgtatttat taattttgga    8820
actgtatgtg tgtgtcatac atcttcatag ttacgagttt aagatggatg gaaatatcga    8880
tctaggatag gtatacatgt tgatgtgggt tttactgatg catatacatg atggcatatg    8940
cagcatctat tcatatgctc taaccttgag tacctatcta ttataataaa caagtatgtt    9000
ttataattat tttgatcttg atatacttgg atgatgcat atgcagcagc tatatgtgga    9060 ttttttttagc cctgccttca tacgctattt atttgcttgg tactgtttct tttgtcgatg    9120
```

```
ctcaccctgt tgtttggtgt tacttctgca ggtcgactct agaggatcca cacgacacca    9180
tgtccgcccg cgaggtgcac atcgacgtga acaacaagac cggccacacc ctccagctgg    9240
aggacaagac caagctcgac ggcggcaggt ggcgcacctc cccgaccaac gtggccaacg    9300
accagatcaa gaccttcgtg gccgaatcca acggcttcat gaccggcacc gagggcacca    9360
tctactactc aattaatggc gaggccgaga tcagcctcta cttcgacaac ccgttcgccg    9420
gctccaacaa atacgacggc cactccaaca agtcccagta cgagatcatc acccagggcg    9480
gctccggcaa ccagtcccac gtgacctaca ccatccagac cacctcctcc cgctacggcc    9540
acaagtcctg agtcatgagt catgagtcag ttaacctaga cttgtccatc ttctggattg    9600
gccaacttaa ttaatgtatg aaataaaagg atgcacacat agtgacatgc taatcactat    9660
aatgtgggca tcaaagttgt gtgttatgtg taattactag ttatctgaat aaaagagaaa    9720
gagatcatcc atatttctta tcctaaatga atgtcacgtg tctttataat tctttgatga    9780
accagatgca tttcattaac caaatccata tacatataaa tattaatcat atataattaa    9840
tatcaattgg gttagcaaaa caaatctagt ctaggtgtgt tttgcgaatg cggccgcgga    9900
ccgaattggg gatctgcatg aaagaaactg tcgcactgct gaaccgcacc ttgtcacttt    9960
catcgaacac gacctgtgcc aagatgacg gtgctgcgt ctaagtgagg ctgaattgcc    10020
ttggacagaa gcggactccc tacaattagt taggccaaac ggtgcatcca tgtgtagctc    10080
cgggctcggc ctgtatcgcc atctgcaata gcatccatgg agctcgttcc atgtagttgg    10140
agatgaacca atgatcgggc gtgtggacgt atgttcctgt gtactccgat agtagagtac    10200
gtgttagctc tttcatggtg caagtgaaat ttgtgttggt ttaattaccc ctacgttagt    10260
tgcgggacag gagacacatc atgaatttaa aggcgatgat gtcctctcct gtaatgttat    10320
tcttttgatg tgatgaatca aaatgtcata taaacatttt gttgctcttt agttaggcct    10380
gatcgtagaa cgaaatgctc gtgtagcggg gctacgagcc tatgacgcaa taacactggt    10440
ttgccggccc ggagtcgctt gacaaaaaaa agcatgttaa gtttatttac aattcaaaac    10500
ctaacatatt atattccctc aaagcaggtt cacgatcaca cctgtaccta aaaaaaacat    10560
gaagaatata ttactccatt attatgagat gaaccacttg gcaagagtgg taagctatat    10620
aaaaaaatga acattattac gagatgttat atgccattat attgattcga agatatatgt    10680
ttctttctcc cacgggcacc taacggatac atgataaggc caaggcagat cacgggaaat    10740
tattcgaata catgttacgc cctattgccg gaaaaaaaat gcagggcagg tgttggccgt    10800
agcgatttaa gcacttaagc tggaggttgc cacacttgga tgcaagcgtc tgacccttct    10860
aaaaaatcgg cggctttgtc cgtatccgta tcccctatcc aacatctagc tggccacacg    10920
acggggctgg gcagatcgtg gatgccgggt cgacgtcgat cgtcagccat catagaccaa    10980
tcgaccatct gttatggatg cttgctagct agactagtca gacataaaat ttggatactt    11040
tctcccaact gggagacggg gactgatgtg cagctgcacg tgagctaaat ttttccctat    11100
aaatatgcat gaaatactgc attatcttgc cacagccact gccacagcca gataacaagt    11160
gcagctggta gcacgcaacg catagctctg gacttgtagc taggtagcca accggatcca    11220
cacgacacca tgctcgacac caacaaggtg tacgagatca gcaaccacgc caacggcctc    11280
tacgccgcca cctacctctc cctcgacgac tccggcgtgt ccctcatgaa caagaacgac    11340
gacgacatcg acgactacaa cctcaagtgg ttcctcttcc cgatcgacga cgaccagtac    11400
atcatcacct cctacgccgc caacaactgc aaggtgtgga acgtgaacaa cgacaagatt    11460
aatgtgtcaa cctactcctc caccaactcc atccagaagt ggcagatcaa ggccaacggc    11520
```

```
tcctcctacg tgatccagtc cgacaacggc aaggtgctca ccgccggcac cggccaggcc    11580
ctcggcctca tccgcctcac cgacgagtcc tccaacaacc cgaaccagca atggaacctg    11640
acgtccgtgc agaccatcca gctcccgcag aagccgatca tcgacaccaa gctcaaggac    11700
tacccgaagt actcccgac cggcaacatc gacaacggca cctccccgca gctcatgggc     11760
tggaccctcg tgccgtgcat catggtgaac gacccgaaca tcgacaagaa cacccagatc    11820
aagaccaccc cgtactacat cctcaagaag taccagtact ggcagagggc cgtgggctcc    11880
aacgtcgcgc tccgcccgca cgagaagaag tcctacacct acgagtgggg caccgagatc    11940
gaccagaaga ccaccatcat caacaccctc ggcttccaga tcaacatcga cagcggcatg    12000
aagttcgaca tcccggaggt gggcggcggt accgacgaga tcaagaccca gctcaacgag    12060
gagctcaaga tcgagtattc acatgagacg aagatcatgg agaagtacca ggagcagtcc    12120
gagatcgaca acccgaccga ccagtccatg aactccatcg gcttcctcac catcacctcc    12180
ctggagctct accgctacaa cggctccgag atccgcatca tgcagatcca gacctccgac    12240
aacgacacct acaacgtgac ctcctacccg aaccaccagc aggccctgct gctgctgacc    12300
aaccactcct acgaggaggt ggaggagatc accaacatcc cgaagtccac cctcaagaag    12360
ctcaagaagt actacttctg agtcatgagt catgagtcag ttaacctaga cttgtccatc    12420
ttctggattg gccaacttaa ttaatgtatg aaataaaagg atgcacacat agtgacatgc    12480
taatcactat aatgtgggca tcaaagttgt gtgttatgtg taattactag ttatctgaat    12540
aaaagagaaa gagatcatcc atatttctta tcctaaatga atgtcacgtg tctttataat    12600
tctttgatga accagatgca tttcattaac caaatccata tacatataaa tattaatcat    12660
atataattaa tatcaattgg gttagcaaaa caaatctagt ctaggtgtgt tttgcgaatt    12720
atcgatgggc cccggccgaa gctggccgcg gaccgaattc ccatggagtc aaagattcaa    12780
atagaggacc taacagaact cgccgtaaag actggcgaac agttcataca gagtctctta    12840
cgactcaatg acaagaagaa aatcttcgtc aacatggtgg agcacgacac gcttgtctac    12900
tccaaaaata tcaaagatac agtctcagaa gaccaaaggg caattgagac ttttcaacaa    12960
agggtaatat ccggaaacct cctcggattc cattgcccag ctatctgtca ctttattgtg    13020
aagatagtgg aaaaggaagg tggctcctac aaatgccatc attgcgataa aggaaaggcc    13080
atcgttgaag atgcctctgc cgacagtggt cccaaagatg gacccccacc cacgaggagc    13140
atcgtggaaa aagaagacgt tccaaccacg tcttcaaagc aagtggattg atgtgatatc    13200
tccactgacg taagggatga cgcacaatcc cactatcctt cgcaagaccc ttcctctata    13260
taaggaagtt catttcattt ggagaggaca gggtacccgg ggatccacca tgtctccgga    13320
gaggagacca gttgagatta ggccagctac agcagctgat atggccgcgg tttgtgtatat   13380 cgttaaccat tacattgaga cgtctacagt gaactttagg acagagccac aaacaccaca    13440
agagtggatt gatgatctag agaggttgca agatagatac ccttggttgg ttgctgaggt    13500
tgagggtgtt gtggctggta ttgcttacgc tgggccctgg aaggctagga acgcttacga    13560
ttggacagtt gagagtactg tttacgtgtc acataggcat caaaggttgg gcctaggatc    13620
cacattgtac acacatttgc ttaagtctat ggaggcgcaa ggttttaagt ctgtggttgc    13680
tgttataggc cttccaaacg atccatctgt taggttgcat gaggctttgg gatacacagc    13740
ccggggtaca ttgcgcgcag ctggatacaa gcatggtgga tggcatgatg ttggtttttg    13800
gcaaagggat tttgagttgc cagctcctcc aaggccagtt aggccagtta cccagatctg    13860
```

```
agtcgacctg caggcatgcc cgctgaaatc accagtctct ctctacaaat ctatctctct    13920
ctataataat gtgtgagtag ttcccagata agggaattag ggttcttata gggtttcgct    13980
catgtgttga gcatataaga aacccttagt atgtatttgt atttgtaaaa tacttctatc    14040
aataaaattt ctaattccta aaaccaaaat ccagggcgag ctcgaattcg agctcgagcc    14100
cgggtggatc ctctagagtc gacctgcaga agcttcggtc cggcgcgcct ctagttgaag    14160
acacgttcat gtcttcatcg taagaagaca ctcagtagtc ttcggccaga atggcctaac    14220
tcaaggccat cgtggcctct tgctcttcag gatgaagagc tatgtttaaa cgtgcaagcg    14280
ctactagaca attcagtaca ttaaaaacgt ccgcaatgtg ttattaagtt gtctaagcgt    14340
caatttggaa caagtggcta tcgccagata taagaacttc gatccgaaat atcgtttcaa    14400
aactagaaaa cagcgcggct ttggctaagc cgcgcactat ataggatttt gggcaccttt    14460
tgatggaacg tgaaagcgta ctgcgcacta gttatttagg ttgaaccttg gatatacggt    14520
tctcactgcg ccaatgcaag gcttgaaact tggttagtaa tacgtactcc ctccgttcct    14580
ttttatttgt cgctggatag tgcaatttg cactatcgag cgacaaataa aaagaaacgg    14640
agggagtata tgattgtcag atgtagatat gtttatttat atatcacata cagatatata    14700
aaacagatca cttttcaga tatacagttc caatgtcagc cctgatcacc ctgtcataaa      14760
ttgcacgttt ctaattgatg ttgcttcatg gtcgtcatga gaaccttctg aagaaatcga    14820
tgaaggttgc caacctttca aagtttcaga aaccactttg catgtacact aagggctggt    14880
ttggcagccc aaaaccagcc agcgttttcc tggtcttttc tcccgggaga agcccatgc     14940 atagattgtc cctggattat ttatctgtgt cctttggcta aaaattcgtc ccaatttcct    15000
gtaggaaact acctcggcct tgggaggcca ggcgattctc caccgcctcg tctcgtccat    15060
ccttcgatgc tcacgcgtgc ctcctcggat gctatcctca ggcgattctc cgtcgtctcg    15120
tctcatccat cctcacgcgc gcctcctccg acgctatccc caggcgattc tccaccgtct    15180
cgtctcatcc atcctcatgt acgcctcgtc cgatgctatc cccagacgat tttccgtcgt    15240
ctcatctcct tcatgctcgc gcgcgcctcc tccgacgcta tccccaggcg attttttctgc   15300 cgtctcgtct ccttcatgcc cgcgcgcgcc tcctccgacg ctatccccag gcgattttcc    15360
gccgtctcgt ctccttcatg cccgcgcgtg cctcctccga cgctattccc acgagcgcct    15420
ccgccgccgc tatccccaga cgattttccg ctgtctcgtc tccttcatgc ccgcgcgccc    15480
ctcctccgac gctatcccca cgagcgcctc cgccgccgct ccaccgtctt cccgccgcc    15540 atccccttaa ttcctataga tctgacccc gctctacttt cgttggcata ctttttgcttg    15600 gtgtgcgcgg gctggagtgg aaggttgcgc attcgatcac gggggagaag tggatcttgg    15660
gtcttggcag gctagggcgg ttgccaggac gccgtggtgt gcattcatgg gtcctataaa    15720
tctttatcat taccgcctta ggagctagtt gtagttcaca catcatatcc ttttctgctc    15780
gacatcgtct ggggatgccc taggtgccct accgaccta cggcattgtc ttgacctcta    15840
ttagactcta tgtcatctag agccttcttg ggtggccttt tgaccccaaa gcgacccat    15900 gatcttaccc taacgaggtc tcccttggtg gggcaagatc cactttgtcc acttaactga    15960
agatctgatc ctcatcttga aatctttaat cccaaggtga ctctacgtcg tatgtggatg    16020
ctccgggtaa cctgccaacc cggatcaccc taagatctct ttcctaaggg gcgagatcta    16080
ggttcctacg agaaagaaga cgaccctgca ccattgcggt ccgtccggtc cagagtgcga    16140
acgtccggat gcgacacagg gaaggagtcg ctcctgcagc gaggtcgcag actgtccaca    16200
cagcctcaga aggcaccgcc agacaataca tgtaataccc actctgtaag aaaaaacctaa   16260
```

```
aaggagaaag tatattcctt tatctatatg tgtgttatat ttctactcac catcacatgt      16320
gaacatctca cttacacaaa taaataatta acaaaagaca ctcaaataaa ttatgcatca      16380
tgctcgacct tattttgtgt gcattctgtt acaatataaa aataatataa aaaacatata      16440
ttaatatcaa aatttggaga tttaacccta atatgcaaat cggagtttag aggaaagaaa      16500
gaaaaatgct atacaaaata aaggaataaa tatataaata aaggtaaaac tattaatact      16560
ggtatattaa tttgaacagt tgacctaatt atgaatatca caactggttt gaattcaaat      16620
atgaaatcca agaatttgga aataggaaaa atggagataa gaataaagga aaagaattct      16680
taactcggat gggcctggga aacgaatttc ggcccacttc ctgtgtcctt agctgtgcgg      16740
ctcagtccag tg                                                         16752

<210> SEQ ID NO 2
<211> LENGTH: 16695
<212> TYPE: DNA
<213> ORGANISM: Artificial
<220> FEATURE:
<223> OTHER INFORMATION: synthetic

<400> SEQUENCE: 2
gagcatatcc agcaccagct ggtaccaagg tcgggtctct gtgctagtgc tattagctag        60
tgtaaggagc gagtaggtca gttaaggctg gtgcgtcgtg agggctgtct tgtgtgtagc       120
tacagcagac ggttcatcag aaggattatt cgtgcagtat atacagtaca actagacaat       180
gatgttgatg attggtctag agctagaggc ctatagccct atactactgt gtattgtccg       240
ccgttttagt tttttggtcc catcccatca atgcaaccgc cttgttttgc tccaattgtc       300
ccgttcctgc gcctcgcttt tgctctgtcg catcgcatac aaaaaaaaaa acgccgcgcc       360
ggctttgaat cgcgcccccc aactgctcca accaggcaac ggacacggcc accgtccgtg       420
tcgcgagcaa aaaacaaaa agaggaacgt gtccaggacg aagcagtcca ctgccgctgt       480
ggccggcaaa agatctggtt gagcacatgg agattggaga aggttggttg gttcttctgg       540
aaacgccaat gaatggggc actgacatgt actcttaaca tgtagtgcaa tccagagatc       600
ggatatccag acactggcag cacgatcgcc tcgcgccgta gatcacgcac gcaaattact       660
gaagaccatt cacaaaaaaa aaaaaacaca caggggctag cgtgccccac accaaaccca       720
agtgctgcgt tgcacgcagg ggagcgaaaa aaaacaataa tgctcactgt cacgtcgcgt       780 atccaaccc gcggacgtct cggctctcag cagcagcaca cggggcacct cacgatgccg       840
ttctcgttgc actccgtgca ccgccggaac ccgccgccgc attcgtcgcc ctcctcctcc       900
tcctccgcct cgtcttcgtc acccacgtac accttgcagc tgcccgagca gacatcgcag       960
agcacgaacc gcatgtcccc gcaggcctcg cacgcgccgg cgtcgccgcc gtgtgggccg      1020
gccgtcgacg cagcgctctc gcacccggcc agcctcggcg cgagctcccc ggcctcgtgc      1080
agccgcttca gctcctcggc gttgcccacg agctccccgt ccacgaagag gctggggagg      1140
gcggcgggcg tgccgccggc ttggccgagc ccgaggccga aaggccgcg gagctcgtcc      1200 cggaacccgc ggtgcatgga cacgtcgcgc tcgtcgaggc gcacgccgta gcccttgagg      1260
atggcgcgcg ccaggcagca gtcctcgtgc gtggcgcgca cgccgcgcag cgacgtgaag      1320
tagagcaccg ccctccgcgg cggcagcgcc ttcccctccc cgccgctcgt cggggcggcg      1380
tcgggccgag gcatcggcat cggcagcggc gtcaccttgg cggacgccgc gaggtcctgc      1440
gcaggcgccg tggcgaccgg gaacgagaag gagtggcgcc cgaacggcgc gcccagcagc      1500
```

```
gggggagcggt cctcgaggcc ggccatgagc gcccacgcgt cgatgtcctc gggctcgttg    1560
ggcggcgtca tggtgggcgt gcgcggcgcc agcctcgtgg gcgcgggctc cggcgcccgc    1620
ggcagggcct tgtccagctc cagggacccg agcgtggacg acgtgagccg caccacgtgg    1680
acgccgacgt cgctggggca ccgagccggg aacgactggc tgcgcggcag cggtgacggg    1740
cagtaccgga ggtcgtgacg ggcctgcctt gaggtggtgc accccatggc accaatgtac    1800
acacacggcc aaagcgccaa gtgggctgca gactgcctgc caatgtgatc aagcagccag    1860
gagcagagac ggatctctgg ggatcggggt ttctggggtt taggatcttt atactactct    1920
gtcattgggg atataaaact aggagtgtgg ttaattagga ctcgatagat aagtttacca    1980
caagcgcgtg aaatggtcta cccgatgatg tgattggcct aaaaagaaca agaagagtat    2040
ttggagctac tgaacattct cttttcctga agataactaa ttttggaac attcagactt     2100 gggagtctgg acttttggag ggaagttcaa attgtggtct gcctctgcca tgtgttgttt    2160
tttagtcgga gagtggccct cattttttt gtcctgttta gctttatagt cgtagcagct     2220
agtagcgaaa tttaaccttg gattatggcc gtgttagtca aacaatcatt gatttatttc    2280
ctccctttcg cgctgctttt cctgtacgca tctccgctgc ccttgattcg aggaccctgt    2340
tcacaacaca gggctctggc tttggagcct ctcgtttgta gcacttgcac gtagttaccc    2400
ggaccgaagc ttcaacacag atctgatagt ttaaacgctc ttcaactgga agagcggtta    2460 cccgaccga agcttcggcc ggggcccatc gatatccgcg gcatgcctg cagtgcagcg      2520 tgacccggtc gtgcccctct ctagagataa tgagcattgc atgtctaagt tataaaaaat    2580
taccacatat ttttttttgtc acacttgttt gaagtgcagt ttatctatct ttatacatat   2640
atttaaactt tactctacga ataatataat ctatagtact acaataatat cagtgtttta    2700
gagaatcata taaatgaaca gttagacatg gtctaaagga caattgagta ttttgacaac    2760
aggactctac agttttatct ttttagtgtg catgtgttct cctttttttt tgcaaatagc    2820
ttcacctata taatacttca tccattttat tagtacatcc attagggtt tagggttaat     2880 ggttttata gactaatttt tttagtacat ctattttatt ctattttagc ctctaaatta     2940
agaaaactaa aactctattt tagttttttt atttaataat ttagatataa aatagaataa    3000
aataaagtga ctaaaaatta aacaaatacc ctttaagaaa ttaaaaaaac taaggaaaca    3060
tttttcttgt ttcgagtaga taatgccagc ctgttaaacg ccgtcgacga gtctaacgga    3120
caccaaccag cgaaccagca gcgtcgcgtc gggccaagcg aagcagacgg cacggcatct    3180
ctgtcgctgc ctctggaccc ctctcgagag ttccgctcca ccgttggact tgctccgctg    3240
tcggcatcca gaaattgcgt ggcggagcgg cagacgtgag ccggcacggc aggcggcctc    3300
ctcctcctct cacggcaccg gcagctacgg gggattcctt tcccaccgct ccttcgcttt    3360
cccttcctcg cccgccgtaa taaatagaca ccccctccac accctctttc cccaacctcg    3420
tgttgttcgg agcgcacaca cacacaacca gatctccccc aaatccaccc gtcggcacct    3480
ccgcttcaag gtacgccgct cgtcctcccc cccccccct ctctaccttc tctagatcgg     3540
cgttccggtc catggttagg gcccggtagt tctacttctg ttcatgtttg tgttagatcc    3600
gtgtttgtgt tagatccgtg ctgctagcgt tcgtacacgg atgcgacctg tacgtcagac    3660
acgttctgat tgctaacttg ccagtgtttc tctttgggga atcctgggat ggctctagcc    3720
gttccgcaga cgggatcgat ttcatgattt tttttgtttc gttgcatagg gtttggtttg    3780
cccttttcct ttatttcaat atatgccgtg cacttgtttt tcgggtcatc ttttcatgct    3840 ttttttttgtc ttggttgtga tgatgtggtc tggttgggcg gtcgttctag atcggagtag   3900
```

```
aattctgttt caaactacct ggtggattta ttaattttgg atctgtatgt gtgtgccata    3960
catattcata gttacgaatt gaagatgatg gatggaaata tcgatctagg ataggtatac    4020
atgttgatgc gggttttact gatgcatata cagagatgct ttttgttcgc ttggttgtga    4080
tgatgtggtg tggttgggcg gtcgttcatt cgttctagat cggagtagaa tactgtttca    4140
aactacctgg tgtatttatt aattttggaa ctgtatgtgt gtgtcataca tcttcatagt    4200
tacgagttta agatggatgg aaatatcgat ctaggatagg tatacatgtt gatgtgggtt    4260
ttactgatgc atatacatga tggcatatgc agcatctatt catatgctct aaccttgagt    4320
acctatctat tataataaac aagtatgttt tataattatt ttgatcttga tatacttgga    4380
tgatggcata tgcagcagct atatgtggat ttttttagcc ctgccttcat acgctattta    4440
tttgcttggt actgtttctt ttgtcgatgc tcaccctgtt gtttggtgtt acttctgcag    4500
gtcgactcta gaggatccaa caatggagaa caacatacag aatcagtgcg tccctacaa    4560 ctgcctcaac aatcctgaag tagagattct caacgaagag aggtcgactg gcagattgcc    4620
gttagacatc tccctgtccc ttacacgttt cctgttgtct gagtttgttc caggtgtggg    4680
agttgcgttt ggcctcttcg acctcatctg gggcttcatc actccatctg attggagcct    4740 cttctcttctc cagattgaac agttgattga acaaaggatt gagaccttgg aaaggaatcg    4800
ggccatcact acccttcgtg gcttagcaga cagctatgag atctacattg aagcactaag    4860
agagtgggaa gccaatccta acaatgccca actgagagaa gatgtgcgta tacgctttgc    4920
taacacagat gatgctttga tcacagccat caacaacttc acccttacca gcttcgagat    4980
ccctcttctc tcggtctatg ttcaagctgc taacctgcac ttgtcactac tgcgcgacgc    5040
tgtgtcgttt gggcaaggtt ggggactgga catagctact gtcaacaatc actacaacag    5100
actcatcaat ctgattcatc gatacacgaa acattgtttg gatacctaca atcagggatt    5160
ggagaacctg agaggtacta acactcgcca atgggccagg ttcaatcagt tcaggagaga    5220
ccttacactt actgtgttag acatagttgc tctctttccg aactacgatg ttcgtaccta    5280
tccgattcaa acgtcatccc aacttacaag ggagatctac accagttcag tcattgaaga    5340
ctctccagtt tctgcgaaca tacccaatgg tttcaacagg gctgagtttg gagtcagacc    5400
accccatctc atggacttca tgaactcttt gtttgtgact gcagagactg ttagatccca    5460
aactgtgtgg ggaggacact tagttagctc acgcaacacg gctggcaatc gtatcaactt    5520
tcctagttac ggggtcttca atcccggggg cgccatctgg attgcagatg aagatccacg    5580
tcctttctat cggaccttgt cagatcctgt cttcgtccga ggaggctttg gcaatcctca    5640
ctatgtactc ggtcttaggg gagtggcctt tcaacaaact ggtacgaatc acacccgcac    5700
attcaggaac tccgggacca ttgactctct agatgagata ccacctcaag acaacagcgg    5760
cgcaccttgg aatgactact cccatgtgct gaatcatgtt acctttgtgc gctggccagg    5820
tgagatctca ggttccgact catggagagc accaatgttc tcttggacgc atcgtagcgc    5880 taccccccaca acaccattg atccagagag aatcactcag attcccttgg tgaaggcaca    5940
cacacttcag tcaggaacta cagttgtaag agggccgggg ttcacgggag gagacattct    6000
tcgacgcact agtggaggac cattcgcgta caccattgtc aacatcaatg gcaacttcc    6060 ccaaaggtat cgtgccagga tacgctatgc ctctactacc aatctaagaa tctacgttac    6120
ggttgcaggt gaacggatct ttgctggtca gttcaacaag acaatggata ccggtgatcc    6180
acttacattc caatctttct cctacgccac tatcaacacc gcgttcacct ttccaatgag    6240
```

```
ccagagcagt ttcacagtag gtgctgatac cttcagttca ggcaacgaag tgtacattga    6300
caggtttgag ttgattccag ttactgccac actcgagtaa ggatccgtcg acctgcagcc    6360
aagctttcgc gagctcgaga tccccgacat atgccccggt tcgttgcga  ctaacatgag    6420 ttcttggaca aatttgattg gacctgatga gatgatccaa cccgaggata tagcaaagct    6480
cgttcgtgca gcaatggaac ggccaaaccg tgcttttgtc cccaagaatg aggtgctatg    6540
catgaaggaa tctacccgtt gatgtccaac agtctcaggg ttaatgtcta tgtatcttaa    6600
ataatgttgt cggtatttty taatctcata tagattttca ctgtgcgacg caaaaatatt    6660
aaataaatat tattattatc tacgttttga ttgagatatc atcaatatta taataaaaat    6720
atccattaaa cacgatttga tacaaatgac agtcaataat ctgatttgaa tatttattaa    6780
ttgtaacgaa ttcataaaag atcgaataga aaatactgca ctgcaaatga aaattaacac    6840
atactaataa atgcgtcaaa tatctttgcc aagatcaagc ggagtgaggg cctcatatcc    6900
ggtctcagtt acaagcacgg tatccccgaa gcgcgctcca ccaatgccct cgacatagat    6960
gccgggctcg acgctgagga cattgcctac cttgagcatg gtctcagcgc cggctttaag    7020
ctcaatccca tcccaatctg aatatcctat cccgcgccca gtccggtgta agaacgggtc    7080
tgtccatcca cctctgttgg gaattccggt ccgggtcacc tttgtccacc aagatggaac    7140
tgcggccagc ttgcatgcct gcagtgcagc gtgacccggt cgtgcccctc tctagagata    7200
atgagcattg catgtctaag ttataaaaaa ttaccacata ttttttttgt cacacttgtt    7260
tgaagtgcag tttatctatc tttatacata tatttaaact ttactctacg aataatataa    7320
tctatagtac tacaataata tcagtgtttt agagaatcat ataaatgaac agttagacat    7380
ggtctaaagg acaattgagt attttgacaa caggactcta cagttttatc ttttttagtgt    7440 gcatgtgttc tcctttttt ttgcaaatag cttcacctat ataatacttc atccatttta    7500
ttagtacatc catttagggt ttagggttaa tggtttttat agactaattt ttttagtaca    7560
tctattttat tctattttag cctctaaatt aagaaaacta aaactctatt ttagtttttt    7620
tatttaataa tttagatata aaatagaata aaataaagtg actaaaaatt aaacaaatac    7680
cctttaagaa attaaaaaaa ctaaggaaac atttttcttg tttcgagtag ataatgccag    7740
cctgttaaac gccgtcgacg agtctaacgg acaccaacca gcgaaccagc agcgtcgcgt    7800
cgggccaagc gaagcagacg gcacggcatc tctgtcgctg cctctggacc cctctcgaga    7860
gttccgctcc accgttggac ttgctccgct gtcggcatcc agaaattgcg tggcggagcg    7920
gcagacgtga gccggcacgg caggcggcct cctcctcctc tcacggcacc ggcagctacg    7980
ggggattcct ttcccaccgc tccttcgctt tcccttcctc gcccgccgta ataaatagac    8040
accccctcca caccctcttt ccccaacctc gtgttgttcg gagcgcacac acacacaacc    8100
agatctcccc caaatccacc cgtcggcacc tccgcttcaa ggtacgccgc tcgtcctccc    8160
cccccccccc tctctacctt ctctagatcg gcgttccggt ccatggttag ggcccggtag    8220
ttctacttct gttcatgttt gtgttagatc cgtgtttgtg ttagatccgt gctgctagcg    8280
ttcgtacacg gatgcgacct gtacgtcaga cacgttctga ttgctaactt gccagtgttt    8340
ctctttgggg aatcctggga tggctctagc cgttccgcag acgggatcga tttcatgatt    8400 tttttgttt cgttgcatag ggtttggttt gcccttttcc tttatttcaa tatatgccgt    8460
gcacttgttt gtcgggtcat cttttcatgc ttttttttgt cttggttgtg atgatgtggt    8520
ctggttgggc ggtcgttcta gatcggagta gaattctgtt tcaaactacc tggtggattt    8580
attaattttg gatctgtatg tgtgtgccat acatattcat agttacgaat tgaagatgat    8640
```

```
ggatggaaat atcgatctag gataggtata catgttgatg cgggttttac tgatgcatat    8700
acagagatgc ttttgttcg cttggttgtg atgatgtggt gtggttgggc ggtcgttcat    8760
tcgttctaga tcggagtaga atactgtttc aaactacctg gtgtatttat taattttgga    8820
actgtatgtg tgtgtcatac atcttcatag ttacgagttt aagatggatg gaaatatcga    8880
tctaggatag gtatacatgt tgatgtgggt tttactgatg catatacatg atggcatatg    8940
cagcatctat tcatatgctc taaccttgag tacctatcta ttataataaa caagtatgtt    9000
ttataattat tttgatcttg atatacttgg atgatggcat atgcagcagc tatatgtgga    9060
ttttttagc cctgccttca tacgctattt atttgcttgg tactgtttct tttgtcgatg     9120
ctcaccctgt tgtttggtgt tacttctgca ggtcgactct agaggatcca cacgacacca    9180
tgtccgcccg cgaggtgcac atcgacgtga acaacaagac cggccacacc ctccagctgg    9240
aggacaagac caagctcgac ggcggcaggt ggcgcacctc cccgaccaac gtggccaacg    9300
accagatcaa gaccttcgtg gccgaatcca acggcttcat gaccggcacc gagggcacca    9360
tctactactc aattaatggc gaggccgaga tcagcctcta cttcgacaac ccgttcgccg    9420
gctccaacaa atacgacggc cactccaaca agtcccagta cgagatcatc acccagggcg    9480
gctccggcaa ccagtcccac gtgacctaca ccatccagac cacctcctcc cgctacggcc    9540
acaagtcctg agtcatgagt catgagtcag ttaacctaga cttgtccatc ttctggattg    9600
gccaacttaa ttaatgtatg aaataaaagg atgcacacat agtgacatgc taatcactat    9660
aatgtgggca tcaaagttgt gtgttatgtg taattactag ttatctgaat aaaagagaaa    9720
gagatcatcc atatttctta tcctaaatga atgtcacgtg tctttataat tctttgatga    9780
accagatgca tttcattaac caaatccata tacatataaa tattaatcat atataattaa    9840
tatcaattgg gttagcaaaa caaatctagt ctaggtgtgt tttgcgaatg cggccgcgga    9900
ccgaattggg gatctgcatg aaagaaactg tcgcactgct gaaccgcacc ttgtcacttt    9960
catcgaacac gacctgtgcc caagatgacg gtgctgcggt ctaagtgagg ctgaattgcc   10020
ttggacagaa gcggactccc tacaattagt taggccaaac ggtgcatcca tgtgtagctc   10080
cgggctcggg ctgtatcgcc atctgcaata gcatccatgg agctcgttcc atgtagttgg   10140
agatgaacca atgatcgggc gtgtggacgt atgttcctgt gtactccgat agtgagagtac  10200
gtgttagctc tttcatggtg caagtgaaat ttgtgttggg ttaattaccc ctacgttagt   10260
tgcgggacag gagacacatc atgaatttaa aggcgatgat gtcctctcct gtaatgttat   10320
tcttttgatg tgatgaatca aaatgtcata taaaacattt gttgctcttt agttaggcct   10380
gatcgtagaa cgaaatgctc gtgtagcggg gctacgagcc tatgacgcaa taacactggt   10440
ttgccggccc ggagtcgctt gacaaaaaaa agcatgttaa gtttatttac aattcaaaac   10500
ctaacatatt atattccctc aaagcaggtt cacgatcaca cctgtaccta aaaaaaacat   10560
gaagaatata ttactccatt attatgagat gaaccacttg gcaagagtgg taagctatat   10620
aaaaaaatga acattattac gagatgttat atgccattat attgattcga agatatatgt   10680
ttctttctcc cacgggcacc taacggatac atgataaggc caaggcagat cacgggaaat   10740
tattcgaata catgttacgc cctattgccg gaaaaaaaat gcagggcagg tgttggccgt   10800
agcgatttaa gcacttaagc tggaggttgc cacacttgga tgcaagcgtc tgaccttct    10860
aaaaaatcgg cggctttgtc cgtatccgta tcccctatcc aacatctagc tggccacacg   10920
acggggctgg gcagatcgtg gatgccgggt cgacgtcgat cgtcagccat catagaccaa   10980
```

```
tcgaccatct gttatggatg cttgctagct agactagtca gacataaaat ttggatactt   11040
tctcccaact gggagacggg gactgatgtg cagctgcacg tgagctaaat ttttccctat   11100
aaatatgcat gaaatactgc attatcttgc cacagccact gccacagcca gataacaagt   11160
gcagctggta gcacgcaacg catagctctg gacttgtagc taggtagcca accggatcca   11220
cacgacacca tgctcgacac caacaaggtg tacgagatca gcaaccacgc caacggcctc   11280
tacgccgcca cctacctctc cctcgacgac tccggcgtgt ccctcatgaa caagaacgac   11340
gacgacatcg acgactacaa cctcaagtgg ttcctcttcc cgatcgacga cgaccagtac   11400
atcatcacct cctacgccgc caacaactgc aaggtgtgga acgtgaacaa cgacaagatt   11460
aatgtgtcaa cctactcctc caccaactcc atccagaagt ggcagatcaa ggccaacggc   11520
tcctcctacg tgatccagtc cgacaacggc aaggtgctca ccgccggcac cggccaggcc   11580
ctcggcctca tccgcctcac cgacgagtcc tccaacaacc cgaaccagca atggaacctg   11640
acgtccgtgc agaccatcca gctcccgcag aagccgatca tcgacaccaa gctcaaggac   11700
tacccgaagt actcccgac cggcaacatc gacaacggcc cctccccgca gctcatgggc   11760
tggacccteg tgccgtgcat catggtgaac gacccgaaca tcgacaagaa cacccagatc   11820
aagaccaccc cgtactacat cctcaagaag taccagtact ggcagagggc cgtgggctcc   11880
aacgtcgcgc tccgcccgca cgagaagaag tcctacacct acgagtgggg caccgagatc   11940
gaccagaaga ccaccatcat caacaccctc ggcttccaga tcaacatcga cagcggcatg   12000
aagttcgaca tcccggaggt gggcggcggt accgacgaga tcaagaccca gctcaacgag   12060
gagctcaaga tcgagtattc acatgagacg aagatcatgg agaagtacca ggagcagtcc   12120
gagatcgaca cccgaccga ccagtccatg aactccatcg gcttcctcac catcacctcc   12180
ctggagctct accgctacaa cggctccgag atccgcatca tgcagatcca gcctccgac   12240
aacgacacct acaacgtgac ctcctacccg aaccaccagc aggccctgct gctgctgacc   12300
aaccactcct acgaggaggt ggaggagatc accaacatcc cgaagtccac cctcaagaag   12360
ctcaagaagt actacttctg agtcatgagt catgagtcag ttaacctaga cttgtccatc   12420
ttctggattg gccaacttaa ttaatgtatg aaataaaagg atgcacacat agtgacatgc   12480
taatcactat aatgtgggca tcaaagttgt gtgttatgtg taattactag ttatctgaat   12540
aaaagagaaa gagatcatcc atatttctta tcctaaatga atgtcacgtg tctttataat   12600
tctttgatga accagatgca tttcattaac caaatccata tacatataaa tattaatcat   12660
atataattaa tatcaattgg gttagcaaaa caaatctagt ctaggtgtgt tttgcgaatt   12720
atcgatgggc cccggccgaa gctggccgcg gaccgaattc ccatggagtc aaagattcaa   12780
atagaggacc taacagaact cgccgtaaag actggcgaac agttcataca gagtctctta   12840
cgactcaatg acaagaagaa aatcttcgtc aacatggtgg agcacgacac gcttgtctac   12900
tccaaaaata tcaaagatac agtctcagaa gaccaaaggg caattgagac ttttcaacaa   12960
agggtaatat ccggaaacct cctcggattc cattgcccag ctatctgtca ctttattgtg   13020
aagatagtgg aaaaggaagg tggctcctac aaatgccatc attgcgataa aggaaaggcc   13080
atcgttgaag atgcctctgc cgacagtggt cccaaagatg gacccccacc cacgaggagc   13140
atcgtggaaa aagaagacgt tccaaccacg tcttcaaagc aagtggattg atgtgatatc   13200
tccactgacg taagggatga cgcacaatcc cactatcctt cgcaagaccc ttcctctata   13260
taaggaagtt catttcattt ggagaggaca gggtacccgg ggatccacca tgtctccgga   13320
gaggagacca gttgagatta ggccagctac agcagctgat atggccgcgg tttgtgatat   13380
```

```
cgttaaccat tacattgaga cgtctacagt gaactttagg acagagccac aaacaccaca    13440
agagtggatt gatgatctag agaggttgca agatagatac ccttggttgg ttgctgaggt    13500
tgagggtgtt gtggctggta ttgcttacgc tgggccctgg aaggctagga acgcttacga    13560
ttggacagtt gagagtactg tttacgtgtc acataggcat caaaggttgg gcctaggatc    13620
cacattgtac acacatttgc ttaagtctat ggaggcgcaa ggttttaagt ctgtggttgc    13680
tgttataggc cttccaaacg atccatctgt taggttgcat gaggctttgg gatacacagc    13740
ccggggtaca ttgcgcgcag ctggatacaa gcatggtgga tggcatgatg ttggtttttg    13800
gcaaagggat tttgagttgc cagctcctcc aaggccagtt aggccagtta cccagatctg    13860
agtcgacctg caggcatgcc cgctgaaatc accagtctct ctctacaaat ctatctctct    13920
ctataataat gtgtgagtag ttcccagata agggaattag ggttcttata gggtttcgct    13980
catgtgttga gcatataaga aacccttagt atgtatttgt atttgtaaaa tacttctatc    14040
aataaaattt ctaattccta aaccaaaat ccagggcgag ctcgaattcg agctcgagcc    14100
cgggtggatc ctctagagtc gacctgcaga agcttcggtc cggcgcgcct ctagttgaag    14160
acacgttcat gtcttcatcg taagaagaca ctcagtagtc ttcggccaga atggcctaac    14220
tcaaggccat cgtggcctct tgctcttcag gatgaagagc tatgtttaaa cgtgcaagcg    14280
cttttgtagc acttgcacgt agttacccgg atataagaac ttcgatccga aatatcgttt    14340
caaaactaga aaacagcgcg gctttggcta agccgcgcac tatataggat tttgggcacc    14400
ttttgatgga acgtgaaagc gtactgcgca ctagttattt aggttgaacc ttggatatac    14460
ggttctcact gcgccaatgc aaggcttgaa acttggttag taatacgtac tccctccgtt    14520 tcttttatt tgtcgctgga tagtgcaatt ttgcactatc gagcgacaaa taaaagaaa     14580 cggagggagt atatgattgt cagatgtaga tatgtttatt tatatatcac atacagatat    14640
ataaaacaga tcactttttc agatatacag ttccaatgtc agccctgatc accctgtcat    14700
aaattgcacg tttctaattg atgttgcttc atggtcgtca tgagaacctt ctgaagaaat    14760
cgatgaaggt tgccaacctt tcaaagtttc agaaaccact ttgcatgtac actaagggct    14820
ggtttggcag cccaaaacca gccagcgttt tcctggtctt ttctcccggg agaaagccca    14880
tgcatagatt gtccctggat tatttatctg tgtcctttgg ctaaaaattc gtcccaattt    14940
cctgtaggaa actacctcgg ccttgggagg ccaggcgatt ctccaccgcc tcgtctcgtc    15000
catccttcga tgctcacgcg tgcctcctcg gatgctatcc tcaggcgatt ctccgtcgtc    15060
tcgtctcatc catcctcacg cgcgcctcct ccgacgctat cccaggcga ttctccaccg     15120 tctcgtctca tccatcctca tgtacgcctc gtccgatgct atccccagac gattttccgt    15180
cgtctcatct ccttcatgct cgcgcgcgcc tcctccgacg ctatccccag gcgattttc     15240 tgccgtctcg tctccttcat gcccgcgcgc gcctcctccg acgctatccc caggcgattt    15300
tccgccgtct cgtctccttc atgcccgcgc gtgcctcctc cgacgctatt ccacgagcg    15360 cctccgccgc cgctatcccc agacgatttt ccgctgtctc gtctccttca tgcccgcgcg    15420
cccctcctcc gacgctatcc ccacgagcgc ctcgccgcc gctccaccgt cttcccgcc      15480 gccatcccct taattcctat agatctggac cccgctctac tttcgttggc atacttttgc    15540
ttggtgtgcg cgggctggag tggaaggttg cgcattcgat cacggggggag aagtggatct    15600 tgggtcttgg caggctaggg cggttgccag gacgccgtgg tgtgcattca tgggtcctat    15660
aaatctttat cattaccgcc ttaggagcta gttgtagttc acacatcata tccttttctg    15720
```

| | | | | |
|---|---|---|---|---|
| ctcgacatcg | tctggggatg | ccctaggtgc | cctaccgacc | ctacggcatt | gtcttgacct | 15780 |
| ctattagact | ctatgtcatc | tagagccttc | ttgggtggcc | ttttgacccc | aaagcgaccc | 15840 |
| tatgatctta | ccctaacgag | gtctcccttg | gtggggcaag | atccactttg | tccacttaac | 15900 |
| tgaagatctg | atcctcatct | tgaaatcttt | aatcccaagg | tgactctacg | tcgtatgtgg | 15960 |
| atgctccggg | taacctgcca | acccggatca | ccctaagatc | tctttcctaa | ggggcgagat | 16020 |
| ctaggttcct | acgagaaaga | agacgaccct | gcaccattgc | ggtccgtccg | gtccagagtg | 16080 |
| cgaacgtccg | gatgcgacac | agggaaggag | tcgctcctgc | agcgaggtcg | cagactgtcc | 16140 |
| acacagcctc | agaaggcacc | gccagacaat | acatgtaata | cccactctgt | aagaaaaacc | 16200 |
| taaaaggaga | agtatattc | ctttatctat | atgtgtgtta | tatttctact | caccatcaca | 16260 |
| tgtgaacatc | tcacttacac | aaataaataa | ttaacaaaag | acactcaaat | aaattatgca | 16320 |
| tcatgctcga | ccttatttg | tgtgcattct | gttacaatat | aaaaataata | taaaaaacat | 16380 |
| atattaatat | caaaatttgg | agatttaacc | ctaatatgca | aatcggagtt | tagaggaaag | 16440 |
| aaagaaaaat | gctatacaaa | ataaaggaat | aaatatataa | ataaaggtaa | aactattaat | 16500 |
| actggtatat | taatttgaac | agttgaccta | attatgaata | tcacaactgg | tttgaattca | 16560 |
| aatatgaaat | ccaagaattt | ggaaatagga | aaatgagga | taagaataaa | ggaaaagaat | 16620 |
| tcttaactcg | gatgggcctg | ggaaacgaat | ttcggcccac | ttcctgtgtc | cttagctgtg | 16680 |
| cggctcagtc | cagtg | | | | | 16695 |

<210> SEQ ID NO 3
<211> LENGTH: 16699
<212> TYPE: DNA
<213> ORGANISM: Artificial
<220> FEATURE:
<223> OTHER INFORMATION: synthetic

<400> SEQUENCE: 3

| | | | | |
|---|---|---|---|---|
| gagcatatcc | agcaccagct | ggtaccaagg | tcgggtctct | gtgctagtgc | tattagctag | 60 |
| tgtaaggagc | gagtaggtca | gttaaggctg | gtgcgtcgtg | agggctgtct | tgtgtgtagc | 120 |
| tacagcagac | ggttcatcag | aaggattatt | cgtgcagtat | atacagtaca | actagacaat | 180 |
| gatgttgatg | attggtctag | agctagaggc | ctatagccct | atactactgt | gtattgtccg | 240 |
| ccgttttagt | ttttggtcc | catcccatca | atgcaaccgc | cttgttttgc | tccaattgtc | 300 |
| ccgttcctgc | gcctcgcttt | tgctctgtcg | catcgcatac | aaaaaaaaa | acgccgcgcc | 360 |
| ggctttgaat | cgcgcccccc | aactgctcca | accaggcaac | ggacacggcc | accgtccgtg | 420 |
| tcgcgagcaa | aaaacaaaa | agaggaacgc | gtccaggacg | aagcagtcca | ctgccgctgt | 480 |
| ggccggcaaa | agatctggtt | gagcacatgg | agattggaga | aggttggttg | gttcttctgg | 540 |
| aaacgccaat | gaatggggggc | actgacatgt | actcttaaca | tgtagtgcaa | tccagagatc | 600 |
| ggatatccag | acactggcag | cacgatcgcc | tcgcgccgta | gatcacgcac | gcaaattact | 660 |
| gaagaccatt | cacaaaaaaa | aaaaacaca | caggggctag | cgtgccccac | accaaaccca | 720 |
| agtgctgcgt | tgcacgcagg | ggagcgaaaa | aaaacaataa | tgctcactgt | cacgtcgcgt | 780 |
| atccaacccc | gcggacgtct | cggctctcag | cagcagcaca | cggggcacct | cacgatgccg | 840 |
| ttctcgttgc | actccgtgca | ccgccggaac | ccgccgccgc | attcgtcgcc | ctcctcctcc | 900 |
| tcctccgcct | cgtcttcgtc | acccacgtac | accttgcagc | tgcccgagca | gacatcgcag | 960 |
| agcacgaacc | gcatgtcccc | gcaggcctcg | cacgcgccgg | cgtcgccgcc | gtgtgggccg | 1020 |
| gccgtcgacg | cagcgctctc | gcacccggcc | agcctcggcg | cgagctcccc | ggcctcgtgc | 1080 |

```
agccgcttca gctcctcggc gttgcccacg agctccccgt ccacgaagag gctggggagg      1140
gcggcgggcg tgccgccggc ttggccgagc ccgaggccga aaggccgcg gagctcgtcc       1200 cggaacccgc ggtgcatgga cacgtcgcgc tcgtcgaggc gcacgccgta gcccttgagg      1260
atggcgcgcg ccaggcagca gtcctcgtgc gtggcgcgca cgccgcgcag cgacgtgaag      1320
tagagcaccg ccctccgcgg cggcagcgcc ttcccctccc cgccgctcgt cggggcggcg      1380 tcggccgag gcatcggcat cggcagcggc gtcaccttgg cggacgccgc gaggtcctgc       1440
gcaggcgccg tggcgaccgg gaacgagaag gagtggcgcc cgaacggcgc gcccagcagc     1500
ggggagcggt cctcgaggcc ggccatgagc gcccacgcgt cgatgtcctc gggctcgttg      1560
ggcggcgtca tggtgggcgt gcgcggcgcc agcctcgtgg gcgcgggctc cggcgcccgc      1620
ggcagggcct tgtccagctc cagggacccg agcgtggacg acgtgagccg caccacgtgg     1680
acgccgacgt cgctggggca ccgagccggg aacgactggc tgcgcggcag cggtgacggg     1740
cagtaccgga ggtcgtgacg ggcctgcctt gaggtggtgc accccatggc accaatgtac     1800
acacacggcc aaagcgccaa gtgggctgca gactgcctgc caatgtgatc aagcagccag     1860
gagcagagac ggatctctgg ggatcgggt ttctggggtt taggatcttt atactactct      1920
gtcattgggg atataaaact aggagtgtgg ttaattagga ctcgatagat aagtttacca     1980
caagcgcgtg aaatggtcta cccgatgatg tgattggcct aaaagaaca agaagagtat     2040 ttggagctac tgaacattct cttttcctga agataactaa ttttggaac attcagactt     2100 gggagtctgg acttttggag ggaagttcaa attgtggtct gcctctgcca tgtgttgttt     2160
tttagtcgga gagtggccct catttttttt gtcctgttta gctttatagt cgtagcagct    2220
agtagcgaaa tttaaccttg gattatggcc gtgttagtca aacaatcatt gatttatttc     2280 ctcccttcg cgctgctttt cctgtacgca tctccgctgc ccttgattcg aggaccctgt      2340
tcacaacaca gggctctggc tttgagcct ctcgtttgta gcacttgcac gtagttaccc      2400
ggaccgaagc ttcaacacag atctgatagt ttaaacgctc ttcaactgga agagcggtta    2460
cccggaccga agcttcggcc ggggcccatc gatatccgcg ggcatgcctg cagtgcagcg     2520
tgacccggtc gtgcccctct ctagagataa tgagcattgc atgtctaagt tataaaaaat    2580
taccacatat ttttttttgtc acacttgttt gaagtgcagt ttatctatct ttatacatat    2640
atttaaactt tactctacga ataatataat ctatagtact acaataatat cagtgtttta    2700
gagaatcata taaatgaaca gttagacatg gtctaaagga caattgagta ttttgacaac    2760
aggactctac agttttatct ttttagtgtg catgtgttct cctttttttt tgcaaatagc    2820
ttcacctata taatacttca tccatttat tagtacatcc atttagggtt tagggttaat    2880 ggttttata gactaatttt tttagtcat ctattttatt ctattttagc ctctaaatta     2940
agaaaactaa aactctattt tagttttttt atttaataat ttagatataa aatagaataa    3000
aataaagtga ctaaaatta aacaaatacc ctttaagaaa ttaaaaaaac taaggaaaca    3060
tttttcttgt ttcgagtaga taatgccagc ctgttaaacg ccgtcgacga gtctaacgga    3120
caccaaccag cgaaccagca gcgtcgcgtc gggccaagcg aagcagacgg cacggcatct    3180
ctgtcgctgc ctctggaccc ctctcgagag ttccgctcca ccgttggact tgctccgctg     3240
tcggcatcca gaaattgcgt ggcggagcgg cagacgtgag ccggcacggc aggcggcctc    3300
ctcctcctct cacggcaccg gcagctacgg gggattcctt tcccaccgct ccttcgcttt    3360
cccttcctcg cccgccgtaa taaatagaca ccccctccac accctctttc cccaacctcg    3420
```

```
tgttgttcgg agcgcacaca cacacaacca gatctccccc aaatccaccc gtcggcacct    3480
ccgcttcaag gtacgccgct cgtcctcccc cccccccct ctctaccttc tctagatcgg     3540
cgttccggtc catggttagg gcccggtagt tctacttctg ttcatgtttg tgttagatcc    3600
gtgtttgtgt tagatccgtg ctgctagcgt tcgtacacgg atgcgacctg tacgtcagac    3660
acgttctgat tgctaacttg ccagtgtttc tctttgggga atcctgggat ggctctagcc    3720
gttccgcaga cgggatcgat ttcatgattt ttttgtttc gttgcatagg gtttggtttg     3780
cccttttcct ttatttcaat atatgccgtg cacttgtttg tcgggtcatc ttttcatgct    3840 ttttttgtc ttggttgtga tgatgtggtc tggttgggcg gtcgttctag atcggagtag     3900
aattctgttt caaactacct ggtggattta ttaattttgg atctgtatgt gtgtgccata    3960
catattcata gttacgaatt gaagatgatg gatggaaata tcgatctagg ataggtatac    4020
atgttgatgc gggttttact gatgcatata cagagatgct ttttgttcgc ttggttgtga   4080
tgatgtggtg tggttgggcg gtcgttcatt cgttctagat cggagtagaa tactgtttca    4140
aactacctgg tgtatttatt aattttggaa ctgtatgtgt gtgtcataca tcttcatagt    4200
tacgagttta agatggatgg aaatatcgat ctaggatagg tatacatgtt gatgtgggtt    4260
ttactgatgc atatacatga tggcatatgc agcatctatt catatgctct aaccttgagt    4320
acctatctat tataataaac aagtatgttt tataattatt ttgatcttga tatacttgga    4380
tgatggcata tgcagcagct atatgtggat ttttttagcc ctgccttcat acgctattta    4440
tttgcttggt actgtttctt ttgtcgatgc tcaccctgtt gtttggtgtt acttctgcag    4500
gtcgactcta gaggatccaa caatggagaa caacatacag aatcagtgcg tcccctacaa    4560
ctgcctcaac aatcctgaag tagagattct caacgaagag aggtcgactg gcagattgcc    4620
gttagacatc tccctgtccc ttacacgttt cctgttgtct gagtttgttc caggtgtggg    4680
agttgcgttt ggcctcttcg acctcatctg gggcttcatc actccatctg attggagcct    4740
ctttcttctc cagattgaac agttgattga acaaaggatt gagaccttgg aaaggaatcg    4800
ggccatcact acccttcgtg gcttagcaga cagctatgag atctacattg aagcactaag    4860
agagtgggaa gccaatccta acaatgccca actgagagaa gatgtgcgta tacgctttgc    4920
taacacagat gatgctttga tcacagccat caacaacttc acccttacca gcttcgagat    4980
ccctcttctc tcggtctatg ttcaagctgc taacctgcac ttgtcactac tgcgcgacgc    5040
tgtgtcgttt gggcaaggtt ggggactgga catagctact gtcaacaatc actacaacag    5100
actcatcaat ctgattcatc gatacacgaa acattgtttg gatacctaca atcagggatt    5160
ggagaacctg agaggtacta acactcgcca atgggccagg ttcaatcagt tcaggagaga    5220
ccttacactt actgtgttag acatagttgc tctctttccg aactacgatg ttcgtaccta    5280
tccgattcaa acgtcatccc aacttacaag ggagatctac accagttcag tcattgaaga    5340
ctctccagtt tctgcgaaca tacccaatgg tttcaacagg gctgagtttg gagtcagacc    5400
accccatctc atggacttca tgaactcttt gtttgtgact gcagagactg ttagatccca    5460
aactgtgtgg ggaggacact tagttagctc acgcaacacg gctggcaatc gtatcaactt    5520
tcctagttac ggggtcttca atcccggggg cgccatctgg attgcagatg aagatccacg    5580
tcctttctat cggaccttgt cagatcctgt cttcgtccga ggaggctttg gcaatcctca    5640
ctatgtactc ggtcttaggg gagtggcctt tcaacaaact ggtacgaatc acacccgcac    5700
attcaggaac tccgggacca ttgactctct agatgagata ccacctcaag acaacagcgg    5760
cgcaccttgg aatgactact cccatgtgct gaatcatgtt acctttgtgc gctggccagg    5820
```

```
tgagatctca ggttccgact catggagagc accaatgttc tcttggacgc atcgtagcgc   5880
tacccccaca aacaccattg atccagagag aatcactcag attcccttgg tgaaggcaca   5940
cacacttcag tcaggaacta cagttgtaag agggccgggg ttcacgggag gagacattct   6000
tcgacgcact agtggaggac cattcgcgta caccattgtc aacatcaatg gcaacttcc    6060 ccaaaggtat cgtgccagga tacgctatgc ctctactacc aatctaagaa tctacgttac   6120
ggttgcaggt gaacggatct ttgctggtca gttcaacaag acaatggata ccggtgatcc   6180
acttacattc caatctttct cctacgccac tatcaacacc gcgttcacct ttccaatgag   6240
ccagagcagt ttcacagtag gtgctgatac cttcagttca ggcaacgaag tgtacattga   6300
caggtttgag ttgattccag ttactgccac actcgagtaa ggatccgtcg acctgcagcc   6360
aagctttcgc gagctcgaga tccccgacat atgccccggt ttcgttgcga ctaacatgag   6420
ttcttggaca aatttgattg gacctgatga gatgatccaa cccgaggata tagcaaagct   6480
cgttcgtgca gcaatggaac ggccaaaccg tgcttttgtc cccaagaatg aggtgctatg   6540
catgaaggaa tctacccgtt gatgtccaac agtctcaggg ttaatgtcta tgtatcttaa   6600
ataatgttgt cggtattttg taatctcata tagattttca ctgtgcgacg caaaaatatt   6660
aaataaatat tattattatc tacgttttga ttgagatatc atcaatatta aataaaaat   6720 atccattaaa cacgatttga tacaaatgac agtcaataat ctgatttgaa tatttattaa   6780
ttgtaacgaa ttacataaag atcgaataga aaatactgca ctgcaaatga aaattaacac   6840
atactaataa atgcgtcaaa tatctttgcc aagatcaagc ggagtgaggg cctcatatcc   6900
ggtctcagtt acaagcacgg tatccccgaa gcgcgctcca ccaatgccct cgacatagat   6960
gccgggctcg acgctgagga cattgcctac cttgagcatg gtctcagcgc cggctttaag   7020
ctcaatccca tcccaatctg aatatcctat cccgcgccca gtccggtgta agaacgggtc   7080
tgtccatcca cctctgttgg gaattccggt ccgggtcacc tttgtccacc aagatggaac   7140
tgcggccagc ttgcatgcct gcagtgcagc gtgacccggt cgtgcccctc tctagagata   7200
atgagcattg catgtctaag ttataaaaaa ttaccacata ttttttttgt cacacttgtt   7260
tgaagtgcag tttatctatc tttatacata tatttaaact ttactctacg aataatataa   7320
tctatagtac tacaataata tcagtgtttt agagaatcat ataaatgaac agttagacat   7380
ggtctaaagg acaattgagt attttgacaa caggactcta cagttttatc ttttttagtgt  7440 gcatgtgttc tcctttttt ttgcaaatag cttcacctat ataatacttc atccatttta    7500
ttagtacatc catttagggt ttagggttaa tggttttta agactaattt ttttagtaca    7560 tctatttat tctattttag cctctaaatt aagaaaacta aaactctatt ttagtttttt    7620
tatttaataa tttagatata aaatagaata aaataaagtg actaaaaatt aaacaaatac   7680
cctttaagaa attaaaaaaa ctaaggaaac attttttcttg tttcgagtag ataatgccag   7740
cctgttaaac gccgtcgacg agtctaacgg acaccaacca gcgaaccagc agcgtcgcgt   7800
cgggccaagc gaagcagacg gcacggcatc tctgtcgctg cctctggacc cctctcgaga   7860
gttccgctcc accgttggac ttgctccgct gtcggcatcc agaaattgcg tggcggagcg   7920
gcagacgtga gccggcacgg caggcggcct cctcctcctc tcacggcacc ggcagctacg   7980
ggggattcct ttcccaccgc tccttcgctt tccttcctc gcccgccgta ataaatagac    8040
accccctcca cacctctttt ccccaacctc gtgttgttcg gagcgcacac acacacaacc   8100
agatctcccc caaatccacc cgtcggcacc tccgcttcaa ggtacgccgc tcgtcctccc   8160
```

```
cccccccccc tctctacctt ctctagatcg gcgttccggt ccatggttag ggcccggtag    8220
ttctacttct gttcatgttt gtgttagatc cgtgtttgtg ttagatccgt gctgctagcg    8280
ttcgtacacg gatgcgacct gtacgtcaga cacgttctga ttgctaactt gccagtgttt    8340
ctctttgggg aatcctggga tggctctagc cgttccgcag acgggatcga tttcatgatt    8400
ttttttgttt cgttgcatag ggtttggttt gccctttttcc tttatttcaa tatatgccgt   8460
gcacttgttt gtcgggtcat cttttcatgc ttttttttgt cttggttgtg atgatgtggt    8520
ctggttgggc ggtcgttcta gatcggagta gaattctgtt tcaaactacc tggtggattt    8580
attaattttg gatctgtatg tgtgtgccat acatattcat agttacgaat tgaagatgat    8640
ggatggaaat atcgatctag gataggtata catgttgatg cgggttttac tgatgcatat    8700
acagagatgc ttttgttcg cttggttgtg atgatgtggt gtggttgggc ggtcgttcat     8760
tcgttctaga tcggagtaga atactgtttc aaactacctg gtgtatttat taattttgga   8820
actgtatgtg tgtgtcatac atcttcatag ttacgagttt aagatggatg gaaatatcga    8880
tctaggatag gtatacatgt tgatgtgggt tttactgatg catatacatg atggcatatg    8940
cagcatctat tcatatgctc taaccttgag tacctatcta ttataataaa caagtatgtt    9000
ttataattat tttgatcttg atatacttgg atgatggcat atgcagcagc tatatgtgga    9060 ttttttagc cctgccttca tacgctattt atttgcttgg tactgtttct tttgtcgatg     9120
ctcaccctgt tgtttggtgt tacttctgca ggtcgactct agaggatcca cacgacacca    9180
tgtccgcccg cgaggtgcac atcgacgtga acaacaagac cggccacacc ctccagctgg    9240
aggacaagac caagctcgac ggcggcaggt ggcgcacctc cccgaccaac gtggccaacg    9300
accagatcaa gaccttcgtg gccgaatcca acggcttcat gaccggcacc gagggcacca    9360
tctactactc aattaatggc gaggccgaga tcagcctcta cttcgacaac ccgttcgccg    9420
gctccaacaa atacgacggc cactccaaca gtcccagta cgagatcatc acccagggcg     9480
gctccggcaa ccagtcccac gtgacctaca ccatccagac cacctcctcc cgctacggcc    9540
acaagtcctg agtcatgagt catgagtcag ttaacctaga cttgtccatc ttctggattg    9600
gccaacttaa ttaatgtatg aaataaaagg atgcacacat agtgacatgc taatcactat    9660
aatgtgggca tcaaagttgt gtgttatgtg taattactag ttatctgaat aaaagagaaa    9720
gagatcatcc atatttctta tcctaaatga atgtcacgtg tctttataat tctttgatga    9780
accagatgca tttcattaac caaatccata tacatataaa tattaatcat ataaattaa     9840 tatcaattgg gttagcaaaa caaatctagt ctaggtgtgt tttgcgaatg cggccgcgga    9900
ccgaattggg gatctgcatg aaagaaactg tcgcactgct gaaccgcacc ttgtcacttt    9960
catcgaacac gacctgtgcc caagatgacg gtgctgcggt ctaagtgagg ctgaattgcc   10020
ttggacagaa gcggactccc tacaattagt taggccaaac ggtgcatcca tgtgtagctc   10080
cgggctcggg ctgtatcgcc atctgcaata gcatccatgg agctcgttcc atgtagttgg   10140
agatgaacca atgatcgggc gtgtggacgt atgttcctgt gtactccgat agtagagtac   10200
gtgttagctc tttcatggtg caagtgaaat ttgtgttggt ttaattaccc ctacgttagt   10260
tgcgggacag gagacacatc atgaatttaa aggcgatgat gtcctctcct gtaatgttat   10320
tcttttgatg tgatgaatca aatgtcata taaaacattt gttgctcttt agttaggcct     10380
gatcgtagaa cgaaatgctc gtgtagcggg gctacgagcc tatgacgcaa taacactggt   10440
ttgccggccc ggagtcgctt gacaaaaaaa agcatgttaa gttatttac aattcaaaac     10500 ctaacatatt atattccctc aaagcaggtt cacgatcaca cctgtaccta aaaaaaacat   10560
```

```
gaagaatata ttactccatt attatgagat gaaccacttg gcaagagtgg taagctatat    10620
aaaaaaatga acattattac gagatgttat atgccattat attgattcga agatatatgt    10680
ttctttctcc cacgggcacc taacggatac atgataaggc caaggcagat cacgggaaat    10740
tattcgaata catgttacgc cctattgccg gaaaaaaat gcagggcagg tgttggccgt     10800
agcgatttaa gcacttaagc tggaggttgc cacacttgga tgcaagcgtc tgacccttct    10860
aaaaaatcgg cggctttgtc cgtatccgta tcccctatcc aacatctagc tggccacacg    10920
acggggctgg gcagatcgtg gatgccgggt cgacgtcgat cgtcagccat catagaccaa    10980
tcgaccatct gttatggatg cttgctagct agactagtca gacataaaat ttggatactt    11040
tctcccaact gggagacggg gactgatgtg cagctgcacg tgagctaaat ttttccctat    11100
aaatatgcat gaaatactgc attatcttgc cacagccact gccacagcca gataacaagt    11160
gcagctggta gcacgcaacg catagctctg gacttgtagc taggtagcca accggatcca    11220
cacgacacca tgctcgacac caacaaggtg tacgagatca gcaaccacgc caacggcctc    11280
tacgccgcca cctacctctc cctcgacgac tccggcgtgt ccctcatgaa caagaacgac    11340
gacgacatcg acgactacaa cctcaagtgg ttcctcttcc cgatcgacga cgaccagtac    11400
atcatcacct cctacgccgc caacaactgc aaggtgtgga acgtgaacaa cgacaagatt    11460
aatgtgtcaa cctactcctc caccaactcc atccagaagt ggcagatcaa ggccaacggc    11520
tcctcctacg tgatccagtc cgacaacggc aaggtgctca ccgccggcac cggccaggcc    11580
ctcggcctca tccgcctcac cgacgagtcc tccaacaacc cgaaccagca atggaacctg    11640
acgtccgtgc agaccatcca gctcccgcag aagccgatca tcgacaccaa gctcaaggac    11700
tacccgaagt actccccgac cggcaacatc gacaacggca cctccccgca gctcatgggc    11760
tggaccctcg tgccgtgcat catggtgaac gacccgaaca tcgacaagaa cacccagatc    11820
aagaccaccc cgtactacat cctcaagaag taccagtact ggcagagggc cgtgggctcc    11880
aacgtcgcgc tccgcccgca cgagaagaag tcctacacct acgagtgggg caccgagatc    11940
gaccagaaga ccaccatcat caacaccctc ggcttccaga tcaacatcga cagcggcatg    12000
aagttcgaca tcccggaggt gggcggcggt accgacgaga tcaagaccca gctcaacgag    12060
gagctcaaga tcgagtattc acatgagacg aagatcatgg agaagtacca ggagcagtcc    12120
gagatcgaca acccgaccga ccagtccatg aactccatcg gcttcctcac catcacctcc    12180
ctggagctct accgctacaa cggctccgag atccgcatca tgcagatcca gacctccgac    12240
aacgacacct acaacgtgac ctcctacccg aaccaccagc aggccctgct gctgctgacc    12300
aaccactcct acgaggaggt ggaggagatc accaacatcc cgaagtccac cctcaagaag    12360
ctcaagaagt actacttctg agtcatgagt catgagtcag ttaacctaga cttgtccatc    12420
ttctggattg gccaacttaa ttaatgtatg aaataaaagg atgcacacat agtgacatgc    12480
taatcactat aatgtgggca tcaaagttgt gtgttatgtg taattactag ttatctgaat    12540
aaaagagaaa gagatcatcc atatttctta tcctaaatga atgtcacgtg tctttataat    12600
tctttgatga accagatgca tttcattaac caaatccata tacatataaa tattaatcat    12660
atataattaa tatcaattgg gttagcaaaa caaatctagt ctaggtgtgt tttgcgaatt    12720
atcgatgggc cccggccgaa gctggccgcg gaccgaattc ccatggagtc aaagattcaa    12780
atagaggacc taacagaact cgccgtaaag actggcgaac agttcataca gagtctctta    12840
cgactcaatg acaagaagaa aatcttcgtc aacatggtgg agcacgacac gcttgtctac    12900
```

```
tccaaaaata tcaaagatac agtctcagaa gaccaaaggg caattgagac ttttcaacaa   12960
agggtaatat ccggaaacct cctcggattc cattgcccag ctatctgtca ctttattgtg   13020
aagatagtgg aaaaggaagg tggctcctac aaatgccatc attgcgataa aggaaaggcc   13080
atcgttgaag atgcctctgc cgacagtggt cccaaagatg acccccacc cacgaggagc    13140 atcgtggaaa aagaagacgt tccaaccacg tcttcaaagc aagtggattg atgtgatatc   13200
tccactgacg taagggatga cgcacaatcc cactatcctt cgcaagaccc ttcctctata   13260
taaggaagtt catttcattt ggagaggaca gggtacccgg ggatccacca tgtctccgga   13320
gaggagacca gttgagatta ggccagctac agcagctgat atggccgcgg tttgtgatat   13380
cgttaaccat tacattgaga cgtctacagt gaactttagg acagagccac aaacaccaca   13440
agagtggatt gatgatctag agaggttgca agatagatac ccttggttgg ttgctgaggt   13500
tgagggtgtt gtggctggta ttgcttacgc tgggccctgg aaggctagga acgcttacga   13560
ttggacagtt gagagtactg tttacgtgtc acataggcat caaaggttgg gcctaggatc   13620
cacattgtac acacatttgc ttaagtctat ggaggcgcaa ggttttaagt ctgtggttgc   13680
tgttataggc cttccaaacg atccatctgt taggttgcat gaggctttgg gatacacagc   13740
ccggggtaca ttgcgcgcag ctggatacaa gcatggtgga tggcatgatg ttggtttttg   13800
gcaaagggat tttgagttgc cagctcctcc aaggccagtt aggccagtta cccagatctg   13860
agtcgacctg caggcatgcc cgctgaaatc accagtctct ctctacaaat ctatctctct   13920
ctataataat gtgtgagtag ttcccagata agggaattag ggttcttata gggtttcgct   13980
catgtgttga gcatataaga aacccttagt atgtatttgt atttgtaaaa tacttctatc   14040
aataaaattt ctaattccta aaaccaaaat ccagggcgag ctcgaattcg agctcgagcc   14100
cgggtggatc tctagagtc gacctgcaga agcttcggtc cggcgcgcct ctagttgaag   14160
acacgttcat gtcttcatcg taagaagaca ctcagtagtc ttcggccaga atggcctaac   14220
tcaaggccat cgtggcctct tgctcttcag gatgaagagc tatgtttaaa cgtgcaagcg   14280
cttttgtagc acttgcacgt agttacccgg ccagatataa gaacttcgat ccgaaatatc   14340
gtttcaaaac tagaaaacag cgcggctttg gctaagccgc gcactatata ggattttggg   14400 cacctttga tggaacgtga aagcgtactg cgcactagtt atttaggttg aaccttggat    14460
atacggttct cactgcgcca atgcaaggct tgaaacttgg ttagtaatac gtactccctc   14520
cgtttctttt tatttgtcgc tggatagtgc aattttgcac tatcgagcga caaataaaaa   14580
gaaacggagg gagtatatga ttgtcagatg tagatatgtt tatttatata tcacatacag   14640
atatataaaa cagatcactt tttcagatat acagttccaa tgtcagccct gatcaccctg   14700
tcataaattg cacgtttcta attgatgttg cttcatggtc gtcatgagaa ccttctgaag   14760
aaatcgatga aggttgccaa cctttcaaag tttcagaaac cactttgcat gtacactaag   14820
ggctggtttg gcagcccaaa accagccagc gtttcctgg tcttttctcc cgggagaaag    14880
cccatgcata gattgtccct ggattattta tctgtgtcct ttggctaaaa attcgtccca   14940
atttcctgta ggaaactacc tcggccttgg gaggccaggc gattctccac cgcctcgtct   15000
cgtccatcct tcgatgctca cgcgtgcctc tcggatgct atcctcaggc gattctccgt    15060
cgtctcgtct catccatcct cacgcgcgcc tcctccgacg ctatcccag gcgattctcc    15120 accgtctcgt ctcatccatc ctcatgtacg cctcgtccga tgctatcccc agacgatttt   15180
ccgtcgtctc atctccttca tgctcgcgcg cgcctcctcc gacgctatcc ccaggcgatt   15240
tttctgccgt ctcgtctcct tcatgcccgc gcgcgcctcc tccgacgcta tccccaggcg   15300
```

-continued

```
attttccgcc gtctcgtctc cttcatgccc gcgcgtgcct cctccgacgc tattcccacg    15360
agcgcctccg ccgccgctat ccccagacga ttttccgctg tctcgtctcc ttcatgcccg    15420
cgcgccccct ctccgacgct atccccacga gcgcctccgc cgccgctcca ccgtcttccc    15480
cgccgccatc cccttaattc ctatagatct ggaccccgct ctactttcgt tggcatactt    15540
ttgcttggtg tgcgcgggct ggagtggaag gttgcgcatt cgatcacggg ggagaagtgg    15600
atcttgggtc ttggcaggct agggcggttg ccaggacgcc gtggtgtgca ttcatgggtc    15660
ctataaatct ttatcattac cgccttagga gctagttgta gttcacacat catatccttt    15720
tctgctcgac atcgtctggg gatgccctag gtgccctacc gacccctacgg cattgtcttg    15780 acctctatta gactctatgt catctagagc cttcttgggt ggccttttga ccccaaagcg    15840
accctatgat cttaccctaa cgaggtctcc cttggtgggg caagatccac tttgtccact    15900
taactgaaga tctgatcctc atcttgaaat ctttaatccc aaggtgactc tacgtcgtat    15960
gtggatgctc cgggtaacct gccaacccgg atcaccctaa gatctctttc ctaaggggcg    16020
agatctaggt tcctacgaga aagaagacga ccctgcacca ttgcggtccg tccggtccag    16080
agtgcgaacg tccggatgcg acacagggaa ggagtcgctc ctgcagcgag gtcgcagact    16140
gtccacacag cctcagaagg caccgccaga caatacatgt aatacccact ctgtaagaaa    16200
aacctaaaag gagaaagtat attcctttat ctatatgtgt gttatatttc tactcaccat    16260
cacatgtgaa catctcactt acacaaataa ataattaaca aaagacactc aaataaatta    16320
tgcatcatgc tcgaccttat tttgtgtgca ttctgttaca atataaaaat aatataaaaa    16380
acatatatta atatcaaaat ttggagattt aaccctaata tgcaaatcgg agtttagagg    16440
aaagaaagaa aaatgctata caaaataaag gaataaatat ataaataaag gtaaaactat    16500
taatactggt atattaattt gaacagttga cctaattatg aatatcacaa ctggtttgaa    16560
ttcaaatatg aaatccaaga atttggaaat aggaaaaatg gagataagaa taaaggaaaa    16620
gaattcttaa ctcggatggg cctgggaaac gaatttcggc ccacttcctg tgtccttagc    16680
tgtgcggctc agtccagtg                                                16699
```

```
<210> SEQ ID NO 4
<211> LENGTH: 27
<212> TYPE: DNA
<213> ORGANISM: Artificial
<220> FEATURE:
<223> OTHER INFORMATION: synthetic

<400> SEQUENCE: 4
tttggaacaa gtggctatcg ccagata                                          27

<210> SEQ ID NO 5
<211> LENGTH: 27
<212> TYPE: DNA
<213> ORGANISM: Artificial
<220> FEATURE:
<223> OTHER INFORMATION: synthetic

<400> SEQUENCE: 5
tttaatgtac tgaattgtct agtagcg                                          27

<210> SEQ ID NO 6
<211> LENGTH: 27
<212> TYPE: DNA
<213> ORGANISM: Artificial
<220> FEATURE:
```

<223> OTHER INFORMATION: synthetic

<400> SEQUENCE: 6
tttcggatcg aagttcttat atctggc                                              27

<210> SEQ ID NO 7
<211> LENGTH: 27
<212> TYPE: DNA
<213> ORGANISM: Artificial
<220> FEATURE:
<223> OTHER INFORMATION: synthetic

<400> SEQUENCE: 7
tttgtagcac ttgcacgtag ttacccg                                              27

<210> SEQ ID NO 8
<211> LENGTH: 35
<212> TYPE: DNA
<213> ORGANISM: Artificial
<220> FEATURE:
<223> OTHER INFORMATION: synthetic

<400> SEQUENCE: 8
cgcttttgta gcacttgcac gtagttaccc ggata                                     35

<210> SEQ ID NO 9
<211> LENGTH: 64
<212> TYPE: DNA
<213> ORGANISM: Artificial
<220> FEATURE:
<223> OTHER INFORMATION: synthetic

<400> SEQUENCE: 9
aacgtgcaag cgcttttgta gcacttgcac gtagttaccc ggatataaga acttcgatcc          60
gaaa                                                                      64

<210> SEQ ID NO 10
<211> LENGTH: 68
<212> TYPE: DNA
<213> ORGANISM: Artificial
<220> FEATURE:
<223> OTHER INFORMATION: synthetic

<400> SEQUENCE: 10
aacgtgcaag cgcttttgta gcacttgcac gtagttaccc ggccagatat aagaacttcg          60
atccgaaa                                                                  68

<210> SEQ ID NO 11
<211> LENGTH: 31
<212> TYPE: DNA
<213> ORGANISM: Artificial
<220> FEATURE:
<223> OTHER INFORMATION: synthetic

<400> SEQUENCE: 11
cgcttttgta gcacttgcac gtagttaccc g                                         31

<210> SEQ ID NO 12
<211> LENGTH: 31
<212> TYPE: DNA
<213> ORGANISM: Artificial
<220> FEATURE:
<223> OTHER INFORMATION: synthetic

<400> SEQUENCE: 12
tatccgggta actacgtgca agtgctacaa a                                        31

<210> SEQ ID NO 13
<211> LENGTH: 31
<212> TYPE: DNA
<213> ORGANISM: Artificial
<220> FEATURE:
<223> OTHER INFORMATION: synthetic

<400> SEQUENCE: 13
tggccgggta actacgtgca agtgctacaa a                                        31

<210> SEQ ID NO 14
<211> LENGTH: 1227
<212> TYPE: DNA
<213> ORGANISM: Artificial
<220> FEATURE:
<223> OTHER INFORMATION: synthetic

<400> SEQUENCE: 14
ttataggcct tccaaacgat ccatctgtta ggttgcatga ggctttggga tacacagccc          60
ggggtacatt gcgcgcagct ggatacaagc atggtggatg gcatgatgtt ggttttttggc       120
aaagggattt tgagttgcca gctcctccaa ggccagttag gccagttacc cagatctgag       180
tcgacctgca ggcatgcccg ctgaaatcac cagtctctct ctacaaatct atctctctct       240
ataataatgt gtgagtagtt cccagataag ggaattaggg ttcttatagg gtttcgctca       300
tgtgttgagc atataagaaa cccttagtat gtatttgtat ttgtaaaata cttctatcaa       360
taaaatttct aattcctaaa accaaaatcc agggcgagct cgaattcgag ctcgagcccg       420
ggtggatcct ctagagtcga cctgcagaag cttcggtccg gcgcgcctct agttgaagac       480
acgttcatgt cttcatcgta agaagacact cagtagtctt cggccagaat ggcctaactc       540
aaggccatcg tggcctcttg ctcttcagga tgaagagcta tgtttaaacg tgcaagcgct       600
tttgtagcac ttgcacgtag ttacccgact agacaattca gtacattaaa aacgtccgca       660
atgtgttatt aagttgtcta agcgtcaatt tggaacaagt ggctatcgcc agatataaga       720
acttcgatcc gaaatatcgt ttcaaaacta gaaaacagcg cggctttggc taagccgcgc       780
actatatagg attttgggca ccttttgatg gaacgtgaaa gcgtactgcg cactagttat       840
ttaggttgaa ccttggatat acggttctca ctgcgccaat gcaaggcttg aaacttggtt       900
agtaatacgt actccctccg tttctttta tttgtcgctg atagtgcaa ttttgcacta         960
tcgagcgaca aataaaaaga aacgagggga gtatatgatt gtcagatgta gatatgttta      1020
tttatatatc acatacagat atataaaaca gatcactttt tcagatatac agttccaatg      1080
tcagccctga tcaccctgtc ataaattgca cgtttctaat tgatgttgct tcatggtcgt      1140
catgagaacc ttctgaagaa atcgatgaag gttgccaacc tttcaaagtt tcagaaacca      1200
ctttgcatgt acactaaggg ctggttt                                           1227

<210> SEQ ID NO 15
<211> LENGTH: 27
<212> TYPE: DNA
<213> ORGANISM: Artificial
<220> FEATURE:
<223> OTHER INFORMATION: synthetic

<400> SEQUENCE: 15
cgctactaga caattcagta cattaaa                                             27

<210> SEQ ID NO 16
<211> LENGTH: 23
<212> TYPE: DNA
<213> ORGANISM: Artificial
<220> FEATURE:
<223> OTHER INFORMATION: synthetic

<400> SEQUENCE: 16
tagcacttgc acgtagttac ccg                                              23

<210> SEQ ID NO 17
<211> LENGTH: 25
<212> TYPE: DNA
<213> ORGANISM: Artificial
<220> FEATURE:
<223> OTHER INFORMATION: synthetic

<400> SEQUENCE: 17
tacgctgggc cctggaaggc tagga                                            25

<210> SEQ ID NO 18
<211> LENGTH: 25
<212> TYPE: DNA
<213> ORGANISM: Artificial
<220> FEATURE:
<223> OTHER INFORMATION: synthetic

<400> SEQUENCE: 18
gatggacgag acgaggcggt ggaga                                            25

<210> SEQ ID NO 19
<211> LENGTH: 46
<212> TYPE: DNA
<213> ORGANISM: Artificial
<220> FEATURE:
<223> OTHER INFORMATION: synthetic

<400> SEQUENCE: 19
tgcaagcgct tttgtagcac ttgcacgtag ttacccgact agacaa                     46

<210> SEQ ID NO 20
<211> LENGTH: 16779
<212> TYPE: DNA
<213> ORGANISM: Artificial
<220> FEATURE:
<223> OTHER INFORMATION: synthetic

<400> SEQUENCE: 20
gagcatatcc agcaccagct ggtaccaagg tcgggtctct gtgctagtgc tattagctag      60
tgtaaggagc gagtaggtca gttaaggctg gtgcgtcgtg agggctgtct tgtgtgtagc     120
tacagcagac ggttcatcag aaggattatt cgtgcagtat atacagtaca actagacaat     180
gatgttgatg attggtctag agctagaggc ctatagccct atactactgt gtattgtccg     240
ccgttttagt ttttggtcc catcccatca atgcaaccgc cttgttttgc tccaattgtc      300
ccgttcctgc gcctcgcttt tgctctgtcg catcgcatac aaaaaaaaaa acgccgcgcc     360
ggctttgaat cgcgccccc aactgctcca accaggcaac ggacacggcc accgtccgtg      420
tcgcgagcaa aaaacaaaa agaggaacgc gtccaggacg aagcagtcca ctgccgctgt     480
ggccggcaaa agatctggtt gagcacatgg agattggaga aggttggttg gttcttctgg     540
aaacgccaat gaatggggc actgacatgt actcttaaca tgtagtgcaa tccagagatc      600
ggatatccag acactggcag cacgatcgcc tcgcgccgta gatcacgcac gcaaattact     660

```
gaagaccatt cacaaaaaaa aaaaaacaca caggggctag cgtgcccac accaaaccca    720 agtgctgcgt tgcacgcagg ggagcgaaaa aaaacaataa tgctcactgt cacgtcgcgt    780
atccaacccc gcggacgtct cggctctcag cagcagcaca cggggcacct cacgatgccg    840
ttctcgttgc actccgtgca ccgccggaac ccgccgccgc attcgtcgcc ctcctcctcc    900
tcctccgcct cgtcttcgtc acccacgtac accttgcagc tgcccgagca gacatcgcag    960
agcacgaacc gcatgtcccc gcaggcctcg cacgcgccgg cgtcgccgcc gtgtgggccg   1020
gccgtcgacg cagcgctctc gcacccggcc agcctcggcg cgagctcccc ggcctcgtgc   1080
agccgcttca gctcctcggc gttgcccacg agctccccgt ccacgaagag gctggggagg   1140
gcggcgggcg tgccgccggc ttggccgagc ccgaggccga aaggccgcg gagctcgtcc   1200 cggaacccgc ggtgcatgga cacgtcgcgc tcgtcgaggc gcacgccgta gcccttgagg   1260
atggcgcgcg ccaggcagca gtcctcgtgc gtggcgcgca cgccgcgcag cgacgtgaag   1320
tagagcaccg ccctccgcgg cggcagcgcc ttcccctccc cgccgctcgt cggggcggcg   1380
tcgggccgag gcatcggcat cggcagcggc gtcaccttgg cggacgccgc gaggtcctgc   1440
gcaggcgccg tggcgaccgg gaacgagaag gagtggcgcc cgaacggcgc gcccagcagc   1500
ggggagcggt cctcgaggcc ggccatgagc gcccacgcgt cgatgtcctc gggctcgttg   1560
ggcggcgtca tggtgggcgt gcgcggcgcc agcctcgtgg gcgcgggctc cggcgcccgc   1620
ggcagggcct tgtccagctc cagggacccg agcgtggacg acgtgagccg caccacgtgg   1680
acgccgacgt cgctggggca ccgagccggg aacgactggc tgcgcggcag cggtgacggg   1740
cagtaccgga ggtcgtgacg ggcctgcctt gaggtggtgc accccatggc accaatgtac   1800
acacacggcc aaagcgccaa gtgggctgca gactgcctgc caatgtgatc aagcagccag   1860
gagcagagac ggatctctgg ggatcggggt ttctggggtt taggatcttt atactactct   1920
gtcattgggg atataaaact aggagtgtgg ttaattagga ctcgatagat aagtttacca   1980
caagcgcgtg aaatggtcta cccgatgatg tgattggcct aaaaagaaca agaagagtat   2040
ttggagctac tgaacattct cttttcctga agataactaa ttttggaac attcagactt   2100 gggagtctgg actttggag ggaagttcaa attgtggtct gcctctgcca tgtgttgttt   2160
tttagtcgga gagtggccct cattttttt gtcctgttta gctttatagt cgtagcagct   2220
agtagcgaaa tttaaccttg gattatggcc gtgttagtca aacaatcatt gatttatttc   2280
ctccctttcg cgctgctttt cctgtacgca tctccgctgc ccttgattcg aggaccctgt   2340
tcacaacaca gggctctggc tttgagcct ctcgtttgta gcacttgcac gtagttaccc   2400
ggaccgaagc ttcaacacag atctgatagt ttaaacgctc ttcaactgga agagcggtta   2460 cccgaccga agcttcggcc ggggcccatc gatatccgcg gcatgcctg cagtgcagcg   2520 tgacccggtc gtgcccctct ctagagataa tgagcattgc atgtctaagt tataaaaaat   2580
taccacatat tttttttgtc acacttgttt gaagtgcagt ttatctatct ttatacatat   2640
atttaaactt tactctacga ataatataat ctatagtact acaataatat cagtgtttta   2700
gagaatcata taaatgaaca gttagacatg gtctaaagga caattgagta ttttgacaac   2760
aggactctac agttttatct ttttagtgtg catgtgttct ccttttttt tgcaaatagc   2820 ttcacctata taatacttca tccatttat tagtacatcc atttagggtt tagggttaat   2880 ggttttata gactaatttt tttagtacat ctattttatt ctattttagc ctctaaatta   2940
agaaaactaa aactctattt tagtttttt atttaataat ttagatataa aatagaataa   3000
```

```
aataaagtga ctaaaaatta aacaaatacc ctttaagaaa ttaaaaaaac taaggaaaca   3060
ttttttcttgt ttcgagtaga taatgccagc ctgttaaacg ccgtcgacga gtctaacgga  3120
caccaaccag cgaaccagca gcgtcgcgtc gggccaagcg aagcagacgg cacggcatct   3180
ctgtcgctgc ctctggaccc ctctcgagag ttccgctcca ccgttggact tgctccgctg   3240
tcggcatcca gaaattgcgt ggcggagcgg cagacgtgag ccggcacggc aggcggcctc   3300
ctcctcctct cacggcaccg gcagctacgg gggattcctt tcccaccgct ccttcgcttt   3360
cccttcctcg cccgccgtaa taaatagaca ccccctccac accctctttc cccaacctcg   3420
tgttgttcgg agcgcacaca cacacaacca gatctccccc aaatccaccc gtcggcacct   3480
ccgcttcaag gtacgccgct cgtcctcccc ccccccccct ctctaccttc tctagatcgg   3540
cgttccggtc catggttagg gcccggtagt tctacttctg ttcatgtttg tgttagatcc   3600
gtgtttgtgt tagatccgtg ctgctagcgt tcgtacacgg atgcgacctg tacgtcagac   3660
acgttctgat tgctaacttg ccagtgtttc tctttgggga atcctgggat ggctctagcc   3720
gttccgcaga cgggatcgat ttcatgattt tttttgtttc gttgcatagg gtttggtttg   3780
ccctttcct  ttatttcaat atatgccgtg cacttgtttg tcgggtcatc ttttcatgct   3840
tttttttgtc ttggttgtga tgatgtggtc tggttgggcg gtcgttctag atcggagtag   3900
aattctgttt caaactacct ggtggattta ttaattttgg atctgtatgt gtgtgccata   3960
catattcata gttacgaatt gaagatgatg gatggaaata tcgatctagg ataggtatac   4020
atgttgatgc gggttttact gatgcatata cagagatgct ttttgttcgc ttggttgtga   4080
tgatgtggtg tggttgggcg gtcgttcatt cgttctagat cggagtagaa tactgtttca   4140
aactacctgg tgtatttatt aattttggaa ctgtatgtgt gtgtcataca tcttcatagt   4200
tacgagttta agatggatgg aaatatcgat ctaggatagg tatacatgtt gatgtgggtt   4260
ttactgatgc atatacatga tggcatatgc agcatctatt catatgctct aaccttgagt   4320
acctatctat tataataaac aagtatgttt tataattatt ttgatcttga tatacttgga   4380
tgatggcata tgcagcagct atatgtggat tttttttagcc ctgccttcat acgctattta   4440
tttgcttggt actgtttctt ttgtcgatgc tcaccctgtt gtttggtgtt acttctgcag   4500
gtcgactcta gaggatccaa caatggagaa caacatacag aatcagtgcg tcccctacaa   4560
ctgcctcaac aatcctgaag tagagattct caacgaagag aggtcgactg gcagattgcc   4620
gttagacatc tccctgtccc ttacacgttt cctgttgtct gagtttgttc caggtgtggg   4680
agttgcgttt ggcctcttcg acctcatctg gggcttcatc actccatctg attggagcct   4740
cttttcttctc cagattgaac agttgattga acaaaggatt gagaccttgg aaaggaatcg   4800
ggccatcact acccttcgtg gcttagcaga cagctatgag atctacattg aagcactaag   4860
agagtgggaa gccaatccta acaatgccca actgagagaa gatgtgcgta tacgctttgc   4920
taacacagat gatgctttga tcacagccat caacaacttc acccttacca gcttcgagat   4980
ccctcttctc tcggtctatg ttcaagctgc taacctgcac ttgtcactac tgcgcgacgc   5040
tgtgtcgttt gggcaaggtt ggggactgga catagctact gtcaacaatc actacaacag   5100
actcatcaat ctgattcatc gatacacgaa acattgtttg gatacctaca atcagggatt   5160
ggagaacctg agaggtacta acactcgcca atgggccagg ttcaatcagt tcaggagaga   5220
ccttacactt actgtgttag acatagttgc tctctttccg aactacgatg ttcgtaccta   5280
tccgattcaa acgtcatccc aacttacaag ggagatctac accagttcag tcattgaaga   5340
ctctccagtt tctgcgaaca tacccaatgg tttcaacagg gctgagtttg gagtcagacc   5400
```

```
acccatctc atggacttca tgaactcttt gtttgtgact gcagagactg ttagatccca    5460
aactgtgtgg ggaggacact tagttagctc acgcaacacg gctggcaatc gtatcaactt    5520
tcctagttac ggggtcttca atcccggggg cgccatctgg attgcagatg aagatccacg    5580
tcctttctat cggaccttgt cagatcctgt cttcgtccga ggaggctttg gcaatcctca    5640
ctatgtactc ggtcttaggg gagtggcctt tcaacaaact ggtacgaatc acacccgcac    5700
attcaggaac tccgggacca ttgactctct agatgagata ccacctcaag acaacagcgg    5760
cgcaccttgg aatgactact cccatgtgct gaatcatgtt acctttgtgc gctggccagg    5820
tgagatctca ggttccgact catggagagc accaatgttc tcttggacgc atcgtagcgc    5880
taccccacca aacaccattg atccagagag aatcactcag attcccttgg tgaaggcaca    5940
cacacttcag tcaggaacta cagttgtaag agggccgggg ttcacgggag agacattct    6000 tcgacgcact agtggaggac cattcgcgta caccattgtc aacatcaatg gcaacttcc    6060 ccaaaggtat cgtgccagga tacgctatgc ctctactacc aatctaagaa tctacgttac    6120
ggttgcaggt gaacggatct tgctggtca gttcaacaag acaatggata ccggtgatcc    6180
acttacattc caatctttct cctacgccac tatcaacacc gcgttcacct ttccaatgag    6240
ccagagcagt ttcacagtag gtgctgatac cttcagttca ggcaacgaag tgtacattga    6300
caggtttgag ttgattccag ttactgccac actcgagtaa ggatccgtcg acctgcagcc    6360
aagctttcgc gagctcgaga tccccgacat atgccccggt tcgttgcga ctaacatgag    6420 ttcttggaca aatttgattg gacctgatga gatgatccaa cccgaggata tagcaaagct    6480
cgttcgtgca gcaatggaac ggccaaaccg tgcttttgtc cccaagaatg aggtgctatg    6540
catgaaggaa tctacccgtt gatgtccaac agtctcaggg ttaatgtcta tgtatcttaa    6600
ataatgttgt cggtatttg taatctcata tagattttca ctgtgcgacg caaaaatatt    6660
aaataaatat tattattatc tacgttttga ttgagatatc atcaatatta taataaaaat    6720
atccattaaa cacgatttga tacaaatgac agtcaataat ctgatttgaa tatttattaa    6780
ttgtaacgaa ttcataaaag atcgaataga aatactgca ctgcaaatga aaattaacac    6840
atactaataa atgcgtcaaa tatctttgcc aagatcaagc ggagtgaggg cctcatatcc    6900
ggtctcagtt acaagcacgg tatccccgaa gcgcgctcca ccaatgccct cgacatagat    6960
gccgggctcg acgctgagga cattgcctac cttgagcatg gtctcagcgc cggctttaag    7020
ctcaatccca tcccaatctg aatatcctat cccgcgccca gtccggtgta agaacgggtc    7080
tgtccatcca cctctgttgg gaattccggt ccgggtcacc tttgtccacc aagatggaac    7140
tgcggccagc ttgcatgcct gcagtgcagc gtgacccggt cgtgcccctc tctagagata    7200
atgagcattg catgtctaag ttataaaaaa ttaccacata tttttttgt cacacttgtt    7260 tgaagtgcag tttatctatc tttatacata tatttaaact ttactctacg aataatataa    7320
tctatagtac tacaataata tcagtgtttt agagaatcat ataaatgaac agttagacat    7380
ggtctaaagg acaattgagt attttgacaa caggactcta cagtttatc ttttagtgt    7440 gcatgtgttc tccttttttt ttgcaaatag cttcacctat ataatacttc atccatttta    7500
ttagtacatc catttagggt ttagggttaa tggtttttat agactaattt ttttagtaca    7560 tctatttat tctattttag cctctaaatt aagaaaacta aaactctat ttagttttt    7620 tatttaataa tttagatata aaatagaata aaataaagtg actaaaaatt aaacaaatac    7680
cctttaagaa attaaaaaaa ctaaggaaac attttttcttg tttcgagtag ataatgccag    7740
```

```
cctgttaaac gccgtcgacg agtctaacgg acaccaacca gcgaaccagc agcgtcgcgt    7800
cgggccaagc gaagcagacg gcacggcatc tctgtcgctg cctctggacc cctctcgaga    7860
gttccgctcc accgttggac ttgctccgct gtcggcatcc agaaattgcg tggcggagcg    7920
gcagacgtga gccggcacgg caggcggcct cctcctcctc tcacggcacc ggcagctacg    7980
ggggattcct ttcccaccgc tccttcgctt tcccttcctc gcccgccgta ataaatagac    8040
accccctcca caccctcttt ccccaacctc gtgttgttcg gagcgcacac acacacaacc    8100
agatctcccc caaatccacc cgtcggcacc tccgcttcaa ggtacgccgc tcgtcctccc    8160
cccccccccc tctctacctt ctctagatcg gcgttccggt ccatggttag ggcccggtag    8220
ttctacttct gttcatgttt gtgttagatc cgtgtttgtg ttagatccgt gctgctagcg    8280
ttcgtacacg gatgcgacct gtacgtcaga cacgttctga ttgctaactt gccagtgttt    8340
ctctttgggg aatcctggga tggctctagc cgttccgcag acgggatcga tttcatgatt    8400
ttttttgttt cgttgcatag ggtttggttt gcccttttcc tttatttcaa tatatgccgt    8460
gcacttgttt gtcgggtcat cttttcatgc ttttttttgt cttggttgtg atgatgtggt    8520
ctggttgggc ggtcgttcta gatcggagta gaattctgtt tcaaactacc tggtggattt    8580
attaattttg gatctgtatg tgtgtgccat acatattcat agttacgaat tgaagatgat    8640
ggatggaaat atcgatctag dataggtata catgttgatg cgggttttac tgatgcatat    8700
acagagatgc ttttgttcg cttggttgtg atgatgtggt gtggttgggc ggtcgttcat    8760
tcgttctaga tcggagtaga atactgtttc aaactacctg gtgtatttat taattttgga    8820
actgtatgtg tgtgtcatac atcttcatag ttacgagttt aagatggatg gaaatatcga    8880
tctaggatag gtatacatgt tgatgtgggt tttactgatg catatacatg atggcatatg    8940
cagcatctat tcatatgctc taaccttgag tacctatcta ttataataaa caagtatgtt    9000
ttataattat tttgatcttg atatacttgg atgatggcat atgcagcagc tatatgtgga    9060
ttttttagc cctgccttca tacgctattt atttgcttgg tactgtttct tttgtcgatg    9120
ctcaccctgt tgtttggtgt tacttctgca ggtcgactct agaggatcca cacgacacca    9180
tgtccgcccg cgaggtgcac atcgacgtga acaacaagac cggccacacc ctccagctgg    9240
aggacaagac caagctcgac ggcggcaggt ggcgcacctc cccgaccaac gtggccaacg    9300
accagatcaa gaccttcgtg gccgaatcca acggcttcat gaccggcacc gagggcacca    9360
tctactactc aattaatggc gaggccgaga tcagcctcta cttcgacaac ccgttcgccg    9420
gctccaacaa atacgacggc cactccaaca gtcccagta cgagatcatc acccagggcg    9480
gctccggcaa ccagtcccac gtgacctaca ccatccagac cacctcctcc cgctacggcc    9540
acaagtcctg agtcatgagt catgagtcag ttaacctaga cttgtccatc ttctggattg    9600
gccaacttaa ttaatgtatg aaataaaagg atgcacacat agtgacatgc taatcactat    9660
aatgtgggca tcaaagttgt gtgttatgtg taattactag ttatctgaat aaaagagaaa    9720
gagatcatcc atatttctta tcctaaatga atgtcacgtg tctttataat tctttgatga    9780
accagatgca tttcattaac caaatccata tacatataaa tattaatcat atataattaa    9840
tatcaattgg gttagcaaaa caaatctagt ctaggtgtgt tttgcgaatg cggccgcgga    9900
ccgaattggg gatctgcatg aaagaaactg tcgcactgct gaaccgcacc ttgtcacttt    9960
catcgaacac gacctgtgcc caagatgacg gtgctgcggt ctaagtgagg ctgaattgcc   10020
ttggacagaa gcggactccc tacaattagt taggccaaac ggtgcatcca tgtgtagctc   10080
cgggctcggg ctgtatcgcc atctgcaata gcatccatgg agctcgttcc atgtagttgg   10140
```

```
agatgaacca atgatcgggc gtgtggacgt atgttcctgt gtactccgat agtagagtac   10200
gtgttagctc tttcatggtg caagtgaaat ttgtgttggt ttaattaccc ctacgttagt   10260
tgcgggacag gagacacatc atgaatttaa aggcgatgat gtcctctcct gtaatgttat   10320
tcttttgatg tgatgaatca aaatgtcata taaaacattt gttgctcttt agttaggcct   10380
gatcgtagaa cgaaatgctc gtgtagcggg gctacgagcc tatgacgcaa taacactggt   10440
ttgccggccc ggagtcgctt gacaaaaaaa agcatgttaa gtttatttac aattcaaaac   10500
ctaacatatt atattccctc aaagcaggtt cacgatcaca cctgtaccta aaaaaaacat   10560
gaagaatata ttactccatt attatgagat gaaccacttg gcaagagtgg taagctatat   10620
aaaaaaatga acattattac gagatgttat atgccattat attgattcga agatatatgt   10680
ttctttctcc cacgggcacc taacggatac atgataaggc caaggcagat cacgggaaat   10740
tattcgaata catgttacgc cctattgccg gaaaaaaaat gcagggcagg tgttggccgt   10800
agcgatttaa gcacttaagc tggaggttgc cacacttgga tgcaagcgtc tgacccttct   10860
aaaaaatcgg cggctttgtc cgtatccgta tcccctatcc aacatctagc tggccacacg   10920
acggggctgg gcagatcgtg gatgccgggt cgacgtcgat cgtcagccat catagaccaa   10980
tcgaccatct gttatggatg cttgctagct agactagtca gacataaaat ttggatactt   11040
tctcccaact gggagacggg gactgatgtg cagctgcacg tgagctaaat ttttccctat   11100
aaatatgcat gaaatactgc attatcttgc cacagccact gccacagcca gataacaagt   11160
gcagctggta gcacgcaacg catagctctg gacttgtagc taggtagcca accggatcca   11220
cacgacacca tgctcgacac caacaaggtg tacgagatca gcaaccacgc caacggcctc   11280
tacgccgcca cctacctctc cctcgacgac tccggcgtgt ccctcatgaa caagaacgac   11340
gacgacatcg acgactacaa cctcaagtgg ttcctcttcc cgatcgacga cgaccagtac   11400
atcatcacct cctacgccgc caacaactgc aaggtgtgga acgtgaacaa cgacaagatt   11460
aatgtgtcaa cctactcctc caccaactcc atccagaagt ggcagatcaa ggccaacggc   11520
tcctcctacg tgatccagtc cgacaacggc aaggtgctca ccgccggcac cggccaggcc   11580
ctcggcctca tccgcctcac cgacgagtcc tccaacaacc cgaaccagca atggaacctg   11640
acgtccgtgc agaccatcca gctcccgcag aagccgatca tcgacaccaa gctcaaggac   11700
tacccgaagt actcccccgac cggcaacatc gacaacggca cctccccgca gctcatgggc   11760
tggaccctcg tgccgtgcat catggtgaac gacccgaaca tcgacaagaa cacccagatc   11820
aagaccaccc cgtactacat cctcaagaag taccagtact ggcagagggc cgtgggctcc   11880
aacgtcgcgc tccgcccgca cgagaagaag tcctacacct acgagtgggg caccgagatc   11940
gaccagaaga ccaccatcat caacaccctc ggcttccaga tcaacatcga cagcggcatg   12000
aagttcgaca tcccggaggt gggcggcggt accgacgaga tcaagaccca gctcaacgag   12060
gagctcaaga tcgagtattc acatgagacg aagatcatgg agaagtacca ggagcagtcc   12120
gagatcgaca acccgaccga ccagtccatg aactccatcg gcttcctcac catcacctcc   12180
ctggagctct accgctacaa cggctccgag atccgcatca tgcagatcca gacctccgac   12240
aacgacacct acaacgtgac ctcctacccg aaccaccagc aggccctgct gctgctgacc   12300
aaccactcct acgaggaggt ggaggagatc accaacatcc cgaagtccac cctcaagaag   12360
ctcaagaagt actacttctg agtcatgagt catgagtcag ttaacctaga cttgtccatc   12420
ttctggattg gccaacttaa ttaatgtatg aaataaaagg atgcacacat agtgacatgc   12480
```

```
taatcactat aatgtgggca tcaaagttgt gtgttatgtg taattactag ttatctgaat    12540
aaaagagaaa gagatcatcc atatttctta tcctaaatga atgtcacgtg tctttataat    12600
tctttgatga accagatgca tttcattaac caaatccata tacatataaa tattaatcat    12660
atataattaa tatcaattgg gttagcaaaa caaatctagt ctaggtgtgt tttgcgaatt    12720
atcgatgggc cccggccgaa gctggccgcg gaccgaattc ccatggagtc aaagattcaa    12780
atagaggacc taacagaact cgccgtaaag actggcgaac agttcataca gagtctctta    12840
cgactcaatg acaagaagaa aatcttcgtc aacatggtgg agcacgacac gcttgtctac    12900
tccaaaaata tcaaagatac agtctcagaa gaccaaaggg caattgagac ttttcaacaa    12960
agggtaatat ccggaaacct cctcggattc cattgcccag ctatctgtca ctttattgtg    13020
aagatagtgg aaaaggaagg tggctcctac aaatgccatc attgcgataa aggaaaggcc    13080
atcgttgaag atgcctctgc cgacagtggt cccaaagatg accccccacc cacgaggagc    13140
atcgtggaaa aagaagacgt tccaaccacg tcttcaaagc aagtggattg atgtgatatc    13200
tccactgacg taagggatga cgcacaatcc cactatcctt cgcaagaccc ttcctctata    13260
taaggaagtt catttcattt ggagaggaca gggtacccgg ggatccacca tgtctccgga    13320
gaggagacca gttgagatta ggccagctac agcagctgat atggccgcgg tttgtgatat    13380
cgttaaccat tacattgaga cgtctacagt gaactttagg acagagccac aaacaccaca    13440
agagtggatt gatgatctag agaggttgca agatagatac ccttggttgg ttgctgaggt    13500
tgagggtgtt gtggctggta ttgcttacgc tgggccctgg aaggctagga acgcttacga    13560
ttggacagtt gagagtactg tttacgtgtc acataggcat caaaggttgg gcctaggatc    13620
cacattgtac acacatttgc ttaagtctat ggaggcgcaa ggttttaagt ctgtggttgc    13680
tgttataggc cttccaaacg atccatctgt taggttgcat gaggctttgg gatacacagc    13740
ccggggtaca ttgcgcgcag ctggatacaa gcatggtgga tggcatgatg ttggtttttg    13800
gcaaagggat tttgagttgc cagctcctcc aaggccagtt aggccagtta cccagatctg    13860
agtcgacctg caggcatgcc cgctgaaatc accagtctct ctctacaaat ctatctctct    13920
ctataataat gtgtgagtag ttcccagata agggaattag ggttcttata gggtttcgct    13980
catgtgttga gcatataaga aacccttagt atgtatttgt atttgtaaaa tacttctatc    14040
aataaaattt ctaattccta aaaccaaaat ccagggcgag ctcgaattcg agctcgagcc    14100
cgggtggatc ctctagagtc gacctgcaga agcttcggtc cggcgcgcct ctagttgaag    14160
acacgttcat gtcttcatcg taagaagaca ctcagtagtc ttcggccaga atggcctaac    14220
tcaaggccat cgtggcctct tgctcttcag gatgaagagc tatgtttaaa cgtgcaagcg    14280
cttttgtagc acttgcacgt agttacccga ctagacaatt cagtacatta aaaacgtccg    14340
caatgtgtta ttaagttgtc taagcgtcaa tttggaacaa gtggctatcg ccagatataa    14400
gaacttcgat ccgaaatatc gtttcaaaac tagaaaacag cgcggctttg gctaagccgc    14460
gcactatata ggattttggg caccttttga tggaacgtga aagcgtactg cgcactagtt    14520
atttaggttg aaccttggat atacggttct cactgcgcca atgcaaggct tgaaacttgg    14580
ttagtaatac gtactccctc cgtttctttt tatttgtcgc tggatagtgc aattttgcac    14640
tatcgagcga caaataaaaa gaaacggagg gagtatatga ttgtcagatg tagatatgtt    14700
tatttatata tcacatacag atatataaaa cagatcactt tttcagatat acagttccaa    14760
tgtcagccct gatcaccctg tcataaattg cacgttccta attgatgttg cttcatggtc    14820
gtcatgagaa ccttctgaag aaatcgatga aggttgccaa cctttcaaag tttcagaaac    14880
```

```
cactttgcat gtacactaag ggctggtttg gcagcccaaa accagccagc gttttcctgg    14940
tcttttctcc cgggagaaag cccatgcata gattgtccct ggattattta tctgtgtcct    15000
ttggctaaaa attcgtccca atttcctgta ggaaactacc tcggccttgg gaggccaggc    15060
gattctccac cgcctcgtct cgtccatcct tcgatgctca cgcgtgcctc ctcggatgct    15120
atcctcaggc gattctccgt cgtctcgtct catccatcct cacgcgcgcc tcctccgacg    15180
ctatccccag gcgattctcc accgtctcgt ctcatccatc ctcatgtacg cctcgtccga    15240
tgctatcccc agacgatttt ccgtcgtctc atctccttca tgctcgcgcg cgcctcctcc    15300
gacgctatcc ccaggcgatt tttctgccgt ctcgtctcct tcatgcccgc gcgcgcctcc    15360
tccgacgcta tccccaggcg attttccgcc gtctcgtctc cttcatgccc gcgcgtgcct    15420
cctccgacgc tattcccacg agcgcctccg ccgccgctat ccccagacga ttttccgctg    15480
tctcgtctcc ttcatgcccg cgcgcccctc ctccgacgct atccccacga gcgcctccgc    15540
cgccgctcca ccgtcttccc cgccgccatc cccttaattc ctatagatct ggaccccgct    15600
ctactttcgt tggcatactt tgcttggtg tgcgcgggct ggagtggaag gttgcgcatt     15660
cgatcacggg ggagaagtgg atcttgggtc ttggcaggc agggcggttg ccaggacgcc     15720
gtggtgtgca ttcatgggtc ctataaatct ttatcattac cgccttagga gctagttgta    15780
gttcacacat catatccttt tctgctcgac atcgtctggg gatgccctag gtgccctacc    15840
gaccctacgg cattgtcttg acctctatta gactctatgt catctagagc cttcttgggt    15900
ggccttttga ccccaaagcg accctatgat cttaccctaa cgaggtctcc cttggtgggg    15960
caagatccac tttgtccact taactgaaga tctgatcctc atcttgaaat ctttaatccc    16020
aaggtgactc tacgtcgtat gtggatgctc cgggtaacct gccaacccgg atcaccctaa    16080
gatctctttc ctaaggggcg agatctaggt tcctacgaga agaagacga ccctgcacca     16140 ttgcggtccg tccggtccag agtgcgaacg tccggatgcg acacagggaa ggagtcgctc    16200
ctgcagcgag gtcgcagact gtccacacag cctcagaagg caccgccaga caatacatgt    16260
aatacccact ctgtaagaaa aacctaaaag gagaaagtat attcctttat ctatatgtgt    16320
gttatatttc tactccaccat cacatgtgaa catctcactt acacaaataa ataattaaca    16380
aaagacactc aaataaatta tgcatcatgc tcgaccttat tttgtgtgca ttctgttaca    16440
atataaaaat aatataaaaa acatatatta atatcaaaat ttggagattt aaccctaata    16500
tgcaaatcgg agtttagagg aaagaagaa aaatgctata caaaataaag gaataaatat     16560
ataaataaag gtaaaactat taatactggt atattaattt gaacagttga cctaattatg    16620
aatatcacaa ctggtttgaa ttcaaatatg aaatccaaga atttggaaat aggaaaatg     16680 gagataagaa taaggaaaa gaattcttaa ctcggatggg cctgggaaac gaatttcggc      16740
ccacttcctg tgtccttagc tgtgcggctc agtccagtg                           16779
```

<210> SEQ ID NO 21
<211> LENGTH: 1307
<212> TYPE: PRT
<213> ORGANISM: Unknown
<220> FEATURE:
<223> OTHER INFORMATION: bacterial

<400> SEQUENCE: 21

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln

```
                20                  25                  30
Glu Gln Gly Phe Ile Glu Glu Asp Lys Ala Arg Asn Asp His Tyr Lys
            35                  40                  45
Glu Leu Lys Pro Ile Ile Asp Arg Ile Tyr Lys Thr Tyr Ala Asp Gln
        50                  55                  60
Cys Leu Gln Leu Val Gln Leu Asp Trp Glu Asn Leu Ser Ala Ala Ile
 65                  70                  75                  80
Asp Ser Tyr Arg Lys Glu Lys Thr Glu Thr Arg Asn Ala Leu Ile
                85                  90                  95
Glu Glu Gln Ala Thr Tyr Arg Asn Ala Ile His Asp Tyr Phe Ile Gly
            100                 105                 110
Arg Thr Asp Asn Leu Thr Asp Ala Ile Asn Lys Arg His Ala Glu Ile
            115                 120                 125
Tyr Lys Gly Leu Phe Lys Ala Glu Leu Phe Asn Gly Lys Val Leu Lys
            130                 135                 140
Gln Leu Gly Thr Val Thr Thr Thr Glu His Glu Asn Ala Leu Leu Arg
145                 150                 155                 160
Ser Phe Asp Lys Phe Thr Thr Tyr Phe Ser Gly Phe Tyr Glu Asn Arg
                165                 170                 175
Lys Asn Val Phe Ser Ala Glu Asp Ile Ser Thr Ala Ile Pro His Arg
            180                 185                 190
Ile Val Gln Asp Asn Phe Pro Lys Phe Lys Glu Asn Cys His Ile Phe
            195                 200                 205
Thr Arg Leu Ile Thr Ala Val Pro Ser Leu Arg Glu His Phe Glu Asn
            210                 215                 220
Val Lys Lys Ala Ile Gly Ile Phe Val Ser Thr Ser Ile Glu Glu Val
225                 230                 235                 240
Phe Ser Phe Pro Phe Tyr Asn Gln Leu Leu Thr Gln Thr Gln Ile Asp
                245                 250                 255
Leu Tyr Asn Gln Leu Leu Gly Gly Ile Ser Arg Glu Ala Gly Thr Glu
            260                 265                 270
Lys Ile Lys Gly Leu Asn Glu Val Leu Asn Leu Ala Ile Gln Lys Asn
            275                 280                 285
Asp Glu Thr Ala His Ile Ile Ala Ser Leu Pro His Arg Phe Ile Pro
            290                 295                 300
Leu Phe Lys Gln Ile Leu Ser Asp Arg Asn Thr Leu Ser Phe Ile Leu
305                 310                 315                 320
Glu Glu Phe Lys Ser Asp Glu Glu Val Ile Gln Ser Phe Cys Lys Tyr
                325                 330                 335
Lys Thr Leu Leu Arg Asn Glu Asn Val Leu Glu Thr Ala Glu Ala Leu
            340                 345                 350
Phe Asn Glu Leu Asn Ser Ile Asp Leu Thr His Ile Phe Ile Ser His
            355                 360                 365
Lys Lys Leu Glu Thr Ile Ser Ser Ala Leu Cys Asp His Trp Asp Thr
            370                 375                 380
Leu Arg Asn Ala Leu Tyr Glu Arg Arg Ile Ser Glu Leu Thr Gly Lys
385                 390                 395                 400
Ile Thr Lys Ser Ala Lys Glu Lys Val Gln Arg Ser Leu Lys His Glu
                405                 410                 415
Asp Ile Asn Leu Gln Glu Ile Ile Ser Ala Ala Gly Lys Glu Leu Ser
            420                 425                 430
Glu Ala Phe Lys Gln Lys Thr Ser Glu Ile Leu Ser His Ala His Ala
            435                 440                 445
```

```
Ala Leu Asp Gln Pro Leu Pro Thr Thr Leu Lys Lys Gln Glu Glu Lys
450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
        515                 520                 525

Glu Lys Phe Lys Leu Asn Phe Gln Met Pro Thr Leu Ala Ser Gly Trp
530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
850                 855                 860
```

```
Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
            885                 890                 895

Lys Glu His Pro Glu Thr Pro Ile Ile Gly Ile Asp Arg Gly Glu Arg
        900                 905                 910

Asn Leu Ile Tyr Ile Thr Val Ile Asp Ser Thr Gly Lys Ile Leu Glu
            915                 920                 925

Gln Arg Ser Leu Asn Thr Ile Gln Gln Phe Asp Tyr Gln Lys Lys Leu
        930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
            965                 970                 975

His Glu Ile Val Asp Leu Met Ile His Tyr Gln Ala Val Val Val Leu
        980                 985                 990

Glu Asn Leu Asn Phe Gly Phe Lys Ser Lys Arg Thr Gly Ile Ala Glu
            995                 1000                1005

Lys Ala Val Tyr Gln Gln Phe Glu Lys Met Leu Ile Asp Lys Leu
    1010                1015                1020

Asn Cys Leu Val Leu Lys Asp Tyr Pro Ala Glu Lys Val Gly Gly
    1025                1030                1035

Val Leu Asn Pro Tyr Gln Leu Thr Asp Gln Phe Thr Ser Phe Ala
    1040                1045                1050

Lys Met Gly Thr Gln Ser Gly Phe Leu Phe Tyr Val Pro Ala Pro
    1055                1060                1065

Tyr Thr Ser Lys Ile Asp Pro Leu Thr Gly Phe Val Asp Pro Phe
    1070                1075                1080

Val Trp Lys Thr Ile Lys Asn His Glu Ser Arg Lys His Phe Leu
    1085                1090                1095

Glu Gly Phe Asp Phe Leu His Tyr Asp Val Lys Thr Gly Asp Phe
    1100                1105                1110

Ile Leu His Phe Lys Met Asn Arg Asn Leu Ser Phe Gln Arg Gly
    1115                1120                1125

Leu Pro Gly Phe Met Pro Ala Trp Asp Ile Val Phe Glu Lys Asn
    1130                1135                1140

Glu Thr Gln Phe Asp Ala Lys Gly Thr Pro Phe Ile Ala Gly Lys
    1145                1150                1155

Arg Ile Val Pro Val Ile Glu Asn His Arg Phe Thr Gly Arg Tyr
    1160                1165                1170

Arg Asp Leu Tyr Pro Ala Asn Glu Leu Ile Ala Leu Leu Glu Glu
    1175                1180                1185

Lys Gly Ile Val Phe Arg Asp Gly Ser Asn Ile Leu Pro Lys Leu
    1190                1195                1200

Leu Glu Asn Asp Asp Ser His Ala Ile Asp Thr Met Val Ala Leu
    1205                1210                1215

Ile Arg Ser Val Leu Gln Met Arg Asn Ser Asn Ala Ala Thr Gly
    1220                1225                1230

Glu Asp Tyr Ile Asn Ser Pro Val Arg Asp Leu Asn Gly Val Cys
    1235                1240                1245

Phe Asp Ser Arg Phe Gln Asn Pro Glu Trp Pro Met Asp Ala Asp
    1250                1255                1260

Ala Asn Gly Ala Tyr His Ile Ala Leu Lys Gly Gln Leu Leu Leu
```

```
                1265                1270                 1275

Asn His Leu Lys Glu Ser Lys Asp Leu Lys Leu Gln Asn Gly Ile
        1280                1285                 1290

Ser Asn Gln Asp Trp Leu Ala Tyr Ile Gln Glu Leu Arg Asn
        1295                1300                 1305

<210> SEQ ID NO 22
<211> LENGTH: 16660
<212> TYPE: DNA
<213> ORGANISM: Artificial
<220> FEATURE:
<223> OTHER INFORMATION: synthetic

<400> SEQUENCE: 22
gagcatatcc agcaccagct ggtaccaagg tcgggtctct gtgctagtgc tattagctag    60
tgtaaggagc gagtaggtca gttaaggctg gtgcgtcgtg agggctgtct tgtgtgtagc   120
tacagcagac ggttcatcag aaggattatt cgtgcagtat atacagtaca actagacaat   180
gatgttgatg attggtctag agctagaggc ctatagccct atactactgt gtattgtccg   240
ccgttttagt ttttggtcc catcccatca atgcaaccgc cttgttttgc tccaattgtc    300
ccgttcctgc gcctcgcttt tgctctgtcg catcgcatac aaaaaaaaaa acgccgcgcc   360
ggctttgaat cgcgcccccc aactgctcca accaggcaac ggacacggcc accgtccgtg   420
tcgcgagcaa aaaacaaaa agaggaacgc gtccaggacg aagcagtcca ctgccgctgt    480
ggccggcaaa agatctggtt gagcacatgg agattggaga aggttggttg gttcttctgg   540
aaacgccaat gaatggggc actgacatgt actcttaaca tgtagtgcaa tccagagatc    600
ggatatccag acactggcag cacgatcgcc tcgcgccgta gatcacgcac gcaaattact   660
gaagaccatt cacaaaaaaa aaaaacaca caggggctag cgtgcccac accaaaccca     720 agtgctgcgt tgcacgcagg ggagcgaaaa aaaacaataa tgctcactgt cacgtcgcgt   780
atccaacccc gcggacgtct cggctctcag cagcagcaca cggggcacct cacgatgccg   840
ttctcgttgc actccgtgca ccgccggaac ccgccgccgc attcgtcgcc ctcctcctcc   900
tcctccgcct cgtcttcgtc acccacgtac accttgcagc tgcccgagca gacatcgcag   960
agcacgaacc gcatgtcccc gcaggcctcg cacgcgccgg cgtcgccgcc gtgtgggccg  1020
gccgtcgacg cagcgctctc gcacccggcc agcctcggcg cgagctcccc ggcctcgtgc  1080
agccgcttca gctcctcggc gttgcccacg agctccccgt ccacgaagag gctggggagg  1140
gcggcgggcg tgccgccggc ttggccgagc ccgaggccga aaggccgcg gagctcgtcc    1200 cggaacccgc ggtgcatgga cacgtcgcgc tcgtcgaggc gcacgccgta gcccttgagg  1260
atggcgcgcg ccaggcagca gtcctcgtgc gtggcgcgca cgccgcgcag cgacgtgaag  1320
tagagcaccg ccctccgcgg cggcagcgcc ttcccctccc cgccgctcgt cggggcggcg  1380
tcgggccgag gcatcggcat cggcagcggc gtcaccttgg cggacgccgc gaggtcctgc  1440
gcaggcgccg tggcgaccgg gaacgagaag gagtggcgcc cgaacggcgc gcccagcagc  1500
ggggagcggt cctcgaggcc ggccatgagc gcccacgcgt cgatgtcctc gggctcgttg  1560
ggcggcgtca tggtgggcgt gcggcggcgcc agcctcgtgg gcgcgggctc cggcgcccgc  1620
ggcagggcct tgtccagctc cagggacccg agcgtggacg acgtgagccg caccacgtgg  1680
acgccgacgt cgctcgggca ccgagccggg aacgactggc tgcgcggcag cggtgacggg  1740
cagtaccgga ggtcgtgacg ggcctgcctt gaggtggtgc accccatggc accaatgtac  1800
acacacggcc aaagcgccaa gtgggctgca gactgcctgc caatgtgatc aagcagccag  1860
```

```
gagcagagac ggatctctgg ggatcggggt ttctggggtt taggatcttt atactactct    1920
gtcattgggg atataaaact aggagtgtgg ttaattagga ctcgatagat aagtttacca    1980
caagcgcgtg aaatggtcta cccgatgatg tgattggcct aaaaagaaca agaagagtat    2040
ttggagctac tgaacattct cttttcctga agataactaa ttttttggaac attcagactt   2100 gggagtctgg acttttggag ggaagttcaa attgtggtct gcctctgcca tgtgttgttt    2160
tttagtcgga gagtggccct cattttttt  gtcctgttta gctttatagt cgtagcagct    2220
agtagcgaaa tttaaccttg gattatggcc gtgttagtca acaatcatt  gatttatttc    2280 ctccctttcg cgctgctttt cctgtacgca tctccgctgc ccttgattcg aggaccctgt    2340
tcacaacaca gggctctggc tttggagcct ctcgtttgta gcacttgcac gtagttaccc    2400
ggaccgaagc ttcaacacag atctgatagt ttaaacgctc ttcaactgga agagcggtta    2460
cccggaccga agcttcggcc ggggcccatc gatatccgcg gcatgcctg  cagtgcagcg    2520 tgacccggtc gtgcccctct ctagagataa tgagcattgc atgtctaagt tataaaaaat    2580
taccacatat ttttttttgtc acacttgttt gaagtgcagt ttatctatct ttatacatat   2640
atttaaactt tactctacga ataatataat ctatagtact acaataatat cagtgtttta    2700
gagaatcata taaatgaaca gttagacatg gtctaaagga caattgagta ttttgacaac    2760
aggactctac agttttatct ttttagtgtg catgtgttct cctttttttt tgcaaatagc    2820
ttcacctata taatacttca tccattttat tagtacatcc atttagggtt tagggttaat    2880 ggttttata  gactaatttt tttagtacat ctattttatt ctattttagc ctctaaatta    2940
agaaaactaa aactctattt tagttttttt atttaataat ttagatataa aatagaataa    3000 aataagtga  ctaaaaatta aacaaatacc ctttaagaaa ttaaaaaaac taaggaaaca    3060
tttttcttgt ttcgagtaga taatgccagc ctgttaaacg ccgtcgacga gtctaacgga    3120
caccaaccag cgaaccagca gcgtcgcgtc gggccaagcg aagcagacgg cacggcatct    3180
ctgtcgctgc ctctggaccc ctctcgagag ttccgctcca ccgttggact tgctccgctg    3240
tcggcatcca gaaattgcgt ggcggagcgg cagacgtgag ccggcacggc aggcggcctc    3300
ctcctcctct cacggcaccg gcagctacgg gggattcctt tcccaccgct ccttcgcttt    3360
cccttcctcg cccgccgtaa taaatagaca ccccctccac accctctttc cccaacctcg    3420
tgttgttcgg agcgcacaca cacacaacca gatctccccc aaatccaccc gtcggcacct    3480
ccgcttcaag gtacgccgct cgtcctcccc cccccccct  ctctaccttc tctagatcgg    3540
cgttccggtc catggttagg gcccggtagt tctacttctg ttcatgtttg tgttagatcc    3600
gtgtttgtgt tagatccgtg ctgctagcgt tcgtacacgg atgcgacctg tacgtcagac    3660
acgttctgat tgctaacttg ccagtgtttc tctttggga  atcctgggat ggctctagcc    3720
gttccgcaga cgggatcgat ttcatgattt tttttgtttc gttgcatagg gtttggtttg    3780 ccctttttcct ttatttcaat atatgccgtg cacttgtttg tcgggtcatc ttttcatgct   3840 ttttttttgtc ttggttgtga tgatgtggtc tggttgggcg gtcgttctag atcggagtag   3900
aattctgttt caaactacct ggtggattta ttaattttgg atctgtatgt gtgtgccata    3960
catattcata gttacgaatt gaagatgatg gatggaaata tcgatctagg ataggtatac    4020
atgttgatgc gggttttact gatgcatata cagagatgct ttttgttcgc ttggttgtga    4080
tgatgtggtg tggttgggcg gtcgttcatt cgttctagat cggagtagaa tactgtttca    4140
aactacctgg tgtatttatt aatttggaa  ctgtatgtgt gtgtcataca tcttcatagt    4200
```

-continued

```
tacgagttta agatggatgg aaatatcgat ctaggatagg tatacatgtt gatgtgggtt    4260
ttactgatgc atatacatga tggcatatgc agcatctatt catatgctct aaccttgagt    4320
acctatctat tataataaac aagtatgttt tataattatt ttgatcttga tatacttgga    4380
tgatggcata tgcagcagct atatgtggat tttttttagcc ctgccttcat acgctattta   4440
tttgcttggt actgtttctt ttgtcgatgc tcaccctgtt gtttggtgtt acttctgcag    4500
gtcgactcta gaggatccaa caatggagaa caacatacag aatcagtgcg tcccctacaa    4560
ctgcctcaac aatcctgaag tagagattct caacgaagag aggtcgactg gcagattgcc    4620
gttagacatc tccctgtccc ttacacgttt cctgttgtct gagtttgttc caggtgtggg    4680
agttgcgttt ggcctcttcg acctcatctg gggcttcatc actccatctg attggagcct    4740
ctttcttctc cagattgaac agttgattga acaaaggatt gagaccttgg aaaggaatcg    4800
ggccatcact acccttcgtg gcttagcaga cagctatgag atctacattg aagcactaag    4860
agagtgggaa gccaatccta acaatgccca actgagagaa gatgtgcgta tacgctttgc    4920
taacacagat gatgctttga tcacagccat caacaacttc acccttacca gcttcgagat    4980
ccctcttctc tcggtctatg ttcaagctgc taacctgcac ttgtcactac tgcgcgacgc    5040
tgtgtcgttt gggcaaggtt ggggactgga catagctact gtcaacaatc actacaacag    5100
actcatcaat ctgattcatc gatacacgaa acattgtttg gatacctaca atcagggatt    5160
ggagaacctg agaggtacta acactcgcca atgggccagg ttcaatcagt tcaggagaga    5220
ccttacactt actgtgttag acatagttgc tctctttccg aactacgatg ttcgtaccta    5280
tccgattcaa acgtcatccc aacttacaag ggagatctac accagttcag tcattgaaga    5340
ctctccagtt tctgcgaaca tacccaatgg tttcaacagg gctgagtttg gagtcagacc    5400
accccatctc atggacttca tgaactcttt gtttgtgact gcagagactg ttagatccca    5460
aactgtgtgg ggaggacact tagttagctc acgcaacacg gctggcaatc gtatcaactt    5520
tcctagttac ggggtcttca atcccggggg cgccatctgg attgcagatg aagatccacg    5580
tcctttctat cggaccttgt cagatcctgt cttcgtccga ggaggctttg gcaatcctca    5640
ctatgtactc ggtcttaggg gagtggcctt tcaacaaact ggtacgaatc acacccgcac    5700
attcaggaac tccgggacca ttgactctct agatgagata ccacctcaag acaacagcgg    5760
cgcaccttgg aatgactact cccatgtgct gaatcatgtt acctttgtgc gctggccagg    5820
tgagatctca ggttccgact catggagagc accaatgttc tcttggacgc atcgtagcgc    5880 taccccaca aacaccattg atccagagag aatcactcag attcccttgg tgaaggcaca    5940
cacacttcag tcaggaacta cagttgtaag agggccgggg ttcacgggag agacattct    6000 tcgacgcact agtggaggac cattcgcgta caccattgtc aacatcaatg gcaacttcc    6060 ccaaaggtat cgtgccagga tacgctatgc ctctactacc aatctaagaa tctacgttac    6120
ggttgcaggt gaacggatct ttgctggtca gttcaacaag acaatggata ccggtgatcc    6180
acttacattc caatctttct cctacgccac tatcaacacc gcgttcacct ttccaatgag    6240
ccagagcagt ttcacagtag gtgctgatac cttcagttca ggcaacgaag tgtacattga    6300
caggtttgag ttgattccag ttactgccac actcgagtaa ggatccgtcg acctgcagcc    6360
aagctttcgc gagctcgaga tccccgacat atgccccggt tcgttgcga ctaacatgag    6420 ttcttggaca aatttgattg gacctgatga gatgatccaa cccgaggata tagcaaagct    6480
cgttcgtgca gcaatggaac ggccaaaccg tgcttttgtc cccaagaatg aggtgctatg    6540
catgaaggaa tctacccgtt gatgtccaac agtctcaggg ttaatgtcta tgtatcttaa    6600
```

```
ataatgttgt cggtattttg taatctcata tagattttca ctgtgcgacg caaaaatatt   6660
aaataaatat tattattatc tacgttttga ttgagatatc atcaatatta taataaaaat   6720
atccattaaa cacgatttga tacaaatgac agtcaataat ctgatttgaa tatttattaa   6780
ttgtaacgaa ttcataaag atcgaataga aaatactgca ctgcaaatga aaattaacac   6840
atactaataa atgcgtcaaa tatctttgcc aagatcaagc ggagtgaggg cctcatatcc   6900
ggtctcagtt acaagcacgg tatccccgaa gcgcgctcca ccaatgccct cgacatagat   6960
gccgggctcg acgctgagga cattgcctac cttgagcatg gtctcagcgc cggctttaag   7020
ctcaatccca tcccaatctg aatatcctat cccgcgccca gtccggtgta agaacgggtc   7080
tgtccatcca cctctgttgg gaattccggt ccgggtcacc tttgtccacc aagatggaac   7140
tgcggccagc ttgcatgcct gcagtgcagc gtgacccggt cgtgccctc tctagagata   7200 atgagcattg catgtctaag ttataaaaaa ttaccacata ttttttttgt cacacttgtt   7260
tgaagtgcag tttatctatc tttatacata tatttaaact ttactctacg aataatataa   7320
tctatagtac tacaataata tcagtgtttt agagaatcat ataaatgaac agttagacat   7380
ggtctaaagg acaattgagt attttgacaa caggactcta cagttttatc ttttagtgt    7440 gcatgtgttc tccttttttt ttgcaaatag cttcacctat ataatacttc atccatttta   7500
ttagtacatc catttagggt ttagggttaa tggtttttat agactaattt ttttagtaca   7560 tctatttat tctatttag cctctaaatt aagaaaacta aaactctatt ttagttttt     7620 tatttaataa tttagatata aaatagaata aaataaagtg actaaaaatt aaacaaatac   7680
cctttaagaa attaaaaaaa ctaaggaaac attttcttg tttcgagtag ataatgccag    7740
cctgttaaac gccgtcgacg agtctaacgg acaccaacca gcgaaccagc agcgtcgcgt   7800
cgggccaagc gaagcagacg gcacggcatc tctgtcgctg cctctggacc cctctcgaga   7860
gttccgctcc accgttggac ttgctccgct gtcggcatcc agaaattgcg tggcggagcg   7920
gcagacgtga gccggcacgg caggcggcct cctcctcctc tcacggcacc ggcagctacg   7980
ggggattcct ttcccaccgc tccttcgctt tccttcctc gcccgccgta ataaatagac    8040
accccctcca caccctcttt ccccaacctc gtgttgttcg gagcgcacac acacacaacc   8100
agatctcccc caaatccacc cgtcggcacc tccgcttcaa ggtacgccgc tcgtcctccc   8160 ccccccccc tctctacctt ctctagatcg gcgttccggt ccatggttag ggcccggtag    8220
ttctacttct gttcatgttt gtgttagatc cgtgtttgtg ttagatccgt gctgctagcg   8280
ttcgtacacg gatgcgacct gtacgtcaga cacgttctga ttgctaactt gccagtgttt   8340
ctctttgggg aatcctggga tggctctagc cgttccgcag acgggatcga tttcatgatt   8400
ttttttgttt cgttgcatag ggtttggttt gcccttttcc tttatttcaa tatatgccgt   8460
gcacttgttt gtcgggtcat cttttcatgc ttttttttgt cttggttgtg atgatgtggt   8520
ctggttgggc ggtcgttcta gatcggagta gaattctgtt tcaaactacc tggtggattt   8580
attaattttg gatctgtatg tgtgtgccat acatattcat agttacgaat tgaagatgat   8640
ggatggaaat atcgatctag gataggtata catgttgatg cgggttttac tgatgcatat   8700
acagagatgc ttttgttcg cttggttgtg atgatgtggt gtggttgggc ggtcgttcat    8760
tcgttctaga tcggagtaga atactgtttc aaactacctg gtgtatttat taattttgga   8820
actgtatgtg tgtgtcatac atcttcatag ttacagtttt aagatggatg gaaatatcga   8880
tctaggatag gtatacatgt tgatgtgggt tttactgatg catatacatg atggcatatg   8940
```

```
cagcatctat tcatatgctc taaccttgag tacctatcta ttataataaa caagtatgtt    9000
ttataattat tttgatcttg atatacttgg atgatggcat atgcagcagc tatatgtgga    9060
tttttttagc cctgccttca tacgctattt atttgcttgg tactgtttct tttgtcgatg    9120
ctcaccctgt tgtttggtgt tacttctgca ggtcgactct agaggatcca cacgacacca    9180
tgtccgcccg cgaggtgcac atcgacgtga acaacaagac cggccacacc ctccagctgg    9240
aggacaagac caagctcgac ggcggcaggt ggcgcacctc cccgaccaac gtggccaacg    9300
accagatcaa gaccttcgtg gccgaatcca acggcttcat gaccggcacc gagggcacca    9360
tctactactc aattaatggc gaggccgaga tcagcctcta cttcgacaac ccgttcgccg    9420
gctccaacaa atacgacggc cactccaaca agtcccagta cgagatcatc acccagggcg    9480
gctccggcaa ccagtcccac gtgacctaca ccatccagac cacctcctcc cgctacggcc    9540
acaagtcctg agtcatgagt catgagtcag ttaacctaga cttgtccatc ttctggattg    9600
gccaacttaa ttaatgtatg aaataaaagg atgcacacat agtgacatgc taatcactat    9660
aatgtgggca tcaaagttgt gtgttatgtg taattactag ttatctgaat aaaagagaaa    9720
gagatcatcc atatttctta tcctaaatga atgtcacgtg tctttataat tctttgatga    9780
accagatgca tttcattaac caaatccata tacatataaa tattaatcat atataattaa    9840
tatcaattgg gttagcaaaa caaatctagt ctaggtgtgt tttgcgaatg cggccgcgga    9900
ccgaattggg gatctgcatg aaagaaactg tcgcactgct gaaccgcacc ttgtcacttt    9960
catcgaacac gacctgtgcc aagatgacg gtgctgcggt ctaagtgagg ctgaattgcc      10020
ttggacagaa gcggactccc tacaattagt taggccaaac ggtgcatcca tgtgtagctc    10080
cgggctcggg ctgtatcgcc atctgcaata gcatccatgg agctcgttcc atgtagttgg    10140
agatgaacca atgatcgggc gtgtggacgt atgttcctgt gtactccgat agtagagtac    10200
gtgttagctc tttcatggtg caagtgaaat ttgtgttggt ttaattaccc ctacgttagt    10260
tgcgggacag gagacacatc atgaatttaa aggcgatgat gtcctctcct gtaatgttat    10320
tcttttgatg tgatgaatca aaatgtcata taaaacatt ttgttgctcttt agttaggcct    10380 gatcgtagaa cgaaatgctc gtgtagcggg gctacgagcc tatgacgcaa taacactggt    10440
ttgccggccc ggagtcgctt gacaaaaaaa agcatgttaa gtttatttac aattcaaaac    10500
ctaacatatt atattccctc aaagcaggtt cacgatcaca cctgtaccta aaaaaaacat    10560
gaagaatata ttactccatt attatgagat gaaccacttg gcaagagtgg taagctatat    10620
aaaaaaatga acattattac gagatgttat atgccattat attgattcga agatatatgt    10680 ttcttttctcc cacgggcacc taacggatac atgataaggc caaggcagat cacgggaaat    10740
tattcgaata catgttacgc cctattgccg gaaaaaaaat gcagggcagg tgttggccgt    10800
agcgatttaa gcacttaagc tggaggttgc cacacttgga tgcaagcgtc tgacccttct    10860
aaaaaatcgg cggctttgtc cgtatccgta tccectatcc aacatctagc tggccacacg    10920
acggggctgg gcagatcgtg gatgccgggt cgacgtcgat cgtcagccat catagaccaa    10980
tcgaccatct gttatggatg cttgctagct agactagtca gacataaaat ttggatactt    11040
tctcccaact gggagacggg gactgatgtg cagctgcacg tgagctaaat ttttccctat    11100
aaatatgcat gaaatactgc attatcttgc cacagccact gccacagcca gataacaagt    11160
gcagctggta gcacgcaacg catagctctg gacttgtagc taggtagcca accggatcca    11220
cacgacacca tgctcgacac caacaaggtg tacgagatca gcaaccacgc caacggcctc    11280
tacgccgcca cctacctctc cctcgacgac tccggcgtgt ccctcatgaa caagaacgac    11340
```

```
gacgacatcg acgactacaa cctcaagtgg ttcctcttcc cgatcgacga cgaccagtac  11400
atcatcacct cctacgccgc caacaactgc aaggtgtgga acgtgaacaa cgacaagatt  11460
aatgtgtcaa cctactcctc caccaactcc atccagaagt ggcagatcaa ggccaacggc  11520
tcctcctacg tgatccagtc cgacaacggc aaggtgctca ccgccggcac cggccaggcc  11580
ctcggcctca tccgcctcac cgacgagtcc tccaacaacc cgaaccagca atggaacctg  11640
acgtccgtgc agaccatcca gctcccgcag aagccgatca tcgacaccaa gctcaaggac  11700
tacccgaagt actccccgac cggcaacatc gacaacggca cctccccgca gctcatgggc  11760
tggaccctcg tgccgtgcat catggtgaac gacccgaaca tcgacaagaa cacccagatc  11820
aagaccaccc cgtactacat cctcaagaag taccagtact ggcagagggc cgtgggctcc  11880
aacgtcgcgc tccgcccgca cgagaagaag tcctacacct acgagtgggg caccgagatc  11940
gaccagaaga ccaccatcat caacaccctc ggcttccaga tcaacatcga cagcggcatg  12000
aagttcgaca tcccggaggt gggcggcggt accgacgaga tcaagaccca gctcaacgag  12060
gagctcaaga tcgagtattc acatgagacg aagatcatgg agaagtacca ggagcagtcc  12120
gagatcgaca acccgaccga ccagtccatg aactccatcg gcttcctcac catcacctcc  12180
ctggagctct accgctacaa cggctccgag atccgcatca tgcagatcca gacctccgac  12240
aacgacacct caacgtgac ctcctacccg aaccaccagc aggccctgct gctgctgacc  12300
aaccactcct acgaggaggt ggaggagatc accaacatcc cgaagtccac cctcaagaag  12360
ctcaagaagt actacttctg agtcatgagt catgagtcag ttaacctaga cttgtccatc  12420
ttctggattg gccaacttaa ttaatgtatg aaataaaagg atgcacacat agtgacatgc  12480
taatcactat aatgtgggca tcaaagttgt gtgttatgtg taattactag ttatctgaat  12540
aaaagagaaa gagatcatcc atatttctta tcctaaatga atgtcacgtg tctttataat  12600
tctttgatga accagatgca tttcattaac caaatccata tacatataaa tattaatcat  12660
atataattaa tatcaattgg gttagcaaaa caaatctagt ctaggtgtgt tttgcgaatt  12720
atcgatgggc cccggccgaa gctggccgcg gaccgaattc ccatggagtc aaagattcaa  12780
atagaggacc taacagaact cgccgtaaag actggcgaac agttcataca gagtctctta  12840
cgactcaatg acaagaagaa aatcttcgtc aacatggtgg agcacgacac gcttgtctac  12900
tccaaaaata tcaaagatac agtctcagaa gaccaaaggg caattgagac ttttcaacaa  12960
agggtaatat ccggaaacct cctcggattc cattgcccag ctatctgtca ctttattgtg  13020
aagatagtgg aaaaggaagg tggctcctac aaatgccatc attgcgataa aggaaaggcc  13080
atcgttgaag atgcctctgc cgacagtggt cccaaagatg gaccccacc cacgaggagc  13140 atcgtggaaa aagaagacgt tccaaccacg tcttcaaagc aagtggattg atgtgatatc  13200
tccactgacg taagggatga cgcacaatcc cactatcctt cgcaagaccc ttcctctata  13260
taaggaagtt catttcattt ggagaggaca gggtacccgg ggatccacca tgtctccgga  13320
gaggagacca gttgagatta ggccagctac agcagctgat atggccgcgg tttgtgatat  13380
cgttaaccat tacattgaga cgtctacagt gaactttagg acagagccac aaacaccaca  13440
agagtggatt gatgatctag agaggttgca agatagatac ccttggttgg ttgctgaggt  13500
tgagggtgtt gtggctggta ttgcttacgc tgggccctgg aaggctagga acgcttacga  13560
ttggacagtt gagagtactg tttacgtgtc acataggcat caaaggttgg gcctaggatc  13620
cacattgtac acacatttgc ttaagtctat ggaggcgcaa ggttttaagt ctgtggttgc  13680
```

```
tgttataggc cttccaaacg atccatctgt taggttgcat gaggctttgg gatacacagc    13740
ccggggtaca ttgcgcgcag ctggatacaa gcatggtgga tggcatgatg ttggtttttg    13800
gcaaagggat tttgagttgc cagctcctcc aaggccagtt aggccagtta cccagatctg    13860
agtcgacctg caggcatgcc cgctgaaatc accagtctct ctctacaaat ctatctctct    13920
ctataataat gtgtgagtag ttcccagata agggaattag ggttcttata gggtttcgct    13980
catgtgttga gcatataaga aacccttagt atgtatttgt atttgtaaaa tacttctatc    14040
aataaaattt ctaattccta aaaccaaaat ccagggcgag ctcgaattcg agctcgagcc    14100
cgggtggatc ctctagagtc gacctgcaga agcttcggtc cggcgcgcct ctagttgaag    14160
acacgttcat gtcttcatcg taagaagaca ctcagtagtc ttcggccaga atggcctaac    14220
tcaaggccat cgtggcctct tgctcttcag gatgaagagc tatgtttaaa cgtgcaagta    14280
agaacttcga tccgaaatat cgtttcaaaa ctagaaaaca gcgcggcttt ggctaagccg    14340
cgcactatat aggattttgg gcaccttttg atggaacgtg aaagcgtact gcgcactagt    14400
tatttaggtt gaaccttgga tatacggttc tcactgcgcc aatgcaaggc ttgaaacttg    14460
gttagtaata cgtactccct ccgtttcttt ttatttgtcg ctggatagtg caattttgca    14520
ctatcgagcg acaaataaaa agaaacggag ggagtatatg attgtcagat gtagatatgt    14580
ttatttatat atcacataca gatatataaa acagatcact ttttcagata tacagttcca    14640
atgtcagccc tgatcaccct gtcataaatt gcacgtttct aattgatgtt gcttcatggt    14700
cgtcatgaga accttctgaa gaaatcgatg aaggttgcca acctttcaaa gtttcagaaa    14760
ccactttgca tgtacactaa gggctggttt ggcagcccaa aaccagccag cgttttcctg    14820 gtctttctc ccgggagaaa gcccatgcat agattgtccc tggattattt atctgtgtcc    14880
tttggctaaa aattcgtccc aatttcctgt aggaaactac ctcggccttg ggaggccagg    14940
cgattctcca ccgcctcgtc tcgtccatcc ttcgatgctc acgcgtgcct cctcggatgc    15000
tatcctcagg cgattctccg tcgtctcgtc tcatccatcc tcacgcgcgc ctcctccgac    15060
gctatcccca ggcgattctc caccgtctcg tctcatccat cctcatgtac gcctcgtccg    15120
atgctatccc cagacgattt tccgtcgtct catctccttc atgctcgcgc gcgcctcctc    15180
cgacgctatc cccaggcgat ttttctgccg tctcgtctcc ttcatgcccg cgcgcgcctc    15240
ctccgacgct atccccaggc gattttccgc cgtctcgtct ccttcatgcc cgcgcgtgcc    15300
tcctccgacg ctattccacg agcgcctcc gccgccgcta tccccagacg attttccgct    15360
gtctcgtctc cttcatgccc gcgcgcccct cctccgacgc tatccccacg agcgcctccg    15420
ccgccgctcc accgtcttcc ccgccgccat ccccttaatt cctatagatc tggacccccgc   15480 tctactttcg ttggcatact tttgcttggt gtgcgcgggc tggagtggaa ggttgcgcat    15540
tcgatcacgg gggagaagtg gatcttgggt cttggcaggc tagggcggtt gccaggacgc    15600
cgtggtgtgc attcatgggt cctataaatc tttatcatta ccgccttagg agctagttgt    15660
agttcacaca tcatatcctt ttctgctcga catcgtctgg ggatgcccta ggtgccctac    15720
cgaccctacg gcattgtctt gacctctatt agactctatg tcatctagag ccttcttggg    15780
tggccttttg accccaaagc gaccctatga tcttaccccta acgaggtctc ccttggtggg    15840
gcaagatcca ctttgtccac ttaactgaag atctgatcct catcttgaaa tctttaatcc    15900
caaggtgact ctacgtcgta tgtggatgct ccgggtaacc tgccaacccg gatcacccta    15960
agatctcttt cctaagggc gagatctagg ttcctacgag aaagaagacg accctgcacc    16020
attgcggtcc gtccggtcca gagtgcgaac gtccggatgc gacacaggga aggagtcgct    16080
```

| | | | | |
|---|---|---|---|---|
| cctgcagcga | ggtcgcagac | tgtccacaca | gcctcagaag | gcaccgccag acaatacatg 16140 |
| taatacccac | tctgtaagaa | aaacctaaaa | ggagaaagta | tattccttta tctatatgtg 16200 |
| tgttatattt | ctactcacca | tcacatgtga | acatctcact | tacacaaata aataattaac 16260 |
| aaaagacact | caaataaatt | atgcatcatg | ctcgaccta | ttttgtgtgc attctgttac 16320 |
| aatataaaaa | taatataaaa | aacatatatt | aatatcaaaa | tttggagatt taaccctaat 16380 |
| atgcaaatcg | gagtttagag | gaaagaaaga | aaatgctat | acaaaataaa ggaataaata 16440 |
| tataaataaa | ggtaaaacta | ttaatactgg | tatattaatt | tgaacagttg acctaattat 16500 |
| gaatatcaca | actggtttga | attcaaatat | gaaatccaag | aatttggaaa taggaaaaat 16560 |
| ggagataaga | ataaaggaaa | agaattctta | actcggatgg | gcctgggaaa cgaatttcgg 16620 |
| cccacttcct | gtgtccttag | ctgtgcggct | cagtccagtg | 16660 |

<210> SEQ ID NO 23
<211> LENGTH: 16664
<212> TYPE: DNA
<213> ORGANISM: Artificial
<220> FEATURE:
<223> OTHER INFORMATION: synthetic

<400> SEQUENCE: 23

| | | | | |
|---|---|---|---|---|
| gagcatatcc | agcaccagct | ggtaccaagg | tcgggtctct | gtgctagtgc tattagctag 60 |
| tgtaaggagc | gagtaggtca | gttaaggctg | gtgcgtcgtg | agggctgtct tgtgtgtagc 120 |
| tacagcagac | ggttcatcag | aaggattatt | cgtgcagtat | atacagtaca actagacaat 180 |
| gatgttgatg | attggtctag | agctagaggc | ctatagccct | atactactgt gtattgtccg 240 |
| ccgttttagt | tttttggtcc | catcccatca | atgcaaccgc | cttgttttgc tccaattgtc 300 |
| ccgttcctgc | gcctcgcttt | tgctctgtcg | catcgcatac | aaaaaaaaaa acgccgcgcc 360 |
| ggctttgaat | cgcgcccccc | aactgctcca | accaggcaac | ggacacggcc accgtccgtg 420 |
| tcgcgagcaa | aaaacaaaa | agaggaacgc | gtccaggacg | aagcagtcca ctgccgctgt 480 |
| ggccggcaaa | agatctggtt | gagcacatgg | agattggaga | aggttggttg gttcttctgg 540 |
| aaacgccaat | gaatggggc | actgacatgt | actcttaaca | tgtagtgcaa tccagagatc 600 |
| ggatatccag | acactggcag | cacgatcgcc | tcgcgccgta | gatcacgcac gcaaattact 660 |
| gaagaccatt | cacaaaaaaa | aaaaaacaca | caggggctag | cgtgccccac accaaaccca 720 |
| agtgctgcgt | tgcacgcagg | ggagcgaaaa | aaaacaataa | tgctcactgt cacgtcgcgt 780 |
| atccaaccc | gcggacgtct | cggctctcag | cagcagcaca | cggggcacct cacgatgccg 840 |
| ttctcgttgc | actccgtgca | ccgccggaac | ccgccgccgc | attcgtcgcc ctcctcctcc 900 |
| tcctccgcct | cgtcttcgtc | acccacgtac | accttgcagc | tgcccgagca gacatcgcag 960 |
| agcacgaacc | gcatgtcccc | gcaggcctcg | cacgcgccgg | cgtcgccgcc gtgtgggccg 1020 |
| gccgtcgacg | cagcgctctc | gcacccgccc | agcctcggcg | cgagctcccc ggcctcgtgc 1080 |
| agccgcttca | gctcctcggc | gttgcccacg | agctccccgt | ccacgaagag gctggggagg 1140 |
| gcggcgggcg | tgccgccggc | ttggccgagc | ccgaggccga | aaggccgcg gagctcgtcc 1200 |
| cggaacccgc | ggtgcatgga | cacgtcgcgc | tcgtcgaggc | gcacgccgta gcccttgagg 1260 |
| atggcgcgcg | ccaggcagca | gtcctcgtgc | gtggcgcgca | cgccgcgcag cgacgtgaag 1320 |
| tagagcaccg | ccctccgcgg | cggcagcgcc | ttccctccc | cgccgctcgt cggggcggcg 1380 |
| tcgggccgag | gcatcggcat | cggcagcggc | gtcaccttgg | cggacgccgc gaggtcctgc 1440 |

-continued

```
gcaggcgccg tggcgaccgg gaacgagaag gagtggcgcc cgaacggcgc gcccagcagc    1500
ggggagcggt cctcgaggcc ggccatgagc gcccacgcgt cgatgtcctc gggctcgttg    1560
ggcggcgtca tggtgggcgt gcgcggcgcc agcctcgtgg gcgcgggctc cggcgcccgc    1620
ggcagggcct tgtccagctc cagggacccg agcgtgacg acgtgagccg caccacgtgg     1680
acgccgacgt cgctggggca ccgagccggg aacgactggc tgcgcggcag cggtgacggg    1740
cagtaccgga ggtcgtgacg ggcctgcctt gaggtggtgc accccatggc accaatgtac    1800
acacacggcc aaagcgccaa gtgggctgca gactgcctgc caatgtgatc aagcagccag    1860
gagcagagac ggatctctgg ggatcggggt ttctggggtt taggatcttt atactactct    1920
gtcattgggg atataaaact aggagtgtgg ttaattagga ctcgatagat aagtttacca    1980
caagcgcgtg aaatggtcta cccgatgatg tgattggcct aaaaagaaca agaagagtat    2040
ttggagctac tgaacattct cttttcctga agataactaa ttttggaac attcagactt     2100 gggagtctgg acttttggag ggaagttcaa attgtggtct gcctctgcca tgtgttgttt    2160
tttagtcgga gagtggccct catttttttt gtcctgttta gctttatagt cgtagcagct    2220
agtagcgaaa tttaaccttg gattatggcc gtgttagtca aacaatcatt gatttatttc    2280 ctcccttcg cgctgctttt cctgtacgca tctccgctgc ccttgattcg aggaccctgt     2340
tcacaacaca gggctctggc tttggagcct ctcgtttgta gcacttgcac gtagttaccc    2400
ggaccgaagc ttcaacacag atctgatagt ttaaacgctc ttcaactgga agagcggtta    2460
cccggaccga agcttcggcc ggggcccatc gatatccgcg ggcatgcctg cagtgcagcg    2520
tgacccggtc gtgccctct ctagagataa tgagcattgc atgtctaagt tataaaaaat     2580
taccacatat ttttttgtc acacttgttt gaagtgcagt ttatctatct ttatacatat     2640
atttaaactt tactctacga ataatataat ctatagtact acaataatat cagtgtttta    2700
gagaatcata taaatgaaca gttagacatg gtctaaagga caattgagta ttttgacaac    2760
aggactctac agttttatct ttttagtgtg catgtgttct cctttttttt tgcaaatagc    2820
ttcacctata taatacttca tccattttat tagtacatcc atttagggtt tagggttaat    2880 ggttttata gactaatttt tttagtacat ctattttatt ctattttagc ctctaaatta     2940
agaaaactaa aactctattt tagttttttt atttaataat ttagatataa aatagaataa    3000
aataaagtga ctaaaaatta aacaaatacc ctttaagaaa ttaaaaaaac taaggaaaca    3060
tttttcttgt ttcgagtaga taatgccagc ctgttaaacg ccgtcgacga gtctaacgga    3120
caccaaccag cgaaccagca gcgtcgcgtc gggccaagcg aagcagacgg cacggcatct    3180
ctgtcgctgc ctctggaccc ctctcgagag ttccgctcca ccgttggact tgctccgctg    3240
tcggcatcca gaaattgcgt ggcggagcgg cagacgtgag ccggcacggc aggcggcctc    3300
ctcctcctct cacggcaccg gcagctacgg gggattcctt tcccaccgct ccttcgcttt    3360
cccttcctcg cccgccgtaa taaatagaca ccccctccac accctctttc cccaacctcg    3420
tgttgttcgg agcgcacaca cacacaacca gatctccccc aaatccaccc gtcggcacct    3480
ccgcttcaag gtacgccgct cgtcctcccc ccccccccct ctctaccttc tctagatcgg    3540
cgttccggtc catggttagg gcccggtagt tctacttctg ttcatgtttg tgttagatcc    3600
gtgtttgtgt tagatccgtg ctgctagcgt tcgtacacgg atgcgacctg tacgtcagac    3660
acgttctgat tgctaacttg ccagtgtttc tctttgggga atcctgggat ggctctagcc    3720
gttccgcaga cgggatcgat ttcatgattt ttttgtttc gttgcatagg gtttggtttg     3780 ccctttttcct ttatttcaat atatgccgtg cacttgtttg tcgggtcatc ttttcatgct    3840
```

```
ttttttttgtc ttggttgtga tgatgtggtc tggttgggcg gtcgttctag atcggagtag    3900
aattctgttt caaactacct ggtggattta ttaattttgg atctgtatgt gtgtgccata    3960
catattcata gttacgaatt gaagatgatg gatggaaata tcgatctagg ataggtatac    4020
atgttgatgc gggttttact gatgcatata cagagatgct ttttgttcgc ttggttgtga    4080
tgatgtggtg tggttgggcg gtcgttcatt cgttctagat cggagtagaa tactgtttca    4140
aactacctgg tgtatttatt aattttggaa ctgtatgtgt gtgtcataca tcttcatagt    4200
tacgagttta agatggatgg aaatatcgat ctaggatagg tatacatgtt gatgtgggtt    4260
ttactgatgc atatacatga tggcatatgc agcatctatt catatgctct aaccttgagt    4320
acctatctat tataataaac aagtatgttt tataattatt ttgatcttga tatacttgga    4380
tgatggcata tgcagcagct atatgtggat ttttttagcc ctgccttcat acgctattta    4440
tttgcttggt actgtttctt ttgtcgatgc tcaccctgtt gtttggtgtt acttctgcag    4500
gtcgactcta gaggatccaa caatggagaa caacatacag aatcagtgcg tcccctacaa    4560
ctgcctcaac aatcctgaag tagagattct caacgaagag aggtcgactg gcagattgcc    4620
gttagacatc tccctgtccc ttacacgttt cctgttgtct gagtttgttc caggtgtggg    4680
agttgcgttt ggcctcttcg acctcatctg gggcttcatc actccatctg attggagcct    4740 cttcttctc cagattgaac agttgattga acaaaggatt gagaccttgg aaaggaatcg    4800
ggccatcact acccttcgtg gcttagcaga cagctatgag atctacattg aagcactaag    4860
agagtgggaa gccaatccta acaatgccca actgagagaa gatgtgcgta tacgctttgc    4920
taacacagat gatgctttga tcacagccat caacaacttc acccttacca gcttcgagat    4980
ccctcttctc tcggtctatg ttcaagctgc taacctgcac ttgtcactac tgcgcgacgc    5040
tgtgtcgttt gggcaaggtt ggggactgga catagctact gtcaacaatc actacaacag    5100
actcatcaat ctgattcatc gatacacgaa acattgtttg gatacctaca atcagggatt    5160
ggagaacctg agaggtacta acactcgcca atgggccagg ttcaatcagt tcaggagaga    5220
ccttacactt actgtgttag acatagttgc tctctttccg aactacgatg ttcgtaccta    5280
tccgattcaa acgtcatccc aacttacaag ggagatctac accagttcag tcattgaaga    5340
ctctccagtt tctgcgaaca tacccaatgg tttcaacagg gctgagtttg gagtcagacc    5400
accccatctc atggacttca tgaactcttt gtttgtgact gcagagactg ttagatccca    5460
aactgtgtgg ggaggacact tagttagctc acgcaacacg gctggcaatc gtatcaactt    5520
tcctagttac ggggtcttca atcccggggg cgccatctgg attgcagatg aagatccacg    5580
tcctttctat cggaccttgt cagatcctgt cttcgtccga ggaggctttg gcaatcctca    5640
ctatgtactc ggtcttaggg gagtggcctt tcaacaaact ggtacgaatc acacccgcac    5700
attcaggaac tccgggacca ttgactctct agatgagata ccacctcaag acaacagcgg    5760
cgcaccttgg aatgactact cccatgtgct gaatcatgtt accttttgtgc gctggccagg    5820 tgagatctca ggttccgact catggagagc accaatgttc tcttggacgc atcgtagcgc    5880
tacccccaca aacaccattg atccagagag aatcactcag attcccttgg tgaaggcaca    5940
cacacttcag tcaggaacta cagttgtaag agggccgggg ttcacgggag agacattct    6000 tcgacgcact agtggaggac cattcgcgta caccattgtc aacatcaatg gcaacttcc    6060 ccaaaggtat cgtgccagga tacgctatgc ctctactacc aatctaagaa tctacgttac    6120
ggttgcaggt gaacggatct tgctggtca gttcaacaag acaatggata ccggtgatcc    6180
```

```
acttacattc caatctttct cctacgccac tatcaacacc gcgttcacct ttccaatgag    6240
ccagagcagt ttcacagtag gtgctgatac cttcagttca ggcaacgaag tgtacattga    6300
caggtttgag ttgattccag ttactgccac actcgagtaa ggatccgtcg acctgcagcc    6360
aagctttcgc gagctcgaga tccccgacat atgcccggt ttcgttgcga ctaacatgag     6420
ttcttggaca aatttgattg gacctgatga gatgatccaa cccgaggata tagcaaagct    6480
cgttcgtgca gcaatggaac ggccaaaccg tgcttttgtc cccaagaatg aggtgctatg    6540
catgaaggaa tctacccgtt gatgtccaac agtctcaggg ttaatgtcta tgtatcttaa    6600
ataatgttgt cggtattttg taatctcata tagattttca ctgtgcgacg caaaatatt    6660 aaataaatat tattattatc tacgttttga ttgagatatc atcaatatta taataaaaat    6720
atccattaaa cacgatttga tacaaatgac agtcaataat ctgatttgaa tatttattaa    6780
ttgtaacgaa ttacataaag atcgaataga aaatactgca ctgcaaatga aaattaacac    6840
atactaataa atgcgtcaaa tatctttgcc aagatcaagc ggagtgaggg cctcatatcc    6900
ggtctcagtt acaagcacgg tatccccgaa gcgcgctcca ccaatgccct cgacatagat    6960
gccgggctcg acgctgagga cattgcctac cttgagcatg gtctcagcgc cggctttaag    7020
ctcaatccca tcccaatctg aatatccat ccgcgcca gtccggtgta agaacgggtc      7080
tgtccatcca cctctgttgg gaattccggt ccgggtcacc tttgtccacc aagatggaac    7140
tgcggccagc ttgcatgcct gcagtgcagc gtgacccggt cgtgcccctc tctagagata    7200
atgagcattg catgtctaag ttataaaaaa ttaccacata ttttttttgt cacacttgtt    7260
tgaagtgcag tttatctatc tttatacata tatttaaact ttactctacg aataatataa    7320
tctatagtac tacaataata tcagtgtttt agagaatcat ataaatgaac agttagacat    7380
ggtctaaagg acaattgagt attttgacaa caggactcta cagttttatc ttttttagtgt   7440 gcatgtgttc tccttttttt ttgcaaatag cttcacctat ataatacttc atccatttta   7500
ttagtacatc catttagggt ttagggttaa tggttttat agactaattt ttttagtaca     7560
tctattttat tctatttag cctctaaatt aagaaaacta aaactctatt ttagttttt      7620 tatttaataa tttagatata aaatagaata aaataaagtg actaaaaatt aaacaaatac    7680
cctttaagaa attaaaaaaa ctaaggaaac atttttcttg tttcgagtag ataatgccag    7740
cctgttaaac gccgtcgacg agtctaacgg acaccaacca gcgaaccagc agcgtcgcgt    7800
cgggccaagc gaagcagacg gcacggcatc tctgtcgctg cctctggacc cctctcgaga    7860
gttccgctcc accgttggac ttgctccgct gtcggcatcc agaaattgcg tggcggagcg    7920
gcagacgtga gccggcacgg caggcggcct cctcctcctc tcacggcacc ggcagctacg    7980
ggggattcct ttcccaccgc tccttcgctt tcccttcctc gcccgccgta ataaatagac    8040
accccctcca caccctcttt ccccaacctc gtgttgttcg gagcgcacac acacacaacc    8100
agatctcccc caaatccacc cgtcggcacc tccgcttcaa ggtacgccgc tcgtcctccc    8160
cccccccccc tctctacctt ctctagatcg gcgttccggt ccatggttag ggcccggtag    8220
ttctacttct gttcatgttt gtgttagatc cgtgtttgtg ttagatccgt gctgctagcg    8280
ttcgtacacg gatgcgacct gtacgtcaga cacgttctga ttgctaactt gccagtgttt    8340
ctctttgggg aatcctggga tggctctagc cgttccgcag acgggatcga tttcatgatt    8400
ttttttgttt cgttgcatag ggtttggttt gccctttcc tttatttcaa tatatgccgt     8460
gcacttgttt gtcgggtcat cttttcatgc tttttttgt cttggttgtg atgatgtggt     8520
ctggttgggc ggtcgttcta gatcggagta gaattctgtt tcaaactacc tggtggattt    8580
```

```
attaattttg gatctgtatg tgtgtgccat acatattcat agttacgaat tgaagatgat    8640
ggatggaaat atcgatctag gataggtata catgttgatg cgggttttac tgatgcatat    8700
acagagatgc tttttgttcg cttggttgtg atgatgtggt gtggttgggc ggtcgttcat    8760
tcgttctaga tcggagtaga atactgtttc aaactacctg gtgtatttat taattttgga    8820
actgtatgtg tgtgtcatac atcttcatag ttacgagttt aagatggatg gaaatatcga    8880
tctaggatag gtatacatgt tgatgtgggt tttactgatg catatacatg atggcatatg    8940
cagcatctat tcatatgctc taaccttgag tacctatcta ttataataaa caagtatgtt    9000
ttataattat tttgatcttg atatacttgg atgatggcat atgcagcagc tatatgtgga    9060
ttttttttagc cctgccttca tacgctattt atttgcttgg tactgtttct tttgtcgatg    9120
ctcaccctgt tgtttggtgt tacttctgca ggtcgactct agaggatcca cacgacacca    9180
tgtccgcccg cgaggtgcac atcgacgtga acaacaagac cggccacacc ctccagctgg    9240
aggacaagac caagctcgac ggcggcaggt ggcgcacctc cccgaccaac gtggccaacg    9300
accagatcaa gaccttcgtg gccgaatcca acggcttcat gaccggcacc gagggcacca    9360
tctactactc aattaatggc gaggccgaga tcagcctcta cttcgacaac ccgttcgccg    9420
gctccaacaa atacgacggc cactccaaca agtcccagta cgagatcatc acccagggcg    9480
gctccggcaa ccagtcccac gtgacctaca ccatccagac cacctcctcc cgctacggcc    9540
acaagtcctg agtcatgagt catgagtcag ttaacctaga cttgtccatc ttctggattg    9600
gccaacttaa ttaatgtatg aaataaaagg atgcacacat agtgcatagc taatcactat    9660
aatgtgggca tcaaagttgt gtgttatgtg taattactag ttatctgaat aaaagagaaa    9720
gagatcatcc atatttctta tcctaaatga atgtcacgtg tctttataat tctttgatga    9780
accagatgca tttcattaac caaatccata tacatataaa tattaatcat atataattaa    9840
tatcaattgg gttagcaaaa caaatctagt ctaggtgtgt tttgcgaatg cggccgcgga    9900
ccgaattggg gatctgcatg aaagaaactg tcgcactgct gaaccgcacc ttgtcacttt    9960
catcgaacac gacctgtgcc caagatgacg gtgctgcggt ctaagtgagg ctgaattgcc   10020
ttggacagaa gcggactccc tacaattagt taggccaaac ggtgcatcca tgtgtagctc   10080
cgggctcggg ctgtatcgcc atctgcaata gcatccatgg agctcgttcc atgtagttgg   10140
agatgaacca atgatcgggc gtgtggacgt atgttcctgt gtactccgat agtagagtac   10200
gtgttagctc tttcatggtg caagtgaaat ttgtgttggt ttaattaccc ctacgttagt   10260
tgcgggacag gagacacatc atgaatttaa aggcgatgat gtcctctcct gtaatgttat   10320
tcttttgatg tgatgaatca aaatgtcata taaaacattt gttgctcttt agttaggcct   10380
gatcgtagaa cgaaatgctc gtgtagcggg gctacgagcc tatgacgcaa taacactggt   10440
ttgccggccc ggagtcgctt gacaaaaaaa agcatgttaa gtttatttac aattcaaaac   10500
ctaacatatt atattccctc aaagcaggtt cacgatcaca cctgtaccta aaaaaaacat   10560
gaagaatata ttactccatt attatgagat gaaccacttg gcaagagtgg taagctatat   10620
aaaaaaatga acattattac gagatgttat atgccattat attgattcga agatatatgt   10680
ttctttctcc cacgggcacc taacggatac atgataaggc caaggcagat cacgggaaat   10740
tattcgaata catgttacgc cctattgccg gaaaaaaaat gcagggcagg tgttggccgt   10800
agcgatttaa gcacttaagc tggaggttgc cacacttgga tgcaagcgtc tgacccttct   10860
aaaaaatcgg cggctttgtc cgtatccgta tcccctatcc aacatctagc tggccacacg   10920
```

-continued

```
acggggctgg gcagatcgtg gatgccgggt cgacgtcgat cgtcagccat catagaccaa   10980
tcgaccatct gttatggatg cttgctagct agactagtca gacataaaat ttggatactt   11040
tctcccaact gggagacggg gactgatgtg cagctgcacg tgagctaaat ttttccctat   11100
aaatatgcat gaaatactgc attatcttgc cacagccact gccacagcca gataacaagt   11160
gcagctggta gcacgcaacg catagctctg gacttgtagc taggtagcca accggatcca   11220
cacgacacca tgctcgacac caacaaggtg tacgagatca gcaaccacgc caacggcctc   11280
tacgccgcca cctacctctc cctcgacgac tccggcgtgt ccctcatgaa caagaacgac   11340
gacgacatcg acgactacaa cctcaagtgg ttcctcttcc cgatcgacga cgaccagtac   11400
atcatcacct cctacgccgc caacaactgc aaggtgtgga acgtgaacaa cgacaagatt   11460
aatgtgtcaa cctactcctc caccaactcc atccagaagt ggcagatcaa ggccaacggc   11520
tcctcctacg tgatccagtc cgacaacggc aaggtgctca ccgccggcac cggccaggcc   11580
ctcggcctca tccgcctcac cgacgagtcc tccaacaacc cgaaccagca atggaacctg   11640
acgtccgtgc agaccatcca gctcccgcag aagccgatca tcgacaccaa gctcaaggac   11700
tacccgaagt actccccgac cggcaacatc gacaacggca cctccccgca gctcatgggc   11760
tggaccctcg tgccgtgcat catggtgaac gacccgaaca tcgacaagaa cacccagatc   11820
aagaccaccc cgtactacat cctcaagaag taccagtact ggcagagggc cgtgggctcc   11880
aacgtcgcgc tccgcccgca cgagaagaag tcctacacct acgagtgggg caccgagatc   11940
gaccagaaga ccaccatcat caacaccctc ggcttccaga tcaacatcga cagcggcatg   12000
aagttcgaca tcccggaggt gggcggcggt accgacgaga tcaagaccca gctcaacgag   12060
gagctcaaga tcgagtattc acatgagacg aagatcatgg agaagtacca ggagcagtcc   12120
gagatcgaca acccgaccga ccagtccatg aactccatcg gcttcctcac catcacctcc   12180
ctggagctct accgctacaa cggctccgag atccgcatca tgcagatcca gacctccgac   12240
aacgacacct acaacgtgac ctcctacccg aaccaccagc aggccctgct gctgctgacc   12300
aaccactcct acgaggaggt ggaggagatc accaacatcc cgaagtccac cctcaagaag   12360
ctcaagaagt actacttctg agtcatgagt catgagtcag ttaacctaga cttgtccatc   12420
ttctggattg ccaacttaa ttaatgtatg aaataaaagg atgcacacat agtgacatgc   12480
taatcactat aatgtgggca tcaaagttgt gtgttatgtg taattactag ttatctgaat   12540
aaaagagaaa gagatcatcc atatttctta tcctaaatga atgtcacgtg tctttataat   12600
tctttgatga accagatgca tttcattaac caaatccata tacatataaa tattaatcat   12660
atataattaa tatcaattgg gttagcaaaa caaatctagt ctaggtgtgt tttgcgaatt   12720
atcgatgggc cccggccgaa gctggccgcg gaccgaattc ccatggagtc aaagattcaa   12780
atagaggacc taacagaact cgccgtaaag actggcgaac agttcataca gagtctctta   12840
cgactcaatg acaagaagaa aatcttcgtc aacatggtgg agcacgacac gcttgtctac   12900
tccaaaaata tcaaagatac agtctcagaa gaccaaaggg caattgagac ttttcaacaa   12960
agggtaatat ccggaaacct cctcggattc cattgcccag ctatctgtca ctttattgtg   13020
aagatagtgg aaaaggaagg tggctcctac aaatgccatc attgcgataa aggaaaggcc   13080
atcgttgaag atgcctctgc cgacagtggt cccaaagatg acccccacc cacgaggagc    13140
atcgtggaaa aagaagacgt tccaaccacg tcttcaaagc aagtggattg atgtgatatc   13200
tccactgacg taagggatga cgcacaatcc cactatcctt cgcaagaccc ttcctctata   13260
taaggaagtt catttcattt ggagaggaca gggtacccgg ggatccacca tgtctccgga   13320
```

```
gaggagacca gttgagatta ggccagctac agcagctgat atggccgcgg tttgtgatat    13380
cgttaaccat tacattgaga cgtctacagt gaactttagg acagagccac aaacaccaca    13440
agagtggatt gatgatctag agaggttgca agatagatac ccttggttgg ttgctgaggt    13500
tgagggtgtt gtggctggta ttgcttacgc tgggccctgg aaggctagga acgcttacga    13560
ttggacagtt gagagtactg tttacgtgtc acataggcat caaaggttgg gcctaggatc    13620
cacattgtac acacatttgc ttaagtctat ggaggcgcaa ggttttaagt ctgtggttgc    13680
tgttataggc cttccaaacg atccatctgt taggttgcat gaggctttgg gatacacagc    13740
ccggggtaca ttgcgcgcag ctggatacaa gcatggtgga tggcatgatg ttggtttttg    13800
gcaaagggat tttgagttgc cagctcctcc aaggccagtt aggccagtta cccagatctg    13860
agtcgacctg caggcatgcc cgctgaaatc accagtctct ctctacaaat ctatctctct    13920
ctataataat gtgtgagtag ttcccagata agggaattag ggttcttata gggtttcgct    13980
catgtgttga gcatataaga aacccttagt atgtatttgt atttgtaaaa tacttctatc    14040
aataaaattt ctaattccta aaaccaaaat ccagggcgag ctcgaattcg agctcgagcc    14100 cggggtggatc ctctagagtc gacctgcaga agcttcggtc cggcgcgcct ctagttgaag    14160
acacgttcat gtcttcatcg taagaagaca ctcagtagtc ttcggccaga atggcctaac    14220
tcaaggccat cgtggcctct tgctcttcag gatgaagagc tatgtttaaa cgtgcaagga    14280
tataagaact tcgatccgaa atatcgtttc aaaactagaa aacagcgcgg ctttggctaa    14340
gccgcgcact atataggatt ttgggcacct tttgatggaa cgtgaaagcg tactgcgcac    14400 tagttatttta ggttgaacct tggatatacg gttctcactg cgccaatgca aggcttgaaa    14460
cttggttagt aatacgtact ccctccgttt ctttttattt gtcgctggat agtgcaattt    14520
tgcactatcg agcgacaaat aaaaagaaac ggagggagta tatgattgtc agatgtagat    14580 atgttttattt atatatcaca tacagatata taaaacagat cacttttttca gatatacagt    14640 tccaatgtca gccctgatca ccctgtcata aattgcacgt ttctaattga tgttgcttca    14700
tggtcgtcat gagaaccttc tgaagaaatc gatgaaggtt gccaacccttt caaagtttca    14760 gaaaccactt tgcatgtaca ctaagggctg gtttggcagc ccaaaaccag ccagcgtttt    14820
cctggtcttt tctcccggga gaaagcccat gcatagattg tccctggatt attttatctgt    14880 gtcctttggc taaaaattcg tcccaatttc ctgtaggaaa ctacctcggc cttgggaggc    14940
caggcgattc tccaccgcct cgtctcgtcc atccttcgat gctcacgcgt gcctcctcgg    15000
atgctatcct caggcgattc tccgtcgtct cgtctcatcc atcctcacgc gcgcctcctc    15060
cgacgctatc cccaggcgat tctccaccgt ctcgtctcat ccatcctcat gtacgcctcg    15120
tccgatgcta tccccagacg attttccgtc gtctcatctc cttcatgctc gcgcgcgcct    15180
cctccgacgc tatccccagg cgattttttct gccgtctcgt ctccttcatg cccgcgcgcg    15240
cctcctccga cgctatcccc aggcgatttt ccgccgtctc gtctccttca tgcccgcgcg    15300
tgcctcctcc gacgctattc ccacgagcgc ctccgccgcc gctatcccca gacgattttc    15360
cgctgtctcg tctccttcat gcccgcgcgc ccctcctccg acgctatccc cacgagcgcc    15420
tccgccgccc ctccaccgtc ttccccgccg ccatccccctt aattcctata gatctggacc    15480 ccgtctctact ttcgttggca tactttttgct tggtgtgcgc gggctggagt ggaaggttgc    15540
gcattcgatc acgggggaga agtggatctt gggtcttggc aggctagggc ggttgccagg    15600
acgccgtggt gtgcattcat gggtcctata aatctttatc attaccgcct taggagctag    15660
```

```
ttgtagttca cacatcatat ccttttctgc tcgacatcgt ctggggatgc cctaggtgcc    15720
ctaccgaccc tacggcattg tcttgacctc tattagactc tatgtcatct agagccttct    15780
tgggtggcct tttgaccccca agcgaccct atgatcttac cctaacgagg tctcccttgg    15840
tggggcaaga tccactttgt ccacttaact gaagatctga tcctcatctt gaaatcttta    15900
atcccaaggt gactctacgt cgtatgtgga tgctccgggt aacctgccaa cccggatcac    15960
cctaagatct ctttcctaag gggcgagatc taggttccta cgagaaagaa gacgaccctg    16020
caccattgcg gtccgtccgg tccagagtgc gaacgtccgg atgcgacaca gggaaggagt    16080
cgctcctgca gcgaggtcgc agactgtcca cacagcctca gaaggcaccg ccagacaata    16140
catgtaatac ccactctgta agaaaaacct aaaaggagaa agtatattcc tttatctata    16200
tgtgtgttat atttctactc accatcacat gtgaacatct cacttacaca aataaataat    16260
taacaaaaga cactcaaata aattatgcat catgctcgac cttattttgt gtgcattctg    16320
ttacaatata aaataatat aaaaaacata tattaatatc aaaatttgga gatttaaccc    16380
taatatgcaa atcggagttt agaggaaaga aagaaaaatg ctatacaaaa taaggaata    16440 aatatataaa taaaggtaaa actattaata ctggtatatt aatttgaaca gttgacctaa    16500
ttatgaatat cacaactggt ttgaattcaa atatgaaatc caagaatttg gaaataggaa    16560
aaatggagat aagaataaag gaaaagaatt cttaactcgg atgggcctgg gaacgaatt    16620 tcggcccact tcctgtgtcc ttagctgtgc ggctcagtcc agtg                    16664

<210> SEQ ID NO 24
<211> LENGTH: 27
<212> TYPE: DNA
<213> ORGANISM: Artificial
<220> FEATURE:
<223> OTHER INFORMATION: synthetic

<400> SEQUENCE: 24
tttgcgaatt atcgatgggc cccggcc                                          27

<210> SEQ ID NO 25
<211> LENGTH: 15115
<212> TYPE: DNA
<213> ORGANISM: Artificial
<220> FEATURE:
<223> OTHER INFORMATION: synthetic

<400> SEQUENCE: 25
gagcatatcc agcaccagct ggtaccaagg tcgggtctct gtgctagtgc tattagctag      60
tgtaaggagc gagtaggtca gttaaggctg gtgcgtcgtg agggctgtct tgtgtgtagc     120
tacagcagac ggttcatcag aaggattatt cgtgcagtat atacagtaca actagacaat     180
gatgttgatg attggtctag agctagaggc ctatagccct atactactgt gtattgtccg     240 ccgtttagt ttttggtcc catcccatca atgcaaccgc cttgttttgc tccaattgtc       300
ccgttcctgc gcctcgcttt tgctctgtcg catcgcatac aaaaaaaaaa acgccgcgcc     360
ggctttgaat cgcgcccccc aactgctcca accaggcaac ggacacggcc accgtccgtg     420
tcgcgagcaa aaaacaaaa agaggaacg gtccaggacg aagcagtcca ctgccgctgt      480
ggccggcaaa agatctggtt gagcacatgg agattggaga aggttggttg gttcttctgg     540
aaacgccaat gaatggggc actgacatgt actcttaaca tgtagtgcaa tccagagatc     600
ggatatccag acactggcag cacgatcgcc tcgcgccgta gatcacgcac gcaaattact     660
gaagaccatt cacaaaaaaa aaaaaacaca caggggctag cgtgccccac accaaaccca     720
```

```
agtgctgcgt tgcacgcagg ggagcgaaaa aaaacaataa tgctcactgt cacgtcgcgt    780
atccaacccc gcggacgtct cggctctcag cagcagcaca cggggcacct cacgatgccg    840
ttctcgttgc actccgtgca ccgccggaac ccgccgccgc attcgtcgcc ctcctcctcc    900
tcctccgcct cgtcttcgtc acccacgtac accttgcagc tgcccgagca gacatcgcag    960
agcacgaacc gcatgtcccc gcaggcctcg cacgcgccgg cgtcgccgcc gtgtgggccg   1020
gccgtcgacg cagcgctctc gcacccggcc agcctcggcg cgagctcccc ggcctcgtgc   1080
agccgcttca gctcctcggc gttgcccacg agctccccgt ccacgaagag gctggggagg   1140
gcggcgggcg tgccgccggc ttggccgagc ccgaggccga aaggccgcg gagctcgtcc    1200 cggaacccgc ggtgcatgga cacgtcgcgc tcgtcgaggc gcacgccgta gcccttgagg   1260
atggcgcgcg ccaggcagca gtcctcgtgc gtggcgcgca cgccgcgcag cgacgtgaag   1320
tagagcaccg ccctccgcgg cggcagcgcc ttcccctccc cgccgctcgt cggggcggcg   1380
tcgggccgag gcatcggcat cggcagcggc gtcaccttgg cggacgccgc gaggtcctgc   1440
gcaggcgccg tggcgaccgg gaacgagaag gagtggcgcc cgaacggcgc gcccagcagc   1500
ggggagcggt cctcgaggcc ggccatgagc gcccacgcgt cgatgtcctc gggctcgttg   1560
ggcggcgtca tggtgggcgt gcgcggcgcc agcctcgtgg gcgcgggctc cggcgcccgc   1620
ggcagggcct tgtccagctc cagggacccg agcgtggacg acgtgagccg caccacgtgg   1680
acgccgacgt cgctggggca ccgagccggg aacgactggc tgcgcggcag cggtgacggg   1740
cagtaccgga ggtcgtgacg ggcctgcctt gaggtggtgc accccatggc accaatgtac   1800
acacacggcc aaagcgccaa gtgggctgca gactgcctgc caatgtgatc aagcagccag   1860
gagcagagac ggatctctgg ggatcggggt ttctggggtt taggatcttt atactactct   1920
gtcattgggg atataaaact aggagtgtgg ttaattagga ctcgatagat aagtttacca   1980
caagcgcgtg aaatggtcta cccgatgatg tgattggcct aaaaagaaca agaagagtat   2040
ttggagctac tgaacattct cttttcctga agataactaa ttttggaac attcagactt    2100 gggagtctgg acttttggag ggaagttcaa attgtggtct gcctctgcca tgtgttgttt   2160
tttagtcgga gagtggccct cattttttt gtcctgttta gctttatagt cgtagcagct    2220
agtagcgaaa tttaaccttg gattatggcc gtgttagtca aacaatcatt gatttatttc    2280
ctccctttcg cgctgctttt cctgtacgca tctccgctgc ccttgattcg aggaccctgt   2340
tcacaacaca gggctctggc tttggagcct ctcgtttgta gcacttgcac gtagttaccc   2400
ggaccgaagc ttcaacacag atctgatagt ttaaacgctc ttcaactgga agagcggtta   2460
cccggaccga agcttcggcc ggggcccatc gatatccgcg gcatgcctg  cagtgcagcg    2520 tgacccggtc gtgcccctct ctagagataa tgagcattgc atgtctaagt tataaaaaat   2580
taccacatat ttttttgtc acacttgttt gaagtgcagt ttatctatct ttatacatat    2640
atttaaactt tactctacga ataatataat ctatagtact acaataatat cagtgttta    2700 gagaatcata taaatgaaca gttagacatg gtctaaagga caattgagta ttttgacaac   2760
aggactctac agttttatct ttttagtgtg catgtgttct ccttttttt tgcaaatagc    2820 ttcacctata taatacttca tccatttat tagtacatcc atttagggtt tagggttaat    2880 ggttttttata gactaatttt tttagtacat ctattttatt ctattttagc ctctaaatta   2940
agaaaactaa aactctattt tagttttttt atttaataat ttagatataa aatagaataa   3000
aataaagtga ctaaaaatta aacaaatacc ctttaagaaa ttaaaaaaac taaggaaaca   3060
```

-continued

| | |
|---|---|
| tttttcttgt ttcgagtaga taatgccagc ctgttaaacg ccgtcgacga gtctaacgga | 3120 |
| caccaaccag cgaaccagca gcgtcgcgtc gggccaagcg aagcagacgg cacggcatct | 3180 |
| ctgtcgctgc ctctggaccc ctctcgagag ttccgctcca ccgttggact tgctccgctg | 3240 |
| tcggcatcca gaaattgcgt ggcggagcgg cagacgtgag ccggcacggc aggcggcctc | 3300 |
| ctcctcctct cacggcaccg gcagctacgg gggattcctt tcccaccgct ccttcgcttt | 3360 |
| cccttcctcg cccgccgtaa taaatagaca cccctccac accctctttc cccaacctcg | 3420 |
| tgttgttcgg agcgcacaca cacacaacca gatctccccc aaatccaccc gtcggcacct | 3480 |
| ccgcttcaag gtacgccgct cgtcctcccc ccccccct ctctaccttc tctagatcgg | 3540 |
| cgttccggtc catggttagg gcccggtagt tctacttctg ttcatgtttg tgttagatcc | 3600 |
| gtgtttgtgt tagatccgtg ctgctagcgt tcgtacacgg atgcgacctg tacgtcagac | 3660 |
| acgttctgat tgctaacttg ccagtgtttc tctttgggga atcctgggat ggctctagcc | 3720 |
| gttccgcaga cgggatcgat ttcatgattt tttttgtttc gttgcatagg gtttggtttg | 3780 |
| cccttttcct ttatttcaat atatgccgtg cacttgtttt tcgggtcatc ttttcatgct | 3840 |
| tttttttgtc ttggttgtga tgatgtggtc tggttgggcg gtcgttctag atcggagtag | 3900 |
| aattctgttt caaactacct ggtggattta ttaattttgg atctgtatgt gtgtgccata | 3960 |
| catattcata gttacgaatt gaagatgatg gatggaaata tcgatctagg ataggtatac | 4020 |
| atgttgatgc gggttttact gatgcatata cagagatgct ttttgttcgc ttggttgtga | 4080 |
| tgatgtggtg tggttgggcg gtcgttcatt cgttctagat cggagtagaa tactgtttca | 4140 |
| aactacctgg tgtatttatt aattttggaa ctgtatgtgt gtgtcataca tcttcatagt | 4200 |
| tacgagttta agatggatgg aaatatcgat ctaggatagg tatacatgtt gatgtgggtt | 4260 |
| ttactgatgc atatacatga tggcatatgc agcatctatt catatgctct aaccttgagt | 4320 |
| acctatctat tataataaac aagtatgttt tataattatt ttgatcttga tatacttgga | 4380 |
| tgatggcata tgcagcagct atatgtggat tttttagcc ctgccttcat acgctattta | 4440 |
| tttgcttggt actgtttctt ttgtcgatgc tcaccctgtt gtttggtgtt acttctgcag | 4500 |
| gtcgactcta gaggatccaa caatggagaa caacatacag aatcagtgcg tccctacaa | 4560 |
| ctgcctcaac aatcctgaag tagagattct caacgaagag aggtcgactg cagattgcc | 4620 |
| gttagacatc tccctgtccc ttacacgttt cctgttgtct gagtttgttc caggtgtggg | 4680 |
| agttgcgttt ggcctcttcg acctcatctg gggcttcatc actccatctg attggagcct | 4740 |
| cttttcttctc cagattgaac agttgattga acaaaggatt gagaccttgg aaaggaatcg | 4800 |
| ggccatcact acccttcgtg gcttagcaga cagctatgag atctacattg aagcactaag | 4860 |
| agagtgggaa gccaatccta caatgcccca actgagagaa gatgtgcgta tacgctttgc | 4920 |
| taacacagat gatgctttga tcacagccat caacaacttc acccttacca gcttcgagat | 4980 |
| ccctcttctc tcggtctatg ttcaagctgc taacctgcac ttgtcactac tgcgcgacgc | 5040 |
| tgtgtcgttt gggcaaggtt ggggactgga catagctact gtcaacaatc actacaacag | 5100 |
| actcatcaat ctgattcatc gatacacgaa acattgtttg gatacctaca atcagggatt | 5160 |
| ggagaacctg agaggtacta acactcgcca atgggccagg ttcaatcagt tcaggagaga | 5220 |
| ccttacactt actgtgttag acatagttgc tctctttccg aactacgatg ttcgtaccta | 5280 |
| tccgattcaa acgtcatccc aacttacaag ggagatctac accagttcag tcattgaaga | 5340 |
| ctctccagtt tctgcgaaca tacccaatgg tttcaacagg gctgagtttg gagtcagacc | 5400 |
| accccatctc atggacttca tgaactcttt gtttgtgact gcagagactg ttagatccca | 5460 |

```
aactgtgtgg ggaggacact tagttagctc acgcaacacg gctggcaatc gtatcaactt    5520
tcctagttac ggggtcttca atcccggggg cgccatctgg attgcagatg aagatccacg    5580
tcctttctat cggaccttgt cagatcctgt cttcgtccga ggaggctttg gcaatcctca    5640
ctatgtactc ggtcttaggg gagtggcctt tcaacaaact ggtacgaatc acacccgcac    5700
attcaggaac tccgggacca ttgactctct agatgagata ccacctcaag acaacagcgg    5760
cgcaccttgg aatgactact cccatgtgct gaatcatgtt accttttgtgc gctggccagg    5820 tgagatctca ggttccgact catggagagc accaatgttc tcttggacgc atcgtagcgc    5880
tacccccaca acaccattg atccagagag aatcactcag attcccttgg tgaaggcaca    5940
cacacttcag tcaggaacta cagttgtaag agggccgggg ttcacgggag gagacattct    6000
tcgacgcact agtggaggac cattcgcgta caccattgtc aacatcaatg ggcaacttcc    6060
ccaaaggtat cgtgccagga tacgctatgc ctctactacc aatctaagaa tctacgttac    6120
ggttgcaggt gaacggatct ttgctggtca gttcaacaag acaatggata ccggtgatcc    6180
acttacattc caatctttct cctacgccac tatcaacacc gcgttcacct ttccaatgag    6240
ccagagcagt ttcacagtag gtgctgatac cttcagttca ggcaacgaag tgtacattga    6300
caggtttgag ttgattccag ttactgccac actcgagtaa ggatccgtcg acctgcagcc    6360 aagcttcgc gagctcgaga tccccgacat atgcccggt ttcgttgcga ctaacatgag    6420
ttcttggaca aatttgattg gacctgatga gatgatccaa cccgaggata tagcaaagct    6480
cgttcgtgca gcaatggaac ggccaaaccg tgcttttgtc cccaagaatg aggtgctatg    6540
catgaaggaa tctacccgtt gatgtccaac agtctcaggg ttaatgtcta tgtatcttaa    6600
ataatgttgt cggtattttg taatctcata tagattttca ctgtgcgacg caaaatatt    6660 aaataaatat tattattatc tacgttttga ttgagatatc atcaatatta taataaaaat    6720
atccattaaa cacgtttga tacaaatgac agtcaataat ctgatttgaa tatttattaa    6780
ttgtaacgaa ttacataaag atcgaataga aaatactgca ctgcaaatga aaattaacac    6840
atactaataa atgcgtcaaa tatctttgcc aagatcaagc ggagtgaggg cctcatatcc    6900
ggtctcagtt acaagcacgg tatccccgaa gcgcgctcca ccaatgccct cgacatagat    6960
gccgggctcg acgctgagga cattgcctac cttgagcatg gtctcagcgc cggctttaag    7020
ctcaatccca tcccaatctg aatatccatat cccgcgccca gtccggtgta agaacgggtc    7080
tgtccatcca cctctgttgg gaattccggt ccgggtcacc tttgtccacc aagatggaac    7140
tgcggccagc ttgcatgcct gcagtgcagc gtgacccggt cgtgcccctc tctagagata    7200
atgagcattg catgtctaag ttataaaaaa ttaccacata tttttttgt cacacttgtt    7260 tgaagtgcag tttatctatc tttatacata tatttaaact ttactctacg aataatataa    7320
tctatagtac tacaataata tcagtgtttt agagaatcat ataaatgaac agttagacat    7380
ggtctaaagg acaattgagt attttgacaa caggactcta cagttttatc ttttttagtgt    7440 gcatgtgttc tcctttttt ttgcaaatag cttcacctat ataatacttc atccatttta    7500
ttagtacatc catttagggt ttaggggttaa tggtttttat agactaattt ttttagtaca    7560 tctatttta tctattttag cctctaaatt aagaaaacta aaactctatt ttagttttt    7620 tatttaataa tttagatata aaatagaata aaataaagtg actaaaaatt aaacaaatac    7680
cctttaagaa attaaaaaaa ctaaggaaac attttcttg tttcgagtag ataatgccag    7740
cctgttaaac gccgtcgacg agtctaacgg acaccaacca gcgaaccagc agcgtcgcgt    7800
```

```
cgggccaagc gaagcagacg gcacggcatc tctgtcgctg cctctggacc cctctcgaga   7860
gttccgctcc accgttggac ttgctccgct gtcggcatcc agaaattgcg tggcggagcg   7920
gcagacgtga gccggcacgg caggcggcct cctcctcctc tcacggcacc ggcagctacg   7980
ggggattcct ttcccaccgc tccttcgctt tcccttcctc gcccgccgta ataaatagac   8040
accccctcca caccctcttt ccccaacctc gtgttgttcg gagcgcacac acacacaacc   8100
agatctcccc caaatccacc cgtcggcacc tccgcttcaa ggtacgccgc tcgtcctccc   8160
cccccccccc tctctacctt tctctagatcg gcgttccggt ccatggttag ggcccggtag   8220
ttctacttct gttcatgttt gtgttagatc cgtgtttgtg ttagatccgt gctgctagcg   8280
ttcgtacacg gatgcgacct gtacgtcaga cacgttctga ttgctaactt gccagtgttt   8340
ctctttgggg aatcctggga tggctctagc cgttccgcag acgggatcga tttcatgatt   8400 tttttttgttt cgttgcatag ggtttggttt gcccttttcc tttatttcaa tatatgccgt   8460
gcacttgttt gtcgggtcat cttttcatgc ttttttttgt cttggttgtg atgatgtggt   8520
ctggttgggc ggtcgttcta gatcggagta gaattctgtt tcaaactacc tggtggattt   8580
attaattttg gatctgtatg tgtgtgccat acatattcat agttacgaat tgaagatgat   8640
ggatggaaat atcgatctag dataggtata catgttgatg cgggttttac tgatgcatat   8700
acagagatgc ttttttgttcg cttggttgtg atgatgtggt gtggttgggc ggtcgttcat   8760
tcgttctaga tcggagtaga atactgtttc aaactacctg gtgtatttat taattttgga   8820
actgtatgtg tgtgtcatac atcttcatag ttacgagttt aagatggatg gaaatatcga   8880
tctaggatag gtatacatgt tgatgtgggt tttactgatg catatacatg atggcatatg   8940
cagcatctat tcatatgctc taaccttgag tacctatcta ttataataaa caagtatgtt   9000
ttataattat tttgatcttg atatacttgg atgatggcat atgcagcagc tatatgtgga   9060 ttttttttagc cctgccttca tacgctattt atttgcttgg tactgtttct tttgtcgatg   9120
ctcaccctgt tgtttggtgt tacttctgca ggtcgactct agaggatcca cacgacacca   9180
tgtccgcccg cgaggtgcac atcgacgtga acaacaagac cggccacacc ctccagctgg   9240
aggacaagac caagctcgac ggcggcaggt ggcgcaacct cccgaccaac gtggccaacg   9300
accagatcaa gaccttcgtg gccgaatcca acggcttcat gaccggcacc gagggcacca   9360
tctactactc aattaatggc gaggccgaga tcagcctcta cttcgacaac ccgttcgccg   9420
gctccaacaa atacgacggc cactccaaca gtcccagta cgagatcatc acccagggcg   9480
gctccggcaa ccagtcccac gtgacctaca ccatccagac cacctcctcc cgctacggcc   9540
acaagtcctg agtcatgagt catgagtcag ttaacctaga cttgtccatc ttctggattg   9600
gccaacttaa ttaatgtatg aaataaaagg atgcacacat agtgacatgc taatcactat   9660
aatgtgggca tcaaagttgt gtgttatgtg taattactag ttatctgaat aaaagagaaa   9720
gagatcatcc atatttctta tcctaaatga atgtcacgtg tctttataat tctttgatga   9780
accagatgca tttcattaac caaatccata tacatataaa tattaatcat atataattaa   9840
tatcaattgg gttagcaaaa caaatctagt ctaggtgtgt tttgcgaatg cggccgcgga   9900
ccgaattggg gatctgcatg aaagaaactg tcgcactgct gaaccgcacc ttgtcacttt   9960
catcgaacac gacctgtgcc caagatgacg gtgctgcggt ctaagtgagg ctgaattgcc  10020
ttggacagaa gcggactccc tacaattagt taggccaaac ggtgcatcca tgtgtagctc  10080
cgggctcggg ctgtatcgcc atctgcaata gcatccatgg agctcgttcc atgtagttgg  10140
agatgaacca atgatcgggc gtgtggacgt atgttcctgt gtactccgat agtagagtac  10200
```

```
gtgttagctc tttcatggtg caagtgaaat ttgtgttggt ttaattaccc ctacgttagt   10260
tgcgggacag gagacacatc atgaatttaa aggcgatgat gtcctctcct gtaatgttat   10320
tcttttgatg tgatgaatca aaatgtcata taaaacattt gttgctcttt agttaggcct   10380
gatcgtagaa cgaaatgctc gtgtagcggg gctacgagcc tatgacgcaa taacactggt   10440
ttgccggccc ggagtcgctt gacaaaaaaa agcatgttaa gtttatttac aattcaaaac   10500
ctaacatatt atattccctc aaagcaggtt cacgatcaca cctgtaccta aaaaaaacat   10560
gaagaatata ttactccatt attatgagat gaaccacttg gcaagagtgg taagctatat   10620
aaaaaaatga acattattac gagatgttat atgccattat attgattcga agatatatgt   10680
ttctttctcc cacgggcacc taacggatac atgataaggc caaggcagat cacgggaaat   10740
tattcgaata catgttacgc cctattgccg gaaaaaaaat gcagggcagg tgttggccgt   10800
agcgatttaa gcacttaagc tggaggttgc cacacttgga tgcaagcgtc tgacccttct   10860
aaaaaatcgg cggctttgtc cgtatccgta tcccctatcc aacatctagc tggccacacg   10920
acggggctgg gcagatcgtg gatgccgggt cgacgtcgat cgtcagccat catagaccaa   10980
tcgaccatct gttatggatg cttgctagct agactagtca gacataaaat ttggatactt   11040
tctcccaact gggagacggg gactgatgtg cagctgcacg tgagctaaat tttccctat    11100 aaatatgcat gaaatactgc attatcttgc cacagccact gccacagcca gataacaagt   11160
gcagctggta gcacgcaacg catagctctg gacttgtagc taggtagcca accggatcca   11220
cacgacacca tgctcgacac caacaaggtg tacgagatca gcaaccacgc caacggcctc   11280
tacgccgcca cctacctctc cctcgacgac tccggcgtgt ccctcatgaa caagaacgac   11340
gacgacatcg acgactacaa cctcaagtgg ttcctcttcc cgatcgacga cgaccagtac   11400
atcatcacct cctacgccgc caacaactgc aaggtgtgga acgtgaacaa cgacaagatt   11460
aatgtgtcaa cctactcctc caccaactcc atccagaagt ggcagatcaa ggccaacggc   11520
tcctcctacg tgatccagtc cgacaacggc aaggtgctca ccgccggcac cggccaggcc   11580
ctcggcctca tccgcctcac cgacgagtcc tccaacaacc cgaaccagca atggaacctg   11640
acgtccgtgc agaccatcca gctcccgcag aagccgatca tcgacaccaa gctcaaggac   11700
tacccgaagt actccccgac cggcaacatc gacaacggca cctccccgca gctcatgggc   11760
tggaccctcg tgccgtgcat catggtgaac gacccgaaca tcgacaagaa cacccagatc   11820
aagaccaccc cgtactacat cctcaagaag taccagtact ggcagagggc cgtgggctcc   11880
aacgtcgcgc tccgcccgca cgagaagaag tcctacacct acgagtgggg caccgagatc   11940
gaccagaaga ccaccatcat caacacccct ggcttccaga tcaacatcga cagcggcatg   12000
aagttcgaca tcccggaggt gggcggcggt accgacgaga tcaagaccca gctcaacgag   12060
gagctcaaga tcgagtattc acatgagacg aagatcatgg agaagtacca ggagcagtcc   12120
gagatcgaca cccgaccga ccagtccatg aactccatcg gcttcctcac catcacctcc    12180
ctggagctct accgctacaa cggctccgag atccgcatca tgcagatcca gacctccgac   12240
aacgacacct acaacgtgac ctcctacccg aaccaccagc aggccctgct gctgctgacc   12300
aaccactcct acgaggaggt ggaggagatc accaacatcc cgaagtccac cctcaagaag   12360
ctcaagaagt actacttctg agtcatgagt catgagtcag ttaacctaga cttgtccatc   12420
ttctggattg gccaacttaa ttaatgtatg aaataaaagg atgcacacat agtgacatgc   12480
taatcactat aatgtgggca tcaaagttgt gtgttatgtg taattactag ttatctgaat   12540
```

```
aaaagagaaa gagatcatcc atatttctta tcctaaatga atgtcacgtg tctttataat    12600
tctttgatga accagatgca tttcattaac caaatccata tacatataaa tattaatcat    12660
atataattaa tatcaattgg gttagcaaaa caaatctagt ctaggtgtgt tttgcgaatt    12720
atcgatgggc ccctaagaac ttcgatccga aatatcgttt caaaactaga aaacagcgcg    12780
gctttggcta agccgcgcac tatataggat tttgggcacc ttttgatgga acgtgaaagc    12840
gtactgcgca ctagttattt aggttgaacc ttggatatac ggttctcact gcgccaatgc    12900
aaggcttgaa acttggttag taatacgtac tccctccgtt tcttttttatt tgtcgctgga    12960 tagtgcaatt ttgcactatc gagcgacaaa taaaagaaa cggagggagt atatgattgt    13020
cagatgtaga tatgttttatt tatatatcac atacagatat ataaaacaga tcacttttttc    13080 agatatacag ttccaatgtc agccctgatc accctgtcat aaattgcacg tttctaattg    13140
atgttgcttc atggtcgtca tgagaaccett ctgaagaaat cgatgaaggt tgccaaccett    13200 tcaaagtttc agaaccact ttgcatgtac actaagggct ggtttggcag cccaaaacca    13260
gccagcgttt tcctggtctt ttctcccggg agaaagccca tgcatagatt gtccctggat    13320
tatttatctg tgtcctttgg ctaaaaattc gtcccaattt cctgtaggaa actacctcgg    13380
ccttgggagg ccaggcgatt ctccaccgcc tcgtctcgtc catccttcga tgctcacgcg    13440
tgcctcctcg gatgctatcc tcaggcgatt ctccgtcgtc tcgtctcatc catcctcacg    13500
cgcgcctcct ccgacgctat ccccaggcga ttctccaccg tctcgtctca tccatcctca    13560
tgtacgcctc gtccgatgct atccccagac gattttccgt cgtctcatct ccttcatgct    13620
cgcgcgcgcc tcctccgacg ctatcccag gcgattttcc tgccgtctcg tctccttcat    13680
gcccgcgcgc gcctcctccg acgctatccc caggcgattt tccgccgtct cgtctccttc    13740
atgcccgcgc gtgcctcctc cgacgctatt cccacgagcg cctccgccgc cgctatcccc    13800
agacgatttt ccgctgtctc gtctccttca tgcccgcgcg cccctcctcc gacgctatcc    13860
ccacgagcgc ctccgccgcc gctccaccgt cttcccccgcc gccatcccct taattcctat    13920
agatctggac cccgctctac tttcgttggc atactttttgc ttggtgtgcg cgggctggag    13980
tggaaggttg cgcattcgat cacgggggag aagtggatct tgggtcttgg caggctaggg    14040
cggttgccag gacgccgtgg tgtgcattca tgggtcctat aaatctttat cattaccgcc    14100
ttaggagcta gttgtagttc acacatcata tccttttctg ctcgacatcg tctgggatg    14160 ccctaggtgc cctaccgacc ctacggcatt gtcttgacct ctattagact ctatgtcatc    14220
tagagccttc ttgggtggcc ttttgacccc aaagcgaccc tatgatctta ccctaacgag    14280
gtctcccttg gtggggcaag atccactttg tccacttaac tgaagatctg atcctcatct    14340
tgaaatcttt aatcccaagg tgactctacg tcgtatgtgg atgctccggg taacctgcca    14400
acccggatca ccctaagatc tctttcctaa ggggcgagat ctaggttcct acgagaaaga    14460
agacgaccct gcaccattgc ggtccgtccg gtccagagtg cgaacgtccg gatgcgacac    14520
agggaaggag tcgctcctgc agcgaggtcg cagactgtcc acacagcctc agaaggcacc    14580
gccagacaat acatgtaata cccactctgt aagaaaaacc taaaggaga aagtatattc    14640 ctttatctat atgtgtgtta tatttctact caccatcaca tgtgaacatc tcacttacac    14700
aaataaataa ttaacaaaag acactcaaat aaattatgca tcatgctcga ccttatttttg    14760 tgtgcattct gttacaatat aaaaataata taaaaaacat atattaatat caaaatttgg    14820
agatttaacc ctaatatgca aatcggagtt tagaggaaag aaagaaaaat gctatacaaa    14880
ataaaggaat aaatatataa ataaaggtaa aactattaat actggtatat taatttgaac    14940
```

```
agttgaccta attatgaata tcacaactgg tttgaattca aatatgaaat ccaagaattt     15000
ggaaatagga aaaatggaga taagaataaa ggaaaagaat tcttaactcg gatgggcctg     15060
ggaaacgaat tcggcccac ttcctgtgtc cttagctgtg cggctcagtc cagtg          15115
```

<210> SEQ ID NO 26
<211> LENGTH: 15142
<212> TYPE: DNA
<213> ORGANISM: Artificial
<220> FEATURE:
<223> OTHER INFORMATION: synthetic

<400> SEQUENCE: 26

```
gagcatatcc agcaccagct ggtaccaagg tcgggtctct gtgctagtgc tattagctag       60
tgtaaggagc gagtaggtca gttaaggctg gtgcgtcgtg agggctgtct tgtgtgtagc      120
tacagcagac ggttcatcag aaggattatt cgtgcagtat atacagtaca actagacaat      180
gatgttgatg attggtctag agctagaggc ctatagccct atactactgt gtattgtccg      240
ccgttttagt ttttggtcc catcccatca atgcaaccgc cttgttttgc tccaattgtc       300
ccgttcctgc gcctcgcttt tgctctgtcg catcgcatac aaaaaaaaaa acgccgcgcc      360
ggctttgaat cgcgcccccc aactgctcca accaggcaac ggacacggcc accgtccgtg      420
tcgcgagcaa aaaacaaaa agaggaacgc gtccaggacg aagcagtcca ctgccgctgt       480
ggccggcaaa agatctggtt gagcacatgg agattggaga aggttggttg gttcttctgg      540
aaacgccaat gaatggggc actgacatgt actcttaaca tgtagtgcaa tccagagatc      600
ggatatccag acactggcag cacgatcgcc tcgcgccgta gatcacgcac gcaaattact      660
gaagaccatt cacaaaaaaa aaaaacaca caggggctag cgtgccccac accaaaccca      720
agtgctgcgt tgcacgcagg ggagcgaaaa aaaacaataa tgctcactgt cacgtcgcgt      780
atccaacccc gcggacgtct cggctctcag cagcagcaca cggggcacct cacgatgccg      840
ttctcgttgc actccgtgca ccgccggaac ccgccgccgc attcgtcgcc ctcctcctcc      900
tcctccgcct cgtcttcgtc acccacgtac accttgcagc tgcccgagca gacatcgcag      960
agcacgaacc gcatgtcccc gcaggcctcg cacgcgccgg cgtcgccgcc gtgtgggccg     1020
gccgtcgacg cagcgctctc gcaccccggcc agcctcggcg cgagctcccc ggcctcgtgc    1080
agccgcttca gctcctcggc gttgcccacg agctccccgt ccacgaagag ctggggagg     1140 gcggcgggcg tgccgccggc ttggccgagc ccgaggccga aaggccgcg gagctcgtcc      1200 cggaacccgc ggtgcatgga cacgtcgcgc tcgtcgaggc gcacgccgta gcccttgagg     1260
atggcgcgcg ccaggcagca gtcctcgtgc gtggcgcgca cgccgcgcag cgacgtgaag     1320
tagagcaccg ccctccgcgg cggcagcgcc ttcccctccc cgccgctcgt cggggcggcg     1380
tcgggccgag gcatcggcat cggcagcggc gtcaccttgg cggacgccgc gaggtcctgc     1440
gcaggcgccg tggcgaccgg gaacgagaag gagtggcgcc cgaacggcgc gcccagcagc     1500
ggggagcggt cctcgaggcc ggccatgagc gcccacgcgt cgatgtcctc gggctcgttg     1560
ggcggcgtca tggtgggcgt gcgcggcgcc agcctcgtgg gcgcgggctc cggcgcccgc     1620
ggcagggcct tgtccagctc cagggacccg agcgtggacg acgtgagccg caccacgtgg     1680
acgccgacgt cgctggggca ccgagccggg aacgactggc tgcgcggcag cggtgacggg     1740
cagtaccgga ggtcgtgacg ggcctgcctt gaggtggtgc accccatggc accaatgtac     1800
acacacggcc aaagcgccaa gtgggctgca gactgcctgc caatgtgatc aagcagccag     1860
```

```
gagcagagac ggatctctgg ggatcggggt ttctggggtt taggatctttt atactactct   1920
gtcattgggg atataaaact aggagtgtgg ttaattagga ctcgatagat aagtttacca   1980
caagcgcgtg aaatggtcta cccgatgatg tgattggcct aaaaagaaca agaagagtat   2040
ttggagctac tgaacattct cttttcctga agataactaa ttttttggaac attcagactt   2100
gggagtctgg acttttggag ggaagttcaa attgtggtct gcctctgcca tgtgttgttt   2160
tttagtcgga gagtggccct cattttttttt gtcctgttta gctttatagt cgtagcagct   2220
agtagcgaaa tttaaccttg gattatggcc gtgttagtca aacaatcatt gatttatttc   2280
ctcccctttcg cgctgctttt cctgtacgca tctccgctgc ccttgattcg aggaccctgt   2340
tcacaacaca gggctctggc tttggagcct ctcgtttgta gcacttgcac gtagttaccc   2400
ggaccgaagc ttcaacacag atctgatagt ttaaacgctc ttcaactgga agagcggtta   2460
cccggaccga agcttcggcc ggggcccatc gatatccgcg ggcatgcctg cagtgcagcg   2520
tgacccggtc gtgcccctct ctagagataa tgagcattgc atgtctaagt tataaaaaat   2580
taccacatat ttttttttgtc acacttgttt gaagtgcagt ttatctatct ttatacatat   2640
atttaaactt tactctacga ataatataat ctatagtact acaataatat cagtgtttta   2700
gagaatcata taaatgaaca gttagacatg gtctaaagga caattgagta ttttgacaac   2760
aggactctac agttttatct ttttagtgtg catgtgttct cctttttttt tgcaaatagc   2820
ttcacctata taatacttca tccatttttat tagtacatcc atttagggtt tagggttaat   2880
ggttttttata gactaattttt tttagtacat ctattttatt ctattttagc ctctaaatta   2940
agaaaactaa aactctattt tagttttttt atttaataat ttagatataa aatagaataa   3000
aataaagtga ctaaaaatta aacaaatacc ctttaagaaa ttaaaaaaac taaggaaaca   3060
tttttcttgt ttcgagtaga taatgccagc ctgttaaacg ccgtcgacga gtctaacgga   3120
caccaaccag cgaaccagca gcgtcgcgtc gggccaagcg aagcagacgg cacggcatct   3180
ctgtcgctgc ctctggaccc ctctcgagag ttccgctcca ccgttggact tgctccgctg   3240
tcggcatcca gaaattgcgt ggcggagcgg cagacgtgag ccggcacggc aggcggcctc   3300
ctcctcctct cacggcaccg gcagctacgg gggattcctt tcccaccgct ccttcgcttt   3360
ccctttcctcg cccgccgtaa taaatagaca cccccctccac accctctttc cccaacctcg   3420
tgttgttcgg agcgcacaca cacacaacca gatctccccc aaatccaccc gtcggcacct   3480
ccgcttcaag gtacgccgct cgtcctcccc ccccccccct ctctaccttc tctagatcgg   3540
cgttccggtc catggttagg gcccggtagt tctacttctg ttcatgtttg tgttagatcc   3600
gtgtttgtgt tagatccgtg ctgctagcgt tcgtacacgg atgcgacctg tacgtcagac   3660
acgttctgat tgctaacttg ccagtgtttc tctttgggga atcctgggat ggctctagcc   3720
gttccgcaga cgggatcgat ttcatgattt ttttttgttttc gttgcatagg gtttggtttg   3780
cccttttcct ttatttcaat atatgccgtg cacttgtttg tcgggtcatc ttttcatgct   3840
ttttttttgtc ttggttgtga tgatgtggtc tggttgggcg gtcgttctag atcggagtag   3900
aattctgttt caaactacct ggtggattta ttaattttgg atctgtatgt gtgtgccata   3960
catattcata gttacgaatt gaagatgatg gatggaaata tcgatctagg ataggtatac   4020
atgttgatgc gggttttact gatgcatata cagagatgct ttttgttcgc ttggttgtga   4080
tgatgtggtg tggttgggcg gtcgttcatt cgttctagat cggagtagaa tactgtttca   4140
aactacctgg tgtatttatt aatttttggaa ctgtatgtgt gtgtcataca tcttcatagt   4200
tacgagttta agatggatgg aaatatcgat ctaggatagg tatacatgtt gatgtgggtt   4260
```

```
ttactgatgc atatacatga tggcatatgc agcatctatt catatgctct aaccttgagt    4320
acctatctat tataataaac aagtatgttt tataattatt ttgatcttga tatacttgga    4380
tgatggcata tgcagcagct atatgtggat tttttagcc ctgccttcat acgctattta     4440
tttgcttggt actgtttctt ttgtcgatgc tcaccctgtt gtttggtgtt acttctgcag    4500
gtcgactcta gaggatccaa caatggagaa caacatacag aatcagtgcg tccctacaa     4560 ctgcctcaac aatcctgaag tagagattct caacgaagag aggtcgactg gcagattgcc    4620
gttagacatc tccctgtccc ttacacgttt cctgttgtct gagtttgttc caggtgtggg    4680
agttgcgttt ggcctcttcg acctcatctg gggcttcatc actccatctg attggagcct    4740
ctttcttctc cagattgaac agttgattga acaaaggatt gagaccttgg aaaggaatcg    4800
ggccatcact acccttcgtg gcttagcaga cagctatgag atctacattg aagcactaag    4860
agagtgggaa gccaatccta acaatgccca actgagagaa gatgtgcgta tacgctttgc    4920
taacacagat gatgctttga tcacagccat caacaacttc acccttacca gcttcgagat    4980
ccctcttctc tcggtctatg ttcaagctgc taacctgcac ttgtcactac tgcgcgacgc    5040
tgtgtcgttt gggcaaggtt ggggactgga catagctact gtcaacaatc actacaacag    5100
actcatcaat ctgattcatc gatacacgaa acattgtttg gatacctaca atcagggatt    5160
ggagaacctg agaggtacta acactcgcca atgggccagg ttcaatcagt tcaggagaga    5220
ccttacactt actgtgttag acatagttgc tctctttccg aactacgatg ttcgtaccta    5280
tccgattcaa acgtcatccc aacttacaag ggagatctac accagttcag tcattgaaga    5340
ctctccagtt tctgcgaaca tacccaatgg tttcaacagg gctgagtttg gagtcagacc    5400
accccatctc atggacttca tgaactcttt gtttgtgact gcagagactg ttagatccca    5460
aactgtgtgg ggaggacact tagttagctc acgcaacacg gctggcaatc gtatcaactt    5520
tcctagttac ggggtcttca atcccgggg cgccatctgg gattgcagatg aagatccacg    5580 tcctttctat cggaccttgt cagatcctgt cttcgtccga ggaggctttg gcaatcctca    5640
ctatgtactc ggtcttaggg gagtggcctt caacaaaact ggtacgaatc acacccgcac    5700
attcaggaac tccgggacca ttgactctct agatgagata ccacctcaag acaacagcgg    5760
cgcaccttgg aatgactact cccatgtgct gaatcatgtt acctttgtgc gctggccagg    5820
tgagatctca ggttccgact catggagagc accaatgttc tcttggacgc atcgtagcgc    5880
tacccccaca aacaccattg atccagagag aatcactcag attcccttgg tgaaggcaca    5940
cacacttcag tcaggaacta cagttgtaag agggccgggg ttcacgggag agacattct      6000 tcgacgcact agtggaggac cattcgcgta caccattgtc aacatcaatg gcaacttcc      6060 ccaaaggtat cgtgccagga tacgctatgc ctctactacc aatctaagaa tctacgttac    6120
ggttgcaggt gaacggatct ttgctggtca gttcaacaag acaatggata ccggtgatcc    6180
acttacattc caatctttct cctacgccac tatcaacacc gcgttcacct ttccaatgag    6240
ccagagcagt ttcacagtag gtgctgatac cttcagttca ggcaacgaag tgtacattga    6300
caggtttgag ttgattccag ttactgccac actcgagtaa ggatccgtcg acctgcagcc    6360
aagctttcgc gagctcgaga tccccgacat atgccccggt ttcgttgcga ctaacatgag    6420
ttcttggaca aatttgattg gacctgatga gatgatccaa cccgaggata tagcaaagct    6480
cgttcgtgca gcaatggaac ggccaaaccg tgcttttgtc cccaagaatg aggtgctatg    6540
catgaaggaa tctacccgtt gatgtccaac agtctcaggg ttaatgtcta tgtatcttaa    6600
```

```
ataatgttgt cggtattttg taatctcata tagattttca ctgtgcgacg caaaaatatt   6660
aaataaatat tattattatc tacgttttga ttgagatatc atcaatatta taataaaaat   6720
atccattaaa cacgatttga tacaaatgac agtcaataat ctgatttgaa tatttattaa   6780
ttgtaacgaa ttacataaag atcgaataga aaatactgca ctgcaaatga aaattaacac   6840
atactaataa atgcgtcaaa tatctttgcc aagatcaagc ggagtgaggg cctcatatcc   6900
ggtctcagtt acaagcacgg tatcccgaa gcgcgctcca ccaatgccct cgacatagat   6960
gccgggctcg acgctgagga cattgcctac cttgagcatg gtctcagcgc cggctttaag   7020
ctcaatccca tcccaatctg aatatccat cccgcgccca gtccggtgta agaacgggtc   7080
tgtccatcca cctctgttgg gaattccggt ccgggtcacc tttgtccacc aagatggaac   7140
tgcggccagc ttgcatgcct gcagtgcagc gtgacccggt cgtgcccctc tctagagata   7200
atgagcattg catgtctaag ttataaaaaa ttaccacata ttttttttgt cacacttgtt   7260
tgaagtgcag tttatctatc tttatacata tatttaaact ttactctacg aataatataa   7320
tctatagtac tacaataata tcagtgtttt agagaatcat ataaatgaac agttagacat   7380
ggtctaaagg acaattgagt attttgacaa caggactcta cagttttatc ttttagtgt    7440 gcatgtgttc tcctttttt ttgcaaatag cttcacctat ataatacttc atccatttta    7500
ttagtacatc catttagggt ttagggttaa tggttttat agactaattt ttttagtaca    7560
tctattttat tctattttag cctctaaatt aagaaaacta aaactctatt ttagttttt    7620 tatttaataa tttagatata aaatagaata aaataaagtg actaaaaatt aaacaaatac   7680
cctttaagaa attaaaaaaa ctaaggaaac attttttcttg tttcgagtag ataatgccag   7740
cctgttaaac gccgtcgacg agtctaacgg acaccaacca gcgaaccagc agcgtcgcgt   7800
cgggccaagc gaagcagacg gcacggcatc tctgtcgctg cctctggacc cctctcgaga   7860
gttccgctcc accgttggac ttgctccgct gtcggcatcc agaaattgcg tggcggagcg   7920
gcagacgtga gccggcacgg caggcggcct cctcctcctc tcacggcacc ggcagctacg   7980
ggggattcct ttcccaccgc tccttcgctt tccttcctc gcccgccgta ataaatagac   8040
accccctcca caccctcttt ccccaacctc gtgttgttcg gagcgcacac acacacaacc   8100
agatctcccc caaatccacc cgtcggcacc tccgcttcaa ggtacgccgc tcgtcctccc   8160 ccccccccc tctctacctt ctctagatcg gcgttccggt ccatggttag ggcccggtag   8220
ttctacttct gttcatgttt gtgttagatc cgtgtttgtg ttagatccgt gctgctagcg   8280
ttcgtacacg gatgcgacct gtacgtcaga cacgttctga ttgctaactt gccagtgttt   8340
ctctttgggg aatcctggga tggctctagc cgttccgcag acgggatcga tttcatgatt   8400 tttttgttt cgttgcatag ggtttggttt gcccttttcc tttatttcaa tatatgccgt    8460
gcacttgttt gtcgggtcat cttttcatgc tttttttgt cttggttgtg atgatgtggt    8520
ctggttgggc ggtcgttcta gatcggagta gaattctgtt tcaaactacc tggtggattt   8580
attaattttg gatctgtatg tgtgtgccat acatattcat agttacgaat tgaagatgat   8640
ggatggaaat atcgatctag gataggtata catgttgatg cgggttttac tgatgcatat   8700
acagagatgc tttttgttcg cttggttgtg atgatgtggt gtggttgggc ggtcgttcat   8760
tcgttctaga tcggagtaga atactgtttc aaactacctg gtgtatttat taattttgga   8820
actgtatgtg tgtgtcatac atcttcatag ttacgagttt aagatggatg gaaatatcga   8880
tctaggatat gtatacatgt tgatgtgggt tttactgatg catatacatg atggcatatg   8940
cagcatctat tcatatgctc taaccttgag tacctatcta ttataataaa caagtatgtt   9000
```

```
ttataattat tttgatcttg atatacttgg atgatggcat atgcagcagc tatatgtgga    9060 ttttttagc cctgccttca tacgctattt atttgcttgg tactgtttct tttgtcgatg     9120
ctcaccctgt tgtttggtgt tacttctgca ggtcgactct agaggatcca cacgacacca    9180
tgtccgcccg cgaggtgcac atcgacgtga acaacaagac cggccacacc ctccagctgg    9240
aggacaagac caagctcgac ggcggcaggt ggcgcacctc cccgaccaac gtggccaacg    9300
accagatcaa gaccttcgtg gccgaatcca acggcttcat gaccggcacc gagggcacca    9360
tctactactc aattaatggc gaggccgaga tcagcctcta cttcgacaac ccgttcgccg    9420
gctccaacaa atacgacggc cactccaaca agtcccagta cgagatcatc acccagggcg    9480
gctccggcaa ccagtcccac gtgacctaca ccatccagac cacctcctcc cgctacggcc    9540
acaagtcctg agtcatgagt catgagtcag ttaacctaga cttgtccatc ttctggattg    9600
gccaacttaa ttaatgtatg aaataaaagg atgcacacat agtgacatgc taatcactat    9660
aatgtgggca tcaaagttgt gtgttatgtg taattactag ttatctgaat aaaagagaaa    9720
gagatcatcc atatttctta tcctaaatga atgtcacgtg tctttataat tctttgatga    9780
accagatgca tttcattaac caaatccata tacatataaa tattaatcat atataattaa    9840
tatcaattgg gttagcaaaa caaatctagt ctaggtgtgt tttgcgaatg cggccgcgga    9900
ccgaattggg gatctgcatg aaagaaactg tcgcactgct gaaccgcacc ttgtcacttt    9960
catcgaacac gacctgtgcc caagatgacg gtgctgcggt ctaagtgagg ctgaattgcc   10020
ttggacagaa gcggactccc tacaattagt taggccaaac ggtgcatcca tgtgtagctc   10080
cgggctcggg ctgtatcgcc atctgcaata gcatccatgg agctcgttcc atgtagttgg   10140
agatgaacca atgatcgggc gtgtggacgt atgttcctgt gtactccgat agtgagtac    10200 gtgttagctc tttcatggtg caagtgaaat ttgtgttggt ttaattaccc ctacgttagt   10260
tgcgggacag gagacacatc atgaatttaa aggcgatgat gtcctctcct gtaatgttat   10320
tcttttgatg tgatgaatca aaatgtcata taaaacattt gttgctcttt agttaggcct   10380
gatcgtagaa cgaaatgctc gtgtagcggg gctacgagcc tatgacgcaa taacactggt   10440
ttgccggccc ggagtcgctt gacaaaaaaa agcatgttaa gtttatttac aattcaaaac   10500
ctaacatatt atattccctc aaagcaggtt cacgatcaca cctgtaccta aaaaaaacat   10560
gaagaatata ttactccatt attatgagat gaaccacttg gcaagagtgg taagctatat   10620
aaaaaaatga acattattac gagatgttat atgccattat attgattcga agatatatgt   10680
ttctttctcc cacgggcacc taacggatac atgataaggc caaggcagat cacgggaaat   10740
tattcgaata catgttacgc cctattgccg gaaaaaaat gcagggcagg tgttggccgt    10800
agcgatttaa gcacttaagc tggaggttgc cacacttgga tgcaagcgtc tgacccttct   10860
aaaaaatcgg cggctttgtc cgtatccgta tccccctatcc aacatctagc tggccacacg   10920
acggggctgg gcagatcgtg gatgccgggt cgacgtcgat cgtcagccat catagaccaa   10980
tcgaccatct gttatggatg cttgctagct agactagtca gacataaaat ttggatactt   11040
tctcccaact gggagacggg gactgatgtg cagctgcacg tgagctaaat ttttccctat   11100
aaatatgcat gaaatactgc attatcttgc cacagccact gccacagcca gataacaagt   11160
gcagctggta gcacgcaacg catagctctg gacttgtagc taggtagcca accggatcca   11220
cacgacacca tgctcgacac caacaaggtg tacgagatca gcaaccacgc caacggcctc   11280
tacgccgcca cctacctctc cctcgacgac tccggcgtgt ccctcatgaa caagaacgac   11340
```

```
gacgacatcg acgactacaa cctcaagtgg ttcctcttcc cgatcgacga cgaccagtac    11400
atcatcacct cctacgccgc caacaactgc aaggtgtgga acgtgaacaa cgacaagatt    11460
aatgtgtcaa cctactcctc caccaactcc atccagaagt ggcagatcaa ggccaacggc    11520
tcctcctacg tgatccagtc cgacaacggc aaggtgctca ccgccggcac cggccaggcc    11580
ctcggcctca tccgcctcac cgacgagtcc tccaacaacc cgaaccagca atggaacctg    11640
acgtccgtgc agaccatcca gctcccgcag aagccgatca tcgacaccaa gctcaaggac    11700
tacccgaagt actccccgac cggcaacatc gacaacggca cctccccgca gctcatgggc    11760
tggaccctcg tgccgtgcat catggtgaac gacccgaaca tcgacaagaa cacccagatc    11820
aagaccaccc cgtactacat cctcaagaag taccagtact ggcagagggc cgtgggctcc    11880
aacgtcgcgc tccgcccgca cgagaagaag tcctacacct acgagtgggg caccgagatc    11940
gaccagaaga ccaccatcat caacaccctc ggcttccaga tcaacatcga cagcggcatg    12000
aagttcgaca tcccggaggt gggcggcggt accgacgaga tcaagaccca gctcaacgag    12060
gagctcaaga tcgagtattc acatgagacg aagatcatgg agaagtacca ggagcagtcc    12120
gagatcgaca acccgaccga ccagtccatg aactccatcg gcttcctcac catcacctcc    12180
ctggagctct accgctacaa cggctccgag atccgcatca tgcagatcca gacctccgac    12240
aacgacacct acaacgtgac ctcctacccg aaccaccagc aggccctgct gctgctgacc    12300
aaccactcct acgaggaggt ggaggagatc accaacatcc cgaagtccac cctcaagaag    12360
ctcaagaagt actacttctg agtcatgagt catgagtcag ttaacctaga cttgtccatc    12420
ttctggattg gccaacttaa ttaatgtatg aaataaaagg atgcacacat agtgacatgc    12480
taatcactat aatgtgggca tcaaagttgt gtgttatgtg taattactag ttatctgaat    12540
aaaagagaaa gagatcatcc atatttctta tcctaaatga atgtcacgtg tctttataat    12600
tctttgatga accagatgca tttcattaac caaatccata tacatataaa tattaatcat    12660
atataattaa tatcaattgg gttagcaaaa caaatctagt ctaggtgtgt tttgcgaatt    12720
atcgatgggc cccttttgtag cacttgcacg tagttacccg taagaacttc gatccgaaat    12780
atcgtttcaa aactagaaaa cagcgcggct ttggctaagc cgcgcactat ataggatttt    12840
gggcaccttt tgatggaacg tgaaagcgta ctgcgcacta gttatttagg ttgaaccttg    12900
gatatacggt tctcactgcg ccaatgcaag gcttgaaact tggttagtaa tacgtactcc    12960 ctccgttttct ttttatttgt cgctggatag tgcaattttg cactatcgag cgacaaataa    13020
aaagaaacgg agggagtata tgattgtcag atgtagatat gtttatttat atatcacata    13080
cagatatata aaacagatca cttttttcaga tatacagttc caatgtcagc cctgatcacc    13140
ctgtcataaa ttgcacgttt ctaattgatg ttgcttcatg gtcgtcatga gaaccttctg    13200
aagaaatcga tgaaggttgc caacctttca aagtttcaga aaccactttg catgtacact    13260
aagggctggt ttggcagccc aaaaccagcc agcgttttcc tggtcttttc tcccgggaga    13320
aagcccatgc atagattgtc cctggattat ttatctgtgt cctttggcta aaaattcgtc    13380 ccaattttcct gtaggaaact acctcggcct tgggaggcca ggcgattctc caccgcctcg    13440
tctcgtccat cctcgatgc tcacgcgtgc ctcctcggat gctatcctca ggcgattctc    13500
cgtcgtctcg tctcatccat cctcacgcgc gcctcctccg acgctatccc caggcgattc    13560
tccaccgtct cgtctcatcc atcctcatgt acgcctcgtc cgatgctatc cccagacgat    13620
tttccgtcgt ctcatctcct tcatgctcgc gcgcgcctcc tccgacgcta tccccaggcg    13680 attttttctgc cgtctcgtct ccttcatgcc cgcgcgcgcc tcctccgacg ctatccccag    13740
```

```
gcgattttcc gccgtctcgt ctccttcatg cccgcgcgtg cctcctccga cgctattccc    13800
acgagcgcct ccgccgccgc tatccccaga cgattttccg ctgtctcgtc tccttcatgc    13860
ccgcgcgccc ctcctccgac gctatcccca cgagcgcctc cgccgccgct ccaccgtctt    13920
ccccgccgcc atcccctta ttcctataga tctggacccc gctctacttt cgttggcata    13980
cttttgcttg gtgtgcgcgg gctggagtgg aaggttgcgc attcgatcac gggggagaag    14040
tggatcttgg gtcttggcag gctagggcgg ttgccaggac gccgtggtgt gcattcatgg    14100
gtcctataaa tctttatcat taccgcctta ggagctagtt gtagttcaca catcatatcc    14160
ttttctgctc gacatcgtct ggggatgccc taggtgccct accgacccta cggcattgtc    14220
ttgacctcta ttagactcta tgtcatctag agccttcttg ggtggccttt tgaccccaaa    14280
gcgaccctat gatcttaccc taacgaggtc tcccttggtg gggcaagatc cactttgtcc    14340
acttaactga agatctgatc ctcatcttga aatctttaat cccaaggtga ctctacgtcg    14400
tatgtggatg ctccgggtaa cctgccaacc cggatcaccc taagatctct ttcctaaggg    14460
gcgagatcta ggttcctacg agaaagaaga cgaccctgca ccattgcggt ccgtccggtc    14520
cagagtgcga acgtccggat gcgacacagg gaaggagtcg ctcctgcagc gaggtcgcag    14580
actgtccaca cagcctcaga aggcaccgcc agacaataca tgtaataccc actctgtaag    14640
aaaaacctaa aaggagaaag tatattcctt tatctatatg tgtgttatat ttctactcac    14700
catcacatgt gaacatctca cttacacaaa taaataatta acaaaagaca ctcaaataaa    14760
ttatgcatca tgctcgacct tattttgtgt gcattctgtt acaatataaa aataatataa    14820
aaaacatata ttaatatcaa aatttggaga tttaaccct atatgcaaat cggagtttag    14880
aggaaagaaa gaaaaatgct atacaaaata aaggaataaa tatataaaata aaggtaaaac    14940 tattaatact ggtatattaa tttgaacagt tgacctaatt atgaatatca caactggttt    15000
gaattcaaat atgaaatcca agaatttgga aataggaaaa atggagataa gaataaagga    15060
aaagaattct taactcggat gggcctggga aacgaatttc ggcccacttc ctgtgtcctt    15120
agctgtgcgg ctcagtccag tg                                             15142
```

<210> SEQ ID NO 27
<211> LENGTH: 900
<212> TYPE: DNA
<213> ORGANISM: Artificial
<220> FEATURE:
<223> OTHER INFORMATION: synthetic

<400> SEQUENCE: 27

```
ccgaaccacc agcaggccct gctgctgctg accaaccact cctacgagga ggtggaggag      60
atcaccaaca tcccgaagtc caccctcaag aagctcaaga agtactactt ctgagtcatg     120
agtcatgagt cagttaacct agacttgtcc atcttctgga ttggccaact taattaatgt     180
atgaaataaa aggatgcaca catagtgaca tgctaatcac tataatgtgg gcatcaaagt     240
tgtgtgttat gtgtaattac tagttatctg aataaaagag aaagagatca tccatatttc     300
ttatcctaaa tgaatgtcac gtgtctttat aattctttga tgaaccagat gcatttcatt     360
aaccaaatcc atatacatat aaatattaat catatataat taatatcaat tgggttagca     420
aaacaaatct agtctaggtg tgttttgcga attatcgatg gccccttttg tagcacttgc     480
acgtagttac ccgtaagaac ttcgatccga aatatcgttt caaaactaga aaacagcgcg     540
gctttggcta agccgcgcac tatataggat tttgggcacc ttttgatgga acgtgaaagc     600
```

| | |
|---|---|
| gtactgcgca ctagttattt aggttgaacc ttggatatac ggttctcact gcgccaatgc | 660 |
| aaggcttgaa acttggttag taatacgtac tccctccgtt tcttttatt tgtcgctgga | 720 |
| tagtgcaatt ttgcactatc gagcgacaaa taaaaagaaa cggagggagt atatgattgt | 780 |
| cagatgtaga tatgtttatt tatatatcac atacagatat ataaaacaga tcacttttc | 840 |
| agatatacag ttccaatgtc agccctgatc accctgtcat aaattgcacg tttctaattg | 900 |

```
<210> SEQ ID NO 28
<211> LENGTH: 27
<212> TYPE: DNA
<213> ORGANISM: Artificial
<220> FEATURE:
<223> OTHER INFORMATION: synthetic

<400> SEQUENCE: 28
```

| | |
|---|---|
| tttcagcggg catgcctgca ggtcgac | 27 |

```
<210> SEQ ID NO 29
<211> LENGTH: 15620
<212> TYPE: DNA
<213> ORGANISM: Artificial
<220> FEATURE:
<223> OTHER INFORMATION: synthetic

<400> SEQUENCE: 29
```

| | |
|---|---|
| gagcatatcc agcaccagct ggtaccaagg tcgggtctct gtgctagtgc tattagctag | 60 |
| tgtaaggagc gagtaggtca gttaaggctg gtgcgtcgtg agggctgtct tgtgtgtagc | 120 |
| tacagcagac ggttcatcag aaggattatt cgtgcagtat atacagtaca actagacaat | 180 |
| gatgttgatg attggtctag agctagaggc ctatagccct atactactgt gtattgtccg | 240 |
| ccgttttagt ttttggtcc catcccatca atgcaaccgc cttgttttgc tccaattgtc | 300 |
| ccgttcctgc gcctcgcttt tgctctgtcg catcgcatac aaaaaaaaaa acgccgcgcc | 360 |
| ggctttgaat cgcgcccccc aactgctcca accaggcaac ggacacgcc accgtccgtg | 420 |
| tcgcgagcaa aaaacaaaa agaggaacgc gtccaggacg aagcagtcca ctgccgctgt | 480 |
| ggccggcaaa agatctggtt gagcacatgg agattggaga aggttggttg gttcttctgg | 540 |
| aaacgccaat gaatggggc actgacatgt actcttaaca tgtagtgcaa tccagagatc | 600 |
| ggatatccag acactggcag cacgatcgcc tcgcgccgta gatcacgcac gcaaattact | 660 |
| gaagaccatt cacaaaaaaa aaaaaacaca caggggctag cgtgccccac accaaaccca | 720 |
| agtgctgcgt tgcacgcagg ggagcgaaaa aaaacaataa tgctcactgt cacgtcgcgt | 780 |
| atccaacccc gcggacgtct cggctctcag cagcagcaca cggggcacct cacgatgccg | 840 |
| ttctcgttgc actccgtgca ccgccggaac ccgccgccgc attcgtcgcc ctcctcctcc | 900 |
| tcctccgcct cgtcttcgtc acccacgtac accttgcagc tgcccgagca gacatcgcag | 960 |
| agcacgaacc gcatgtcccc gcaggcctcg cacgcgccgg cgtcgccgcc gtgtgggccg | 1020 |
| gccgtcgacg cagcgctctc gcacccgccc agcctcggcg cgagctcccc ggcctcgtgc | 1080 |
| agccgcttca gctcctcggc gttgcccacg agctccccgt ccacgaagag gctggggagg | 1140 |
| gcggcgggcg tgccgccggc ttggccgagc ccgaggccga aaggccgcg gagctcgtcc | 1200 |
| cggaacccgc ggtgcatgga cacgtcgcgc tcgtcgaggc gcacgccgta gcccttgagg | 1260 |
| atggcgcgcg ccaggcagca gtcctcgtgc gtggcgcgca cgccgcgcag cgacgtgaag | 1320 |
| tagagcaccg ccctccgcgg cggcagcgcc ttcccctccc cgccgctcgt cggggcggcg | 1380 |
| tcgggccgag gcatcggcat cggcagcggc gtcaccttgg cggacgccgc gaggtcctgc | 1440 |

-continued

```
gcaggcgccg tggcgaccgg gaacgagaag gagtggcgcc cgaacggcgc gcccagcagc    1500
ggggagcggt cctcgaggcc ggccatgagc gcccacgcgt cgatgtcctc gggctcgttg    1560
ggcggcgtca tggtgggcgt gcgcggcgcc agcctcgtgg gcgcgggctc cggcgcccgc    1620
ggcagggcct tgtccagctc cagggacccg agcgtggacg acgtgagccg caccacgtgg    1680
acgccgacgt cgctggggca ccgagccggg aacgactggc tgcgcggcag cggtgacggg    1740
cagtaccgga ggtcgtgacg ggcctgcctt gaggtggtgc accccatggc accaatgtac    1800
acacacggcc aaagcgccaa gtgggctgca gactgcctgc caatgtgatc aagcagccag    1860
gagcagagac ggatctctgg ggatcggggt ttctggggtt taggatcttt atactactct    1920
gtcattgggg atataaaact aggagtgtgg ttaattagga ctcgatagat aagtttacca    1980
caagcgcgtg aaatggtcta cccgatgatg tgattggcct aaaaagaaca agaagagtat    2040
ttggagctac tgaacattct cttttcctga agataactaa ttttggaac attcagactt     2100 gggagtctgg acttttggag ggaagttcaa attgtggtct gcctctgcca tgtgttgttt    2160
tttagtcgga gagtggccct cattttttt gtcctgttta gctttatagt cgtagcagct     2220
agtagcgaaa tttaaccttg gattatggcc gtgttagtca aacaatcatt gatttatttc    2280
ctccctttcg cgctgctttt cctgtacgca tctccgctgc ccttgattcg aggaccctgt    2340
tcacaacaca gggctctggc tttggagcct ctcgtttgta gcacttgcac gtagttaccc    2400
ggaccgaagc ttcaacacag atctgatagt ttaaacgctc ttcaactgga agagcggtta    2460
cccggaccga agcttcggcc ggggcccatc gatatccgcg ggcatgcctg cagtgcagcg    2520
tgacccggtc gtgcccctct ctagagataa tgagcattgc atgtctaagt tataaaaaat    2580
taccacatat ttttttgtc acacttgttt gaagtgcagt ttatctatct ttatacatat     2640
atttaaactt tactctacga ataatataat ctatagtact acaataatat cagtgtttta    2700
gagaatcata taaatgaaca gttagacatg gtctaaagga caattgagta ttttgacaac    2760
aggactctac agtttatct ttttagtgtg catgtgttct cctttttttt tgcaaatagc     2820
ttcacctata taatacttca tccatttat tagtacatcc atttagggtt tagggttaat    2880 ggttttata gactaatttt tttagtcat ctatttatt ctatttagc ctctaaatta      2940 agaaaactaa aactctattt tagttttttt atttaataat ttagatataa aatagaataa    3000
aataaagtga ctaaaaatta aacaaatacc ctttaagaaa ttaaaaaaac taaggaaaca    3060
tttttcttgt ttcgagtaga taatgccagc ctgttaaacg ccgtcgacga gtctaacgga    3120
caccaaccag cgaaccagca gcgtcgcgtc gggccaagcg aagcagacgg cacggcatct    3180
ctgtcgctgc ctctggaccc ctctcgagag ttccgctcca ccgttggact tgctccgctg    3240
tcggcatcca gaaattgcgt ggcggagcgg cagacgtgag ccggcacggc aggcggcctc    3300
ctcctcctct cacggcaccg gcagctacgg gggattcctt tcccaccgct ccttcgcttt    3360
cccttcctcg cccgccgtaa taaatagaca ccccctccac accctctttc cccaacctcg    3420
tgttgttcgg agcgcacaca cacacaacca gatctccccc aaatccaccc gtcggcacct    3480
ccgcttcaag gtacgccgct cgtcctcccc ccccccccct ctctaccttc tctagatcgg    3540
cgttccggtc catggttagg gcccggtagt tctacttctg ttcatgtttg tgttagatcc    3600
gtgtttgtgt tagatccgtg ctgctagcgt tcgtacacgg atgcgacctg tacgtcagac    3660
acgttctgat tgctaacttg ccagtgtttc tcttggggga atcctgggat ggctctagcc    3720
gttccgcaga cgggatcgat ttcatgattt tttttgtttc gttgcatagg gtttggtttg    3780
```

```
cccttttcct ttatttcaat atatgccgtg cacttgtttg tcgggtcatc tttttcatgct    3840
tttttttgtc ttggttgtga tgatgtggtc tggttgggcg gtcgttctag atcggagtag    3900
aattctgttt caaactacct ggtggattta ttaattttgg atctgtatgt gtgtgccata    3960
catattcata gttacgaatt gaagatgatg gatggaaata tcgatctagg ataggtatac    4020
atgttgatgc gggttttact gatgcatata cagagatgct ttttgttcgc ttggttgtga    4080
tgatgtggtg tggttgggcg gtcgttcatt cgttctagat cggagtagaa tactgtttca    4140
aactacctgg tgtatttatt aattttggaa ctgtatgtgt gtgtcataca tcttcatagt    4200
tacgagttta agatggatgg aaatatcgat ctaggatagg tatacatgtt gatgtgggtt    4260
ttactgatgc atatacatga tggcatatgc agcatctatt catatgctct aaccttgagt    4320
acctatctat tataataaac aagtatgttt tataattatt ttgatcttga tatacttgga    4380
tgatggcata tgcagcagct atatgtggat ttttttagcc ctgccttcat acgctattta    4440
tttgcttggt actgtttctt ttgtcgatgc tcaccctgtt gtttggtgtt acttctgcag    4500
gtcgactcta gaggatccaa caatggagaa caacatacag aatcagtgcg tcccctacaa    4560
ctgcctcaac aatcctgaag tagagattct caacgaagag aggtcgactg gcagattgcc    4620
gttagacatc tccctgtccc ttacacgttt cctgttgtct gagtttgttc caggtgtggg    4680
agttgcgttt ggcctcttcg acctcatctg gggcttcatc actccatctg attggagcct    4740
cttcttctc cagattgaac agttgattga acaaaggatt gagaccttgg aaaggaatcg    4800
ggccatcact acccttcgtg gcttagcaga cagctatgag atctacattg aagcactaag    4860
agagtgggaa gccaatccta acaatgccca actgagagaa gatgtgcgta tacgctttgc    4920
taacacagat gatgctttga tcacagccat caacaacttc acccttacca gcttcgagat    4980
ccctcttctc tcggtctatg ttcaagctgc taacctgcac ttgtcactac tgcgcgacgc    5040
tgtgtcgttt gggcaaggtt ggggactgga catagctact gtcaacaatc actacaacag    5100
actcatcaat ctgattcatc gatacacgaa acattgtttg gatacctaca atcagggatt    5160
ggagaacctg agaggtacta acactcgcca atgggccagg ttcaatcagt tcaggagaga    5220
ccttacactt actgtgttag acatagttgc tctctttccg aactacgatg ttcgtaccta    5280
tccgattcaa acgtcatccc aacttacaag ggagatctac accagttcag tcattgaaga    5340
ctctccagtt tctgcgaaca tacccaatgg tttcaacagg gctgagtttg gagtcagacc    5400
accccatctc atggacttca tgaactcttt gtttgtgact gcagagactg ttagatccca    5460
aactgtgtgg ggaggacact tagttagctc acgcaacacg gctggcaatc gtatcaactt    5520
tcctagttac ggggtcttca atcccggggg cgccatctgg attgcagatg aagatccacg    5580
tcctttctat cggaccttgt cagatcctgt cttcgtccga ggaggctttg gcaatcctca    5640
ctatgtactc ggtcttaggg gagtggcctt tcaacaaact ggtacgaatc acccgcac     5700
attcaggaac tccgggacca ttgactctct agatgagata ccacctcaag acaacagcgg    5760
cgcaccttgg aatgactact cccatgtgct gaatcatgtt acctttgtgc gctggccagg    5820
tgagatctca ggttccgact catggagagc accaatgttc tcttggacgc atcgtagcgc    5880
taccccaca acaccattg atccagagag aatcactcag attcccttgg tgaaggcaca    5940
cacacttcag tcaggaacta cagttgtaag agggccgggg ttcacgggag agacattct    6000
tcgacgcact agtggaggac cattcgcgta caccattgtc aacatcaatg gcaacttcc    6060
ccaaaggtat cgtgccagga tacgctatgc ctctactacc aatctaagaa tctacgttac    6120
ggttgcaggt gaacggatct ttgctggtca gttcaacaag acaatggata ccggtgatcc    6180
```

```
acttacattc caatctttct cctacgccac tatcaacacc gcgttcacct ttccaatgag    6240
ccagagcagt ttcacagtag gtgctgatac cttcagttca ggcaacgaag tgtacattga    6300
caggtttgag ttgattccag ttactgccac actcgagtaa ggatccgtcg acctgcagcc    6360
aagctttcgc gagctcgaga tccccgacat atgccccggt ttcgttgcga ctaacatgag    6420
ttcttggaca aatttgattg gacctgatga gatgatccaa cccgaggata tagcaaagct    6480
cgttcgtgca gcaatggaac ggccaaaccg tgcttttgtc cccaagaatg aggtgctatg    6540
catgaaggaa tctacccgtt gatgtccaac agtctcaggg ttaatgtcta tgtatcttaa    6600
ataatgttgt cggtattttg taatctcata tagattttca ctgtgcgacg caaaaatatt    6660
aaataaatat tattattatc tacgttttga ttgagatatc atcaatatta taataaaaat    6720
atccattaaa cacgatttga tacaaatgac agtcaataat ctgatttgaa tatttattaa    6780
ttgtaacgaa ttacataaag atcgaataga aaatactgca ctgcaaatga aaattaacac    6840
atactaataa atgcgtcaaa tatctttgcc aagatcaagc ggagtgaggg cctcatatcc    6900
ggtctcagtt acaagcacgg tatccccgaa gcgcgctcca ccaatgccct cgacatagat    6960
gccgggctcg acgctgagga cattgcctac cttgagcatg gtctcagcgc cggctttaag    7020
ctcaatccca tcccaatctg aatatcctat cccgcgccca gtccggtgta agaacgggtc    7080
tgtccatcca cctctgttgg gaattccggt ccgggtcacc tttgtccacc aagatggaac    7140
tgcggccagc ttgcatgcct gcagtgcagc gtgacccggt cgtgccsctc tctagagata    7200
atgagcattg catgtctaag ttataaaaaa ttaccacata ttttttttgt cacacttgtt    7260
tgaagtgcag tttatctatc tttatacata tatttaaact ttactctacg aataatataa    7320
tctatagtac tacaataata tcagtgtttt agagaatcat ataaatgaac agttagacat    7380
ggtctaaagg acaattgagt attttgacaa caggactcta cagttttatc tttttagtgt    7440
gcatgtgttc tccttttttt ttgcaaatag cttcacctat ataatacttc atccatttta    7500
ttagtacatc catttagggt ttagggttaa tggtttttat agactaattt ttttagtaca    7560
tctattttat tctatttag cctctaaatt aagaaaacta aaactctatt ttagtttttt    7620
tatttaataa tttagatata aaatagaata aaataaagtg actaaaaatt aaacaaatac    7680
cctttaagaa attaaaaaaa ctaaggaaac atttttcttg tttcgagtag ataatgccag    7740
cctgttaaac gccgtcgacg agtctaacgg acaccaacca gcgaaccagc agcgtcgcgt    7800
cgggccaagc gaagcagacg gcacggcatc tctgtcgctg cctctggacc cctctcgaga    7860
gttccgctcc accgttggac ttgctccgct gtcggcatcc agaaattgcg tggcggagcg    7920
gcagacgtga gccggacgg caggcggcct cctcctcctc tcacggcacc ggcagctacg    7980
ggggattcct ttcccaccgc tccttcgctt tccttcctc gcccgccgta ataaatagac    8040 acccccctcca caccctcttt ccccaacctc gtgttgttcg gagcgcacac acacacaacc    8100
agatctcccc caaatccacc cgtcggcacc tccgcttcaa ggtacgccgc tcgtcctccc    8160
cccccccccc tctctaccctt ctctagatcg gcgttccggt ccatggttag ggcccggtag    8220
ttctacttct gttcatgttt gtgttagatc cgtgtttgtg ttagatccgt gctgctagcg    8280
ttcgtacacg gatgcgacct gtacgtcaga cacgttctga ttgctaactt gccagtgttt    8340
ctctttgggg aatcctggga tggctctagc cgttccgcag acgggatcga tttcatgatt    8400
ttttttgttt cgttgcatag ggtttggttt gccctttcc tttatttcaa tatatgccgt    8460
gcacttgttt gtcgggtcat cttttcatgc ttttttttgt cttggttgtg atgatgtggt    8520
```

```
ctggttgggc ggtcgttcta gatcggagta gaattctgtt tcaaactacc tggtggattt    8580
attaattttg gatctgtatg tgtgtgccat acatattcat agttacgaat tgaagatgat    8640
ggatggaaat atcgatctag gataggtata catgttgatg cgggttttac tgatgcatat    8700
acagagatgc tttttgttcg cttggttgtg atgatgtggt gtggttgggc ggtcgttcat    8760
tcgttctaga tcggagtaga atactgtttc aaactacctg gtgtatttat taattttgga    8820
actgtatgtg tgtgtcatac atcttcatag ttacgagttt aagatggatg gaaatatcga    8880
tctaggatag gtatacatgt tgatgtgggt tttactgatg catatacatg atggcatatg    8940
cagcatctat tcatatgctc taaccttgag tacctatcta ttataataaa caagtatgtt    9000
ttataattat tttgatcttg atatacttgg atgatggcat atgcagcagc tatatgtgga    9060 ttttttttagc cctgccttca tacgctattt atttgcttgg tactgtttct tttgtcgatg    9120
ctcaccctgt tgtttggtgt tacttctgca ggtcgactct agaggatcca cacgacacca    9180
tgtccgcccg cgaggtgcac atcgacgtga acaacaagac cggccacacc ctccagctgg    9240
aggacaagac caagctcgac ggcggcaggt ggcgcaccte cccgaccaac gtggccaacg    9300
accagatcaa gaccttcgtg gccgaatcca acggcttcat gaccggcacc gagggcacca    9360
tctactactc aattaatggc gaggccgaga tcagcctcta cttcgacaac ccgttcgccg    9420
gctccaacaa atacgacggc cactccaaca gtcccagta cgagatcatc acccagggcg    9480
gctccggcaa ccagtcccac gtgacctaca ccatccagac cacctcctcc cgctacggcc    9540
acaagtcctg agtcatgagt catgagtcag ttaacctaga cttgtccatc ttctggattg    9600
gccaacttaa ttaatgtatg aaataaaagg atgcacacat agtgacatgc taatcactat    9660
aatgtgggca tcaaagttgt gtgttatgtg taattactag ttatctgaat aaaagagaaa    9720
gagatcatcc atatttctta tcctaaatga atgtcacgtg tctttataat tctttgatga    9780
accagatgca tttcattaac caaatccata tacatataaa tattaatcat atataattaa    9840
tatcaattgg gttagcaaaa caaatctagt ctaggtgtgt tttgcgaatg cggccgcgga    9900
ccgaattggg gatctgcatg aaagaaactg tcgcactgct gaaccgcacc ttgtcacttt    9960
catcgaacac gacctgtgcc caagatgacg gtgctgcggt ctaagtgagg ctgaattgcc   10020
ttggacagaa gcggactccc tacaattagt taggccaaac ggtgcatcca tgtgtagctc   10080
cgggctcggg ctgtatcgcc atctgcaata gcatccatgg agctcgttcc atgtagttgg   10140
agatgaacca atgatcgggc gtgtggacgt atgttcctgt gtactccgat agtagagtac   10200
gtgttagctc tttcatggtg caagtgaaat ttgtgttggt ttaattaccc ctacgttagt   10260
tgcgggacag gagacacatc atgaatttaa aggcgatgat gtcctctcct gtaatgttat   10320
tcttttgatg tgatgaatca aaatgtcata taaaacattt gttgctcttt agttaggcct   10380
gatcgtagaa cgaaatgctc gtgtagcggg gctacgagcc tatgacgcaa taacactggt   10440
ttgccggccc ggagtcgctt gacaaaaaaa agcatgttaa gtttatttac aattcaaaac   10500
ctaacatatt atattccctc aaagcaggtt cacgatcaca cctgtaccta aaaaaaacat   10560
gaagaatata ttactccatt attatgagat gaaccacttg gcaagagtgg taagctatat   10620
aaaaaaatga acattattac gagatgttat atgccattat attgattcga agatatatgt   10680
ttctttctcc cacgggcacc taacggatac atgataaggc caaggcagat cacgggaaat   10740
tattcgaata catgttacgc cctattgccg gaaaaaaaat gcagggcagg tgttggccgt   10800
agcgatttaa gcacttaagc tggaggttgc cacacttgga tgcaagcgtc tgacccttct   10860
aaaaaatcgg cggctttgtc cgtatccgta tcccctatcc aacatctagc tggccacacg   10920
```

```
acggggctgg gcagatcgtg gatgccgggt cgacgtcgat cgtcagccat catagaccaa   10980
tcgaccatct gttatggatg cttgctagct agactagtca gacataaaat ttggatactt   11040
tctcccaact gggagacggg gactgatgtg cagctgcacg tgagctaaat ttttccctat   11100
aaatatgcat gaaatactgc attatcttgc cacagccact gccacagcca gataacaagt   11160
gcagctggta gcacgcaacg catagctctg gacttgtagc taggtagcca accggatcca   11220
cacgacacca tgctcgacac caacaaggtg tacgagatca gcaaccacgc caacggcctc   11280
tacgccgcca cctacctctc cctcgacgac tccggcgtgt ccctcatgaa caagaacgac   11340
gacgacatcg acgactacaa cctcaagtgg ttcctcttcc cgatcgacga cgaccagtac   11400
atcatcacct cctacgccgc caacaactgc aaggtgtgga acgtgaacaa cgacaagatt   11460
aatgtgtcaa cctactcctc caccaactcc atccagaagt ggcagatcaa ggccaacggc   11520
tcctcctacg tgatccagtc cgacaacggc aaggtgctca ccgccggcac cggccaggcc   11580
ctcggcctca tccgcctcac cgacgagtcc tccaacaacc cgaaccagca atggaacctg   11640
acgtccgtgc agaccatcca gctcccgcag aagccgatca tcgacaccaa gctcaaggac   11700
tacccgaagt actccccgac cggcaacatc gacaacggca cctccccgca gctcatgggc   11760
tggaccctcg tgccgtgcat catggtgaac gacccgaaca tcgacaagaa cacccagatc   11820
aagaccaccc cgtactacat cctcaagaag taccagtact ggcagagggc cgtgggctcc   11880
aacgtcgcgc tccgcccgca cgagaagaag tcctacacct acgagtgggg caccgagatc   11940
gaccagaaga ccaccatcat caacaccctc ggcttccaga tcaacatcga cagcggcatg   12000
aagttcgaca tcccggaggt gggcggcggt accgacgaga tcaagaccca gctcaacgag   12060
gagctcaaga tcgagtattc acatgagacg aagatcatgg agaagtacca ggagcagtcc   12120
gagatcgaca acccgaccga ccagtccatg aactccatcg gcttcctcac catcacctcc   12180
ctggagctct accgctacaa cggctccgag atccgcatca tgcagatcca gacctccgac   12240
aacgacacct acaacgtgac ctcctacccg aaccaccagc aggccctgct gctgctgacc   12300
aaccactcct acgaggaggt ggaggagatc accaacatcc cgaagtccac cctcaagaag   12360
ctcaagaagt actacttctg agtcatgagt catgagtcag ttaacctaga cttgtccatc   12420
ttctggattg ccaacttaa ttaatgtatg aaataaaagg atgcacacat agtgacatgc   12480
taatcactat aatgtgggca tcaaagttgt gtgttatgtg taattactag ttatctgaat   12540
aaaagagaaa gagatcatcc atatttctta tcctaaatga atgtcacgtg tctttataat   12600
tctttgatga accagatgca tttcattaac caaatccata tacatataaa tattaatcat   12660
ataattaa tatcaattgg gttagcaaaa caaatctagt ctaggtgtgt tttgcgaatt   12720
atcgatgggc cccacctgca ggcatgcccg ctgaaatcac cagtctctct ctacaaatct   12780
atctctctct ataataatgt gtgagtagtt cccagataag ggaattaggg ttcttatagg   12840
gtttcgctca tgtgttgagc atataagaaa cccttagtat gtatttgtat ttgtaaaata   12900
cttctatcaa taaaatttct aattcctaaa accaaaatcc agggcgagct cgaattcgag   12960
ctcgagcccg ggtggatcct ctagagtcga cctgcagaag cttcggtccg gcgcgcctct   13020
agttgaagac acgttcatgt cttcatcgta agaagacact cagtagtctt cggccagaat   13080
ggcctaactc aaggccatcg tggcctcttg ctcttcagga tgaagagcta tgtttaaacg   13140
tgcaagcgct actagacaat tcagtacatt aaaaacgtcc gcaatgtgtt attaagttgt   13200
ctaagcgtca atttggaaca agtggctatc gccagatata agaacttcga tccgaaatat   13260
```

```
cgtttcaaaa ctagaaaaca gcgcggcttt ggctaagccg cgcactatat aggattttgg    13320
gcaccttttg atggaacgtg aaagcgtact gcgcactagt tatttaggtt gaaccttgga    13380
tatacggttc tcactgcgcc aatgcaaggc ttgaaacttg gttagtaata cgtactccct    13440
ccgtttcttt ttatttgtcg ctggatagtg caattttgca ctatcgagcg acaaataaaa    13500
agaaacggag ggagtatatg attgtcagat gtagatatgt ttatttatat atcacataca    13560
gatatataaa acagatcact ttttcagata tacagttcca atgtcagccc tgatcaccct    13620
gtcataaatt gcacgtttct aattgatgtt gcttcatggt cgtcatgaga accttctgaa    13680
gaaatcgatg aaggttgcca acctttcaaa gtttcagaaa ccactttgca tgtacactaa    13740
gggctggttt ggcagcccaa aaccagccag cgttttcctg gtcttttctc ccgggagaaa    13800
gcccatgcat agattgtccc tggattattt atctgtgtcc tttggctaaa aattcgtccc    13860
aatttcctgt aggaaactac ctcggccttg ggaggccagg cgattctcca ccgcctcgtc    13920
tcgtccatcc ttcgatgctc acgcgtgcct cctcggatgc tatcctcagg cgattctccg    13980
tcgtctcgtc tcatccatcc tcacgcgcgc ctcctccgac gctatcccca ggcgattctc    14040
caccgtctcg tctcatccat cctcatgtac gcctcgtccg atgctatccc cagacgattt    14100
tccgtcgtct catctccttc atgctcgcgc gcgcctcctc cgacgctatc cccaggcgat    14160
ttttctgccg tctcgtctcc ttcatgcccg cgcgcgcctc ctccgacgct atccccaggc    14220
gattttccgc cgtctcgtct ccttcatgcc cgcgcgtgcc tcctccgacg ctattcccac    14280
gagcgcctcc gccgccgcta tccccagacg attttccgct gtctcgtctc cttcatgccc    14340
gcgcgccccct cctccgacgc tatccccacg agcgcctccg ccgccgctcc accgtcttcc    14400
ccgccgccat cccccttaatt cctatagatc tggaccccgc tctactttcg ttggcatact    14460
tttgcttggt gtgcgcgggc tggagtggaa ggttgcgcat tcgatcacgg gggagaagtg    14520
gatcttgggt cttggcaggc tagggcggtt gccaggacgc cgtggtgtgc attcatgggt    14580
cctataaatc tttatcatta ccgccttagg agctagttgt agttcacaca tcatatcctt    14640
ttctgctcga catcgtctgg ggatgcccta ggtgccctac cgaccctacg gcattgtctt    14700
gacctctatt agactctatg tcatctagag cccttcttggg tggccttttg accccaaagc    14760
gaccctatga tcttacccta acgaggtctc ccttggtggg gcaagatcca ctttgtccac    14820
ttaactgaag atctgatcct catcttgaaa tctttaatcc caaggtgact ctacgtcgta    14880
tgtggatgct ccgggtaacc tgccaacccg gatcacccta agatctcttt cctaagggc    14940
gagatctagg ttcctacgag aaagaagacg accctgcacc attgcggtcc gtccggtcca    15000
gagtgcgaac gtccggatgc gacacaggga aggagtcgct cctgcagcga ggtcgcagac    15060
tgtccacaca gcctcagaag gcaccgccag acaatacatg taatacccac tctgtaagaa    15120
aaacctaaaa ggagaaagta tattcctttta tctatatgtg tgttatattt ctactcacca    15180
tcacatgtga acatctcact tacacaaata aataattaac aaaagacact caaataaatt    15240
atgcatcatg ctcgacctta ttttgtgtgc attctgttac aatataaaaa taatataaaa    15300
aacatatatt aatatcaaaa tttggagatt taaccctaat atgcaaatcg gagtttagag    15360
gaaagaaaga aaaatgctat acaaaataaa ggaataaata tataaataaa ggtaaaacta    15420
ttaatactgg tatattaatt tgaacagttg acctaattat gaatatcaca actggtttga    15480
attcaaatat gaaatccaag aatttggaaa taggaaaaat ggagataaga ataaggaaa    15540
agaattctta actcggatgg gcctgggaaa cgaattcgg cccacttcct gtgtccttag    15600
ctgtgcggct cagtccagtg                                               15620
```

-continued

<210> SEQ ID NO 30
<211> LENGTH: 15528
<212> TYPE: DNA
<213> ORGANISM: Artificial
<220> FEATURE:
<223> OTHER INFORMATION: synthetic

<400> SEQUENCE: 30

| | | | | | |
|---|---|---|---|---|---|
| gagcatatcc | agcaccagct | ggtaccaagg | tcgggtctct | gtgctagtgc | tattagctag | 60 |
| tgtaaggagc | gagtaggtca | gttaaggctg | gtgcgtcgtg | agggctgtct | tgtgtgtagc | 120 |
| tacagcagac | ggttcatcag | aaggattatt | cgtgcagtat | atacagtaca | actagacaat | 180 |
| gatgttgatg | attggtctag | agctagaggc | ctatagccct | atactactgt | gtattgtccg | 240 |
| ccgtttagt | ttttggtcc | catcccatca | atgcaaccgc | cttgttttgc | tccaattgtc | 300 |
| ccgttcctgc | gcctcgcttt | tgctctgtcg | catcgcatac | aaaaaaaaaa | acgccgcgcc | 360 |
| ggctttgaat | cgcgcccccc | aactgctcca | accaggcaac | ggacacggcc | accgtccgtg | 420 |
| tcgcgagcaa | aaaacaaaa | agaggaacgc | gtccaggacg | aagcagtcca | ctgccgctgt | 480 |
| ggccggcaaa | agatctggtt | gagcacatgg | agattggaga | aggttggttg | gttcttctgg | 540 |
| aaacgccaat | gaatggggc | actgacatgt | actcttaaca | tgtagtgcaa | tccagagatc | 600 |
| ggatatccag | acactggcag | cacgatcgcc | tcgcgccgta | gatcacgcac | gcaaattact | 660 |
| gaagaccatt | cacaaaaaaa | aaaaaacaca | caggggctag | cgtgccccac | accaaaccca | 720 |
| agtgctgcgt | tgcacgcagg | ggagcgaaaa | aaaacaataa | tgctcactgt | cacgtcgcgt | 780 |
| atccaacccc | gcggacgtct | cggctctcag | cagcagcaca | cggggcacct | cacgatgccg | 840 |
| ttctcgttgc | actccgtgca | ccgccggaac | ccgccgccgc | attcgtcgcc | ctcctcctcc | 900 |
| tcctccgcct | cgtcttcgtc | acccacgtac | accttgcagc | tgcccgagca | gacatcgcag | 960 |
| agcacgaacc | gcatgtcccc | gcaggcctcg | cacgcgccgg | cgtcgccgcc | gtgtgggccg | 1020 |
| gccgtcgacg | cagcgctctc | gcacccgccc | agcctcggcg | cgagctcccc | ggcctcgtgc | 1080 |
| agccgcttca | gctcctcggc | gttgcccacg | agctccccgt | ccacgaagag | gctggggagg | 1140 |
| gcggcgggcg | tgccgccggc | ttggccgagc | ccgaggccga | aaggccgcg | gagctcgtcc | 1200 |
| cggaacccgc | ggtgcatgga | cacgtcgcgc | tcgtcgaggc | gcacgccgta | gcccttgagg | 1260 |
| atggcgcgcc | ccaggcagca | gtcctcgtgc | gtggcgcgca | cgccgcgcag | cgacgtgaag | 1320 |
| tagagcaccg | ccctccgcgg | cggcagcgcc | ttccctccc | cgccgctcgt | cggggcggcg | 1380 |
| tcgggccgag | gcatcggcat | cggcagcggc | gtcaccttgg | cggacgccgc | gaggtcctgc | 1440 |
| gcaggcgccg | tggcgaccgg | gaacgagaag | gagtggcgcc | cgaacggcgc | gcccagcagc | 1500 |
| ggggagcggt | cctcgaggcc | ggccatgagc | gcccacgcgt | cgatgtcctc | gggctcgttg | 1560 |
| ggcggcgtca | tggtgggcgt | gcgcggcgcc | agcctcgtgg | gcgcgggctc | cggcgcccgc | 1620 |
| ggcagggcct | tgtccagctc | cagggacccg | agcgtgacg | acgtgagccg | caccacgtgg | 1680 |
| acgccgacgt | cgctggggca | ccgagccggg | aacgactggc | tgcgcggcag | cggtgacggg | 1740 |
| cagtaccgga | ggtcgtgacg | ggcctgcctt | gaggtggtgc | accccatggc | accaatgtac | 1800 |
| acacacggcc | aaagcgccaa | gtgggctgca | gactgcctgc | caatgtgatc | aagcagccag | 1860 |
| gagcagagac | ggatctctgg | ggatcggggt | ttctggggtt | taggatcttt | atactactct | 1920 |
| gtcattgggg | atataaaact | aggagtgtgg | ttaattagga | ctcgatagat | aagtttacca | 1980 |
| caagcgcgtg | aaatggtcta | cccgatgatg | tgattggcct | aaaaagaaca | agaagagtat | 2040 |

```
ttggagctac tgaacattct cttttcctga agataactaa ttttttggaac attcagactt    2100 gggagtctgg acttttggag ggaagttcaa attgtggtct gcctctgcca tgtgttgttt    2160
tttagtcgga gagtggccct cattttttt gtcctgttta gctttatagt cgtagcagct    2220
agtagcgaaa tttaaccttg gattatggcc gtgttagtca aacaatcatt gatttatttc    2280 ctcccttcg cgctgctttt cctgtacgca tctccgctgc ccttgattcg aggaccctgt    2340
tcacaacaca gggctctggc tttggagcct ctcgtttgta gcacttgcac gtagttaccc    2400
ggaccgaagc ttcaacacag atctgatagt ttaaacgctc ttcaactgga agagcggtta    2460
cccggaccga agcttcggcc ggggcccatc gatatccgcg gcatgcctg cagtgcagcg    2520 tgacccggtc gtgcccctct ctagagataa tgagcattgc atgtctaagt tataaaaaat    2580
taccacatat ttttttgtc acacttgttt gaagtgcagt ttatctatct ttatacatat    2640
atttaaactt tactctacga ataatataat ctatagtact acaataatat cagtgttta    2700 gagaatcata taaatgaaca gttagacatg gtctaaagga caattgagta ttttgacaac    2760
aggactctac agtttatct ttttagtgtg catgtgttct ccttttttt tgcaaatagc    2820 ttcacctata taatacttca tccatttat tagtacatcc atttagggtt tagggttaat    2880 ggttttata gactaattt tttagtacat ctattttatt ctattttagc ctctaaatta    2940
agaaaactaa aactctattt tagttttttt atttaataat ttagatataa aatgaataa    3000 aataaagtga ctaaaaatta aacaaatacc ctttaagaaa ttaaaaaaac taggaaaca    3060 tttttcttgt ttcgagtaga taatgccagc ctgttaaacg ccgtcgacga gtctaacgga    3120
caccaaccag cgaaccagca gcgtcgcgtc gggccaagcg aagcagacgg cacggcatct    3180
ctgtcgctgc ctctggaccc ctctcgagag ttccgctcca ccgttggact tgctccgctg    3240
tcggcatcca gaaattgcgt ggcggagcgg cagacgtgag ccggcacggc aggcggcctc    3300
ctcctcctct cacggcaccg gcagctacgg gggattcctt tcccaccgct ccttcgcttt    3360
ccctccctcg cccgccgtaa taaatagaca ccccctccac accctctttc cccaacctcg    3420
tgttgttcgg agcgcacaca cacacaacca gatctccccc aaatccaccc gtcggcacct    3480
ccgcttcaag gtacgccgct cgtcctcccc cccccccct ctctaccttc tctagatcgg    3540
cgttccggtc catggttagg gcccggtagt tctacttctg ttcatgtttg tgttagatcc    3600
gtgtttgtgt tagatccgtg ctgctagcgt tcgtacacgg atgcgacctg tacgtcagac    3660
acgttctgat tgctaacttg ccagtgtttc tctttgggga atcctgggat ggctctagcc    3720
gttccgcaga cgggatcgat ttcatgattt tttttgtttc gttgcatagg tttggtttg    3780 ccctttcct ttatttcaat atatgccgtg cacttgtttg tcgggtcatc ttttcatgct    3840 ttttttgtc ttggttgtga tgatgtggtc tggttgggcg gtcgttctag atcggagtag    3900
aattctgttt caaactacct ggtggattta ttaattttgg atctgtatgt gtgtgccata    3960
catattcata gttacgaatt gaagatgatg gatggaaata tcgatctagg ataggtatac    4020
atgttgatgc gggttttact gatgcatata cagagatgct ttttgttcgc ttggttgtga    4080
tgatgtggtg tggttgggcg gtcgttcatt cgttctagat cggagtagaa tactgtttca    4140
aactacctgg tgtatttatt aattttggaa ctgtatgtgt gtgtcataca tcttcatagt    4200
tacgagttta agatggatgg aaatatcgat ctaggatagg tatacatgtt gatgtgggtt    4260
ttactgatgc atatacatga tggcatatgc agcatctatt catatgctct aaccttgagt    4320
acctatctat tataataaac aagtatgttt tataattatt ttgatcttga tatacttgga    4380
tgatggcata tgcagcagct atatgtggat ttttttagcc ctgccttcat acgctattta    4440
```

-continued

```
tttgcttggt actgtttctt ttgtcgatgc tcaccctgtt gtttggtgtt acttctgcag    4500
gtcgactcta gaggatccaa caatggagaa caacatacag aatcagtgcg tccectacaa    4560
ctgcctcaac aatcctgaag tagagattct caacgaagag aggtcgactg gcagattgcc    4620
gttagacatc tccctgtccc ttacacgttt cctgttgtct gagtttgttc caggtgtggg    4680
agttgcgttt ggcctcttcg acctcatctg gggcttcatc actccatctg attggagcct    4740
ctttcttctc cagattgaac agttgattga acaaaggatt gagaccttgg aaaggaatcg    4800
ggccatcact acccttcgtg gcttagcaga cagctatgag atctacattg aagcactaag    4860
agagtgggaa gccaatccta acaatgccca actgagagaa gatgtgcgta tacgctttgc    4920
taacacagat gatgctttga tcacagccat caacaacttc acccttacca gcttcgagat    4980
ccctcttctc tcggtctatg ttcaagctgc taacctgcac ttgtcactac tgcgcgacgc    5040
tgtgtcgttt gggcaaggtt ggggactgga catagctact gtcaacaatc actacaacag    5100
actcatcaat ctgattcatc gatacacgaa acattgtttg gatacctaca atcagggatt    5160
ggagaacctg agaggtacta acactcgcca atgggccagg ttcaatcagt tcaggagaga    5220
ccttacactt actgtgttag acatagttgc tctctttccg aactacgatg ttcgtaccta    5280
tccgattcaa acgtcatccc aacttacaag ggagatctac accagttcag tcattgaaga    5340
ctctccagtt tctgcgaaca tacccaatgg tttcaacagg gctgagtttg gagtcagacc    5400
accccatctc atggacttca tgaactcttt gtttgtgact gcagagactg ttagatccca    5460
aactgtgtgg ggaggacact tagttagctc acgcaacacg gctggcaatc gtatcaactt    5520
tcctagttac ggggtcttca atcccggggg cgccatctgg attgcagatg aagatccacg    5580
tcctttctat cggaccttgt cagatcctgt cttcgtccga ggaggctttg gcaatcctca    5640
ctatgtactc ggtcttaggg gagtggcctt tcaacaaact ggtacgaatc acacccgcac    5700
attcaggaac tccgggacca ttgactctct agatgagata ccacctcaag acaacagcgg    5760
cgcaccttgg aatgactact cccatgtgct gaatcatgtt acctttgtgc gctggccagg    5820
tgagatctca ggttccgact catggagagc accaatgttc tcttggacgc atcgtagcgc    5880
tacccccaca aacaccattg atccagagag aatcactcag attcccttgg tgaaggcaca    5940
cacacttcag tcaggaacta cagttgtaag agggccgggg ttcacgggag gagacattct    6000
tcgacgcact agtggaggac cattcgcgta caccattgtc aacatcaatg ggcaacttcc    6060
ccaaaggtat cgtgccagga tacgctatgc ctctactacc aatctaagaa tctacgttac    6120
ggttgcaggt gaacggatct ttgctggtca gttcaacaag acaatggata ccggtgatcc    6180
acttacattc caatctttct cctacgccac tatcaacacc gcgttcacct ttccaatgag    6240
ccagagcagt ttcacagtag gtgctgatac cttcagttca ggcaacgaag tgtacattga    6300
caggtttgag ttgattccag ttactgccac actcgagtaa ggatccgtcg acctgcagcc    6360
aagcttcgc gagctcgaga tccccgacat atgccccggt ttcgttgcga ctaacatgag    6420
ttcttggaca aatttgattg gacctgatga gatgatccaa cccgaggata tagcaaagct    6480
cgttcgtgca gcaatggaac ggccaaaccg tgcttttgtc cccaagaatg aggtgctatg    6540
catgaaggaa tctacccgtt gatgtccaac agtctcaggg ttaatgtcta tgtatcttaa    6600
ataatgttgt cggtattttg taatctcata tagattttca ctgtgcgacg caaaaatatt    6660
aaataaatat tattattatc tacgttttga ttgagatatc atcaatatta taataaaaat    6720
atccattaaa cacgatttga tacaaatgac agtcaataat ctgatttgaa tatttattaa    6780
```

```
ttgtaacgaa ttacataaag atcgaataga aaatactgca ctgcaaatga aaattaacac    6840
atactaataa atgcgtcaaa tatctttgcc aagatcaagc ggagtgaggg cctcatatcc    6900
ggtctcagtt acaagcacgg tatccccgaa gcgcgctcca ccaatgccct cgacatagat    6960
gccgggctcg acgctgagga cattgcctac cttgagcatg gtctcagcgc cggctttaag    7020
ctcaatccca tcccaatctg aatatcctat cccgcgccca gtccggtgta agaacgggtc    7080
tgtccatcca cctctgttgg gaattccggt ccgggtcacc tttgtccacc aagatggaac    7140
tgcggccagc ttgcatgcct gcagtgcagc gtgacccggt cgtgcccctc tctagagata    7200
atgagcattg catgtctaag ttataaaaaa ttaccacata ttttttttgt cacacttgtt    7260
tgaagtgcag tttatctatc tttatacata tatttaaact ttactctacg aataatataa    7320
tctatagtac tacaataata tcagtgtttt agagaatcat ataaatgaac agttagacat    7380
ggtctaaagg acaattgagt attttgacaa caggactcta cagttttatc ttttttagtgt    7440 gcatgtgttc tcctttttttt ttgcaaatag cttcacctat ataatacttc atccatttta    7500
ttagtacatc catttagggt ttagggttaa tggttttat agactaattt ttttagtaca    7560
tctattttat tctattttag cctctaaatt aagaaaacta aaactctatt ttagtttttt    7620
tatttaataa tttagatata aaatagaata aaataaagtg actaaaaatt aaacaaaatac   7680 cctttaagaa attaaaaaaa ctaaggaaac attttttcttg tttcgagtag ataatgccag    7740
cctgttaaac gccgtcgacg agtctaacgg acaccaacca gcgaaccagc agcgtcgcgt    7800
cgggccaagc gaagcagacg gcacggcatc tctgtcgctg cctctggacc cctctcgaga    7860
gttccgctcc accgttggac ttgctccgct gtcggcatcc agaaattgcg tggcggagcg    7920
gcagacgtga gccggcacgg caggcggcct cctcctcctc tcacggcacc ggcagctacg    7980
ggggattcct ttcccaccgc tccttcgctt tccctctcctc gcccgccgta ataaatagac    8040
accccctcca caccctcttt ccccaacctc gtgttgttcg gagcgcacac acacacaacc    8100
agatctcccc caaatccacc cgtcggcacc tccgcttcaa ggtacgccgc tcgtcctccc    8160
cccccccccc tctctacctt ctctagatcg gcgttccggt ccatggttag ggcccggtag    8220
ttctacttct gttcatgttt gtgttagatc cgtgtttgtg ttagatccgt gctgctagcg    8280
ttcgtacacg gatgcgacct gtacgtcaga cacgttctga ttgctaactt gccagtgttt    8340
ctctttgggg aatcctggga tggctctagc cgttccgcag acgggatcga tttcatgatt    8400 tttttttgttt cgttgcatag ggtttggttt gcccttttcc tttatttcaa tatatgccgt    8460
gcacttgttt gtcgggtcat cttttcatgc tttttttttgt cttggttgtg atgatgtggt    8520
ctggttgggc ggtcgttcta gatcggagta gaattctgtt tcaaactacc tggtggattt    8580
attaattttg gatctgtatg tgtgtgccat acatattcat agttacgaat tgaagatgat    8640
ggatggaaat atcgatctag dataggtata catgttgatg cgggttttac tgatgcatat    8700
acagagatgc ttttgttcg cttggttgtg atgatgtggt gtggttgggc ggtcgttcat    8760
tcgttctaga tcggagtaga atactgtttc aaactacctg gtgtatttat taattttgga    8820
actgtatgtg tgtgtcatac atcttcatag ttacgagttt aagatggatg gaaatatcga    8880
tctaggatag gtatacatgt tgatgtgggt tttactgatg catatacatg atggcatatg    8940
cagcatctat tcatatgctc taaccttgag tacctatcta ttataataaa caagtatgtt    9000
ttataattat tttgatcttg atatacttgg atgatggcat atgcagcagc tatatgtgga    9060
tttttttagc cctgccttca tacgctattt atttgcttgg tactgttctt tttgtcgatg    9120
ctcaccctgt tgtttggtgt tacttctgca ggtcgactct agaggatcca cacgacacca    9180
```

-continued

```
tgtccgcccg cgaggtgcac atcgacgtga acaacaagac cggccacacc ctccagctgg    9240
aggacaagac caagctcgac ggcggcaggt ggcgcacctc cccgaccaac gtggccaacg    9300
accagatcaa gaccttcgtg gccgaatcca acggcttcat gaccggcacc gagggcacca    9360
tctactactc aattaatggc gaggccgaga tcagcctcta cttcgacaac ccgttcgccg    9420
gctccaacaa atacgacggc cactccaaca agtcccagta cgagatcatc acccagggcg    9480
gctccggcaa ccagtcccac gtgacctaca ccatccagac cacctcctcc cgctacggcc    9540
acaagtcctg agtcatgagt catgagtcag ttaacctaga cttgtccatc ttctggattg    9600
gccaacttaa ttaatgtatg aaataaaagg atgcacacat agtgacatgc taatcactat    9660
aatgtgggca tcaaagttgt gtgttatgtg taattactag ttatctgaat aaaagagaaa    9720
gagatcatcc atatttctta tcctaaatga atgtcacgtg tctttataat tctttgatga    9780
accagatgca tttcattaac caaatccata tacatataaa tattaatcat ataaattaa    9840 tatcaattgg gttagcaaaa caaatctagt ctaggtgtgt tttgcgaatg cggccgcgga    9900
ccgaattggg gatctgcatg aaagaaactg tcgcactgct gaaccgcacc ttgtcacttt    9960
catcgaacac gacctgtgcc caagatgacg gtgctgcggt ctaagtgagg ctgaattgcc   10020
ttggacagaa gcggactccc tacaattagt taggccaaac ggtgcatcca tgtgtagctc   10080
cgggctcggg ctgtatcgcc atctgcaata gcatccatgg agctcgttcc atgtagttgg   10140
agatgaacca atgatcgggc gtgtggacgt atgttcctgt gtactccgat agtagagtac   10200
gtgttagctc tttcatggtg caagtgaaat ttgtgttggt ttaattaccc ctacgttagt   10260
tgcgggacag gagacacatc atgaatttaa aggcgatgat gtcctctcct gtaatgttat   10320
tcttttgatg tgatgaatca aaatgtcata taaaacattt gttgctcttt agttaggcct   10380
gatcgtagaa cgaaatgctc gtgtagcggg gctacgagcc tatgacgcaa taacactggt   10440
ttgccggccc ggagtcgctt gacaaaaaaa agcatgttaa gtttatttac aattcaaaac   10500
ctaacatatt atattccctc aaagcaggtt cacgatcaca cctgtaccta aaaaaaacat   10560
gaagaatata ttactccatt attatgagat gaaccacttg gcaagagtgg taagctatat   10620
aaaaaaatga acattattac gagatgttat atgccattat attgattcga agatatatgt   10680
ttctttctcc cacgggcacc taacggatac atgataaggc caaggcagat cacgggaaat   10740
tattcgaata catgttacgc cctattgccg gaaaaaaaat gcagggcagg tgttggccgt   10800
agcgatttaa gcacttaagc tggaggttgc cacacttgga tgcaagcgtc tgaccttct    10860 aaaaaatcgg cggctttgtc cgtatccgta tcccctatcc aacatctagc tggccacacg   10920
acggggctgg gcagatcgtg gatgccgggt cgacgtcgat cgtcagccat catagaccaa   10980
tcgaccatct gttatggatg cttgctagct agactagtca gacataaaat ttggatactt   11040
tctcccaact gggagacggg gactgatgtg cagctgcacg tgagctaaat ttttccctat   11100
aaatatgcat gaaatactgc attatcttgc cacagccact gccacagcca gataacaagt   11160
gcagctggta gcacgcaacg catagctctg gacttgtagc taggtagcca accggatcca   11220
cacgacacca tgctcgacac caacaaggtg tacgagatca gcaaccacgc caacggcctc   11280
tacgccgcca cctacctctc cctcgacgac tccggcgtgt ccctcatgaa caagaacgac   11340
gacgacatcg acgactacaa cctcaagtgg ttcctcttcc cgatcgacga cgaccagtac   11400
atcatcacct cctacgccgc caacaactgc aaggtgtgga acgtgaacaa cgacaagatt   11460
aatgtgtcaa cctactcctc caccaactcc atccagaagt ggcagatcaa ggccaacggc   11520
```

```
tcctcctacg tgatccagtc cgacaacggc aaggtgctca ccgccggcac cggccaggcc   11580
ctcggcctca tccgcctcac cgacgagtcc tccaacaacc cgaaccagca atggaacctg   11640
acgtccgtgc agaccatcca gctcccgcag aagccgatca tcgacaccaa gctcaaggac   11700
tacccgaagt actccccgac cggcaacatc gacaacggca cctccccgca gctcatgggc   11760
tggaccctcg tgccgtgcat catggtgaac gacccgaaca tcgacaagaa cacccagatc   11820
aagaccaccc cgtactacat cctcaagaag taccagtact ggcagagggc cgtgggctcc   11880
aacgtcgcgc tccgcccgca cgagaagaag tcctacacct acgagtgggg caccgagatc   11940
gaccagaaga ccaccatcat caacaccctc ggcttccaga tcaacatcga cagcggcatg   12000
aagttcgaca tcccggaggt gggcggcggt accgacgaga tcaagaccca gctcaacgag   12060
gagctcaaga tcgagtattc acatgagacg aagatcatgg agaagtacca ggagcagtcc   12120
gagatcgaca acccgaccga ccagtccatg aactccatcg gcttcctcac catcacctcc   12180
ctggagctct accgctacaa cggctccgag atccgcatca tgcagatcca gacctccgac   12240
aacgacacct acaacgtgac ctcctacccg aaccaccagc aggccctgct gctgctgacc   12300
aaccactcct acgaggaggt ggaggagatc accaacatcc cgaagtccac cctcaagaag   12360
ctcaagaagt actacttctg agtcatgagt catgagtcag ttaacctaga cttgtccatc   12420
ttctggattg gccaacttaa ttaatgtatg aaataaaagg atgcacacat agtgacatgc   12480
taatcactat aatgtgggca tcaaagttgt gtgttatgtg taattactag ttatctgaat   12540
aaaagagaaa gagatcatcc atatttctta tcctaaatga atgtcacgtg tctttataat   12600
tctttgatga accagatgca tttcattaac caaatccata tacatataaa tattaatcat   12660
atataattaa tatcaattgg gttagcaaaa caaatctagt ctaggtgtgt tttgcgaatt   12720
atcgatgggc cccacctgca ggcatgcccg ctgaaatcac cagtctctct ctacaaatct   12780
atctctctct ataataatgt gtgagtagtt cccagataag ggaattaggg ttcttatagg   12840
gtttcgctca tgtgttgagc atataagaaa cccttagtat gtatttgtat ttgtaaaata   12900
cttctatcaa taaaatttct aattcctaaa accaaaatcc agggcgagct cgaattcgag   12960
ctcgagcccg ggtggatcct ctagagtcga cctgcagaag cttcggtccg gcgcgcctct   13020
agttgaagac acgttcatgt cttcatcgta agaagacact cagtagtctt cggccagaat   13080
ggcctaactc aaggccatcg tggcctcttg ctcttcagga tgaagagcta tgtttaaacg   13140
tgcaagtaag aacttcgatc cgaaatatcg tttcaaaact agaaacagc gcggctttgg   13200 ctaagccgcg cactatatag gattttgggc acctttgat ggaacgtgaa agcgtactgc   13260
gcactagtta tttaggttga accttggata tacggttctc actgcgccaa tgcaaggctt   13320
gaaacttggt tagtaatacg tactccctcc gtttcttttt atttgtcgct ggatagtgca   13380
attttgcact atcgagcgac aaataaaaag aaacggaggg agtatatgat tgtcagatgt   13440
agatatgttt atttatatat cacatacaga tatataaaac agatcacttt ttcagatata   13500
cagttccaat gtcagccctg atcaccctgt cataaattgc acgtttctaa ttgatgttgc   13560
ttcatggtcg tcatgagaac cttctgaaga atcgatgaa ggttgccaac ctttcaaagt   13620
ttcagaaacc actttgcatg tacactaagg gctggtttgg cagcccaaaa ccagccagcg   13680
ttttcctggt cttttctccc gggagaaagc ccatgcatag attgtccctg gattatttat   13740
ctgtgtcctt tggctaaaaa ttcgtcccaa tttcctgtag gaaactacct cggccttggg   13800
aggccaggcg attctccacc gcctcgtctc gtccatcctt cgatgctcac gcgtgcctcc   13860
tcggatgcta tcctcaggcg attctccgtc gtctcgtctc atccatcctc acgcgcgcct   13920
```

```
cctccgacgc tatccccagg cgattctcca ccgtctcgtc tcatccatcc tcatgtacgc    13980
ctcgtccgat gctatcccca gacgattttc cgtcgtctca tctccttcat gctcgcgcgc    14040
gcctcctccg acgctatccc caggcgattt ttctgccgtc tcgtctcctt catgcccgcg    14100
cgcgcctcct ccgacgctat ccccaggcga ttttccgccg tctcgtctcc ttcatgcccg    14160
cgcgtgcctc ctccgacgct attcccacga gcgcctccgc cgccgctatc cccagacgat    14220
tttccgctgt ctcgtctcct tcatgcccgc gcgcccctcc tccgacgcta tcccacgag    14280 cgcctccgcc gccgctccac cgtcttcccc gccgccatcc ccttaattcc tatagatctg    14340
gaccccgctc tactttcgtt ggcatacttt tgcttggtgt gcgcgggctg gagtggaagg    14400
ttgcgcattc gatcacgggg gagaagtgga tcttgggtct tggcaggcta gggcggttgc    14460
caggacgccg tggtgtgcat tcatgggtcc tataaatctt tatcattacc gccttaggag    14520
ctagttgtag ttcacacatc atatccttt ctgctcgaca tcgtctgggg atgccctagg     14580
tgccctaccg accctacggc attgtcttga cctctattag actctatgtc atctagagcc    14640
ttcttgggtg gccttttgac cccaaagcga ccctatgatc ttaccctaac gaggtctccc    14700
ttggtggggc aagatccact ttgtccactt aactgaagat ctgatcctca tcttgaaatc    14760
tttaatccca aggtgactct acgtcgtatg tggatgctcc gggtaacctg ccaacccgga    14820
tcaccctaag atctctttcc taaggggcga gatctaggtt cctacgagaa agaagacgac    14880
cctgcaccat tgcggtccgt ccggtccaga gtgcgaacgt ccggatgcga cacagggaag    14940
gagtcgctcc tgcagcgagg tcgcagactg tccacacagc ctcagaaggc accgccagac    15000
aatacatgta atacccactc tgtaagaaaa acctaaaagg agaaagtata ttcctttatc    15060
tatatgtgtg ttatatttct actcaccatc acatgtgaac atctcactta cacaaataaa    15120
taattaacaa aagacactca aataaattat gcatcatgct cgaccttatt ttgtgtgcat    15180
tctgttacaa tataaaaata atataaaaaa catatattaa tatcaaaatt tggagattta    15240
accctaatat gcaaatcgga gtttagagga aagaaagaaa aatgctatac aaaataaagg    15300
aataaatata taaataaagg taaaactatt aatactggta tattaatttg aacagttgac    15360
ctaattatga atatcacaac tggtttgaat tcaaatatga aatccaagaa tttgaaaata    15420
ggaaaaatgg agataagaat aaaggaaaag aattcttaac tcggatgggc ctgggaaacg    15480
aatttcggcc cacttcctgt gtccttagct gtgcggctca gtccagtg                 15528
```

<210> SEQ ID NO 31
<211> LENGTH: 15563
<212> TYPE: DNA
<213> ORGANISM: Artificial
<220> FEATURE:
<223> OTHER INFORMATION: synthetic

<400> SEQUENCE: 31

```
gagcatatcc agcaccagct ggtaccaagg tcgggtctct gtgctagtgc tattagctag      60
tgtaaggagc gagtaggtca gttaaggctg gtgcgtcgtg agggctgtct tgtgtgtagc     120
tacagcagac ggttcatcag aaggattatt cgtgcagtat atacagtaca actagacaat     180
gatgttgatg attggtctag agctagaggc ctatagccct atactactgt gtattgtccg     240
ccgttttagt tttttggtcc catcccatca atgcaaccgc cttgttttgc tccaattgtc     300
ccgttcctgc gcctcgcttt tgctctgtcg catcgcatac aaaaaaaaaa acgccgcgcc     360
ggctttgaat cgcgcccccc aactgctcca accaggcaac ggacacggcc accgtccgtg     420
```

```
tcgcgagcaa aaaaacaaaa agaggaacgc gtccaggacg aagcagtcca ctgccgctgt    480
ggccggcaaa agatctggtt gagcacatgg agattggaga aggttggttg gttcttctgg    540
aaacgccaat gaatggggc actgacatgt actcttaaca tgtagtgcaa tccagagatc    600
ggatatccag acactggcag cacgatcgcc tcgcgccgta gatcacgcac gcaaattact    660
gaagaccatt cacaaaaaaa aaaaaacaca caggggctag cgtgccccac accaaaccca    720
agtgctgcgt tgcacgcagg ggagcgaaaa aaaacaataa tgctcactgt cacgtcgcgt    780
atccaacccc gcggacgtct cggctctcag cagcagcaca cggggcacct cacgatgccg    840
ttctcgttgc actccgtgca ccgccggaac ccgccgccgc attcgtcgcc ctcctcctcc    900
tcctccgcct cgtcttcgtc acccacgtac accttgcagc tgcccgagca gacatcgcag    960
agcacgaacc gcatgtcccc gcaggcctcg cacgcgccgg cgtcgccgcc gtgtgggccg   1020
gccgtcgacg cagcgctctc gcacccgcc agcctcggcg cgagctcccc ggcctcgtgc   1080
agccgcttca gctcctcggc gttgcccacg agctccccgt ccacgaagag gctggggagg   1140
gcggcgggcg tgccgccggc ttggccgagc ccgaggccga aaggccgcg gagctcgtcc   1200
cggaacccgc ggtgcatgga cacgtcgcgc tcgtcgaggc gcacgccgta gcccttgagg   1260
atggcgcgc ccaggcagca gtcctcgtgc gtggcgcgca cgccgcgcag cgacgtgaag   1320
tagagcaccg ccctccgcgg cggcagcgcc ttcccctccc cgccgctcgt cggggcggcg   1380
tcgggccgag gcatcggcat cggcagcggc gtcaccttgg cggacgccgc gaggtcctgc   1440
gcaggcgccg tggcgaccgg gaacgagaag gagtggcgcc cgaacggcgc gcccagcagc   1500
ggggagcggt cctcgaggcc ggccatgagc gcccacgcgt cgatgtcctc gggctcgttg   1560
ggcggcgtca tggtgggcgt gcgcggcgcc agcctcgtgg gcgcgggctc cggcgcccgc   1620
ggcagggcct tgtccagctc cagggacccg agcgtgacg acgtgagccg caccacgtgg   1680
acgccgacgt cgctggggca ccgagccggg aacgactggc tgcgcggcag cggtgacggg   1740
cagtaccgga ggtcgtgacg ggcctgcctt gaggtggtgc accccatggc accaatgtac   1800
acacacggcc aaagcgccaa gtgggctgca gactgcctgc caatgtgatc aagcagccag   1860
gagcagagac ggatctctgg ggatcggggt ttctggggtt taggatcttt atactactct   1920
gtcattgggg atataaaact aggagtgtgg ttaattagga ctcgatagat aagtttacca   1980
caagcgcgtg aaatggtcta cccgatgatg tgattggcct aaaaagaaca agaagagtat   2040
ttggagctac tgaacattct cttttcctga agataactaa ttttggaac attcagactt   2100
gggagtctgg acttttggag ggaagttcaa attgtggtct gcctctgcca tgtgttgttt   2160
tttagtcgga gagtggccct cattttttt gtcctgttta gctttatagt cgtagcagct   2220
agtagcgaaa tttaaccttg gattatggcc gtgttagtca aacaatcatt gattatttc   2280
ctccctttcg cgctgctttt cctgtacgca tctccgctgc ccttgattcg aggaccctgt   2340
tcacaacaca gggctctggc tttggagcct ctcgtttgta gcacttgcac gtagttaccc   2400
ggaccgaagc ttcaacacag atctgatagt ttaaacgctc ttcaactgga agagcggtta   2460
cccggaccga agcttcggcc ggggcccatc gatatccgcg gcatgcctg cagtgcagcg   2520
tgacccggtc gtgcccctct ctagagataa tgagcattgc atgtctaagt tataaaaaat   2580
taccacatat ttttttgtc acacttgttt gaagtgcagt ttatctatct ttatacatat   2640
atttaaactt tactctacga ataatataat ctatagtact acaataatat cagtgtttta   2700
gagaatcata taaatgaaca gttagacatg gtctaaagga caattgagta ttttgacaac   2760
aggactctac agttttatct ttttagtgtg catgtgttct cctttttttt tgcaaatagc   2820
```

```
ttcacctata taatacttca tccattttat tagtacatcc atttaggtt tagggttaat      2880 ggttttata  gactaattt  tttagtacat ctattttatt ctattttagc ctctaaatta    2940
agaaaactaa aactctattt tagtttttt  atttaataat ttagatataa aatagaataa    3000
aataaagtga ctaaaaatta aacaaatacc ctttaagaaa ttaaaaaaac taaggaaaca    3060 ttttcttgt  ttcgagtaga taatgccagc ctgttaaacg ccgtcgacga gtctaacgga   3120
caccaaccag cgaaccagca gcgtcgcgtc gggccaagcg aagcagacgg cacggcatct    3180
ctgtcgctgc ctctggaccc ctctcgagag ttccgctcca ccgttggact tgctccgctg    3240
tcggcatcca gaaattgcgt ggcggagcgg cagacgtgag ccggcacggc aggcggcctc    3300
ctcctcctct cacggcaccg gcagctacgg gggattcctt tcccaccgct ccttcgcttt    3360
cccttcctcg cccgccgtaa taaatagaca cccctccac  accctctttc cccaacctcg    3420
tgttgttcgg agcgcacaca cacacaacca gatctccccc aaatccaccc gtcggcacct    3480
ccgcttcaag gtacgccgct cgtcctcccc ccccccccct ctctaccttc tctagatcgg    3540
cgttccggtc catggttagg gcccggtagt tctacttctg ttcatgtttg tgttagatcc    3600
gtgtttgtgt tagatccgtg ctgctagcgt tcgtacacgg atgcgacctg tacgtcagac    3660
acgttctgat tgctaacttg ccagtgtttc tctttgggga atcctgggat ggctctagcc    3720
gttccgcaga cgggatcgat ttcatgattt ttttgtttc  gttgcatagg gtttggtttg    3780
cccttttcct ttatttcaat atatgccgtg cacttgtttg tcgggtcatc ttttcatgct    3840
tttttttgtc ttggttgtga tgatgtggtc tggttgggcg gtcgttctag atcggagtag    3900
aattctgttt caaactacct ggtggattta ttaattttgg atctgtatgt gtgtgccata    3960
catattcata gttacgaatt gaagatgatg gatggaaata tcgatctagg ataggtatac    4020
atgttgatgc gggttttact gatgcatata cagagatgct ttttgttcgc ttggttgtga    4080
tgatgtggtg tggttgggcg gtcgttcatt cgttctagat cggagtagaa tactgtttca    4140
aactacctgg tgtatttatt aattttggaa ctgtatgtgt gtgtcataca tcttcatagt    4200
tacgagttta agatggatgg aaatatcgat ctaggatagg tatacatgtt gatgtgggtt    4260
ttactgatgc atatacatga tggcatatgc agcatctatt catatgctct aaccttgagt    4320
acctatctat tataataaac aagtatgttt tataattatt ttgatcttga tatacttgga    4380
tgatggcata tgcagcagct atatgtggat tttttagcc  ctgccttcat acgctattta    4440
tttgcttggt actgtttctt ttgtcgatgc tcaccctgtt gtttggtgtt acttctgcag    4500
gtcgactcta gaggatccaa caatggagaa caacatacag aatcagtgcg tcccctacaa    4560
ctgcctcaac aatcctgaag tagagattct caacgaagag aggtcgactg gcagattgcc    4620
gttagacatc tccctgtccc ttacacgttt cctgttgtct gagtttgttc caggtgtggg    4680
agttgcgttt ggcctcttcg acctcatctg ggcttcatc  actccatctg attggagcct    4740 cttcttctc  cagattgaac agttgattga acaaaggatt gagaccttgg aaaggaatcg    4800
ggccatcact acccttcgtg gcttagcaga cagctatgag atctacattg aagcactaag    4860
agagtgggaa gccaatccta acaatgccca actgagagaa gatgtgcgta tacgctttgc    4920
taacacagat gatgctttga tcacagccat caacaacttc acccttacca gcttcgagat    4980
ccctcttctc tcggtctatg ttcaagctgc taacctgcac ttgtcactac tgcgcgacgc    5040
tgtgtcgttt gggcaaggtt ggggactgga catagctact gtcaacaatc actacaacag    5100
actcatcaat ctgattcatc gatacacgaa acattgtttg gatacctaca atcagggatt    5160
```

```
ggagaacctg agaggtacta acactcgcca atgggccagg ttcaatcagt tcaggagaga    5220
ccttacactt actgtgttag acatagttgc tctctttccg aactacgatg ttcgtaccta    5280
tccgattcaa acgtcatccc aacttacaag ggagatctac accagttcag tcattgaaga    5340
ctctccagtt tctgcgaaca tacccaatgg tttcaacagg gctgagtttg gagtcagacc    5400
accccatctc atggacttca tgaactcttt gtttgtgact gcagagactg ttagatccca    5460
aactgtgtgg ggaggacact tagttagctc acgcaaacg gctggcaatc gtatcaactt     5520
aactgtgtgg ggaggacact tagttagctc acgcaaacg gctggcaatc gtatcaactt     5520
tcctagttac ggggtcttca atcccggggg cgccatctgg attgcagatg aagatccacg    5580
tcctttctat cggaccttgt cagatcctgt cttcgtccga ggaggctttg caatcctca     5640 ctatgtactc ggtcttaggg gagtggcctt tcaacaaact ggtacgaatc acccgcac      5700 attcaggaac tccgggacca ttgactctct agatgagata ccacctcaag acaacagcgg    5760
cgcaccttgg aatgactact cccatgtgct gaatcatgtt acctttgtgc gctggccagg    5820
tgagatctca ggttccgact catggagagc accaatgttc tcttggacgc atcgtagcgc    5880 taccccaca aacaccattg atccagagag aatcactcag attcccttgg tgaaggcaca     5940
cacacttcag tcaggaacta cagttgtaag agggccgggg ttcacgggag gagacattct    6000
tcgacgcact agtggaggac cattcgcgta caccattgtc aacatcaatg gcaacttcc     6060 ccaaaggtat cgtgccagga tacgctatgc ctctactacc aatctaagaa tctacgttac    6120
ggttgcaggt gaacggatct ttgctggtca gttcaacaag acaatggata ccggtgatcc    6180
acttacattc caatctttct cctacgccac tatcaacacc gcgttcacct ttccaatgag    6240
ccagagcagt ttcacagtag gtgctgatac cttcagttca ggcaacgaag tgtacattga    6300
caggtttgag ttgattccag ttactgccac actcgagtaa ggatccgtcg acctgcagcc    6360
aagctttcgc gagctcgaga tccccgacat atgccccggt ttcgttgcga ctaacatgag    6420
ttcttggaca aatttgattg gacctgatga gatgatccaa cccgaggata tagcaaagct    6480
cgttcgtgca gcaatggaac ggccaaaccg tgcttttgtc cccaagaatg aggtgctatg    6540
catgaaggaa tctacccgtt gatgtccaac agtctcaggg ttaatgtcta tgtatcttaa    6600
ataatgttgt cggtattttg taatctcata tagattttca ctgtgcgacg caaaaatatt    6660
aaataaatat tattattatc tacgttttga ttgagatatc atcaatatta tataaaaat    6720 atccattaaa cacgatttga tacaaatgac agtcaataat ctgatttgaa tatttattaa    6780
ttgtaacgaa ttacataaag atcgaataga aaatactgca ctgcaaatga aaattaacac    6840
atactaataa atgcgtcaaa tatctttgcc aagatcaagc ggagtgaggg cctcatatcc    6900
ggtctcagtt acaagcacgg tatccccgaa gcgcgctcca ccaatgccct cgacatagat    6960
gccgggctcg acgctgagga cattgcctac cttgagcatg gtctcagcgc cggctttaag    7020
ctcaatccca tcccaatctg aatatcctat cccgcgccca gtccggtgta agaacgggtc    7080
tgtccatcca cctctgttgg gaattccggt ccgggtcacc tttgtccacc aagatggaac    7140
tgcggccagc ttgcatgcct gcagtgcagc gtgacccggt cgtgcccctc tctagagata    7200
atgagcattg catgtctaag ttataaaaaa ttaccacata ttttttttgt cacacttgtt    7260
tgaagtgcag tttatctatc tttatacata tatttaaact ttactctacg aataatataa    7320
tctatagtac tacaataata tcagtgtttt agagaatcat ataaatgaac agttagacat    7380
ggtctaaagg acaattgagt attttgacaa caggactcta cagttttatc ttttagtgt     7440 gcatgtgttc tccttttttt ttgcaaatag cttcacctat ataatacttc atccattta     7500 ttagtacatc catttagggt ttagggttaa tggtttttat agactaattt ttttagtaca    7560
```

```
tctattttat tctattttag cctctaaatt aagaaaacta aaactctatt ttagtttttt   7620
tatttaataa tttagatata aaatagaata aaataaagtg actaaaaatt aaacaaatac   7680
cctttaagaa attaaaaaaa ctaaggaaac attttttcttg tttcgagtag ataatgccag  7740
cctgttaaac gccgtcgacg agtctaacgg acaccaacca gcgaaccagc agcgtcgcgt   7800
cgggccaagc gaagcagacg gcacggcatc tctgtcgctg cctctggacc cctctcgaga   7860
gttccgctcc accgttggac ttgctccgct gtcggcatcc agaaattgcg tggcggagcg   7920
gcagacgtga gccggcacgg caggcggcct cctcctcctc tcacggcacc ggcagctacg   7980
ggggattcct ttcccaccgc tccttcgctt tccctcctc gcccgccgta ataaatagac    8040
accccctcca caccctcttt ccccaacctc gtgttgttcg gagcgcacac acacacaacc   8100
agatctcccc caaatccacc cgtcggcacc tccgcttcaa ggtacgccgc tcgtcctccc   8160
ccccccccccc tctctacctt ctctagatcg gcgttccggt ccatggttag ggcccggtag  8220
ttctacttct gttcatgttt gtgttagatc cgtgtttgtg ttagatccgt gctgctagcg   8280
ttcgtacacg gatgcgacct gtacgtcaga cacgttctga ttgctaactt gccagtgttt   8340
ctctttgggg aatcctggga tggctctagc cgttccgcag acgggatcga tttcatgatt   8400
ttttttgttt cgttgcatag ggtttggttt gcccttttcc tttatttcaa tatatgccgt   8460
gcacttgttt gtcgggtcat cttttcatgc tttttttgt cttggttgtg atgatgtggt    8520
ctggttgggc ggtcgttcta gatcggagta gaattctgtt tcaaactacc tggtggattt   8580
attaattttg gatctgtatg tgtgtgccat acatattcat agttacgaat tgaagatgat   8640
ggatggaaat atcgatctag gataggtata catgttgatg cgggttttac tgatgcatat   8700
acagagatgc ttttgttcg cttggttgtg atgatgtggt gtggttgggc ggtcgttcat    8760
tcgttctaga tcggagtaga atactgtttc aaactacctg gtgtatttat taattttgga  8820
actgtatgtg tgtgtcatac atcttctag ttacgagttt aagatggatg gaaatatcga    8880
tctaggatag gtatacatgt tgatgtgggt tttactgatg catatacatg atggcatatg   8940
cagcatctat tcatatgctc taaccttgag tacctatcta ttataataaa caagtatgtt   9000
ttataattat tttgatcttg atatacttgg atgatggcat atgcagcagc tatatgtgga   9060
tttttttagc cctgccttca tacgctattt atttgcttgg tactgtttct tttgtcgatg   9120
ctcaccctgt tgtttggtgt tacttctgca ggtcgactct agaggatcca cacgacacca   9180
tgtccgcccg cgaggtgcac atcgacgtga acaacaagac cggccacacc ctccagctgg   9240
aggacaagac caagctcgac ggcggcaggt ggcgcacctc cccgaccaac gtggccaacg   9300
accagatcaa gaccttcgtg gccgaatcca acggcttcat gaccggcacc gagggcacca   9360
tctactactc aattaatggc gaggccgaga tcagcctcta cttcgacaac ccgttcgccg   9420
gctccaacaa atacgacggc cactccaaca gtcccagta cgagatcatc acccagggcg    9480
gctccggcaa ccagtcccac gtgacctaca ccatccagac cacctcctcc cgctacggcc   9540
acaagtcctg agtcatgagt catgagtcag ttaacctaga cttgtccatc ttctggattg   9600
gccaacttaa ttaatgtatg aaataaaagg atgcacacat agtgacatgc taatcactat   9660
aatgtgggca tcaaagttgt gtgttatgtg taattactag ttatctgaat aaaagagaaa   9720
gagatcatcc atatttctta tcctaaatga atgtcacgtg tctttataat tctttgatga   9780
accagatgca tttcattaac caaatccata tacatataaa tattaatcat atataattaa   9840
tatcaattgg gttagcaaaa caaatctagt ctaggtgtgt tttgcgaatg cggccgcgga   9900
```

```
ccgaattggg gatctgcatg aaagaaactg tcgcactgct gaaccgcacc ttgtcacttt    9960
catcgaacac gacctgtgcc caagatgacg gtgctgcggt ctaagtgagg ctgaattgcc   10020
ttggacagaa gcggactccc tacaattagt taggccaaac ggtgcatcca tgtgtagctc   10080
cgggctcggg ctgtatcgcc atctgcaata gcatccatgg agctcgttcc atgtagttgg   10140
agatgaacca atgatcgggc gtgtggacgt atgttcctgt gtactccgat agtagagtac   10200
gtgttagctc tttcatggtg caagtgaaat tgtgttggt ttaattaccc ctacgttagt   10260
tgcgggacag gagacacatc atgaatttaa aggcgatgat gtcctctcct gtaatgttat   10320
tcttttgatg tgatgaatca aaatgtcata taaaacattt gttgctcttt agttaggcct   10380
gatcgtagaa cgaaatgctc gtgtagcggg gctacgagcc tatgacgcaa taacactggt   10440
ttgccggccc ggagtcgctt gacaaaaaaa agcatgttaa gtttatttac aattcaaaac   10500
ctaacatatt atattccctc aaagcaggtt cacgatcaca cctgtaccta aaaaaaacat   10560
gaagaatata ttactccatt attatgagat gaaccacttg gcaagagtgg taagctatat   10620
aaaaaaatga acattattac gagatgttat atgccttat attgattcga agatatatgt   10680
ttctttctcc cacgggcacc taacggatac atgataaggc caaggcagat cacgggaaat   10740
tattcgaata catgttacgc cctattgccg gaaaaaaaat gcagggcagg tgttggccgt   10800
agcgatttaa gcacttaagc tggaggttgc cacacttgga tgcaagcgtc tgacccttct   10860
aaaaaatcgg cggctttgtc cgtatccgta tcccctatcc aacatctagc tggccacacg   10920
acggggctgg gcagatcgtg gatgccgggt cgacgtcgat cgtcagccat catagaccaa   10980
tcgaccatct gttatggatg cttgctagct agactagtca gacataaaat ttggatactt   11040
tctcccaact gggagacggg gactgatgtg cagctgcacg tgagctaaat ttttccctat   11100
aaatatgcat gaaatactgc attatcttgc cacagccact gccacagcca gataacaagt   11160
gcagctggta gcacgcaacg catagctctg gacttgtagc taggtagcca accggatcca   11220
cacgacacca tgctcgacac caacaaggtg tacgagatca gcaaccacgc caacggcctc   11280
tacgccgcca cctacctctc cctcgacgac tccggcgtgt ccctcatgaa caagaacgac   11340
gacgacatcg acgactacaa cctcaagtgg ttcctcttcc cgatcgacga cgaccagtac   11400
atcatcacct cctacgccgc caacaactgc aaggtgtgga acgtgaacaa cgacaagatt   11460
aatgtgtcaa cctactcctc caccaactcc atccagaagt ggcagatcaa ggccaacggc   11520
tcctcctacg tgatccagtc cgacaacggc aaggtgctca ccgccggcac cggccaggcc   11580
ctcggcctca tccgcctcac cgacgagtcc tccaacaacc cgaaccagca atggaacctg   11640
acgtccgtgc agaccatcca gctcccgcag aagccgatca tcgacaccaa gctcaaggac   11700
tacccgaagt actccccgac cggcaacatc gacaacggca cctccccgca gctcatgggc   11760
tggaccctcg tgccgtgcat catggtgaac gacccgaaca tcgacaagaa cacccagatc   11820
aagaccaccc cgtactacat cctcaagaag taccagtact ggcagagggc cgtgggctcc   11880
aacgtcgcgc tccgcccgca cgagaagaag tcctacacct acgagtgggg caccgagatc   11940
gaccagaaga ccaccatcat caacacccc ggcttccaga tcaacatcga cagcggcatg   12000
aagttcgaca tcccggaggt gggcggcggt accgacgaga tcaagaccca gctcaacgag   12060
gagctcaaga tcgagtattc acatgagacg aagatcatgg agaagtacca ggagcagtcc   12120
gagatcgaca cccgaccga ccagtccatg aactccatcg gcttcctcac catcacctcc   12180
ctggagctct accgctacaa cggctccgag atccgcatca tgcagatcca gacctccgac   12240
aacgacacct acaacgtgac ctcctacccg aaccaccagc aggccctgct gctgctgacc   12300
```

```
aaccactcct acgaggaggt ggaggagatc accaacatcc cgaagtccac cctcaagaag    12360
ctcaagaagt actacttctg agtcatgagt catgagtcag ttaacctaga cttgtccatc    12420
ttctggattg gccaacttaa ttaatgtatg aaataaaagg atgcacacat agtgacatgc    12480
taatcactat aatgtgggca tcaaagttgt gtgttatgtg taattactag ttatctgaat    12540
aaaagagaaa gagatcatcc atatttctta tcctaaatga atgtcacgtg tctttataat    12600
tctttgatga accagatgca tttcattaac caaatccata tacatataaa tattaatcat    12660
atataattaa tatcaattgg gttagcaaaa caaatctagt ctaggtgtgt tttgcgaatt    12720
atcgatgggc cccacctgca ggcatgcccg ctgaaatcac cagtctctct ctacaaatct    12780
atctctctct ataataatgt gtgagtagtt cccagataag ggaattaggg ttcttatagg    12840
gtttcgctca tgtgttgagc atataagaaa cccttagtat gtatttgtat ttgtaaaata    12900
cttctatcaa taaaatttct aattcctaaa accaaaatcc agggcgagct cgaattcgag    12960
ctcgagcccg ggtggatcct ctagagtcga cctgcagaag cttcggtccg gcgcgcctct    13020
agttgaagac acgttcatgt cttcatcgta agaagacact cagtagtctt cggccagaat    13080
ggcctaactc aaggccatcg tggcctcttg ctcttcagga tgaagagcta tgttttaaacg    13140 tgcaagcgct tttgtagcac ttgcacgtag ttacccggat ataagaactt cgatccgaaa    13200
tatcgtttca aaactagaaa acagcgcggc tttggctaag ccgcgcacta tataggattt    13260
tgggcacctt ttgatggaac gtgaaagcgt actgcgcact agttatttag gttgaaccctt   13320 ggatatacgg ttctcactgc gccaatgcaa ggcttgaaac ttggttagta atacgtactc    13380
cctccgtttc ttttttattg tcgctggata gtgcaatttt gcactatcga gcgacaaata    13440
aaaagaaacg gagggagtat atgattgtca gatgtagata tgtttattta tatatcacat    13500
acagatatat aaaacagatc acttttttcag atatacagtt ccaatgtcag ccctgatcac    13560
cctgtcataa attgcacgtt tctaattgat gttgcttcat ggtcgtcatg agaaccttct    13620
gaagaaatcg atgaaggttg ccaacctttc aaagtttcag aaaccacttt gcatgtacac    13680
taagggctgg tttggcagcc caaaaccagc cagcgttttc ctggtctttt ctcccgggag    13740
aaagcccatg catagattgt ccctggatta tttatctgtg tcctttggct aaaaattcgt    13800
cccaatttcc tgtaggaaac tacctcggcc ttgggaggcc aggcgattct ccaccgcctc    13860
gtctcgtcca tccttcgatg ctcacgcgtg cctcctcgga tgctatcctc aggcgattct    13920
ccgtcgtctc gtctcatcca tcctcacgcg cgcctcctcc gacgctatcc ccaggcgatt    13980
ctccaccgtc tcgtctcatc catcctcatg tacgcctcgt ccgatgctat ccccagacga    14040
ttttccgtcg tctcatctcc ttcatgctcg cgcgcgcctc ctccgacgct atccccaggc    14100 gattttctg ccgtctcgtc tccttcatgc ccgcgcgcgc ctcctccgac gctatcccca    14160
ggcgattttc cgccgtctcg tctccttcat gcccgcgcgt gcctcctccg acgctattcc    14220
cacgagcgcc tccgccgccg ctatccccag acgattttcc gctgtctcgt ctccttcatg    14280
cccgcgcgcc cctcctccga cgctatcccc acgagcgcct ccgccgccgc tccaccgtct    14340
tccccgccgc catcccctta attcctatag atctggaccc cgctctactt tcgttggcat    14400
actttgtctt ggtgtgcgcg ggctggagtg gaaggttgcg cattcgatca cgggggagaa    14460
gtggatcttg ggtcttggca ggctagggcg gttgccagga cgccgtggtg tgcattcatg    14520
ggtcctataa atctttatca ttaccgcctt aggagctagt tgtagttcac acatcatatc    14580
cttttctgct cgacatcgtc tggggatgcc ctaggtgccc taccgaccct acggcattgt    14640
```

```
cttgacctct attagactct atgtcatcta gagccttctt gggtggcctt ttgaccccaa    14700 agcgaccota tgatcttacc ctaacgaggt ctcccttggt ggggcaagat ccactttgtc    14760
cacttaactg aagatctgat cctcatcttg aaatctttaa tcccaaggtg actctacgtc    14820
gtatgtggat gctccgggta acctgccaac ccggatcacc ctaagatctc tttcctaagg    14880
ggcgagatct aggttcctac gagaaagaag acgaccctgc accattgcgg tccgtccggt    14940
ccagagtgcg aacgtccgga tgcgacacag ggaaggagtc gctcctgcag cgaggtcgca    15000
gactgtccac acagcctcag aaggcaccgc cagacaatac atgtaatacc cactctgtaa    15060
gaaaaaccta aaaggagaaa gtatattcct ttatctatat gtgtgttata tttctactca    15120
ccatcacatg tgaacatctc acttacacaa ataataatt aacaaaagac actcaaataa    15180
attatgcatc atgctcgacc ttattttgtg tgcattctgt tacaatataa aaataatata    15240
aaaaacatat attaatatca aaatttggag atttaaccct aatatgcaaa tcggagttta    15300
gaggaaagaa agaaaaatgc tatacaaaat aaaggaataa atatataaat aaaggtaaaa    15360
ctattaatac tggtatatta atttgaacag ttgacctaat tatgaatatc acaactggtt    15420
tgaattcaaa tatgaaatcc aagaatttgg aaataggaaa aatggagata agaataaagg    15480
aaaagaattc ttaactcgga tgggcctggg aaacgaattt cggcccactt cctgtgtcct    15540
tagctgtgcg gctcagtcca gtg                                           15563

<210> SEQ ID NO 32
<211> LENGTH: 1003
<212> TYPE: DNA
<213> ORGANISM: Artificial
<220> FEATURE:
<223> OTHER INFORMATION: synthetic

<400> SEQUENCE: 32
taagggaatt agggttctta tagggtttcg ctcatgtgtt gagcatataa gaaacccta       60 gtatgtattt gtatttgtaa aatacttcta tcaataaaat ttctaattcc taaaaccaaa     120
atccagggcg agctcgaatt cgagctcgag cccgggtgga tcctctagag tcgacctgca    180
gaagcttcgg tccggcgcgc ctctagttga agacacgttc atgtcttcat cgtaagaaga    240
cactcagtag tcttcggcca gaatggccta actcaaggcc atcgtggcct cttgctcttc    300
aggatgaaga gctatgttta aacgtgcaag taagaacttc gatccgaaat atcgtttcaa    360
aactagaaaa cagcgcggct ttggctaagc cgcgcactat ataggatttt gggcaccttt    420
tgatggaacg tgaaagcgta ctgcgcacta gttatttagg ttgaaccttg gatatacggt    480
tctcactgcg ccaatgcaag gcttgaaact tggttagtaa tacgtactcc ctccgtttct    540
tttttattgt cgctggatag tgcaattttg cactatcgag cgacaaataa aaagaaacgg    600
agggagtata tgattgtcag atgtagatat gtttatttat atatcacata cagatatata    660
aaacagatca cttttcaga tatacagttc caatgtcagc cctgatcacc ctgtcataaa    720
ttgcacgttt ctaattgatg ttgcttcatg gtcgtcatga gaaccttctg aagaaatcga    780
tgaaggttgc caacctttca aagtttcaga accactttg catgtacact aagggctggt    840
ttggcagccc aaaaccagcc agcgttttcc tggtctttc tcccgggaga agcccatgc     900 atagattgtc cctggattat ttatctgtgt cctttggcta aaaattcgtc ccaatttcct    960
gtaggaaact acctcggcct tgggaggcca ggcgattctc cac                    1003

<210> SEQ ID NO 33
<211> LENGTH: 900
```

```
<212> TYPE: DNA
<213> ORGANISM: Artificial
<220> FEATURE:
<223> OTHER INFORMATION: synthetic

<400> SEQUENCE: 33
ttacccagat ctgagtcgac ctgcaggcat gcccgctgaa atcaccagtc tctctctaca      60
aatctatctc tctctataat aatgtgtgag tagttcccag ataagggaat tagggttctt     120
atagggtttc gctcatgtgt tgagcatata agaaaccctt agtatgtatt tgtatttgta     180
aaatacttct atcaataaaa tttctaattc ctaaaaccaa atccagggc gagctcgaat      240
tcgagctcga gcccgggtgg atcctctaga gtcgacctgc agaagcttcg gtccggcgcg     300
cctctagttg aagacacgtt catgtcttca tcgtaagaag acactcagta gtcttcggcc     360
agaatggcct aactcaaggc catcgtggcc tcttgctctt caggatgaag agctatgttt     420
aaacgtgcaa ggatataaga acttcgatcc gaaatatcgt ttcaaaacta gaaaacagcg     480
cggctttggc taagccgcgc actatatagg attttgggca ccttttgatg gaacgtgaaa     540
gcgtactgcg cactagttat ttaggttgaa ccttggatat acggttctca ctgcgccaat     600
gcaaggcttg aaacttggtt agtaatacgt actccctccg tttcttttta tttgtcgctg     660
gatagtgcaa ttttgcacta tcgagcgaca aataaaaaga aacggaggga gtatatgatt     720
gtcagatgta gatatgttta tttatatatc acatacagat atataaaaca gatcactttt     780
tcagatatac agttccaatg tcagccctga tcaccctgtc ataaattgca cgtttctaat     840
tgatgttgct tcatggtcgt catgagaacc ttctgaagaa atcgatgaag gttgccaacc     900

<210> SEQ ID NO 34
<211> LENGTH: 702
<212> TYPE: DNA
<213> ORGANISM: Artificial
<220> FEATURE:
<223> OTHER INFORMATION: synthetic

<400> SEQUENCE: 34
agaagtacta cttctgagtc atgagtcatg agtcagttaa cctagacttg tccatcttct      60
ggattggcca acttaattaa tgtatgaaat aaaaggatgc acacatagtg acatgctaat     120
cactataatg tgggcatcaa agttgtgtgt tatgtgtaat tactagttat ctgaataaaa     180
gagaaagaga tcatccatat ttcttatcct aaatgaatgt cacgtgtctt tataattctt     240
tgatgaacca gatgcatttc attaaccaaa tccatataca tataaatatt aatcatatat     300
aattaatatc aattgggtta gcaaaacaaa tctagtctag gtgtgttttg cgaattatcg     360
atgggcccct aagaacttcg atccgaaata tcgtttcaaa actagaaaac agcgcggctt     420
tggctaagcc gcgcactata taggattttg ggcaccttt tgatggaacgt gaaagcgtac    480
tgcgcactag ttatttaggt tgaaccttgg atatacggtt ctcactgcgc caatgcaagg     540
cttgaaactt ggttagtaat acgtactccc tccgtttctt tttatttgtc gctggatagt     600
gcaattttgc actatcgagc gacaaataaa agaaacgga gggagtatat gattgtcaga     660
tgtagatatg tttatttata tatcacatac agatatataa aa                        702

<210> SEQ ID NO 35
<211> LENGTH: 700
<212> TYPE: DNA
<213> ORGANISM: Artificial
<220> FEATURE:
<223> OTHER INFORMATION: synthetic
```

```
<400> SEQUENCE: 35
aagtactact tctgagtcat gagtcatgag tcagttaacc tagacttgtc catcttctgg      60
attggccaac ttaattaatg tatgaaataa aaggatgcac acatagtgac atgctaatca     120
ctataatgtg ggcatcaaag ttgtgtgtta tgtgtaatta ctagttatct gaataaaaga    180
gaaagagatc atccatattt cttatcctaa atgaatgtca cgtgtcttta taattctttg    240
atgaaccaga tgcatttcat taaccaaatc catatacata taaatattaa tcatatataa    300
ttaatatcaa ttgggttagc aaaacaaatc tagtctaggt gtgttttgcg aattatcgat    360
gggcccacc tgcaggcatg cccgctgaaa tcaccagtct ctctctacaa atctatctct     420
ctctataata atgtgtgagt agttcccaga taagggaatt agggttctta tagggtttcg    480
ctcatgtgtt gagcatataa gaaaccctta gtatgtattt gtatttgtaa aatacttcta    540
tcaataaaat ttctaattcc taaaaccaaa atccagggcg agctcgaatt cgagctcgag    600
cccgggtgga tcctctagag tcgacctgca gaagcttcgg tccggcgcgc ctctagttga    660
agacacgttc atgtcttcat cgtaagaaga cactcagtag                           700
```

INIR6 TRANSGENIC MAIZE

REFERENCE TO SEQUENCE LISTING SUBMITTED ELECTRONICALLY

The sequence listing contained in the file named "10086WO1_ST25.txt", which was created on Aug. 2, 2021 and electronically filed herewith, is incorporated herein by reference in its entirety.

BACKGROUND

Transgenes which are placed into different positions in the plant genome through non-site specific integration can exhibit different levels of expression (Weising et al., 1988, Ann. Rev. Genet. 22:421-477). Such transgene insertion sites can also contain various undesirable rearrangements of the foreign DNA elements that include deletions and/or duplications. Furthermore, many transgene insertion sites can also comprise selectable or scoreable marker genes which in some instances are no longer required once a transgenic plant event containing the linked transgenes which confer desirable traits are selected.

Commercial transgenic plants typically comprise one or more independent insertions of transgenes at specific locations in the host plant genome that have been selected for features that include expression of the transgene(s) of interest and the transgene-conferred trait(s), absence or minimization of rearrangements, and normal Mendelian transmission of the trait(s) to progeny. An examples of a selected transgenic corn event which confers lepidopteran and coleopteran insect pest tolerance is the DP-4114 transgenic maize event disclosed in U.S. Pat. No. 8,575,434. DP-4114 transgenic maize plants express a Cry1F protein which can confer resistance to European corn borer (ECB, *Ostrinia nubilalis*) infestations as well as cry34Ab1 and cry35Ab1 proteins which can confer resistance to corn rootworm (CRW; *Diabrotica* sp. Including *Diabrotica virgifera virgifera*) infestations. DP-4114 transgenic maize plants also express a phosphinotricin acetyl transferase (PAT) protein which confers tolerance to the herbicide glufosinate.

Methods for removing selectable marker genes and/or duplicated transgenes in transgene insertion sites in plant genomes involving use of site-specific recombinase systems (e.g., cre-lox) as well as for insertion of new genes into transgene insertion sites have been disclosed (Srivastava and Ow; Methods Mol Biol, 2015, 1287:95-103; Dale and Ow, 1991, *Proc. Natl Acad. Sci. USA* 88, 10558-10562; Srivastava and Thomson, Plant Biotechnol J, 2016; 14(2):471-82). Such methods typically require incorporation of the recombination site sequences recognized by the recombinase at particular locations within the transgene.

SUMMARY

Transgenic maize plant cells comprising an INIR6 transgenic locus comprising an originator guide RNA recognition site (OgRRS) in a first DNA junction polynucleotide of a DP-4114 transgenic locus and a cognate guide RNA recognition site (CgRRS) in a second DNA junction polynucleotide of the DP-4114 transgenic locus are provided. Transgenic maize plant cells comprising an INIR6 transgenic locus comprising an insertion and/or substitution in a DNA junction polynucleotide of a DP-4114 transgenic locus of DNA comprising a cognate guide RNA recognition site (CgRRS) are provided. In certain embodiments, the DP-4114 transgenic locus is set forth in SEQ ID NO:1, is present in seed deposited at the ATCC under accession No. PTA-11506 is present in progeny thereof, is present in allelic variants thereof, or is present in other variants thereof. INIR6 transgenic maize plant cells, transgenic maize plant seeds, and transgenic maize plants all comprising a transgenic locus set forth in SEQ ID NO: 2, 3, 20, 22, 23, 25, 26, 29, 30, 31, or an allelic variant thereof are provided. Transgenic maize plant parts including seeds and transgenic maize plants comprising the maize plant cells are also provided.

Methods for obtaining a bulked population of inbred seed comprising selfing the aforementioned transgenic maize plants and harvesting seed comprising the INIR6 transgenic locus from the selfed maize plant are also provided.

Methods of obtaining hybrid maize seed comprising crossing the aforementioned transgenic maize plants to a second maize plant which is genetically distinct from the first maize plant and harvesting seed comprising the INIR6 transgenic locus from the cross are provided. Methods for obtaining a bulked population of seed comprising selfing a transgenic maize plant of comprising SEQ ID NO: 2, 3, 20, 22, 23, 25, 26, 29, 30, 31, or an allelic variant thereof and harvesting transgenic seed comprising the transgenic locus set forth in SEQ ID NO: 2, 3, 20, 22, 23, 25, 26, 29, 30, 31, or an allelic variant thereof are provided.

A DNA molecule comprising SEQ ID NO: 2, 3, 8, 9, 10, 19, 20, 22, 23, 25, 26, 27, 29, 30, 31, 32-35, or an allelic variant thereof is provided. Processed transgenic maize plant products and biological samples comprising the DNA molecules are provided. Nucleic acid molecules adapted for detection of genomic DNA comprising the DNA molecules, wherein said nucleic acid molecule optionally comprises a detectable label are provided. Methods of detecting a maize plant cell comprising an INIR6 transgenic locus comprising the step of detecting a DNA molecule comprising SEQ ID NO: 2, 3, 8, 9, 10, 19, 20, 22, 23, 25, 26, 27, 29, 30, 31, 32-35, or an allelic variant thereof are provided.

Methods of excising the INIR6 transgenic locus from the genome of the aforementioned maize plant cells comprising the steps of: (a) contacting the INIR6 transgenic locus comprising the OgRRS and the CgRRS with: (i) an RNA dependent DNA endonuclease (RdDe); and (ii) a guide RNA (gRNA) capable of hybridizing to the guide RNA hybridization site of the OgRRS and the CgRRS; wherein the RdDe recognizes a OgRRS/gRNA and a CgRRS/gRNA hybridization complex; and, (b) selecting a transgenic plant cell, transgenic plant part, or transgenic plant wherein the INIR6 transgenic locus flanked by the OgRRS and the CgRRS has been excised.

BRIEF DESCRIPTION OF THE DRAWINGS/FIGURES

The patent or application file contains at least one drawing executed in color. Copies of this patent or patent application publication with color drawing(s) will be provided by the Office upon request and payment of the necessary fee.

FIG. 1 shows a diagram of transgene expression cassettes and selectable markers in the DP-4114 transgenic locus. Nucleotides 1-2422 of SEQ ID NO: 1 are 5' flanking plant genomic DNA sequence, nucleotides 2423 to 14347 of SEQ ID NO: 1 are transgenic insert DNA sequence, and nucleotides 14348 to 16752 of SEQ ID NO: 1 are 3' plant genome flanking DNA sequence of the DP-4114 transgenic locus.

Figure 2:
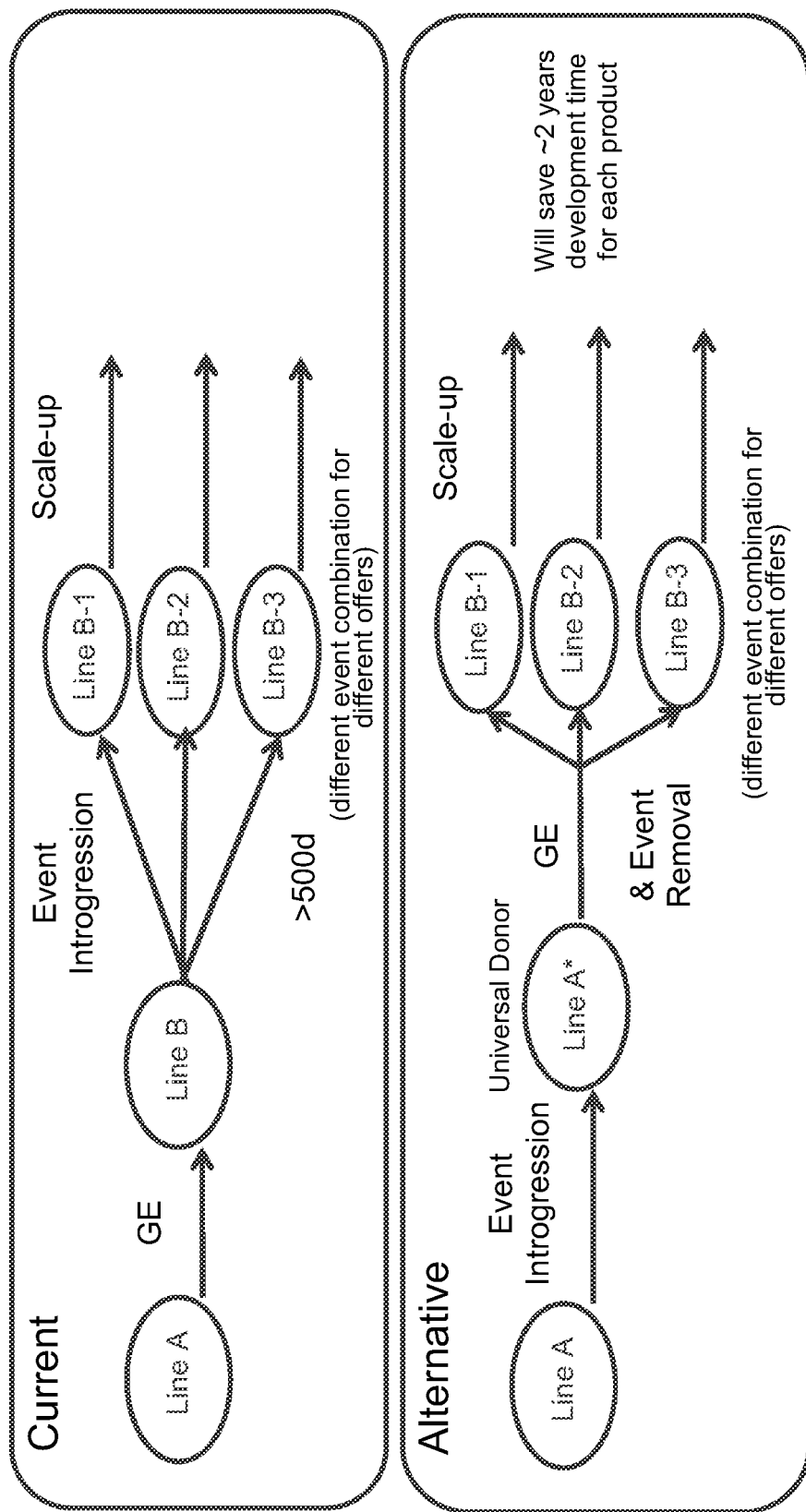

FIG. 2 shows a schematic diagram which compares current breeding strategies for introgression of transgenic events (i.e., transgenic loci) to alternative breeding strategies for introgression of transgenic events where the transgenic events (i.e., transgenic loci) can be removed following introgression to provide different combinations of transgenic traits. In FIG. 2, "GE" refers to genome editing (e.g., including introduction of targeted genetic changes with genome editing molecules and "Event Removal" refers to excision of a transgenic locus (i.e., an "Event") with genome editing molecules.

Figure 3B:
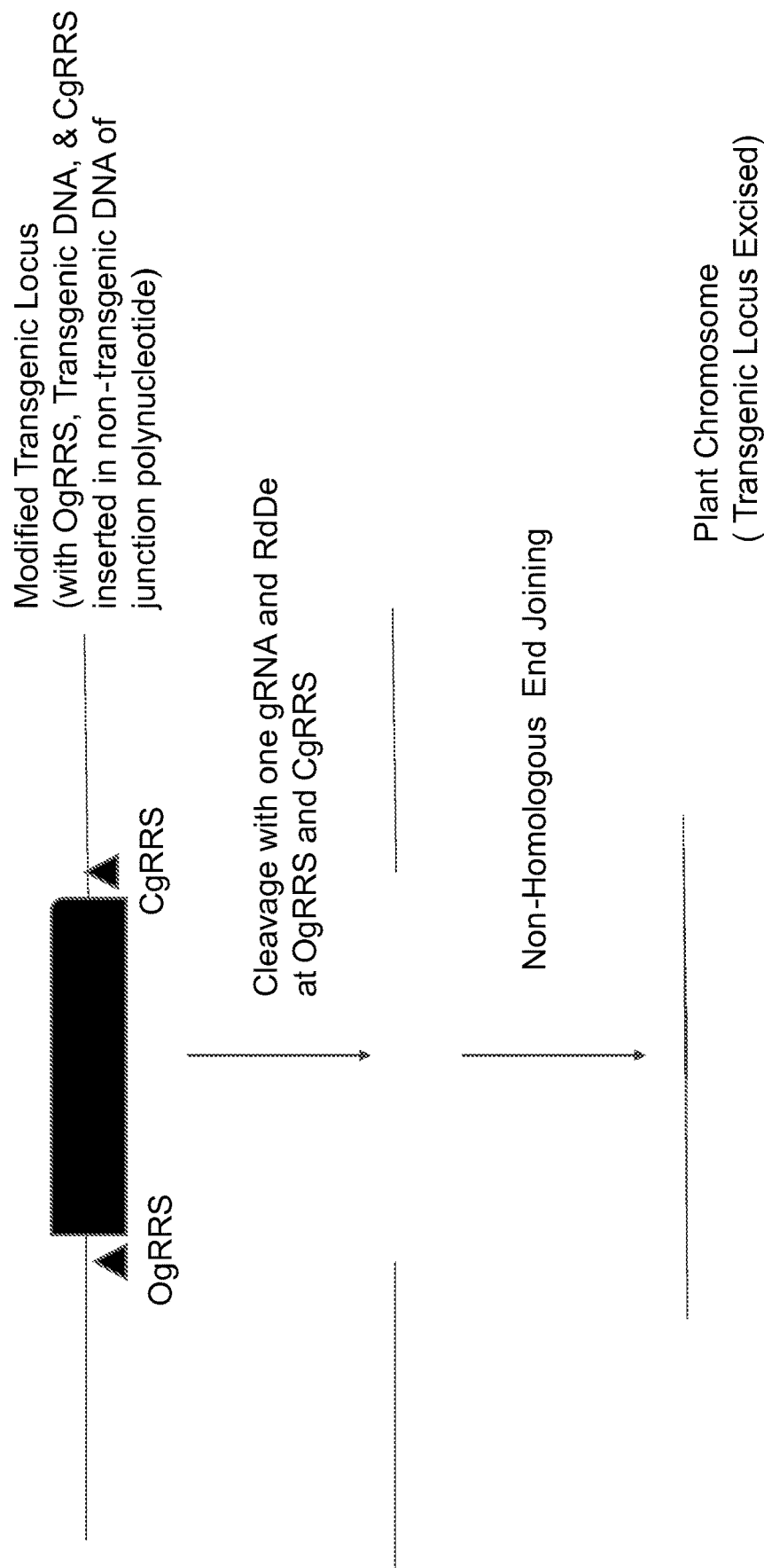
Figure 3C:
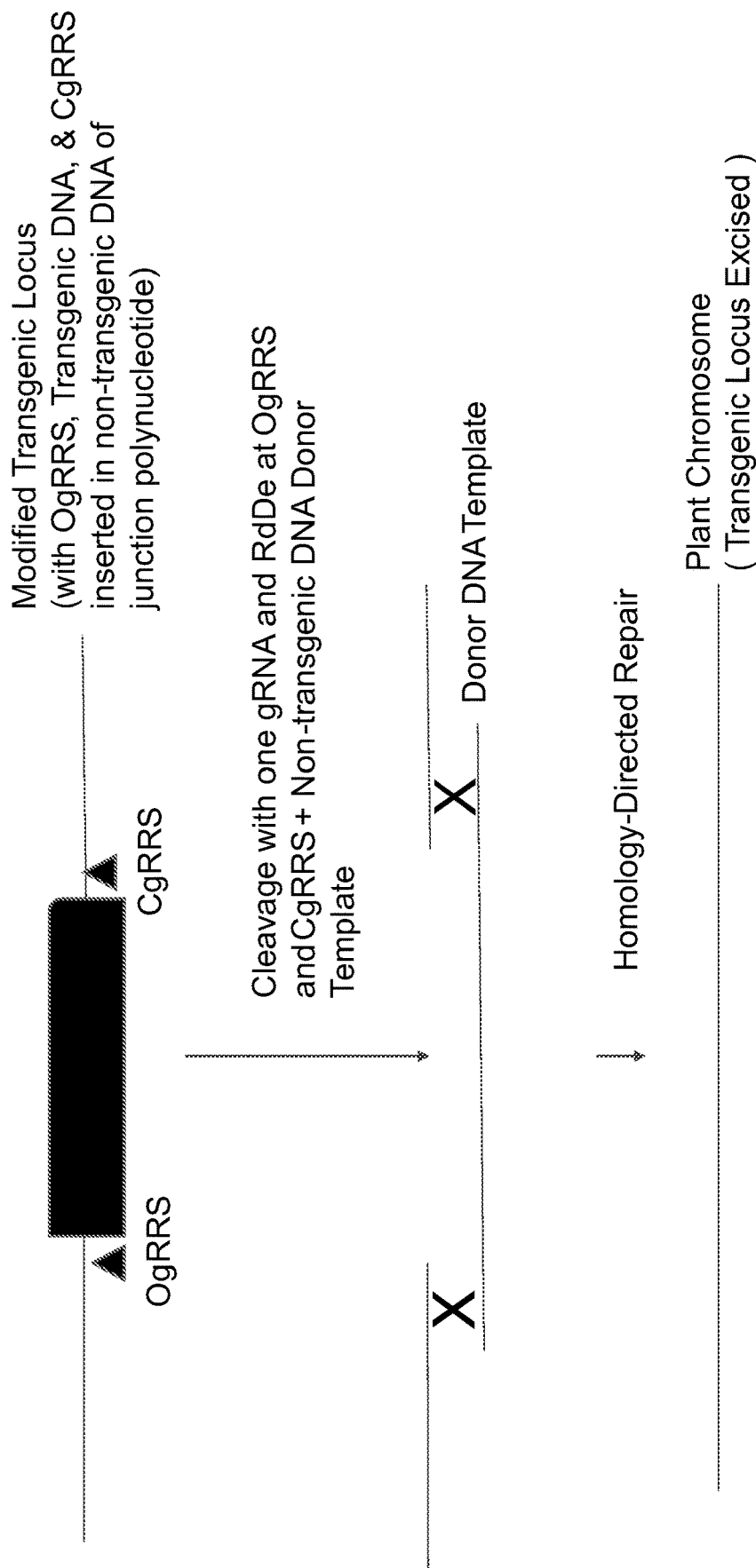

FIG. 3A, B, C. FIG. 3A shows a schematic diagram of a non-limiting example of: (i) an untransformed plant chromosome containing non-transgenic DNA which includes the originator guide RNA recognition site (OgRRS) (top); (ii) the original transgenic locus with the OgRRS in the non-transgenic DNA of the $1^{st}$ junction polynucleotide (middle); and (iii) the modified transgenic locus with a cognate guide RNA inserted into the non-transgenic DNA of the $2^{nd}$ junction polynucleotide (bottom). FIG. 3B shows a schematic diagram of a non-limiting example of a process where a modified transgenic locus with a cognate guide RNA inserted into the non-transgenic DNA of the $2^{nd}$ junction polynucleotide (top) is subjected to cleavage at the OgRRS and CgRRS with one guide RNA (gRNA) that hybridizes to gRNA hybridization site in both the OgRRS and the CgRRS and an RNA dependent DNA endonuclease (RdDe) that recognizes and cleaves the gRNA/OgRRS and the gRNA/CgRRS complex followed by non-homologous end joining processes to provide a plant chromosome where the transgenic locus is excised. FIG. 3C shows a schematic diagram of a non-limiting example of a process where a modified transgenic locus with a cognate guide RNA inserted into the non-transgenic DNA of the $2^{nd}$ junction polynucleotide (top) is subjected to cleavage at the OgRRS and CgRRS with one guide RNA (gRNA) that hybridizes to the gRNA hybridization site in both the OgRRS and the CgRRS and an RNA dependent DNA endonuclease (RdDe) that recognizes and cleaves the gRNA/OgRRS and the gRNA/CgRRS complex in the presence of a donor DNA template. In FIG. 3C, cleavage of the modified transgenic locus in the presence of the donor DNA template which has homology to non-transgenic DNA but lacks the OgRRS in the $1^{st}$ and 2nd junction polynucleotides followed by homology-directed repair processes to provide a plant chromosome where the transgenic locus is excised and non-transgenic DNA present in the untransformed plant chromosome is at least partially restored.

DETAILED DESCRIPTION

Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as well as necessarily defines the exact complements, as is known to one of ordinary skill in the art.

Where a term is provided in the singular, the inventors also contemplate embodiments described by the plural of that term.

The term "about" as used herein means a value or range of values which would be understood as an equivalent of a stated value and can be greater or lesser than the value or range of values stated by 10 percent. Each value or range of values preceded by the term "about" is also intended to encompass the embodiment of the stated absolute value or range of values.

The phrase "allelic variant" as used herein refers to a polynucleotide or polypeptide sequence variant that occurs in a different strain, variety, or isolate of a given organism.

The term "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the phrase "approved transgenic locus" is a genetically modified plant event which has been authorized, approved, and/or de-regulated for any one of field testing, cultivation, human consumption, animal consumption, and/or import by a governmental body. Illustrative and non-limiting examples of governmental bodies which provide such approvals include the Ministry of Agriculture of Argentina, Food Standards Australia New Zealand, National Biosafety Technical Committee (CTNBio) of Brazil, Canadian Food Inspection Agency, China Ministry of Agriculture Biosafety Network, European Food Safety Authority, US Department of Agriculture, US Department of Environmental Protection, and US Food and Drug Administration.

The term "backcross", as used herein, refers to crossing an F1 plant or plants with one of the original parents. A backcross is used to maintain or establish the identity of one parent (species) and to incorporate a particular trait from a second parent (species). The term "backcross generation", as used herein, refers to the offspring of a backcross.

As used herein, the phrase "biological sample" refers to either intact or non-intact (e.g., milled seed or plant tissue, chopped plant tissue, lyophilized tissue) plant tissue. It may also be an extract comprising intact or non-intact seed or plant tissue. The biological sample can comprise flour, meal, syrup, oil, starch, and cereals manufactured in whole or in part to contain crop plant by-products. In certain embodiments, the biological sample is "non-regenerable" (i.e., incapable of being regenerated into a plant or plant part). In certain embodiments, the biological sample refers to a homogenate, an extract, or any fraction thereof containing genomic DNA of the organism from which the biological sample was obtained, wherein the biological sample does not comprise living cells.

As used herein, the terms "correspond," "corresponding," and the like, when used in the context of an nucleotide position, mutation, and/or substitution in any given polynucleotide (e.g., an allelic variant of SEQ ID NO: 1) with respect to the reference polynucleotide sequence (e.g., SEQ ID NO: 1) all refer to the position of the polynucleotide residue in the given sequence that has identity to the residue in the reference nucleotide sequence when the given polynucleotide is aligned to the reference polynucleotide sequence using a pairwise alignment algorithm (e.g., CLUSTAL O 1.2.4 with default parameters).

As used herein, the terms "Cpf1" and "Cas12a" are used interchangeably to refer to the same RNA dependent DNA endonuclease (RdDe). A Cas12a protein provided herein includes the protein of SEQ ID NO: 21.

The term "crossing" as used herein refers to the fertilization of female plants (or gametes) by male plants (or gametes). The term "gamete" refers to the haploid reproductive cell (egg or pollen) produced in plants by meiosis from a gametophyte and involved in sexual reproduction, during which two gametes of opposite sex fuse to form a diploid zygote. The term generally includes reference to a pollen (including the sperm cell) and an ovule (including the ovum). When referring to crossing in the context of achieving the introgression of a genomic region or segment, the skilled person will understand that in order to achieve the introgression of only a part of a chromosome of one plant into the chromosome of another plant, random portions of the genomes of both parental lines recombine during the cross due to the occurrence of crossing-over events in the production of the gametes in the parent lines. Therefore, the genomes of both parents must be combined in a single cell by a cross, where after the production of gametes from the cell and their fusion in fertilization will result in an introgression event.

As used herein, the phrases "DNA junction polynucleotide" and "junction polynucleotide" refers to a polynucleotide of about 18 to about 500 base pairs in length comprised of both endogenous chromosomal DNA of the plant genome and heterologous transgenic DNA which is inserted in the plant genome. A junction polynucleotide can thus comprise about 8, 10, 20, 50, 100, 200, 250, 500, or 1000 base pairs of endogenous chromosomal DNA of the plant genome and about 8, 10, 20, 50, 100, 200, 250, 500, or 1000 base pairs of heterologous transgenic DNA which span the one end of the transgene insertion site in the plant chromosomal DNA. Transgene insertion sites in chromosomes will typically contain both a 5' junction polynucleotide and a 3' junction polynucleotide. In embodiments set forth herein in SEQ ID NO: 1, the 5' junction polynucleotide is located at the 5' end of the sequence and the 3' junction polynucleotide is located at the 3' end of the sequence. In a non-limiting and illustrative example, a 5' junction polynucleotide of a transgenic locus is telomere proximal in a chromosome arm and the 3' junction polynucleotide of the transgenic locus is centromere proximal in the same chromosome arm. In another non-limiting and illustrative example, a 5' junction polynucleotide of a transgenic locus is centromere proximal in a chromosome arm and the 3' junction polynucleotide of the transgenic locus is telomere proximal in the same chromosome arm. The junction polynucleotide which is telomere proximal and the junction polynucleotide which is centromere proximal can be determined by comparing non-transgenic genomic sequence of a sequenced non-transgenic plant genome to the non-transgenic DNA in the junction polynucleotides.

The term "donor," as used herein in the context of a plant, refers to the plant or plant line from which the trait, transgenic event, or genomic segment originates, wherein the donor can have the trait, introgression, or genomic segment in either a heterozygous or homozygous state.

As used herein, the term "DP-4114" is used to refer to any of a transgenic maize locus, transgenic maize plants and parts thereof including seed set forth in U.S. Pat. No. 8,575,434, which is incorporated herein by reference in its entirety. Representative DP-4114 transgenic maize seed have been deposited with American Type Culture Collection (ATCC, Manassas, Va. 20110-2209 USA) under Accession No. PTA-11506. DP-4114 transgenic loci include loci having the sequence of SEQ ID NO:1, the sequence of the DP-4114 locus in the deposited seed of Accession No. PTA-11506 and any progeny thereof, as well as allelic variants and other variants of SEQ ID NO:1

As used herein, the terms "excise" and "delete," when used in the context of a DNA molecule, are used interchangeably to refer to the removal of a given DNA segment or element (e.g., transgene element or transgenic locus or portion thereof) of the DNA molecule.

As used herein, the phrase "elite crop plant" refers to a plant which has undergone breeding to provide one or more trait improvements. Elite crop plant lines include plants which are an essentially homozygous, e.g., inbred or doubled haploid. Elite crop plants can include inbred lines used as is or used as pollen donors or pollen recipients in hybrid seed production (e.g., used to produce F1 plants). Elite crop plants can include inbred lines which are selfed to produce non-hybrid cultivars or varieties or to produce (e.g., bulk up) pollen donor or recipient lines for hybrid seed production. Elite crop plants can include hybrid F1 progeny of a cross between two distinct elite inbred or doubled haploid plant lines.

As used herein, an "event," "a transgenic event," "a transgenic locus" and related phrases refer to an insertion of one or more transgenes at a unique site in the genome of a plant as well as to DNA fragments, plant cells, plants, and plant parts (e.g., seeds) comprising genomic DNA containing the transgene insertion. Such events typically comprise both a 5' and a 3' DNA junction polynucleotide and confer one or more useful traits including herbicide tolerance, insect resistance, male sterility, and the like.

As used herein, the phrases "endogenous sequence," "endogenous gene," "endogenous DNA," "endogenous polynucleotide," and the like refer to the native form of a polynucleotide, gene or polypeptide in its natural location in the organism or in the genome of an organism.

The terms "exogenous" and "heterologous" as are used synonymously herein to refer to any polynucleotide (e.g., DNA molecule) that has been inserted into a new location in the genome of a plant. Non-limiting examples of an exogenous or heterologous DNA molecule include a synthetic DNA molecule, a non-naturally occurring DNA molecule, a DNA molecule found in another species, a DNA molecule found in a different location in the same species, and/or a DNA molecule found in the same strain or isolate of a species, where the DNA molecule has been inserted into a new location in the genome of a plant.

As used herein, the term "F1" refers to any offspring of a cross between two genetically unlike individuals.

The term "gene," as used herein, refers to a hereditary unit consisting of a sequence of DNA that occupies a specific location on a chromosome and that contains the genetic instruction for a particular characteristics or trait in an organism. The term "gene" thus includes a nucleic acid (for example, DNA or RNA) sequence that comprises coding sequences necessary for the production of an RNA, or a polypeptide or its precursor. A functional polypeptide can be encoded by a full length coding sequence or by any portion of the coding sequence as long as the desired activity or functional properties (e.g., enzymatic activity, pesticidal activity, ligand binding, and/or signal transduction) of the RNA or polypeptide are retained.

The term "identifying," as used herein with respect to a plant, refers to a process of establishing the identity or distinguishing character of a plant, including exhibiting a certain trait, containing one or more transgenes, and/or containing one or more molecular markers.

As used herein, the term "INIR6" is used to refer either individually collectively to items that include any or all of the DP-4114 transgenic maize loci which have been modified as disclosed herein, modified DP-4114 transgenic maize plants and parts thereof including seed, and DNA obtained therefrom.

The term "isolated" as used herein means having been removed from its natural environment.

As used herein, the terms "include," "includes," and "including" are to be construed as at least having the features to which they refer while not excluding any additional unspecified features.

As used herein, the phrase "introduced transgene" is a transgene not present in the original transgenic locus in the genome of an initial transgenic event or in the genome of a progeny line obtained from the initial transgenic event. Examples of introduced transgenes include exogenous transgenes which are inserted in a resident original transgenic locus.

As used herein, the terms "introgression", "introgressed" and "introgressing" refer to both a natural and artificial process, and the resulting plants, whereby traits, genes or DNA sequences of one species, variety or cultivar are moved into the genome of another species, variety or cultivar, by crossing those species. The process may optionally be completed by backcrossing to the recurrent parent. Examples of introgression include entry or introduction of a gene, a transgene, a regulatory element, a marker, a trait, a trait locus, or a chromosomal segment from the genome of one plant into the genome of another plant.

The phrase "marker-assisted selection", as used herein, refers to the diagnostic process of identifying, optionally followed by selecting a plant from a group of plants using the presence of a molecular marker as the diagnostic characteristic or selection criterion. The process usually involves detecting the presence of a certain nucleic acid sequence or polymorphism in the genome of a plant.

The phrase "molecular marker", as used herein, refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), microsatellite markers (e.g. SSRs), sequence-characterized amplified region (SCAR) markers, Next Generation Sequencing (NGS) of a molecular marker, cleaved amplified polymorphic sequence (CAPS) markers or isozyme markers or combinations of the markers described herein which defines a specific genetic and chromosomal location.

As used herein the terms "native" or "natural" define a condition found in nature. A "native DNA sequence" is a DNA sequence present in nature that was produced by natural means or traditional breeding techniques but not generated by genetic engineering (e.g., using molecular biology/transformation techniques).

The term "offspring", as used herein, refers to any progeny generation resulting from crossing, selfing, or other propagation technique.

The phrase "operably linked" refers to a juxtaposition wherein the components so described are in a relationship permitting them to function in their intended manner. For instance, a promoter is operably linked to a coding sequence if the promoter affects its transcription or expression. When the phrase "operably linked" is used in the context of a PAM site and a guide RNA hybridization site, it refers to a PAM site which permits cleavage of at least one strand of DNA in a polynucleotide with an RNA dependent DNA endonuclease or RNA dependent DNA nickase which recognize the PAM site when a guide RNA complementary to guide RNA hybridization site sequences adjacent to the PAM site is present. A OgRRS and its CgRRS are operably linked to junction polynucleotides when they can be recognized by a gRNA and an RdDe to provide for excision of the transgenic locus or portion thereof flanked by the junction polynucleotides.

As used herein, the term "plant" includes a whole plant and any descendant, cell, tissue, or part of a plant. The term "plant parts" include any part(s) of a plant, including, for example and without limitation: seed (including mature seed and immature seed); a plant cutting; a plant cell; a plant cell culture; or a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. Regenerable cells in a plant cell or tissue culture may be embryos, protoplasts, meristematic cells, callus, pollen, leaves, anthers, roots, root tips, silk, flowers, kernels, ears, cobs, husks, or stalks. In contrast, some plant cells are not capable of being regenerated to produce plants and are referred to herein as "non-regenerable" plant cells.

The term "purified," as used herein defines an isolation of a molecule or compound in a form that is substantially free of contaminants normally associated with the molecule or compound in a native or natural environment and means having been increased in purity as a result of being separated from other components of the original composition. The term "purified nucleic acid" is used herein to describe a nucleic acid sequence which has been separated from other compounds including, but not limited to polypeptides, lipids and carbohydrates.

The term "recipient", as used herein, refers to the plant or plant line receiving the trait, transgenic event or genomic segment from a donor, and which recipient may or may not have the have trait, transgenic event or genomic segment itself either in a heterozygous or homozygous state.

As used herein the term "recurrent parent" or "recurrent plant" describes an elite line that is the recipient plant line in a cross and which will be used as the parent line for successive backcrosses to produce the final desired line.

As used herein the term "recurrent parent percentage" relates to the percentage that a backcross progeny plant is identical to the recurrent parent plant used in the backcross. The percent identity to the recurrent parent can be determined experimentally by measuring genetic markers such as SNPs and/or RFLPs or can be calculated theoretically based on a mathematical formula.

The terms "selfed," "selfing," and "self," as used herein, refer to any process used to obtain progeny from the same plant or plant line as well as to plants resulting from the process. As used herein, the terms thus include any fertilization process wherein both the ovule and pollen are from the same plant or plant line and plants resulting therefrom. Typically, the terms refer to self-pollination processes and progeny plants resulting from self-pollination.

The term "selecting", as used herein, refers to a process of picking out a certain individual plant from a group of individuals, usually based on a certain identity, trait, characteristic, and/or molecular marker of that individual.

As used herein, the phrase "originator guide RNA recognition site" or the acronym "OgRRS" refers to an endogenous DNA polynucleotide comprising a protospacer adjacent motif (PAM) site operably linked to a guide RNA hybridization site. In certain embodiments, an OgRRS can be located in an untransformed plant chromosome or in non-transgenic DNA of a DNA junction polynucleotide of both an original transgenic locus and a modified transgenic locus. In certain embodiments, an OgRRS can be located in transgenic DNA of a DNA junction polynucleotide of both an original transgenic locus and a modified transgenic locus. In certain embodiments, an OgRRS can be located in both transgenic DNA and non-transgenic DNA of a DNA junction polynucleotide of both an original transgenic locus and a modified transgenic locus (i.e., can span transgenic and non-transgenic DNA in a DNA junction polynucleotide).

As used herein the phrase "cognate guide RNA recognition site" or the acronym "CgRRS" refer to a DNA polynucleotide comprising a PAM site operably linked to a guide RNA hybridization site, where the CgRRS is absent from transgenic plant genomes comprising a first original transgenic locus that is unmodified and where the CgRRS and its corresponding OgRRS can hybridize to a single gRNA. A CgRRS can be located in transgenic DNA of a DNA junction polynucleotide of a modified transgenic locus, in transgenic DNA of a DNA junction polynucleotide of a modified transgenic locus, or in both transgenic and non-transgenic DNA of a modified transgenic locus (i.e., can span transgenic and non-transgenic DNA in a DNA junction polynucleotide).

As used herein, the phrase "a transgenic locus excision site" refers to the DNA which remains in the genome of a plant or in a DNA molecule (e.g., an isolated or purified DNA molecule) wherein a segment comprising, consisting essentially of, or consisting of a transgenic locus has been deleted. In a non-limiting and illustrative example, a transgenic locus excision site can thus comprise a contiguous segment of DNA comprising at least 10 base pairs of DNA that is telomere proximal to the deleted transgenic locus or to the deleted segment of the transgenic locus and at least 10 base pairs of DNA that is centromere proximal to the deleted transgenic locus or to the deleted segment of the transgenic locus.

As used herein, the phrase "transgene element" refers to a segment of DNA comprising, consisting essentially of, or consisting of a promoter, a 5' UTR, an intron, a coding region, a 3'UTR, or a polyadenylation signal. Polyadenylation signals include transgene elements referred to as "terminators" (e.g., NOS, pinII, rbcs, Hsp17, TubA).

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

Genome editing molecules can permit introduction of targeted genetic change conferring desirable traits in a variety of crop plants (Zhang et al. Genome Biol. 2018; 19: 210; Schindele et al. FEBS Lett. 2018; 592(12):1954). Desirable traits introduced into crop plants such as maize and soybean include herbicide tolerance, improved food and/or feed characteristics, male-sterility, and drought stress tolerance. Nonetheless, full realization of the potential of genome editing methods for crop improvement will entail efficient incorporation of the targeted genetic changes in germplasm of different elite crop plants adapted for distinct growing conditions. Such elite crop plants will also desirably comprise useful transgenic loci which confer various traits including herbicide tolerance, pest resistance (e.g.; insect, nematode, fungal disease, and bacterial disease resistance), conditional male sterility systems for hybrid seed production, abiotic stress tolerance (e.g., drought tolerance), improved food and/or feed quality, and improved industrial use (e.g., biofuel). Provided herein are methods whereby targeted genetic changes are efficiently combined with desired subsets of transgenic loci in elite progeny plant lines (e.g., elite inbreds used for hybrid seed production or for inbred varietal production). Also provided are plant genomes containing modified transgenic loci which can be selectively excised with a single gRNA molecule. Such modified transgenic loci comprise an originator guide RNA recognition site (OgRRS) which is identified in non-transgenic DNA of a first junction polynucleotide of the transgenic locus and cognate guide RNA recognition site (CgRRS) which is introduced (e.g., by genome editing methods) into a second junction polynucleotide of the transgenic locus and which can hybridize to the same gRNA as the OgRRS, thereby permitting excision of the modified transgenic locus with a single guide RNA. An originator guide RNA recognition site (OgRRS) comprises endogenous DNA found in untransformed plants and in endogenous non-transgenic DNA of junction polynucleotides of transgenic plants containing a modified or unmodified transgenic locus. The OgRRS located in non-transgenic DNA of a first DNA junction polynucleotide is used to design a related cognate guide RNA recognition site (CgRRS) which is introduced (e.g., by genome editing methods) into the second junction polynucleotide of the transgenic locus. A CgRRS is thus present in junction polynucleotides of modified transgenic loci provided herein and is absent from endogenous DNA found in untransformed plants and absent from endogenous non-transgenic DNA found in junction sequences of transgenic plants containing an unmodified transgenic locus. Also provided are unique transgenic locus excision sites created by excision of such modified transgenic loci, DNA molecules comprising the modified transgenic loci, unique transgenic locus excision sites and/or plants comprising the same, biological samples containing the DNA, nucleic acid markers adapted for detecting the DNA molecules, and related methods of identifying the elite crop plants comprising unique transgenic locus excision sites.

Also provided herein are methods whereby targeted genetic changes are efficiently combined with desired subsets of transgenic loci in elite progeny plant lines (e.g., elite inbreds used for hybrid seed production or for inbred varietal production). Examples of such methods include those illustrated in FIG. 2. In certain embodiments, INIR6 transgenic loci provided here are characterized by polynucleotide sequences that can facilitate as necessary the removal of the INIR6 transgenic loci from the genome. Useful applications of such INIR6 transgenic loci and related methods of making include targeted excision of a INIR6 transgenic locus or portion thereof in certain breeding lines to facilitate recovery of germplasm with subsets of transgenic traits tailored for specific geographic locations and/or grower preferences. Other useful applications of such INIR6 transgenic loci and related methods of making include removal of transgenic traits from certain breeding lines when it is desirable to replace the trait in the breeding line without disrupting other transgenic loci and/or non-transgenic loci. In certain embodiments, maize genomes containing INIR6 transgenic loci or portions thereof which can be selectively excised with one or more gRNA molecules and RdDe (RNA dependent DNA endonucleases) which form gRNA/target DNA complexes. Such selectively excisable INIR6 transgenic loci can comprise an originator guide RNA recognition site (OgRRS) which is identified in non-transgenic DNA, transgenic DNA, or a combination thereof in of a first junction polynucleotide of the transgenic locus and cognate guide RNA recognition site (CgRRS) which is introduced (e.g., by genome editing methods) into a second junction polynucleotide of the transgenic locus and which can hybridize to the same gRNA as the OgRRS, thereby permitting excision of the modified transgenic locus or portions thereof with a single guide RNA (e.g., as shown in FIGS. 3A and B). In certain embodiments, an originator guide RNA recognition site (OgRRS) comprises endogenous DNA found in untransformed plants and in endogenous non-transgenic DNA of junction polynucleotides of transgenic plants containing a modified or unmodified transgenic locus. In certain embodiments, an originator guide RNA recognition site (OgRRS) comprises exogenous transgenic DNA of junction polynucleotides of transgenic plants containing a modified or unmodified transgenic locus. The OgRRS located in non-transgenic DNA transgenic DNA, or a combination thereof in of a first DNA junction polynucleotide is used to design a related cognate guide RNA recognition site (CgRRS) which is introduced (e.g., by genome editing methods) into the second junction polynucleotide of the transgenic locus. A CgRRS is thus present in junction polynucleotides of modified transgenic loci provided herein and is absent from endogenous DNA found in untransformed plants and absent from junction sequences of transgenic plants containing an unmodified transgenic locus. A CgRRS is also absent from a combination of non-transgenic and transgenic DNA found in junction sequences of transgenic plants containing an unmodified transgenic locus. Examples of OgRRS polynucleotide sequences in or near a 5' junction polynucleotide in an DP-4114 transgenic locus include SEQ ID NO: 7. OgRRS polynucleotide sequences located in a first junction polynucleotide can be introduced into the second junction polynucleotide using donor DNA templates as illustrated in FIG. 3C and as elsewhere described herein. A donor DNA template for introducing the SEQ ID NO: 7 OgRRS into the 3' junction polynucleotide of an DP-4114 locus includes the donor DNA template formed by annealing SEQ ID NO: 11 and 12 or by annealing SEQ ID NO: 11 and 13. Double stranded breaks in a 3' junction polynucleotide of SEQ ID NO: 1 can be introduced with gRNAs encoded by SEQ ID NO: 4, 5, and/or 6 and a Cas12a nuclease. Integration of the SEQ ID NO: 11/12 or 11/13 donor DNA template into the 3' junction polynucleotide of an DP-4114 locus at the double stranded breaks introduced by the gRNAs encoded by SEQ ID NO: 4, 5, and/or 6 and a Cas12a nuclease can provide an INIR6 locus comprising the CgRRS sequence set forth in SEQ ID NO: 8, 9, or 10. Double stranded breaks in a 3' junction polynucleotide of SEQ ID NO: 1 can be introduced with gRNAs encoded by SEQ ID NO: 4, 5, and/or 6. Another donor DNA template adapted for insertion of the OgRRS of SEQ ID NO: 7 in a 3' junction polynucleotide of a DP-4114 transgenic locus can comprise SEQ ID NO: 14. Double stranded breaks in a 3' junction polynucleotide of SEQ ID NO: 1 can be introduced with gRNAs encoded by SEQ ID NO: 5 and a Cas12a nuclease. A donor DNA template of SEQ ID NO: 14 or the equivalent thereof having longer or shorter homology arms can be used to obtain the CgRRS insertion in the 3' junction polynucleotide that is set forth in SEQ ID NO: 19. An INIR6 transgenic locus containing this CgRRS insertion is set forth in SEQ ID NO: 20. In certain embodiments, an INIR6 transgenic locus can comprise any of the aforementioned CgRRS insertions as well as a deletion of either: (i) the PAT selectable marker cassette and optionally the 3' junction polynucleotide (e.g., as in SEQ ID NO: 25); or (ii) DNA comprising, consisting essentially of, or consisting of the CaMV35S promoter and operably linked PAT coding region while retaining the CaMV35S terminator element of the DP-4114 locus (e.g., as in SEQ ID NO: 29). Double stranded breaks which delete the PAT selectable marker cassette and a 3' junction polynucleotide of SEQ ID NO: 1 can be introduced with gRNAs encoded by SEQ ID NO: 4 (guide RNA-1) and SEQ ID NO: 24 (guide RNA-4) and a Cas12a nuclease. A donor DNA template of SEQ ID NO: 27 or the equivalent thereof having longer or shorter homology arms can be used to obtain the INIR6 transgenic locus comprising the deletion of the PAT selectable marker cassette and a 3' junction polynucleotide and the CgRRS insertion that is set forth in SEQ ID NO: 26. A donor DNA template of SEQ ID NO: 27 or the equivalent thereof having longer or shorter homology arms can be used to obtain the INIR6 transgenic locus comprising the deletion of the PAT selectable marker cassette and a 3' junction polynucleotide and the CgRRS insertion that is set forth in SEQ ID NO: 26.

Also provided herein are allelic variants of any of the INIR6 transgenic loci or DNA molecules provided herein. In certain embodiments, such allelic variants of INIR6 transgenic loci include sequences having at least 85%, 90%, 95%, 98%, or 99% sequence identity across the entire length or at least 20, 40, 100, 500, 1,000, 2,000, 4,000, 6,000, 8,000, 9,000, 10,000, 12,000, 14,000, 16,000, or 16,752 nucleotides of SEQ ID NO: 2, 3, 20, 22, 23, 25, 26, 29, 30, or 31. In certain embodiments, such allelic variants of INIR6 DNA molecules include sequences having at least 85%, 90%, 95%, 98%, or 99% sequence identity across the entire length of SEQ ID NO: 2, 3, 8, 9, 10, 19, 20, 22, 23, 25, 26, 27, 29, 30, 31, or 32-35.

Also provided are unique transgenic locus excision sites created by excision of INIR6 transgenic loci or selectively excisable INIR6 transgenic loci, DNA molecules comprising the INIR6 transgenic loci or unique fragments thereof (i.e., fragments of an INIR6 locus which are not found in an DP-4114 transgenic locus). INIR6 plants comprising the same, biological samples containing the DNA, nucleic acid markers adapted for detecting the DNA molecules, and related methods of identifying maize plants comprising unique INIR6 transgenic locus excision sites and unique fragments of a INIR6 transgenic locus. DNA molecules comprising unique fragments of an INIR6 transgenic locus are diagnostic for the presence of an INIR6 transgenic locus or fragments thereof in a maize plant, maize cell, maize seed, products obtained therefrom (e.g., seed meal or stover), and biological samples.

Methods provided herein can be used to excise any transgenic locus where the first and second junction sequences comprising the endogenous non-transgenic genomic DNA and the heterologous transgenic DNA which are joined at the site of transgene insertion in the plant genome are known or have been determined. In certain embodiments provided herein, transgenic loci can be removed from crop plant lines to obtain crop plant lines with tailored combinations of transgenic loci and optionally targeted genetic changes. Such first and second junction sequences are readily identified in new transgenic events by inverse PCR techniques using primers which are complementary the inserted transgenic sequences. In certain embodiments, the first and second junction sequences of transgenic loci are published. An example of a transgenic locus which can be improved and used in the methods provided herein is the maize DP-4114 transgenic locus. The maize DP-4114 transgenic locus and its transgenic junction sequences are also depicted in FIG. 1. Maize plants comprising the DP-4114 transgenic locus and seed thereof have been cultivated, been placed in commerce, and have been described in a variety of publications by various governmental bodies. Databases which have compiled descriptions of the DP-4114 transgenic locus include the International Service for the Acquisition of Agri-biotech Applications (ISAAA) database (available on the world wide web internet site "isaaa.org/gmapprovaldatabase/event"), the GenBit LLC database (available on the world wide web internet site "genbitgroup.com/en/gmo/gmodatabase"), and the Biosafety Clearing-House (BCH) database (available on the http internet site "bch.cbd.int/database/organisms").

Sequences of the junction polynucleotides as well as the transgenic insert(s) of the DP-4114 transgenic locus which can be improved by the methods provided herein are set forth or otherwise provided in SEQ ID NO: 1, U.S. Pat. No. 8,575,434, the sequence of the DP-4114 locus in the deposited seed of ATCC accession No. PTA-11506, and elsewhere in this disclosure. In certain embodiments provided herein, the DP-4114 transgenic locus set forth in SEQ ID NO: 1 or present in the deposited seed of ATCC accession No. PTA-11506 is referred to as an "original DP-4114 transgenic locus." Allelic or other variants of the sequence set forth SEQ ID NO: 1, the patent references set forth therein and incorporated herein by reference in their entireties, and elsewhere in this disclosure which may be present in certain variant DP-4114 transgenic plant loci (e.g., progeny of deposited seed of accession No. PTA-11506 which contain allelic variants of SEQ ID NO:1 or progeny originating from transgenic plant cells comprising the original DP4114 transgenic locus set forth in U.S. Pat. No. 8,575,434) can also be improved by identifying sequences in the variants that correspond to the SEQ ID NO: 1 by performing a pairwise alignment (e.g., using CLUSTAL O 1.2.4 with default parameters) and making corresponding changes in the allelic or other variant sequences. Such allelic or other variant sequences include sequences having at least 85%, 90%, 95%, 98%, or 99% sequence identity across the entire length or at least 20, 40, 100, 500, 1,000, 2,000, 4,000, 8,000, 10,000, 12,000, 14,350, 15,000, or 16,652 nucleotides of SEQ ID NO: 1. Also provided are plants, plant parts including seeds, genomic DNA, and/or DNA obtained from INIR6 plants which comprise one or more modifications (e.g., via insertion of a CgRRS in a junction polynucleotide sequence) which provide for selective excision of the INIR6 transgenic locus or a portion thereof. Also provided herein are methods of detecting plants, genomic DNA, and/or DNA obtained from plants comprising a INIR6 transgenic locus which contains one or more of a CgRRS, deletions of selectable marker genes, deletions of non-essential DNA, and/or a transgenic locus excision site. A first junction polynucleotide of a DP-4114 transgenic locus can comprise either one of the junction polynucleotides found at the 5' end or the 3' end of any one of the sequences set forth in SEQ ID NO: 1, allelic variants thereof, or other variants thereof. In certain embodiments, a 5' junction polynucleotide of a DP-4114 transgenic locus can comprise DNA spanning the plant genomic DNA/transgene insert junction at nucleotides 2422 and 2423 of SEQ ID NO: 1. In certain embodiments, a 3' junction polynucleotide of a DP-4114 transgenic locus can comprise DNA spanning the plant genomic DNA/transgene insert junction at nucleotides 14347 and 14348 of SEQ ID NO: 1. An OgRRS can be found within non-transgenic DNA, transgenic DNA, or a combination thereof in either one of the junction polynucleotides of any one of SEQ ID NO: 1, allelic variants thereof, or other variants thereof. A second junction polynucleotide of a transgenic locus can comprise either one of the junction polynucleotides found at the 5' or 3' end of any one of the sequences set forth in SEQ ID NO: 1, allelic variants thereof, or other variants thereof. A CgRRS can be introduced within transgenic, non-transgenic DNA, or a combination thereof of either one of the junction polynucleotides of any one of SEQ ID NO: 1, allelic variants thereof, or other variants thereof to obtain an INIR6 transgenic locus. In certain embodiments, the OgRRS is found in non-transgenic DNA or transgenic DNA of the 5' junction polynucleotide of a transgenic locus of any one of SEQ ID NO: 1, allelic variants thereof, or other variants thereof and the corresponding CgRRS is introduced into the transgenic DNA, non-transgenic DNA, or a combination thereof in the 3' junction polynucleotide of the DP-4114 transgenic locus of SEQ ID NO: 1, allelic variants thereof, or other variants thereof to obtain an INIR6 transgenic locus. In other embodiments, the OgRRS is found in non-transgenic DNA or transgenic DNA of the 3' junction polynucleotide of the DP-4114 transgenic locus of any one of SEQ ID NO: 1, allelic variants thereof, or other variants thereof and the corresponding CgRRS is introduced into the transgenic DNA, non-transgenic DNA, or a combination thereof in the 5' junction polynucleotide of the transgenic locus of SEQ ID NO: 1, allelic variants thereof, or other variants thereof to obtain an INIR6 transgenic locus.

In certain embodiments, the CgRRS is comprised in whole or in part of an exogenous DNA molecule that is introduced into a DNA junction polynucleotide by genome editing. In certain embodiments, the guide RNA hybridization site of the CgRRS is operably linked to a pre-existing PAM site in the transgenic DNA or non-transgenic DNA of the transgenic plant genome. In other embodiments, the guide RNA hybridization site of the CgRRS is operably linked to a new PAM site that is introduced in the DNA junction polynucleotide by genome editing. A CgRRS can be located in non-transgenic plant genomic DNA of a DNA junction polynucleotide of an INIR6 transgenic locus, in transgenic DNA of a DNA junction polynucleotide of an INIR6 transgenic locus or can span the junction of the transgenic and non-transgenic DNA of a DNA junction polynucleotide of an INIR6 transgenic locus. An OgRRS can likewise be located in non-transgenic plant genomic DNA of a DNA junction polynucleotide of an INIR6 transgenic locus, in transgenic DNA of a DNA junction polynucleotide of an INIR6 transgenic locus, or can span the junction of the transgenic and non-transgenic DNA of a DNA junction polynucleotide of an INIR6 transgenic locus Methods provided herein can be used in a variety of breeding schemes to obtain elite crop plants comprising subsets of desired modified transgenic loci comprising an OgRRS and a CgRRS operably linked to junction polynucleotide sequences and transgenic loci excision sites where undesired transgenic loci or portions thereof have been removed (e.g., by use of the OgRRS and a CgRRS). Such methods are useful at least insofar as they allow for production of distinct useful donor plant lines each having unique sets of modified transgenic loci and, in some instances, targeted genetic changes that are tailored for distinct geographies and/or product offerings. In an illustrative and non-limiting example, a different product lines comprising transgenic loci conferring only two of three types of herbicide tolerance (e.g., glyphosate, glufosinate, and dicamba) can be obtained from a single donor line comprising three distinct transgenic loci conferring resistance to all three herbicides. In certain aspects, plants comprising the subsets of undesired transgenic loci and transgenic loci excision sites can further comprise targeted genetic changes. Such elite crop plants can be inbred plant lines or can be hybrid plant lines. In certain embodiments, at least two transgenic loci (e.g., transgenic loci including an INIR6 and another modified transgenic locus wherein an OgRRS and a CgRRS site is operably linked to a first and a second junction sequence and optionally a selectable marker gene and/or non-essential DNA are deleted) are introgressed into a desired donor line comprising elite crop plant germplasm and then subjected to genome editing molecules to recover plants comprising one of the two introgressed transgenic loci as well as a transgenic loci excision site introduced by excision of the other transgenic locus or portion thereof by the genome editing molecules. In certain embodiments, the genome editing molecules can be used to remove a transgenic locus and introduce targeted genetic changes in the crop plant genome. Introgression can be achieved by backcrossing plants comprising the transgenic loci to a recurrent parent comprising the desired elite germplasm and selecting progeny with the transgenic loci and recurrent parent germplasm. Such backcrosses can be repeated and/or supplemented by molecular assisted breeding techniques using SNP or other nucleic acid markers to select for recurrent parent germplasm until a desired recurrent parent percentage is obtained (e.g., at least about 95%, 96%, 97%, 98%, or 99% recurrent parent percentage). A non-limiting, illustrative depiction of a scheme for obtaining plants with both subsets of transgenic loci and the targeted genetic changes is shown in the FIG. 2 (bottom "Alternative" panel), where two or more of the transgenic loci ("Event" in FIG. 2) are provided in Line A and then moved into elite crop plant germplasm by introgression. In the non-limiting FIG. 2 illustration, introgression can be achieved by crossing a "Line A" comprising two or more of the modified transgenic loci to the elite germplasm and then backcrossing progeny of the cross comprising the transgenic loci to the elite germplasm as the recurrent parent) to obtain a "Universal Donor" (e.g., Line A+ in FIG. 2) comprising two or more of the modified transgenic loci. This elite germplasm containing the modified transgenic loci (e.g., "Universal Donor" of FIG. 2) can then be subjected to genome editing molecules which can excise at least one of the transgenic loci ("Event Removal" in FIG. 2) and introduce other targeted genetic changes ("GE" in FIG. 2) in the genomes of the elite crop plants containing one of the transgenic loci and a transgenic locus excision site corresponding to the removal site of one of the transgenic loci. Such selective excision of transgenic loci or portion thereof can be effected by contacting the genome of the plant comprising two transgenic loci with gene editing molecules (e.g., RdDe and gRNAs, TALENS, and/or ZFN) which recognize one transgenic loci but not another transgenic loci. Genome editing molecules that provide for selective excision of a first modified transgenic locus comprising an OgRRS and a CgRRS include a gRNA that hybridizes to the OgRRS and CgRRS of the first modified transgenic locus and an RdDe that recognizes the gRNA/OgRRS and gRNA/CgRRS complexes. Distinct plant lines with different subsets of transgenic loci and desired targeted genetic changes are thus recovered (e.g., "Line B-1," "Line B-2," and "Line B-3" in FIG. 2). In certain embodiments, it is also desirable to bulk up populations of inbred elite crop plants or their seed comprising the subset of transgenic loci and a transgenic locus excision site by selfing. In certain embodiments, inbred progeny of the selfed maize plants comprising the INIR6 transgenic loci can be used as a pollen donor or recipient for hybrid seed production. Such hybrid seed and the progeny grown therefrom can comprise a subset of desired transgenic loci and a transgenic loci excision site.

Hybrid plant lines comprising elite crop plant germplasm, at least one transgenic locus and at least one transgenic locus excision site, and in certain aspects, additional targeted genetic changes are also provided herein. Methods for production of such hybrid seed can comprise crossing elite crop plant lines where at least one of the pollen donor or recipient comprises at least the transgenic locus and a transgenic locus excision site and/or additional targeted genetic changes. In certain embodiments, the pollen donor and recipient will comprise germplasm of distinct heterotic groups and provide hybrid seed and plants exhibiting heterosis. In certain embodiments, the pollen donor and recipient can each comprise a distinct transgenic locus which confers either a distinct trait (e.g., herbicide tolerance or insect resistance), a different type of trait (e.g., tolerance to distinct herbicides or to distinct insects such as coleopteran or lepidopteran insects), or a different mode-of-action for the same trait (e.g., resistance to coleopteran insects by two distinct modes-of-action or resistance to lepidopteran insects by two distinct modes-of-action). In certain embodiments, the pollen recipient will be rendered male sterile or conditionally male sterile. Methods for inducing male sterility or conditional male sterility include emasculation (e.g., detasseling), cytoplasmic male sterility, chemical hybridizing agents or systems, a transgenes or transgene systems, and/or mutation(s) in one or more endogenous plant genes. Descriptions of various male sterility systems that can be adapted for use with the elite crop plants provided herein are described in Wan et al. Molecular Plant; 12, 3, (2019):321-342 as well as in U.S. Pat. No. 8,618,358; US 20130031674; and US 2003188347.

In certain embodiments, it will be desirable to use genome editing molecules to make modified transgenic loci by introducing a CgRRS into the transgenic loci, to excise modified transgenic loci comprising an OgRRS and a CgRRS, and/or to make targeted genetic changes in elite crop plant or other germplasm. Techniques for effecting genome editing in crop plants (e.g., maize,) include use of morphogenic factors such as Wuschel (WUS), Ovule Development Protein (ODP), and/or Babyboom (BBM) which can improve the efficiency of recovering plants with desired genome edits. In some aspects, the morphogenic factor comprises WUS1, WUS2, WUS3, WOX2A, WOX4, WOX5, WOX9, BBM2, BMN2, BMN3, and/or ODP2. In certain embodiments, compositions and methods for using WUS, BBM, and/or ODP, as well as other techniques which can be adapted for effecting genome edits in elite crop plant and other germplasm, are set forth in US 20030082813, US 20080134353, US 20090328252, US 20100100981, US 20110165679, US 20140157453, US 20140173775, and US 20170240911, which are each incorporated by reference in their entireties. In certain embodiments, the genome edits can be effected in regenerable plant parts (e.g., plant embryos) of elite crop plants by transient provision of gene editing molecules or polynucleotides encoding the same and do not necessarily require incorporating a selectable marker gene into the plant genome (e.g., US 20160208271 and US 20180273960, both incorporated herein by reference in their entireties; Svitashev et al. Nat Commun. 2016; 7:13274).

In certain embodiments, edited transgenic plant genomes, transgenic plant cells, parts, or plants containing those genomes, and DNA molecules obtained therefrom, can comprise a desired subset of transgenic loci and/or comprise at least one transgenic locus excision site. In certain embodiments, a segment comprising an INIR6 transgenic locus comprising an OgRRS in non-transgenic DNA of a 1st junction polynucleotide sequence and a CgRRS in a 2nd junction polynucleotide sequence is deleted with a gRNA and RdDe that recognize the OgRRS and the CgRRS to produce an INIR6 transgenic locus excision site. In certain embodiments, the transgenic locus excision site can comprise a contiguous segment of DNA comprising at least 10 base pairs of DNA that is telomere proximal to the deleted segment of the transgenic locus and at least 10 base pairs of DNA that is centromere proximal to the deleted segment of the transgenic locus wherein the transgenic DNA (i.e., the heterologous DNA) that has been inserted into the crop plant genome has been deleted. In certain embodiments where a segment comprising a transgenic locus has been deleted, the transgenic locus excision site can comprise a contiguous segment of DNA comprising at least 10 base pairs DNA that is telomere proximal to the deleted segment of the transgenic locus and at least 10 base pairs of DNA that is centromere proximal DNA to the deleted segment of the transgenic locus wherein the heterologous transgenic DNA and at least 1, 2, 5, 10, 20, 50, or more base pairs of endogenous DNA located in a 5' junction sequence and/or in a 3' junction sequence of the original transgenic locus that has been deleted. In such embodiments where DNA comprising the transgenic locus is deleted, a transgenic locus excision site can comprise at least 10 base pairs of DNA that is telomere proximal to the deleted segment of the transgenic locus and at least 10 base pairs of DNA that is centromere proximal to the deleted segment of the transgenic locus wherein all of the transgenic DNA is absent and either all or less than all of the endogenous DNA flanking the transgenic DNA sequences are present. In certain embodiments where a segment consisting essentially of an original transgenic locus has been deleted, the transgenic locus excision site can be a contiguous segment of at least 10 base pairs of DNA that is telomere proximal to the deleted segment of the transgenic locus and at least 10 base pairs of DNA that is centromere proximal to the deleted segment of the transgenic locus wherein less than all of the heterologous transgenic DNA that has been inserted into the crop plant genome is excised. In certain aforementioned embodiments where a segment consisting essentially of an original transgenic locus has been deleted, the transgenic locus excision site can thus contain at least 1 base pair of DNA or 1 to about 2 or 5, 8, 10, 20, or 50 base pairs of DNA comprising the telomere proximal and/or centromere proximal heterologous transgenic DNA that has been inserted into the crop plant genome. In certain embodiments where a segment consisting of an original transgenic locus has been deleted, the transgenic locus excision site can contain a contiguous segment of DNA comprising at least 10 base pairs of DNA that is telomere proximal to the deleted segment of the transgenic locus and at least 10 base pairs of DNA that is centromere proximal to the deleted segment of the transgenic locus wherein the heterologous transgenic DNA that has been inserted into the crop plant genome is deleted. In certain embodiments where DNA consisting of the transgenic locus is deleted, a transgenic locus excision site can comprise at least 10 base pairs of DNA that is telomere proximal to the deleted segment of the transgenic locus and at least 10 base pairs of DNA that is centromere proximal to the deleted segment of the transgenic locus wherein all of the heterologous transgenic DNA that has been inserted into the crop plant genome is deleted and all of the endogenous DNA flanking the heterologous sequences of the transgenic locus is present. In any of the aforementioned embodiments or in other embodiments, the continuous segment of DNA comprising the transgenic locus excision site can further comprise an insertion of 1 to about 2, 5, 10, 20, or more nucleotides between the DNA that is telomere proximal to the deleted segment of the transgenic locus and the DNA that is centromere proximal to the deleted segment of the transgenic locus. Such insertions can result either from endogenous DNA repair and/or recombination activities at the double stranded breaks introduced at the excision site and/or from deliberate insertion of an oligonucleotide. Plants, edited plant genomes, biological samples, and DNA molecules (e.g., including isolated or purified DNA molecules) comprising the INIR6 transgenic loci excision sites are provided herein.

In other embodiments, a segment comprising a INIR6 transgenic locus (e.g., a transgenic locus comprising an OgRRS in non-transgenic DNA of a $1^{st}$ junction sequence and a CgRRS in a $2^{nd}$ junction sequence) can be deleted with a gRNA and RdDe that recognize the OgRRS and the CgRRS and replaced with DNA comprising the endogenous non-transgenic plant genomic DNA present in the genome prior to transgene insertion. A non-limiting example of such replacements can be visualized in FIG. 3C, where the donor DNA template can comprise the endogenous non-transgenic plant genomic DNA present in the genome prior to transgene insertion along with sufficient homology to non-transgenic DNA on each side of the excision site to permit homology-directed repair. In certain embodiments, the endogenous non-transgenic plant genomic DNA present in the genome prior to transgene insertion can be at least partially restored. In certain embodiments, the endogenous non-transgenic plant genomic DNA present in the genome prior to transgene insertion can be essentially restored such that no more than about 5, 10, or 20 to about 50, 80, or 100 nucleotides are changed relative to the endogenous DNA at the essentially restored excision site.

In certain embodiments, edited transgenic plant genomes and transgenic plant cells, plant parts, or plants containing those edited genomes, comprising a modification of an original transgenic locus, where the modification comprises an OgRRS and a CgRRS which are operably linked to a $1^{st}$ and a $2^{nd}$ junction sequence, respectively or irrespectively, and optionally further comprise a deletion of a segment of the original transgenic locus. In certain embodiments, the modification comprises two or more separate deletions and/or there is a modification in two or more original transgenic plant loci. In certain embodiments, the deleted segment comprises, consists essentially of, or consists of a segment of non-essential DNA in the transgenic locus. Illustrative examples of non-essential DNA include but are not limited to synthetic cloning site sequences, duplications of transgene sequences; fragments of transgene sequences, and *Agrobacterium* right and/or left border sequences. In certain embodiments, the non-essential DNA is a duplication and/or fragment of a promoter sequence and/or is not the promoter sequence operably linked in the cassette to drive expression of a transgene. In certain embodiments, excision of the non-essential DNA improves a characteristic, functionality, and/or expression of a transgene of the transgenic locus or otherwise confers a recognized improvement in a transgenic plant comprising the edited transgenic plant genome. In certain embodiments, the non-essential DNA does not comprise DNA encoding a selectable marker gene. In certain embodiments of an edited transgenic plant genome, the modification comprises a deletion of the non-essential DNA and a deletion of a selectable marker gene. The modification producing the edited transgenic plant genome could occur by excising both the non-essential DNA and the selectable marker gene at the same time, e.g., in the same modification step, or the modification could occur step-wise. For example, an edited transgenic plant genome in which a selectable marker gene has previously been removed from the transgenic locus can comprise an original transgenic locus from which a non-essential DNA is further excised and vice versa. In certain embodiments, the modification comprising deletion of the non-essential DNA and deletion of the selectable marker gene comprises excising a single segment of the original transgenic locus that comprises both the non-essential DNA and the selectable marker gene. Such modification would result in one excision site in the edited transgenic genome corresponding to the deletion of both the non-essential DNA and the selectable marker gene. In certain embodiments, the modification comprising deletion of the non-essential DNA and deletion of the selectable marker gene comprises excising two or more segments of the original transgenic locus to achieve deletion of both the non-essential DNA and the selectable marker gene. Such modification would result in at least two excision sites in the edited transgenic genome corresponding to the deletion of both the non-essential DNA and the selectable marker gene. In certain embodiments of an edited transgenic plant genome, prior to excision, the segment to be deleted is flanked by operably linked protospacer adjacent motif (PAM) sites in the original or unmodified transgenic locus and/or the segment to be deleted encompasses an operably linked PAM site in the original or unmodified transgenic locus. In certain embodiments, following excision of the segment, the resulting edited transgenic plant genome comprises PAM sites flanking the deletion site in the modified transgenic locus. In certain embodiments of an edited transgenic plant genome, the modification comprises a modification of a DP-4114 transgenic locus.

In certain embodiments, improvements in a transgenic plant locus are obtained by introducing a new cognate guide RNA recognition site (CgRRS) which is operably linked to a DNA junction polynucleotide of the transgenic locus in the transgenic plant genome. Such CgRRS sites can be recognized by RdDe and a single suitable guide RNA directed to the CgRRS and the originator gRNA Recognition Site (OgRRS) to provide for cleavage within the junction polynucleotides which flank an INIR6 transgenic locus. In certain embodiments, the CgRRS/gRNA and OgRRS/gRNA hybridization complexes are recognized by the same class of RdDe (e.g., Class 2 type II or Class 2 type V) or by the same RdDe (e.g., both the CgRRS/gRNA and OgRRS/gRNA hybridization complexes recognized by the same Cas9 or Cas 12 RdDe). Such CgRRS and OgRRS can be recognized by RdDe and suitable guide RNAs containing crRNA sufficiently complementary to the guide RNA hybridization site DNA sequences adjacent to the PAM site of the CgRRS and the OgRRS to provide for cleavage within or near the two junction polynucleotides. Suitable guide RNAs can be in the form of a single gRNA comprising a crRNA or in the form of a crRNA/tracrRNA complex. In the case of the OgRRS site, the PAM and guide RNA hybridization site are endogenous DNA polynucleotide molecules found in the plant genome. In certain embodiments where the CgRRS is introduced into the plant genome by genome editing, gRNA hybridization site polynucleotides introduced at the CgRRS are at least 17 or 18 nucleotides in length and are complementary to the crRNA of a guide RNA. In certain embodiments, the gRNA hybridization site sequence of the OgRRS and/or the CgRRS is about 17 or 18 to about 24 nucleotides in length. The gRNA hybridization site sequence of the OgRRS and the gRNA hybridization site of the CgRRS can be of different lengths or comprise different sequences so long as there is sufficient complementarity to permit hybridization by a single gRNA and recognition by a RdDe that recognizes and cleaves DNA at the gRNA/OgRRS and gRNA/CgRRS complex. In certain embodiments, the guide RNA hybridization site of the CgRRS comprise about a 17 or 18 to about 24 nucleotide sequence which is identical to the guide RNA hybridization site of the OgRRS. In other embodiments, the guide RNA hybridization site of the CgRRS comprise about a 17 or 18 to about 24 nucleotide sequence which has one, two, three, four, or five nucleotide insertions, deletions or substitutions when compared to the guide RNA hybridization site of the OgRRS. Certain CgRRS comprising a gRNA hybridization site containing has one, two, three, four, or five nucleotide insertions, deletions or substitutions when compared to the guide RNA hybridization site of the OgRRS can undergo hybridization with a gRNA which is complementary to the OgRRS gRNA hybridization site and be cleaved by certain RdDe. Examples of mismatches between gRNAs and guide RNA hybridization sites which allow for RdDe recognition and cleavage include mismatches resulting from both nucleotide insertions and deletions in the DNA which is hybridized to the gRNA (e.g., Lin et al., doi: 10.1093/nar/gku402). In certain embodiments, an operably linked PAM site is co-introduced with the gRNA hybridization site polynucleotide at the CgRRS. In certain embodiments, the gRNA hybridization site polynucleotides are introduced at a position adjacent to a resident endogenous PAM sequence in the junction polynucleotide sequence to form a CgRRS where the gRNA hybridization site polynucleotides are operably linked to the endogenous PAM site. In certain embodiments, non-limiting features of the OgRRS, CgRRS, and/or the gRNA hybridization site polynucleotides thereof include: (i) absence of significant homology or sequence identity (e.g., less than 50% sequence identity across the entire length of the OgRRS, CgRRS, and/or the gRNA hybridization site sequence) to any other endogenous or transgenic sequences present in the transgenic plant genome or in other transgenic genomes of the maize plant being transformed and edited; (ii) absence of significant homology or sequence identity (e.g., less than 50% sequence identity across the entire length of the sequence) of a sequence of a first OgRRS and a first CgRRS to a second OgRRS and a second CgRRS which are operably linked to junction polynucleotides of a distinct transgenic locus; (iii) the presence of some sequence identity (e.g., about 25%, 40%, or 50% to about 60%, 70%, or 80%) between the OgRRS sequence and endogenous sequences present at the site where the CgRRS sequence is introduced; and/or (iv) optimization of the gRNA hybridization site polynucleotides for recognition by the RdDe and guide RNA when used in conjunction with a particular PAM sequence. In certain embodiments, the first and second OgRRS as well as the first and second CgRRS are recognized by the same class of RdDe (e.g., Class 2 type II or Class 2 type V) or by the same RdDe (e.g., Cas9 or Cas 12 RdDe). In certain embodiments, the first OgRRS site in a first junction polynucleotide and the CgRRS introduced in the second junction polynucleotide to permit excision of a first transgenic locus by a first single guide RNA and a single RdDe. Such nucleotide insertions or genome edits used to introduce CgRRS in a transgenic plant genome can be effected in the plant genome by using gene editing molecules (e.g., RdDe and guide RNAs, RNA dependent nickases and guide RNAs, Zinc Finger nucleases or nickases, or TALE nucleases or nickases) which introduce blunt double stranded breaks or staggered double stranded breaks in the DNA junction polynucleotides. In the case of DNA insertions, the genome editing molecules can also in certain embodiments further comprise a donor DNA template or other DNA template which comprises the heterologous nucleotides for insertion to form the CgRRS. Guide RNAs can be directed to the junction polynucleotides by using a pre-existing PAM site located within or adjacent to a junction polynucleotide of the transgenic locus. Non-limiting examples of such pre-existing PAM sites present in junction polynucleotides, which can be used either in conjunction with an inserted heterologous sequence to form a CgRRS or which can be used to create a double stranded break to insert or create a CgRRS, include PAM sites recognized by a Cas12a enzyme. Non-limiting examples where a CgRRS are created in a DNA sequence are illustrated in Example 2.

Transgenic loci comprising OgRRS and CgRRS in a first and a second junction polynucleotides can be excised from the genomes of transgenic plants by contacting the transgenic loci with RdDe or RNA directed nickases, and a suitable guide RNA directed to the OgRRS and CgRRS. A non-limiting example where a modified transgenic locus is excised from a plant genome by use of a gRNA and an RdDe that recognizes an OgRRS/gRNA and a CgRRS/gRNA complex and introduces dsDNA breaks in both junction polynucleotides nd repaired by NHEJ is depicted in FIG. 3B. In the depicted example set forth in FIG. 3B, the OgRRS site and the CgRRS site are absent from the plant chromosome comprising the transgene excision site that results from the process. In other embodiments provided herein where a modified transgenic locus is excised from a plant genome by use of a gRNA and an RdDe that recognizes an OgRRS/gRNA and a CgRRS/gRNA complex and repaired by NHEJ or microhomology-mediated end joining (MMEJ), the OgRRS and/or other non-transgenic sequences that were originally present prior to transgene insertion are partially or essentially restored.

In certain embodiments, edited transgenic plant genomes provided herein can lack one or more selectable and/or scoreable markers found in an original event (transgenic locus). Original DP-4114 transgenic loci (events), including those set forth in SEQ ID NO: 1), U.S. Pat. No. 8,575,434, the sequence of the DP-4114 locus in the deposited seed of accession No. PTA-11506 and progeny thereof, contain a selectable marker gene encoding a phosphinotricin acetyl transferase (PAT) protein which confers tolerance to the herbicide glufosinate. In certain embodiments provided herein, the DNA element comprising, consisting essentially of, or consisting of the PAT selectable marker gene of an DP-4114 transgenic locus is absent from an INIR6 transgenic locus. The PAT selectable marker cassette can be excised from an original DP-4114 transgenic locus by contacting the transgenic locus with one or more gene editing molecules which introduce double stranded breaks in the transgenic locus at the 5' and 3' end of the expression cassette comprising the PAT selectable marker transgene (e.g., an RdDe and guide RNAs directed to PAM sites located at the 5' and 3' end of the expression cassette comprising the PAT selectable marker transgene) and selecting for plant cells, plant parts, or plants wherein the selectable marker has been excised. Examples of an INIR6 transgenic locus comprising a deletion of a PAT selectable marker transgene and a 3' border sequence include the INIR6 transgenic locus of SEQ ID NO: 25 and allelic variants thereof. Examples of an INIR6 transgenic locus comprising a deletion of a PAT selectable marker transgene and a CgRRS include the INIR6 transgenic locus of SEQ ID NO: 26 and variants thereof. In certain embodiments, a DNA fragment comprising, consisting essentially of, or consisting of the CaMV35S promoter and operably linked PAT coding region of the DP-4114 transgenic locus is deleted while leaving in place the CaMV35S terminator of the PAT selectable marker cassette in the INIR6 transgenic locus. In certain embodiments, the PinII terminator which is operably linked to Cry35Ab1 coding region is thus placed in tandem with the CaMV35S promoter in the INIR6 transgenic locus. Examples of an INIR6 transgenic locus comprising, consisting essentially of, or consisting of a deletion of the CaMV35S promoter and operably linked PAT coding region of a DP-4114 transgenic locus include am INIR6 transgenic locus which can be obtained with a Cas12a nuclease and a guide RNAs which cleave DNA located between the PinII terminator which is operably linked to the Cry35Ab1 coding region (e.g., guide RNA-4; SEQ ID NO: 24) and DNA located between the 3' end of the PAT coding region and the 5' end of the CaMV35S promoter (e.g., Guide RNA NO: 5; SEQ ID NO: 28). Examples of an INIR6 transgenic locus comprising a deletion of the CaMV35S promoter and operably linked PAT coding region of a DP-4114 transgenic locus include the INIR6 transgenic locus of SEQ ID NO: 29, 30, and variants thereof. Examples of an INIR6 transgenic locus comprising a CgRRS and a deletion of the CaMV35S promoter and operably linked PAT coding region of a DP-4114 transgenic locus include the INIR6 transgenic locus of SEQ ID NO: 31 and variants thereof. In certain embodiments, the selectable or scoreable marker transgene can be inactivated. Inactivation can be achieved by modifications including insertion, deletion, and/or substitution of one or more nucleotides in a promoter element, 5' or 3' untranslated region (UTRs), intron, coding region, and/or 3' terminator and/or polyadenylation site of the selectable marker transgene. Such modifications can inactivate the selectable marker transgene by eliminating or reducing promoter activity, introducing a missense mutation, and/or introducing a pre-mature stop codon. In certain embodiments, the selectable PAT marker transgene can be replaced by an introduced transgene. In certain embodiments, an original transgenic locus that was contacted with gene editing molecules which introduce double stranded breaks in the transgenic locus at the 5' and 3' end of the expression cassette comprising the PAT selectable marker transgene can also be contacted with a suitable donor DNA template comprising an expression cassette flanked by DNA homologous to remaining DNA in the transgenic locus located 5' and 3' to the selectable marker excision site. In certain embodiments, a coding region of the PAT selectable marker transgene can be replaced with another coding region such that the replacement coding region is operably linked to the promoter and 3' terminator or polyadenylation site of the PAT selectable marker transgene.

In certain embodiments, edited transgenic plant genomes provided herein can comprise additional new introduced transgenes (e.g., expression cassettes) inserted into the transgenic locus of a given event. Introduced transgenes inserted at the transgenic locus of an event subsequent to the event's original isolation can be obtained by inducing a double stranded break at a site within an original transgenic locus (e.g., with genome editing molecules including an RdDe and suitable guide RNA(s); a suitable engineered zinc-finger nuclease; a TALEN protein and the like) and providing an exogenous transgene in a donor DNA template which can be integrated at the site of the double stranded break (e.g. by homology-directed repair (HDR) or by non-homologous end-joining (NHEJ)). In certain embodiments, an OgRRS and a CgRRS located in a $1^{st}$ junction polynucleotide and a $2^{nd}$ junction polynucleotide, respectively, can be used to delete the transgenic locus and replace it with one or more new expression cassettes. In certain embodiments, such deletions and replacements are effected by introducing dsDNA breaks in both junction polynucleotides and providing the new expression cassettes on a donor DNA template (e.g., in FIG. 3C, the donor DNA template can comprise an expression cassette flanked by DNA homologous to non-transgenic DNA located telomere proximal and centromere proximal to the excision site). Suitable expression cassettes for insertion include DNA molecules comprising promoters which are operably linked to DNA encoding proteins and/or RNA molecules which confer useful traits which are in turn operably linked to polyadenylation sites or terminator elements. In certain embodiments, such expression cassettes can also comprise 5' UTRs, 3' UTRs, and/or introns. Useful traits include biotic stress tolerance (e.g., insect resistance, nematode resistance, or disease resistance), abiotic stress tolerance (e.g., heat, cold, drought, and/or salt tolerance), herbicide tolerance, and quality traits (e.g., improved fatty acid compositions, protein content, starch content, and the like). Suitable expression cassettes for insertion include expression cassettes which confer insect resistance, herbicide tolerance, biofuel use, or male sterility traits contained in any of the transgenic events set forth in US Patent Application Public. Nos. 20090038026, 20130031674, 20150361446, 20170088904, 20150267221, 201662346688, and 20200190533 as well as in U.S. Pat. Nos. 6,342,660, 7,323,556, 8,575,434, 6,040,497, 8,759,618, 7,157,281, 6,852,915, 7,705,216, 10,316,330, 8,618,358, 8,450,561, 8,212,113, 9,428,765, 7,897,748, 8,273,959, 8,093,453, 8,901,378, 9,994,863, 7,928,296, and 8,466,346, each of which are incorporated herein by reference in their entireties.

In certain embodiments, INIR6 plants provided herein, including plants with one or more transgenic loci, modified transgenic loci, and/or comprising transgenic loci excision sites can further comprise one or more targeted genetic changes introduced by one or more of gene editing molecules or systems. Also provided are methods where the targeted genetic changes are introduced and one or more transgenic loci are removed from plants either in series or in parallel (e.g., as set forth in the non-limiting illustration in FIG. 2, bottom "Alternative" panel, where "GE" can represent targeted genetic changes induced by gene editing molecules and "Event Removal" represents excision of one or more transgenic loci with gene editing molecules). Such targeted genetic changes include those conferring traits such as improved yield, improved food and/or feed characteristics (e.g., improved oil, starch, protein, or amino acid quality or quantity), improved nitrogen use efficiency, improved biofuel use characteristics (e.g., improved ethanol production), male sterility/conditional male sterility systems (e.g., by targeting endogenous MS26, MS45 and MSCA1 genes), herbicide tolerance (e.g., by targeting endogenous ALS, EPSPS, HPPD, or other herbicide target genes), delayed flowering, non-flowering, increased biotic stress resistance (e.g., resistance to insect, nematode, bacterial, or fungal damage), increased abiotic stress resistance (e.g., resistance to drought, cold, heat, metal, or salt), enhanced lodging resistance, enhanced growth rate, enhanced biomass, enhanced tillering, enhanced branching, delayed flowering time, delayed senescence, increased flower number, improved architecture for high density planting, improved photosynthesis, increased root mass, increased cell number, improved seedling vigor, improved seedling size, increased rate of cell division, improved metabolic efficiency, and increased meristem size in comparison to a control plant lacking the targeted genetic change. Types of targeted genetic changes that can be introduced include insertions, deletions, and substitutions of one or more nucleotides in the crop plant genome. Sites in endogenous plant genes for the targeted genetic changes include promoter, coding, and non-coding regions (e.g., 5' UTRs, introns, splice donor and acceptor sites and 3' UTRs). In certain embodiments, the targeted genetic change comprises an insertion of a regulatory or other DNA sequence in an endogenous plant gene.

Non-limiting examples of regulatory sequences which can be inserted into endogenous plant genes with gene editing molecules to effect targeted genetic changes which confer useful phenotypes include those set forth in US Patent Application Publication 20190352655, which is incorporated herein by reference in its entirety, such as: (a) auxin response element (AuxRE) sequence; (b) at least one D1-4 sequence (Ulmasov et al. (1997) Plant Cell, 9:1963-1971), (c) at least one DR5 sequence (Ulmasov et al. (1997) Plant Cell, 9:1963-1971); (d) at least one m5-DR5 sequence (Ulmasov et al. (1997) Plant Cell, 9:1963-1971); (e) at least one P3 sequence; (f) a small RNA recognition site sequence bound by a corresponding small RNA (e.g., an siRNA, a microRNA (miRNA), a trans-acting siRNA as described in U.S. Pat. No. 8,030,473, or a phased sRNA as described in U.S. Pat. No. 8,404,928; both of these cited patents are incorporated by reference herein); (g) a microRNA (miRNA) recognition site sequence; (h) the sequence recognizable by a specific binding agent includes a microRNA (miRNA) recognition sequence for an engineered miRNA wherein the specific binding agent is the corresponding engineered mature miRNA; (i) a transposon recognition sequence; (j) a sequence recognized by an ethylene-responsive element binding-factor-associated amphiphilic repression (EAR) motif; (k) a splice site sequence (e.g., a donor site, a branching site, or an acceptor site; see, for example, the splice sites and splicing signals set forth in the internet site lemur[dot]amu[dot]edu[dot]pl/share/ERISdb/home.html); (l) a recombinase recognition site sequence that is recognized by a site-specific recombinase; (m) a sequence encoding an RNA or amino acid aptamer or an RNA riboswitch, the specific binding agent is the corresponding ligand, and the change in expression is upregulation or downregulation; (n) a hormone responsive element recognized by a nuclear receptor or a hormone-binding domain thereof; (o) a transcription factor binding sequence; and (p) a polycomb response element (see Xiao et al. (2017) Nature Genetics, 49:1546-1552, doi: 10.1038/ng.3937). Non limiting examples of target maize genes that can be subjected to targeted gene edits to confer useful traits include: (a) ZmIPK1 (herbicide tolerant and phytate reduced maize; Shukla et al., Nature. 2009; 459:437-41); (b) ZmGL2 (reduced epicuticular wax in leaves; Char et al. Plant Biotechnol J. 2015; 13:1002); (c) ZmMTL (induction of haploid plants; Kelliher et al. Nature. 2017; 542:105); (d) Wx1 (high amylopectin content; US 20190032070; incorporated herein by reference in its entirety); (e) TMS5 (thermosensitive male sterile; Li et al. J Genet Genomics. 2017; 44:465-8); (f) ALS (herbicide tolerance; Svitashev et al.; Plant Physiol. 2015; 169:931-45); and (g) ARGOS8 (drought stress tolerance; Shi et al., Plant Biotechnol J. 2017; 15:207-16). Non-limiting examples of target genes in crop plants including maize which can be subjected to targeted genetic changes which confer useful phenotypes include those set forth in US Patent Application Nos. 20190352655, 20200199609, 20200157554, and 20200231982, which are each incorporated herein in their entireties; and Zhang et al. (Genome Biol. 2018; 19: 210).

Gene editing molecules of use in methods provided herein include molecules capable of introducing a double-strand break ("DSB") or single-strand break ("SSB") in double-stranded DNA, such as in genomic DNA or in a target gene located within the genomic DNA as well as accompanying guide RNA or donor DNA template polynucleotides. Examples of such gene editing molecules include: (a) a nuclease comprising an RNA-guided nuclease, an RNA-guided DNA endonuclease or RNA directed DNA endonuclease (RdDe), a class 1 CRISPR type nuclease system, a type II Cas nuclease, a Cas9, a nCas9 nickase, a type V Cas nuclease, a Cas12a nuclease, a nCas12a nickase, a Cas12d (CasY), a Cas12e (CasX), a Cas12b (C2c1), a Cas12c (C2c3), a Cas12i, a Cas12j, a Cas14, an engineered nuclease, a codon-optimized nuclease, a zinc-finger nuclease (ZFN) or nickase, a transcription activator-like effector nuclease (TAL-effector nuclease or TALEN) or nickase (TALE-nickase), an Argonaute, and a meganuclease or engineered meganuclease; (b) a polynucleotide encoding one or more nucleases capable of effectuating site-specific alteration (including introduction of a DSB or SSB) of a target nucleotide sequence; (c) a guide RNA (gRNA) for an RNA-guided nuclease, or a DNA encoding a gRNA for an RNA-guided nuclease; (d) donor DNA template polynucleotides; and (e) other DNA templates (dsDNA, ssDNA, or combinations thereof) suitable for insertion at a break in genomic DNA (e.g., by non-homologous end joining (NHEJ) or microhomology-mediated end joining (MMEJ).

CRISPR-type genome editing can be adapted for use in the plant cells and methods provided herein in several ways. CRISPR elements, e.g., gene editing molecules comprising CRISPR endonucleases and CRISPR guide RNAs including single guide RNAs or guide RNAs in combination with tracrRNAs or scoutRNA, or polynucleotides encoding the same, are useful in effectuating genome editing without remnants of the CRISPR elements or selective genetic markers occurring in progeny. In certain embodiments, the CRISPR elements are provided directly to the eukaryotic cell (e.g., plant cells), systems, methods, and compositions as isolated molecules, as isolated or semi-purified products of a cell free synthetic process (e.g., in vitro translation), or as isolated or semi-purified products of in a cell-based synthetic process (e.g., such as in a bacterial or other cell lysate). In certain embodiments, genome-inserted CRISPR elements are useful in plant lines adapted for use in the methods provide herein. In certain embodiments, plants or plant cells used in the systems, methods, and compositions provided herein can comprise a transgene that expresses a CRISPR endonuclease (e.g., a Cas9, a Cpf1-type or other CRISPR endonuclease). In certain embodiments, one or more CRISPR endonucleases with unique PAM recognition sites can be used. Guide RNAs (sgRNAs or crRNAs and a tracrRNA) to form an RNA-guided endonuclease/guide RNA complex which can specifically bind sequences in the gDNA target site that are adjacent to a protospacer adjacent motif (PAM) sequence. The type of RNA-guided endonuclease typically informs the location of suitable PAM sites and design of crRNAs or sgRNAs. G-rich PAM sites, e.g., 5'-NGG are typically targeted for design of crRNAs or sgRNAs used with Cas9 proteins. Examples of PAM sequences include 5'-NGG (*Streptococcus pyogenes*), 5'-NNAGAA (*Streptococcus thermophilus* CRISPR1), 5'-NGGNG (*Streptococcus thermophilus* CRISPR3), 5'-NNGRRT or 5'-NNGRR (*Staphylococcus aureus* Cas9, SaCas9), and 5'-NNNGATT (*Neisseria meningitidis*). T-rich PAM sites (e.g., 5'-TTN or 5'-TTTV, where "V" is A, C, or G) are typically targeted for design of crRNAs or sgRNAs used with Cas12a proteins. In some instances, Cas12a can also recognize a 5'-CTA PAM motif. Other examples of potential Cas12a PAM sequences include TTN, CTN, TCN, CCN, TTTN, TCTN, TTCN, CTTN, ATTN, TCCN, TTGN, GTTN, CCCN, CCTN, TTAN, TCGN, CTCN, ACTN, GCTN, TCAN, GCCN, and CCGN (wherein N is defined as any nucleotide). Cpf1 (i.e., Cas12a) endonuclease and corresponding guide RNAs and PAM sites are disclosed in US Patent Application Publication 2016/0208243 A1, which is incorporated herein by reference for its disclosure of DNA encoding Cpf1 endonucleases and guide RNAs and PAM sites. Introduction of one or more of a wide variety of CRISPR guide RNAs that interact with CRISPR endonucleases integrated into a plant genome or otherwise provided to a plant is useful for genetic editing for providing desired phenotypes or traits, for trait screening, or for gene editing mediated trait introgression (e.g., for introducing a trait into a new genotype without backcrossing to a recurrent parent or with limited backcrossing to a recurrent parent). Multiple endonucleases can be provided in expression cassettes with the appropriate promoters to allow multiple genome site editing.

CRISPR technology for editing the genes of eukaryotes is disclosed in US Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in US Patent Application Publication 2016/0208243 A1. Other CRISPR nucleases useful for editing genomes include Cas12b and Cas12c (see Shmakov et al. (2015) Mol. Cell, 60:385-397; Harrington et al. (2020) Molecular Cell doi: 10.1016/j.molcel.2020.06.022) and CasX and CasY (see Burstein et al. (2016) Nature, doi:10.1038/nature21059; Harrington et al. (2020) Molecular Cell doi:10.1016/j.molcel.2020.06.022), or Cas12j (Pausch et al, (2020) Science 10.1126/science.abb1400). Plant RNA promoters for expressing CRISPR guide RNA and plant codon-optimized CRISPR Cas9 endonuclease are disclosed in International Patent Application PCT/US2015/018104 (published as WO 2015/131101 and claiming priority to U.S. Provisional Patent Application 61/945,700). Methods of using CRISPR technology for genome editing in plants are disclosed in US Patent Application Publications US 2015/0082478A1 and US 2015/0059010A1 and in International Patent Application PCT/US2015/038767 A1 (published as WO 2016/007347 and claiming priority to U.S. Provisional Patent Application 62/023,246). All of the patent publications referenced in this paragraph are incorporated herein by reference in their entirety. In certain embodiments, an RNA-guided endonuclease that leaves a blunt end following cleavage of the target site is used. Blunt-end cutting RNA-guided endonucleases include Cas9, Cas12c, and Cas 12h (Yan et al., 2019). In certain embodiments, an RNA-guided endonuclease that leaves a staggered single stranded DNA overhanging end following cleavage of the target site following cleavage of the target site is used. Staggered-end cutting RNA-guided endonucleases include Cas12a, Cas12b, and Cas12e.

The methods can also use sequence-specific endonucleases or sequence-specific endonucleases and guide RNAs that cleave a single DNA strand in a dsDNA target site. Such cleavage of a single DNA strand in a dsDNA target site is also referred to herein and elsewhere as "nicking" and can be effected by various "nickases" or systems that provide for nicking. Nickases that can be used include nCas9 (Cas9 comprising a D10A amino acid substitution), nCas12a (e.g., Cas12a comprising an R1226A amino acid substitution; Yamano et al., 2016), Cas12i (Yan et al. 2019), a zinc finger nickase e.g., as disclosed in Kim et al., 2012), a TALE nickase (e.g., as disclosed in Wu et al., 2014), or a combination thereof. In certain embodiments, systems that provide for nicking can comprise a Cas nuclease (e.g., Cas9 and/or Cas12a) and guide RNA molecules that have at least one base mismatch to DNA sequences in the target editing site (Fu et al., 2019). In certain embodiments, genome modifications can be introduced into the target editing site by creating single stranded breaks (i.e., "nicks") in genomic locations separated by no more than about 10, 20, 30, 40, 50, 60, 80, 100, 150, or 200 base pairs of DNA. In certain illustrative and non-limiting embodiments, two nickases (i.e., a CAS nuclease which introduces a single stranded DNA break including nCas9, nCas12a, Cas12i, zinc finger nickases, TALE nickases, combinations thereof, and the like) or nickase systems can directed to make cuts to nearby sites separated by no more than about 10, 20, 30, 40, 50, 60, 80 or 100 base pairs of DNA. In instances where an RNA guided nickase and an RNA guide are used, the RNA guides are adjacent to PAM sequences that are sufficiently close (i.e., separated by no more than about 10, 20, 30, 40, 50, 60, 80, 100, 150, or 200 base pairs of DNA). For the purposes of gene editing, CRISPR arrays can be designed to contain one or multiple guide RNA sequences corresponding to a desired target DNA sequence; see, for example, Cong et al. (2013) Science, 339:819-823; Ran et al. (2013) Nature Protocols, 8:2281-2308. At least 16 or 17 nucleotides of gRNA sequence are required by Cas9 for DNA cleavage to occur; for Cpf1 at least 16 nucleotides of gRNA sequence are needed to achieve detectable DNA cleavage and at least 18 nucleotides of gRNA sequence were reported necessary for efficient DNA cleavage in vitro; see Zetsche et al. (2015) Cell, 163:759-771. In practice, guide RNA sequences are generally designed to have a length of 17-24 nucleotides (frequently 19, 20, or 21 nucleotides) and exact complementarity (i.e., perfect base-pairing) to the targeted gene or nucleic acid sequence; guide RNAs having less than 100% complementarity to the target sequence can be used (e.g., a gRNA with a length of 20 nucleotides and 1-4 mismatches to the target sequence) but can increase the potential for off-target effects. The design of effective guide RNAs for use in plant genome editing is disclosed in US Patent Application Publication 2015/0082478 A1, the entire specification of which is incorporated herein by reference. More recently, efficient gene editing has been achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing); see, for example, Cong et al. (2013) Science, 339:819-823; Xing et al. (2014) BMC Plant Biol., 14:327-340. Chemically modified sgRNAs have been demonstrated to be effective in genome editing; see, for example, Hendel et al. (2015) Nature Biotechnol., 985-991. The design of effective gRNAs for use in plant genome editing is disclosed in US Patent Application Publication 2015/0082478 A1, the entire specification of which is incorporated herein by reference.

Genomic DNA may also be modified via base editing. Both adenine base editors (ABE) which convert A/T base pairs to G/C base pairs in genomic DNA as well as cytosine base pair editors (CBE) which effect C to T substitutions can be used in certain embodiments of the methods provided herein. In certain embodiments, useful ABE and CBE can comprise genome site specific DNA binding elements (e.g., RNA-dependent DNA binding proteins including catalytically inactive Cas9 and Cas12 proteins or Cas9 and Cas12 nickases) operably linked to adenine or cytidine deaminases and used with guide RNAs which position the protein near the nucleotide targeted for substitution. Suitable ABE and CBE disclosed in the literature (Kim, Nat Plants, 2018 March; 4(3):148-151) can be adapted for use in the methods set forth herein. In certain embodiments, a CBE can comprise a fusion between a catalytically inactive Cas9 (dCas9) RNA dependent DNA binding protein fused to a cytidine deaminase which converts cytosine (C) to uridine (U) and selected guide RNAs, thereby effecting a C to T substitution; see Komor et al. (2016) Nature, 533:420-424. In other embodiments, C to T substitutions are effected with Cas9 nickase [Cas9n(D10A)] fused to an improved cytidine deaminase and optionally a bacteriophage Mu dsDNA (double-stranded DNA) end-binding protein Gam; see Komor et al., Sci Adv. 2017 August; 3(8):eaao4774. In other embodiments, adenine base editors (ABEs) comprising an adenine deaminase fused to catalytically inactive Cas9 (dCas9) or a Cas9 D10A nickase can be used to convert A/T base pairs to G/C base pairs in genomic DNA (Gaudelli et al., (2017) Nature 551(7681):464-471.

In certain embodiments, zinc finger nucleases or zinc finger nickases can also be used in the methods provided herein. Zinc-finger nucleases are site-specific endonucleases comprising two protein domains: a DNA-binding domain, comprising a plurality of individual zinc finger repeats that each recognize between 9 and 18 base pairs, and a DNA-cleavage domain that comprises a nuclease domain (typically FokI). The cleavage domain dimerizes in order to cleave DNA; therefore, a pair of ZFNs are required to target non-palindromic target polynucleotides. In certain embodiments, zinc finger nuclease and zinc finger nickase design methods which have been described (Urnov et al. (2010) Nature Rev. Genet., 11:636-646; Mohanta et al. (2017) Genes vol. 8, 12: 399; Ramirez et al. Nucleic Acids Res. (2012); 40(12): 5560-5568; Liu et al. (2013) Nature Communications, 4: 2565) can be adapted for use in the methods set forth herein. The zinc finger binding domains of the zinc finger nuclease or nickase provide specificity and can be engineered to specifically recognize any desired target DNA sequence. The zinc finger DNA binding domains are derived from the DNA-binding domain of a large class of eukaryotic transcription factors called zinc finger proteins (ZFPs). The DNA-binding domain of ZFPs typically contains a tandem array of at least three zinc "fingers" each recognizing a specific triplet of DNA. A number of strategies can be used to design the binding specificity of the zinc finger binding domain. One approach, termed "modular assembly", relies on the functional autonomy of individual zinc fingers with DNA. In this approach, a given sequence is targeted by identifying zinc fingers for each component triplet in the sequence and linking them into a multifinger peptide. Several alternative strategies for designing zinc finger DNA binding domains have also been developed. These methods are designed to accommodate the ability of zinc fingers to contact neighboring fingers as well as nucleotide bases outside their target triplet. Typically, the engineered zinc finger DNA binding domain has a novel binding specificity, compared to a naturally-occurring zinc finger protein. Engineering methods include, for example, rational design and various types of selection. Rational design includes, for example, the use of databases of triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, e.g., U.S. Pat. Nos. 6,453,242 and 6,534,261, both incorporated herein by reference in their entirety. Exemplary selection methods (e.g., phage display and yeast two-hybrid systems) can be adapted for use in the methods described herein. In addition, enhancement of binding specificity for zinc finger binding domains has been described in U.S. Pat. No. 6,794,136, incorporated herein by reference in its entirety. In addition, individual zinc finger domains may be linked together using any suitable linker sequences. Examples of linker sequences are publicly known, e.g., see U.S. Pat. Nos. 6,479,626; 6,903,185; and 7,153,949, incorporated herein by reference in their entirety. The nucleic acid cleavage domain is non-specific and is typically a restriction endonuclease, such as FokI. This endonuclease must dimerize to cleave DNA. Thus, cleavage by FokI as part of a ZFN requires two adjacent and independent binding events, which must occur in both the correct orientation and with appropriate spacing to permit dimer formation. The requirement for two DNA binding events enables more specific targeting of long and potentially unique recognition sites. FokI variants with enhanced activities have been described and can be adapted for use in the methods described herein; see, e.g., Guo et al. (2010) *J. Mol. Biol.*, 400:96-107.

Transcription activator like effectors (TALEs) are proteins secreted by certain *Xanthomonas* species to modulate gene expression in host plants and to facilitate the colonization by and survival of the bacterium. TALEs act as transcription factors and modulate expression of resistance genes in the plants. Recent studies of TALEs have revealed the code linking the repetitive region of TALEs with their target DNA-binding sites. TALEs comprise a highly conserved and repetitive region consisting of tandem repeats of mostly 33 or 34 amino acid segments. The repeat monomers differ from each other mainly at amino acid positions 12 and 13. A strong correlation between unique pairs of amino acids at positions 12 and 13 and the corresponding nucleotide in the TALE-binding site has been found. The simple relationship between amino acid sequence and DNA recognition of the TALE binding domain allows for the design of DNA binding domains of any desired specificity. TALEs can be linked to a non-specific DNA cleavage domain to prepare genome editing proteins, referred to as TAL-effector nucleases or TALENs. As in the case of ZFNs, a restriction endonuclease, such as FokI, can be conveniently used. Methods for use of TALENs in plants have been described and can be adapted for use in the methods described herein, see Mahfouz et al. (2011) Proc. Natl. Acad. Sci. USA, 108:2623-2628; Mahfouz (2011) GM Crops, 2:99-103; and Mohanta et al. (2017) *Genes* vol. 8, 12: 399). TALE nickases have also been described and can be adapted for use in methods described herein (Wu et al.; Biochem Biophys Res Commun. (2014); 446(1):261-6; Luo et al; *Scientific Reports* 6, Article number: 20657 (2016)).

Embodiments of the donor DNA template molecule having a sequence that is integrated at the site of at least one double-strand break (DSB) in a genome include double-stranded DNA, a single-stranded DNA, a single-stranded DNA/RNA hybrid, and a double-stranded DNA/RNA hybrid. In embodiments, a donor DNA template molecule that is a double-stranded (e.g., a dsDNA or dsDNA/RNA hybrid) molecule is provided directly to the plant protoplast or plant cell in the form of a double-stranded DNA or a double-stranded DNA/RNA hybrid, or as two single-stranded DNA (ssDNA) molecules that are capable of hybridizing to form dsDNA, or as a single-stranded DNA molecule and a single-stranded RNA (ssRNA) molecule that are capable of hybridizing to form a double-stranded DNA/ RNA hybrid; that is to say, the double-stranded polynucleotide molecule is not provided indirectly, for example, by expression in the cell of a dsDNA encoded by a plasmid or other vector. In various non-limiting embodiments of the method, the donor DNA template molecule that is integrated (or that has a sequence that is integrated) at the site of at least one double-strand break (DSB) in a genome is double-stranded and blunt-ended; in other embodiments the donor DNA template molecule is double-stranded and has an overhang or "sticky end" consisting of unpaired nucleotides (e.g., 1, 2, 3, 4, 5, or 6 unpaired nucleotides) at one terminus or both termini. In an embodiment, the DSB in the genome has no unpaired nucleotides at the cleavage site, and the donor DNA template molecule that is integrated (or that has a sequence that is integrated) at the site of the DSB is a blunt-ended double-stranded DNA or blunt-ended double-stranded DNA/RNA hybrid molecule, or alternatively is a single-stranded DNA or a single-stranded DNA/RNA hybrid molecule. In another embodiment, the DSB in the genome has one or more unpaired nucleotides at one or both sides of the cleavage site, and the donor DNA template molecule that is integrated (or that has a sequence that is integrated) at the site of the DSB is a double-stranded DNA or double-stranded DNA/RNA hybrid molecule with an overhang or "sticky end" consisting of unpaired nucleotides at one or both termini, or alternatively is a single-stranded DNA or a single-stranded DNA/RNA hybrid molecule; in embodiments, the donor DNA template molecule DSB is a double-stranded DNA or double-stranded DNA/RNA hybrid molecule that includes an overhang at one or at both termini, wherein the overhang consists of the same number of unpaired nucleotides as the number of unpaired nucleotides created at the site of a DSB by a nuclease that cuts in an off-set fashion (e.g., where a Cas12 nuclease effects an off-set DSB with 5-nucleotide overhangs in the genomic sequence, the donor DNA template molecule that is to be integrated (or that has a sequence that is to be integrated) at the site of the DSB is double-stranded and has 5 unpaired nucleotides at one or both termini). In certain embodiments, one or both termini of the donor DNA template molecule contain no regions of sequence homology (identity or complementarity) to genomic regions flanking the DSB; that is to say, one or both termini of the donor DNA template molecule contain no regions of sequence that is sufficiently complementary to permit hybridization to genomic regions immediately adjacent to the location of the DSB. In embodiments, the donor DNA template molecule contains no homology to the locus of the DSB, that is to say, the donor DNA template molecule contains no nucleotide sequence that is sufficiently complementary to permit hybridization to genomic regions immediately adjacent to the location of the DSB. In embodiments, the donor DNA template molecule is at least partially double-stranded and includes 2-20 base-pairs, e. g., 2, 3, 4, 5, 6, 7, 8, 9, 10, 11, 12, 13, 14, 15, 16, 17, 18, 19, or 20 base-pairs; in embodiments, the donor DNA template molecule is double-stranded and blunt-ended and consists of 2-20 base-pairs, e.g., 2, 3, 4, 5, 6, 7, 8, 9, 10, 11, 12, 13, 14, 15, 16, 17, 18, 19, or 20 base-pairs; in other embodiments, the donor DNA template molecule is double-stranded and includes 2-20 base-pairs, e.g., 2, 3, 4, 5, 6, 7, 8, 9, 10, 11, 12, 13, 14, 15, 16, 17, 18, 19, or 20 base-pairs and in addition has at least one overhang or "sticky end" consisting of at least one additional, unpaired nucleotide at one or at both termini. In an embodiment, the donor DNA template molecule that is integrated (or that has a sequence that is integrated) at the site of at least one double-strand break (DSB) in a genome is a blunt-ended double-stranded DNA or a blunt-ended double-stranded DNA/RNA hybrid molecule of about 18 to about 300 base-pairs, or about 20 to about 200 base-pairs, or about 30 to about 100 base-pairs, and having at least one phosphorothioate bond between adjacent nucleotides at a 5' end, 3' end, or both 5' and 3' ends. In embodiments, the donor DNA template molecule includes single strands of at least 11, at least 18, at least 20, at least 30, at least 40, at least 60, at least 80, at least 100, at least 120, at least 140, at least 160, at least 180, at least 200, at least 240, at least 280, or at least 320 nucleotides. In embodiments, the donor DNA template molecule has a length of at least 2, at least 3, at least 4, at least 5, at least 6, at least 7, at least 8, at least 9, at least 10, or at least 11 base-pairs if double-stranded (or nucleotides if single-stranded), or between about 2 to about 320 base-pairs if double-stranded (or nucleotides if single-stranded), or between about 2 to about 500 base-pairs if double-stranded (or nucleotides if single-stranded), or between about 5 to about 500 base-pairs if double-stranded (or nucleotides if single-stranded), or between about 5 to about 300 base-pairs if double-stranded (or nucleotides if single-stranded), or between about 11 to about 300 base-pairs if double-stranded (or nucleotides if single-stranded), or about 18 to about 300 base-pairs if double-stranded (or nucleotides if single-stranded), or between about 30 to about 100 base-pairs if double-stranded (or nucleotides if single-stranded). In embodiments, the donor DNA template molecule includes chemically modified nucleotides (see, e.g., the various modifications of internucleotide linkages, bases, and sugars described in Verma and Eckstein (1998) Annu. Rev. Biochem., 67:99-134); in embodiments, the naturally occurring phosphodiester backbone of the donor DNA template molecule is partially or completely modified with phosphorothioate, phosphorodithioate, or methylphosphonate internucleotide linkage modifications, or the donor DNA template molecule includes modified nucleoside bases or modified sugars, or the donor DNA template molecule is labelled with a fluorescent moiety (e.g., fluorescein or rhodamine or a fluorescent nucleoside analogue) or other detectable label (e.g., biotin or an isotope). In another embodiment, the donor DNA template molecule contains secondary structure that provides stability or acts as an aptamer. Other related embodiments include double-stranded DNA/RNA hybrid molecules, single-stranded DNA/RNA hybrid donor molecules, and single-stranded donor DNA template molecules (including single-stranded, chemically modified donor DNA template molecules), which in analogous procedures are integrated (or have a sequence that is integrated) at the site of a double-strand break. Donor DNA templates provided herein include those comprising CgRRS sequences flanked by DNA with homology to a donor polynucleotide and include the donor DNA template set forth in SEQ ID NO: 14, SEQ ID NO: 27, and equivalents thereof with longer or shorter homology arms. Other DNA donor templates useful for effecting deletions in 3' junction polynucleotides include those set forth in SEQ ID NO: 32 and 33 as well as equivalents thereof with longer and shorter homology arms. Other DNA donor templates useful for effecting deletions of a PAT selectable marker cassette and a 3' junction polynucleotide include those set forth on SEQ ID NO: 34 and equivalents thereof with longer and shorter homology arms. Other DNA donor templates useful for effecting deletions of a CaMV35S promoter and PAT coding region of a PAT selectable marker cassette include those set forth on SEQ ID NO: 35 and equivalents thereof with longer and shorter homology arms. In certain embodiments, a donor DNA template can comprise an adapter molecule (e.g., a donor DNA template formed by annealing SEQ ID NO: 11 and 12 or by annealing SEQ ID NO: 11 and 13) with cohesive ends which can anneal to an overhanging cleavage site (e.g., introduced by a Cas12a nuclease and suitable gRNAs). In certain embodiments, integration of the donor DNA templates can be facilitated by use of a bacteriophage lambda exonuclease, a bacteriophage lambda beta SSAP protein, and an *E. coli* SSB essentially as set forth in US Patent Application Publication 20200407754, which is incorporated herein by reference in its entirety.

Donor DNA template molecules used in the methods provided herein include DNA molecules comprising, from 5' to 3', a first homology arm, a replacement DNA, and a second homology arm, wherein the homology arms containing sequences that are partially or completely homologous to genomic DNA (gDNA) sequences flanking a target site-specific endonuclease cleavage site in the gDNA. In certain embodiments, the replacement DNA can comprise an insertion, deletion, or substitution of 1 or more DNA base pairs relative to the target gDNA. In an embodiment, the donor DNA template molecule is double-stranded and perfectly base-paired through all or most of its length, with the possible exception of any unpaired nucleotides at either terminus or both termini. In another embodiment, the donor DNA template molecule is double-stranded and includes one or more non-terminal mismatches or non-terminal unpaired nucleotides within the otherwise double-stranded duplex. In an embodiment, the donor DNA template molecule that is integrated at the site of at least one double-strand break (DSB) includes between 2-20 nucleotides in one (if single-stranded) or in both strands (if double-stranded), e. g., 2, 3, 4, 5, 6, 7, 8, 9, 10, 11, 12, 13, 14, 15, 16, 17, 18, 19, or 20 nucleotides on one or on both strands, each of which can be base-paired to a nucleotide on the opposite strand (in the case of a perfectly base-paired double-stranded polynucleotide molecule). Such donor DNA templates can be integrated in genomic DNA containing blunt and/or staggered double stranded DNA breaks by homology-directed repair (HDR). In certain embodiments, a donor DNA template homology arm can be about 20, 50, 100, 200, 400, or 600 to about 800, or 1000 base pairs in length. In certain embodiments, a donor DNA template molecule can be delivered to a plant cell) in a circular (e.g., a plasmid or a viral vector including a geminivirus vector) or a linear DNA molecule. In certain embodiments, a circular or linear DNA molecule that is used can comprise a modified donor DNA template molecule comprising, from 5' to 3', a first copy of the target sequence-specific endonuclease cleavage site sequence, the first homology arm, the replacement DNA, the second homology arm, and a second copy of the target sequence-specific endonuclease cleavage site sequence. Without seeking to be limited by theory, such modified donor DNA template molecules can be cleaved by the same sequence-specific endonuclease that is used to cleave the target site gDNA of the eukaryotic cell to release a donor DNA template molecule that can participate in HDR-mediated genome modification of the target editing site in the plant cell genome. In certain embodiments, the donor DNA template can comprise a linear DNA molecule comprising, from 5' to 3', a cleaved target sequence-specific endonuclease cleavage site sequence, the first homology arm, the replacement DNA, the second homology arm, and a cleaved target sequence-specific endonuclease cleavage site sequence. In certain embodiments, the cleaved target sequence-specific endonuclease sequence can comprise a blunt DNA end or a blunt DNA end that can optionally comprise a 5' phosphate group. In certain embodiments, the cleaved target sequence-specific endonuclease sequence comprises a DNA end having a single-stranded 5' or 3' DNA overhang. Such cleaved target sequence-specific endonuclease cleavage site sequences can be produced by either cleaving an intact target sequence-specific endonuclease cleavage site sequence or by synthesizing a copy of the cleaved target sequence-specific endonuclease cleavage site sequence. Donor DNA templates can be synthesized either chemically or enzymatically (e.g., in a polymerase chain reaction (PCR)). Donor DNA templates provided herein include those comprising CgRRS sequences flanked by DNA with homology to a donor polynucleotide.

INIR6 transgenic loci comprising deletions in a 5' or a 3' junction polynucleotide and/or deletions of all or a portion of the PAT selectable marker cassette are also provided herein. An INIR6-4 locus of SEQ ID NO: 22 comprising a deletion in a 3' junction polynucleotide can be obtained by using a Cas12a nuclease, gRNA-1 (encoded by SEQ ID NO: 4), gRNA-2 (encoded by SEQ ID NO: 5), and the DNA donor template of SEQ ID NO: 32. An INIR6-5 locus of SEQ ID NO: 23 comprising a deletion in a 3' junction polynucleotide deletion can be obtained by using a Cas12a nuclease, gRNA-2 (encoded by SEQ ID NO: 5), gRNA-3 (encoded by SEQ ID NO: 6), and the DNA donor template of SEQ ID NO: 33. An INIR6-6 locus of SEQ ID NO: 25 comprising a deletion in a 3' junction polynucleotide and deletion of a PAT selectable marker cassette can be obtained by using a Cas12a nuclease, gRNA-1 (encoded by SEQ ID NO: 4), gRNA-4 (encoded by SEQ ID NO: 24), and the DNA donor template of SEQ ID NO: 34. An INIR6-8 locus of SEQ ID NO: 29 comprising a deletion of the CaMV35S promoter and PAT coding region of the PAT selectable marker cassette can be obtained by using a Cas12a nuclease, gRNA-4 (encoded by SEQ ID NO: 24), gRNA-5 (encoded by SEQ ID NO: 28), and the DNA donor template of SEQ ID NO: 35.

Various treatments are useful in delivery of gene editing molecules and/or other molecules to a DP-4114 or INIR6 plant cell. In certain embodiments, one or more treatments is employed to deliver the gene editing or other molecules (e.g., comprising a polynucleotide, polypeptide or combination thereof) into a eukaryotic or plant cell, e.g., through barriers such as a cell wall, a plasma membrane, a nuclear envelope, and/or other lipid bilayer. In certain embodiments, a polynucleotide-, polypeptide-, or RNP-containing composition comprising the molecules are delivered directly, for example by direct contact of the composition with a plant cell. Aforementioned compositions can be provided in the form of a liquid, a solution, a suspension, an emulsion, a reverse emulsion, a colloid, a dispersion, a gel, liposomes, micelles, an injectable material, an aerosol, a solid, a powder, a particulate, a nanoparticle, or a combination thereof can be applied directly to a plant, plant part, plant cell, or plant explant (e.g., through abrasion or puncture or otherwise disruption of the cell wall or cell membrane, by spraying or dipping or soaking or otherwise directly contacting, by microinjection). For example, a plant cell or plant protoplast is soaked in a liquid genome editing molecule-containing composition, whereby the agent is delivered to the plant cell. In certain embodiments, the agent-containing composition is delivered using negative or positive pressure, for example, using vacuum infiltration or application of hydrodynamic or fluid pressure. In certain embodiments, the agent-containing composition is introduced into a plant cell or plant protoplast, e.g., by microinjection or by disruption or deformation of the cell wall or cell membrane, for example by physical treatments such as by application of negative or positive pressure, shear forces, or treatment with a chemical or physical delivery agent such as surfactants, liposomes, or nanoparticles; see, e.g., delivery of materials to cells employing microfluidic flow through a cell-deforming constriction as described in US Published Patent Application 2014/0287509, incorporated by reference in its entirety herein. Other techniques useful for delivering the agent-containing composition to a eukaryotic cell, plant cell or plant protoplast include: ultrasound or sonication; vibration, friction, shear stress, vortexing, cavitation; centrifugation or application of mechanical force; mechanical cell wall or cell membrane deformation or breakage; enzymatic cell wall or cell membrane breakage or permeabilization; abrasion or mechanical scarification (e.g., abrasion with carborundum or other particulate abrasive or scarification with a file or sandpaper) or chemical scarification (e.g., treatment with an acid or caustic agent); and electroporation. In certain embodiments, the agent-containing composition is provided by bacterially mediated (e.g., *Agrobacterium* sp., *Rhizobium* sp., *Sinorhizobium* sp., *Mesorhizobium* sp., *Bradyrhizobium* sp., *Azobacter* sp., *Phyllobacterium* sp.) transfection of the plant cell or plant protoplast with a polynucleotide encoding the genome editing molecules (e.g., RNA dependent DNA endonuclease, RNA dependent DNA binding protein, RNA dependent nickase, ABE, or CBE, and/or guide RNA); see, e.g., Broothaerts et al. (2005) *Nature*, 433:629-633). Any of these techniques or a combination thereof are alternatively employed on the plant explant, plant part or tissue or intact plant (or seed) from which a plant cell is optionally subsequently obtained or isolated; in certain embodiments, the agent-containing composition is delivered in a separate step after the plant cell has been isolated.

In some embodiments, one or more polynucleotides or vectors driving expression of one or more genome editing molecules or trait-conferring genes (e.g., herbicide tolerance, insect resistance, and/or male sterility) are introduced into a DP-4114 or INIR6 plant cell. In certain embodiments, a polynucleotide vector comprises a regulatory element such as a promoter operably linked to one or more polynucleotides encoding genome editing molecules and/or trait-conferring genes. In such embodiments, expression of these polynucleotides can be controlled by selection of the appropriate promoter, particularly promoters functional in a eukaryotic cell (e.g., plant cell); useful promoters include constitutive, conditional, inducible, and temporally or spatially specific promoters (e.g., a tissue specific promoter, a developmentally regulated promoter, or a cell cycle regulated promoter). Developmentally regulated promoters that can be used in plant cells include Phospholipid Transfer Protein (PLTP), fructose-1,6-bisphosphatase protein, NAD (P)-binding Rossmann-Fold protein, adipocyte plasma membrane-associated protein-like protein, Rieske [2Fe-2S] iron-sulfur domain protein, chlororespiratory reduction 6 protein, D-glycerate 3-kinase, chloroplastic-like protein, chlorophyll a-b binding protein 7, chloroplastic-like protein, ultraviolet-B-repressible protein, Soul heme-binding family protein, Photosystem I reaction center subunit psi-N protein, and short-chain dehydrogenase/reductase protein that are disclosed in US Patent Application Publication No. 20170121722, which is incorporated herein by reference in its entirety and specifically with respect to such disclosure. In certain embodiments, the promoter is operably linked to nucleotide sequences encoding multiple guide RNAs, wherein the sequences encoding guide RNAs are separated by a cleavage site such as a nucleotide sequence encoding a microRNA recognition/cleavage site or a self-cleaving ribozyme (see, e.g., Ferré-D'Amaré and Scott (2014) Cold Spring Harbor Perspectives Biol., 2:a003574). In certain embodiments, the promoter is an RNA polymerase III promoter operably linked to a nucleotide sequence encoding one or more guide RNAs. In certain embodiments, the RNA polymerase III promoter is a plant U6 spliceosomal RNA promoter, which can be native to the genome of the plant cell or from a different species, e.g., a U6 promoter from maize, tomato, or soybean such as those disclosed U.S. Patent Application Publication 2017/0166912, or a homologue thereof; in an example, such a promoter is operably linked to DNA sequence encoding a first RNA molecule including a Cas12a gRNA followed by an operably linked and suitable 3' element such as a U6 poly-T terminator. In another embodiment, the RNA polymerase III promoter is a plant U3, 7SL (signal recognition particle RNA), U2, or U5 promoter, or chimerics thereof, e.g., as described in U.S. Patent Application Publication 20170166912. In certain embodiments, the promoter operably linked to one or more polynucleotides is a constitutive promoter that drives gene expression in eukaryotic cells (e.g., plant cells). In certain embodiments, the promoter drives gene expression in the nucleus or in an organelle such as a chloroplast or mitochondrion. Examples of constitutive promoters for use in plants include a CaMV 35S promoter as disclosed in U.S. Pat. Nos. 5,858,742 and 5,322,938, a rice actin promoter as disclosed in U.S. Pat. No. 5,641,876, a maize chloroplast aldolase promoter as disclosed in U.S. Pat. No. 7,151,204, and the nopaline synthase (NOS) and octopine synthase (OCS) promoters from *Agrobacterium tumefaciens*. In certain embodiments, the promoter operably linked to one or more polynucleotides encoding elements of a genome-editing system is a promoter from figwort mosaic virus (FMV), a RUBISCO promoter, or a pyruvate phosphate dikinase (PPDK) promoter, which is active in photosynthetic tissues. Other contemplated promoters include cell-specific or tissue-specific or developmentally regulated promoters, for example, a promoter that limits the expression of the nucleic acid targeting system to germline or reproductive cells (e.g., promoters of genes encoding DNA ligases, recombinases, replicases, or other genes specifically expressed in germline or reproductive cells). In certain embodiments, the genome alteration is limited only to those cells from which DNA is inherited in subsequent generations, which is advantageous where it is desirable that expression of the genome-editing system be limited in order to avoid genotoxicity or other unwanted effects. All of the patent publications referenced in this paragraph are incorporated herein by reference in their entirety.

Expression vectors or polynucleotides provided herein may contain a DNA segment near the 3' end of an expression cassette that acts as a signal to terminate transcription and directs polyadenylation of the resultant mRNA and may also support promoter activity. Such a 3' element is commonly referred to as a "3'-untranslated region" or "3'-UTR" or a "polyadenylation signal." In some cases, plant gene-based 3' elements (or terminators) consist of both the 3'-UTR and downstream non-transcribed sequence (Nuccio et al., 2015). Useful 3' elements include: *Agrobacterium tumefaciens* nos 3', tml 3', tmr 3', tms 3', ocs 3', and tr7 3' elements disclosed in U.S. Pat. No. 6,090,627, incorporated herein by reference, and 3' elements from plant genes such as the heat shock protein 17, ubiquitin, and fructose-1,6-biphosphatase genes from wheat (*Triticum aestivum*), and the glutelin, lactate dehydrogenase, and beta-tubulin genes from rice (*Oryza sativa*), disclosed in US Patent Application Publication 2002/0192813 A1. All of the patent publications referenced in this paragraph are incorporated herein by reference in their entireties.

In certain embodiments, the DP-4114 or INIR6 plant cells used herein can comprise haploid, diploid, or polyploid plant cells or plant protoplasts, for example, those obtained from a haploid, diploid, or polyploid plant, plant part or tissue, or callus. In certain embodiments, plant cells in culture (or the regenerated plant, progeny seed, and progeny plant) are haploid or can be induced to become haploid; techniques for making and using haploid plants and plant cells are known in the art, see, e.g., methods for generating haploids in *Arabidopsis thaliana* by crossing of a wild-type strain to a haploid-inducing strain that expresses altered forms of the centromere-specific histone CENH3, as described by Maruthachalam and Chan in "How to make haploid *Arabidopsis thaliana*", protocol available at www[dot]openwetware[dot]org/images/d/d3/Haploid_Arabidopsis_protocol [dot] pdf; (Ravi et al. (2014) *Nature Communications*, 5:5334, doi: 10.1038/ncomms6334). Haploids can also be obtained in a wide variety of monocot plants (e.g., maize, wheat, rice, sorghum, barley) by crossing a plant comprising a mutated CENH3 gene with a wildtype diploid plant to generate haploid progeny as disclosed in U.S. Pat. No. 9,215,849, which is incorporated herein by reference in its entirety. Haploid-inducing maize lines that can be used to obtain haploid maize plants and/or cells include Stock 6, MHI (Moldovian Haploid Inducer), indeterminate gametophyte (ig) mutation, KEMS, RWK, ZEM, ZMS, KMS, and well as transgenic haploid inducer lines disclosed in U.S. Pat. No. 9,677,082, which is incorporated herein by reference in its entirety. Examples of haploid cells include but are not limited to plant cells obtained from haploid plants and plant cells obtained from reproductive tissues, e.g., from flowers, developing flowers or flower buds, ovaries, ovules, megaspores, anthers, pollen, megagametophyte, and microspores. In certain embodiments where the plant cell or plant protoplast is haploid, the genetic complement can be doubled by chromosome doubling (e.g., by spontaneous chromosomal doubling by meiotic non-reduction, or by using a chromosome doubling agent such as colchicine, oryzalin, trifluralin, pronamide, nitrous oxide gas, anti-microtubule herbicides, anti-microtubule agents, and mitotic inhibitors) in the plant cell or plant protoplast to produce a doubled haploid plant cell or plant protoplast wherein the complement of genes or alleles is homozygous; yet other embodiments include regeneration of a doubled haploid plant from the doubled haploid plant cell or plant protoplast. Another embodiment is related to a hybrid plant having at least one parent plant that is a doubled haploid plant provided by this approach. Production of doubled haploid plants provides homozygosity in one generation, instead of requiring several generations of self-crossing to obtain homozygous plants. The use of doubled haploids is advantageous in any situation where there is a desire to establish genetic purity (i.e., homozygosity) in the least possible time. Doubled haploid production can be particularly advantageous in slow-growing plants or for producing hybrid plants that are offspring of at least one doubled-haploid plant.

In certain embodiments, the DP-4114 or INIR6 plant cells used in the methods provided herein can include non-dividing cells. Such non-dividing cells can include plant cell protoplasts, plant cells subjected to one or more of a genetic and/or pharmaceutically-induced cell-cycle blockage, and the like.

In certain embodiments, the DP-4114 or INIR6 plant cells in used in the methods provided herein can include dividing cells. Dividing cells can include those cells found in various plant tissues including leaves, meristems, and embryos. These tissues include dividing cells from young maize leaf, meristems and scutellar tissue from about 8 or 10 to about 12 or 14 days after pollination (DAP) embryos. The isolation of maize embryos has been described in several publications (Brettschneider, Becker, and Lörz 1997; Leduc et al. 1996; Frame et al. 2011; K. Wang and Frame 2009). In certain embodiments, basal leaf tissues (e.g., leaf tissues located about 0 to 3 cm from the ligule of a maize plant; Kirienko, Luo, and Sylvester 2012) are targeted for HDR-mediated gene editing. Methods for obtaining regenerable plant structures and regenerating plants from the NHEJ-, MMEJ-, or HDR-mediated gene editing of plant cells provided herein can be adapted from methods disclosed in US Patent Application Publication No. 20170121722, which is incorporated herein by reference in its entirety and specifically with respect to such disclosure. In certain embodiments, single plant cells subjected to the HDR-mediated gene editing will give rise to single regenerable plant structures. In certain embodiments, the single regenerable plant cell structure can form from a single cell on, or within, an explant that has been subjected to the NHEJ-, MMEJ-, or HDR-mediated gene editing.

In some embodiments, methods provided herein can include the additional step of growing or regenerating an INIR6 plant from a INIR6 plant cell that had been subjected to the gene editing or from a regenerable plant structure obtained from that INIR6 plant cell. In certain embodiments, the plant can further comprise an inserted transgene, a target gene edit, or genome edit as provided by the methods and compositions disclosed herein. In certain embodiments, callus is produced from the plant cell, and plantlets and plants produced from such callus. In other embodiments, whole seedlings or plants are grown directly from the plant cell without a callus stage. Thus, additional related aspects are directed to whole seedlings and plants grown or regenerated from the plant cell or plant protoplast having a target gene edit or genome edit, as well as the seeds of such plants. In certain embodiments wherein the plant cell or plant protoplast is subjected to genetic modification (for example, genome editing by means of, e.g., an RdDe), the grown or regenerated plant exhibits a phenotype associated with the genetic modification. In certain embodiments, the grown or regenerated plant includes in its genome two or more genetic or epigenetic modifications that in combination provide at least one phenotype of interest. In certain embodiments, a heterogeneous population of plant cells having a target gene edit or genome edit, at least some of which include at least one genetic or epigenetic modification, is provided by the method; related aspects include a plant having a phenotype of interest associated with the genetic or epigenetic modification, provided by either regeneration of a plant having the phenotype of interest from a plant cell or plant protoplast selected from the heterogeneous population of plant cells having a target gene or genome edit, or by selection of a plant having the phenotype of interest from a heterogeneous population of plants grown or regenerated from the population of plant cells having a targeted genetic edit or genome edit. Examples of phenotypes of interest include herbicide resistance, improved tolerance of abiotic stress (e.g., tolerance of temperature extremes, drought, or salt) or biotic stress (e.g., resistance to nematode, bacterial, or fungal pathogens), improved utilization of nutrients or water, modified lipid, carbohydrate, or protein composition, improved flavor or appearance, improved storage characteristics (e.g., resistance to bruising, browning, or softening), increased yield, altered morphology (e.g., floral architecture or color, plant height, branching, root structure). In an embodiment, a heterogeneous population of plant cells having a target gene edit or genome edit (or seedlings or plants grown or regenerated therefrom) is exposed to conditions permitting expression of the phenotype of interest; e.g., selection for herbicide resistance can include exposing the population of plant cells having a target gene edit or genome edit (or seedlings or plants grown or regenerated therefrom) to an amount of herbicide or other substance that inhibits growth or is toxic, allowing identification and selection of those resistant plant cells (or seedlings or plants) that survive treatment. Methods for obtaining regenerable plant structures and regenerating plants from plant cells or regenerable plant structures can be adapted from published procedures (Roest and Gilissen, Acta Bot. Neerl., 1989, 38(1), 1-23; Bhaskaran and Smith, Crop Sci. 30(6):1328-1337; Ikeuchi et al., Development, 2016, 143: 1442-1451). Methods for obtaining regenerable plant structures and regenerating plants from plant cells or regenerable plant structures can also be adapted from US Patent Application Publication No. 20170121722, which is incorporated herein by reference in its entirety and specifically with respect to such disclosure. Also provided are heterogeneous or homogeneous populations of such plants or parts thereof (e.g., seeds), succeeding generations or seeds of such plants grown or regenerated from the plant cells or plant protoplasts, having a target gene edit or genome edit. Additional related aspects include a hybrid plant provided by crossing a first plant grown or regenerated from a plant cell or plant protoplast having a target gene edit or genome edit and having at least one genetic or epigenetic modification, with a second plant, wherein the hybrid plant contains the genetic or epigenetic modification; also contemplated is seed produced by the hybrid plant. Also envisioned as related aspects are progeny seed and progeny plants, including hybrid seed and hybrid plants, having the regenerated plant as a parent or ancestor. The plant cells and derivative plants and seeds disclosed herein can be used for various purposes useful to the consumer or grower. In other embodiments, processed products are made from the INIR6 plant or its seeds, including: (a) maize seed meal (defatted or non-defatted); (b) extracted proteins, oils, sugars, and starches; (c) fermentation products; (d) animal feed or human food products (e.g., feed and food comprising maize seed meal (defatted or non-defatted) and other ingredients (e.g., other cereal grains, other seed meal, other protein meal, other oil, other starch, other sugar, a binder, a preservative, a humectant, a vitamin, and/or mineral; (e) a pharmaceutical; (f) raw or processed biomass (e.g., cellulosic and/or lignocellulosic material); and (g) various industrial products.

EMBODIMENTS

Various embodiments of the plants, genomes, methods, biological samples, and other compositions described herein are set forth in the following sets of numbered embodiments.

1a. A transgenic maize plant cell comprising an INIR6 transgenic locus comprising an originator guide RNA recognition site (OgRRS) in a first DNA junction polynucleotide of a DP-4114 transgenic locus and a cognate guide RNA recognition site (CgRRS) in a second DNA junction polynucleotide of the DP-4114 transgenic locus.

1b. A transgenic maize plant cell comprising an INIR6 transgenic locus comprising an insertion and/or substitution of DNA in a DNA junction polynucleotide of a DP-4114 transgenic locus with DNA comprising a cognate guide RNA recognition site (CgRRS), a deletion of a 5' or 3' DNA junction polynucleotide of the DP-4114 transgenic locus, a deletion of a phosphinotricin acetyltransferase (PAT) selectable marker gene of the DP-4114 transgenic locus, and/or a deletion of DNA comprising, consisting essentially of, or consisting of the CaMV35S promoter and operably linked PAT coding region of the DP-4114 transgenic locus.

2. The transgenic maize plant cell of embodiment 1a or 1b, wherein said CgRRS comprises the DNA molecule set forth in SEQ ID NO: 8, 9, 10, or 19; and/or wherein said DP-4114 transgenic locus is set forth in SEQ ID NO: 1, is present in seed deposited at the ATCC under accession No. PTA-11506, is present in progeny thereof, is present in allelic variants thereof, or is present in other variants thereof.

3. The transgenic maize plant cell of embodiments 1a, 1b, or 2, wherein said INIR6 transgenic locus comprises the DNA molecule set forth in SEQ ID NO: 2, 3, 20, 22, 23, 25, 26, 29, 30, 31, or an allelic variant thereof.

4. A transgenic maize plant part comprising the maize plant cell of any one of embodiments 1a, 1b, 2, or 3, wherein said maize plant part is optionally a seed.

5. A transgenic maize plant comprising the maize plant cell of any one of embodiments 1a, 1b, 2, or 3.

6. A method for obtaining a bulked population of inbred seed comprising selfing the transgenic maize plant of embodiment 5 and harvesting seed comprising the INIR6 transgenic locus from the selfed maize plant.

7. A method of obtaining hybrid maize seed comprising crossing the transgenic maize plant of embodiment 5 to a second maize plant which is genetically distinct from the first maize plant and harvesting seed comprising the INIR6 transgenic locus from the cross.

8. A DNA molecule comprising SEQ ID NO: 2, 3, 8, 9, 10, 19, 20, 22, 23, 25, 26, 27, 29, 30, 31, 32, 33, 34, 35, or an allelic variant thereof.

9. A processed transgenic maize plant product comprising the DNA molecule of embodiment 8.

10. A biological sample containing the DNA molecule of embodiment 8.

11. A nucleic acid molecule adapted for detection of genomic DNA comprising the DNA molecule of embodiment 8, wherein said nucleic acid molecule optionally comprises a detectable label.

12. A method of detecting a maize plant cell comprising the INIR6 transgenic locus of any one of embodiments 1a, 1b, 2, or 3, comprising the step of detecting DNA molecule comprising SEQ ID NO: 2, 3, 8, 9, 10, 19, 20, 22, 23, 25, 26, 27, 29, 30, 31, 32, 33, 34, 35, or an allelic variant thereof.

13. A method of excising the INIR6 transgenic locus from the genome of the maize plant cell of any one of embodiments 1a, 1b, 2, or 3, comprising the steps of:

(a) contacting the edited transgenic plant genome of the plant cell of embodiment 5 with: (i) an RNA dependent DNA endonuclease (RdDe); and (ii) a guide RNA (gRNA) capable of hybridizing to the guide RNA hybridization site of the OgRRS and the CgRRS; wherein the RdDe recognizes a OgRRS/gRNA and a CgRRS/gRNA hybridization complex; and, (b) selecting a transgenic plant cell, transgenic plant part, or transgenic plant wherein the INIR6 transgenic locus flanked by the OgRRS and the CgRRS has been excised.

14. The method of embodiment 13, wherein the INIR6 transgenic locus of the maize plant cell comprises the CgRRS of SEQ ID NO: 26, 19, 8, 9, or 10 and the guide RNA comprises an RNA sequence encoded by SEQ ID NO: 16.

15. The method of embodiment 14, wherein the maize plant cell comprises the INIR6 transgenic locus of SEQ ID NO: 2, 3, 20, 26, 31, or an allelic variant thereof.

EXAMPLES

Example 1. Introduction of a CgRRS in a 3' Junction Polynucleotide of a DP-4114 Transgenic Locus Transgenic plant genomes containing one or more of the following transgenic loci (events) are contacted with:
(i) an ABE or CBE and guide RNAs which recognize the indicated target DNA sites (protospacer (guide RNA coding) plus PAM site) in the 5' or 3' junction polynucleotides of the event to introduce a CgRRS in the junction polynucleotide;
(ii) an RdDe and guide RNAs which recognize the indicated target DNA site (guide RNA coding plus PAM site) in the 5' or 3' junction polynucleotides of the event as well as a donor DNA template spanning the double stranded DNA break site in the junction polynucleotide to introduce a CgRRS in a junction polynucleotide.
Plant cells, callus, parts, or whole plants comprising the introduced CgRRS in the transgenic plant genome are selected.

TABLE 1

Examples of OgRRS and CgRRS in DP-4114

| CORN EVENT NAME | OgRRS | CgRRS |
|---|---|---|
| DP-4114 | tttgtagcacttgcacgt agttacccg (SEQ ID NO: 7; located in 5' junction polynucleotide of SEQ ID NO: 1) | cgcttttgtagcacttgcacgtag ttacccggata (SEQ ID NO: 8; inserted into 3' junction polynucleotide) |
| | | aacgtgcaagcgcttttgtagcact tgcacgtagttacccggatataaga acttcgatccgaaa (SEQ ID NO: 9; inserted into 3' junction polynucleotide) |
| | | aacgtgcaagcgcttttgtagcact tgcacgtagttacccggccagatat aagaacttcgatccgaaa (SEQ ID NO: 10; inserted into 3' junction polynucleotide) |

Example 2. Insertion of a CgRRS Element in the 3'-Junction of the DP-4114 Event

Two plant gene expression vectors are prepared. Plant expression cassettes for expressing a bacteriophage lambda exonuclease, a bacteriophage lambda beta SSAP protein, and an E. coli SSB are constructed essentially as set forth in US Patent Application Publication 20200407754, which is incorporated herein by reference in its entirety. A DNA sequence encoding a tobacco c2 nuclear localization signal (NLS) is fused in-frame to the DNA sequences encoding the exonuclease, the bacteriophage lambda beta SSAP protein, and the E. coli SSB to provide a DNA sequence encoding the c2 NLS-Exo, c2 NLS lambda beta SSAP, and c2 NLS-SSB fusion proteins that are set forth in SEQ ID NO: 135, SEQ ID NO: 134, and SEQ ID NO: 133 of US Patent Application Publication 20200407754, respectively, and incorporated herein by reference in its entirety. DNA sequences encoding the c2 NLS-Exo, c2 NLS lambda beta SSAP, and c2NLS-SSB fusion proteins are operably linked to a OsUBI1, ZmUBI1, OsACT promoter and a OsUbi1, ZmUBI1, OsACT polyadenylation site respectively, to provide the exonuclease, SSAP, and SSB plant expression cassettes.

A DNA donor template sequence (SEQ ID NO: 14) that targets the 3'-T-DNA junction polynucleotide of the DP-4114 event (SEQ ID NO:1; FIG. 1) for HDR-mediated insertion of a 27 base pair OgRRS sequence (SEQ ID NO: 7) that is identical to a Cas12a recognition site at the 5'-junction polynucleotide of the DP-4114 T-DNA insert is constructed. The DNA donor sequence includes a replacement template with desired insertion region (27 base pairs long) flanked on both sides by homology arms about 500-635 bp in length. The homology arms match (i.e., are homologous to) gDNA (genomic DNA) regions flanking the target gDNA insertion site (SEQ ID NO: 15). The replacement template region comprising the donor DNA is flanked at each end by DNA sequences identical to the DP-4114 3'-T-DNA junction polynucleotide sequence recognized by a Cas12a RNA-guided nuclease and a gRNA (e.g., encoded by SEQ ID NO: 5).

A plant expression cassette that provides for expression of the RNA-guided sequence-specific Cas12a endonuclease is constructed. A plant expression cassette that provides for expression of a guide RNA (e.g., encoded by SEQ ID NO: 5) complementary to sequences adjacent to the insertion site is constructed. An *Agrobacterium* superbinary plasmid transformation vector containing a cassette that provides for the expression of a suitable plant selectable marker (e.g., a glyphosate tolerant EPSPS, a neomycin phosphotransferase (nptII), a hygromycin phosphotransferase (hptII), or a phosphomannose isomerase (pmi)) is constructed. Once the cassettes, donor sequence and *Agrobacterium* superbinary plasmid transformation vector are constructed, they are combined to generate two maize transformation plasmids.

A maize transformation plasmid is constructed with the selectable marker cassette, the RNA-guided sequence-specific endonuclease cassette, the guide RNA cassette, and the DP-4114 5'-T_DNA junction sequence DNA donor sequence into the *Agrobacterium* superbinary plasmid transformation vector (the control vector).

A maize transformation plasmid is constructed with the selectable marker cassette, the RNA-guided sequence-specific endonuclease cassette, the guide RNA cassette, the SSB cassette, the lambda beta SSAP cassette, the Exo cassette, and the DP-4114 5'-DNA junction sequence donor DNA template sequence (e.g., SEQ ID NO: 14) into the *Agrobacterium* superbinary plasmid transformation vector (the lambda red vector).

All constructs are transformed into *Agrobacterium* strain LBA4404.

Maize transformations are performed based on published methods (e.g., Ishida et. al, Nature Protocols 2007; 2, 1614-1621; U.S. Pat. Nos. 7,064,248; 8,212,113; 8,450,561; 8,455,720; all incorporated herein by reference in their entireties). In certain instances, immature embryos approximately 1.8-2.2 mm in size, are isolated from surface sterilized ears 10-14 days after pollination. Embryos are placed in an *Agrobacterium* suspension made with infection medium at a concentration of OD 600=1.0. Acetosyringone (200 µM) is added to the infection medium at the time of use. Embryos and *Agrobacterium* are placed on a rocker shaker at slow speed for 15 minutes. Embryos are then poured onto the surface of a plate of co-culture medium. Excess liquid media is removed by tilting the plate and drawing off all liquid with a pipette. Embryos are flipped as necessary to maintain a scutelum up orientation. Co-culture plates are placed in a box with a lid and cultured in the dark at 22° C. for 3 days. Embryos are then transferred to resting medium, maintaining the scutellum up orientation. Embryos remain on resting medium for 7 days at 27-28° C. Embryos that produced callus are transferred to Selection 1 medium with a suitable concentration of the selection agent for the selectable marker gene selected and cultured for an additional, suitable time period (e.g. 7 days). In some instances, glyphosate is used as the selection agent for a glyphosate tolerant EPSPS selectable marker (e.g., as in U.S. Pat. No. 8,212,113, incorporated herein by reference in its entirety). In some instances, kanamycin, paromomycin, or G418 is used as the selection agent for a nptII selectable marker (e.g., as in U.S. Pat. No. 8,450,561, incorporated herein by reference in its entirety). In some instances, hygromycin is used as the selection agent for an hptII selectable marker (e.g., as in U.S. Pat. No. 7,064,248, incorporated herein by reference in its entirety). In some instances, media comprising mannose as a sole carbon source is used as the selection agent for a pmi selectable marker (as in U.S. Pat. No. 8,455,720, incorporated herein by reference in its entirety). Callused embryos are placed on Selection 2 medium with a suitable concentration of the selection agent and cultured for 14 days at 27-28° C. Growing calli resistant to the selection agent are transferred to Pre-Regeneration media with a suitable concentration of the selection agent to initiate shoot development. Calli remained on Pre-Regeneration media for a suitable time period (e.g., 7 days). Calli beginning to initiate shoots are transferred to Regeneration medium with a suitable concentration of the selection agent in Phytatrays and cultured in light at 27-28° C. Shoots that reached the top of the Phytatray with intact roots are isolated into Shoot Elongation medium prior to transplant into soil and gradual acclimatization to greenhouse conditions.

When a sufficient amount of viable tissue is obtained, it can be screened for insertion at the DP-4114 junction sequence, using a PCR-based approach. The PCR primer on the 5'-end is 5'-tacgctgggccctggaaggctagga-3' (SEQ ID NO: 17). The PCR primer on the 3'-end is 5'-gatggacga-gacgaggcggtggaga-3' (SEQ ID NO: 18). The above primers that flank donor DNA homology arms are used to amplify the DP-4114 3'-junction polynucleotide sequence. The correct donor sequence insertion will produce a 1563 bp product. A unique DNA fragment comprising the CgRRS in the DP-4114 3' junction polynucleotide is set forth in SEQ ID NO: 19. Amplicons can be sequenced directly using an amplicon sequencing approach or ligated to a convenient plasmid vector for Sanger sequencing. Those plants in which the DP-4114 junction sequence now contains the intended Cas12a recognition sequence are selected and grown to maturity. The T-DNA encoding the Cas12a reagents can be segregated away from the modified junction sequence in a subsequent generation. The resultant INIR6 transgenic locus (SEQ ID NO: 20) comprising the CgRRS and OgRRS (e.g., which each comprise SEQ ID NO: 7) can be excised using Cas12a and a suitable gRNA which hybridizes to DNA comprising SEQ ID NO: 7 at both the OgRRS and the CgRRS.

The breadth and scope of the present disclosure should not be limited by any of the above-described embodiments.

What is claimed is:

1. A DNA molecule comprising SEQ ID NO: 34.
2. A biological sample containing the DNA molecule of claim 1.
3. The biological sample of claim 2, wherein the biological sample comprises non-intact plant tissue.
4. The biological sample of claim 3, wherein the non-intact plant tissue is milled seed, chopped plant tissue, or lyophilized tissue.

* * * * *

UNITED STATES PATENT AND TRADEMARK OFFICE
CERTIFICATE OF CORRECTION

PATENT NO. : 11,753,648 B2
APPLICATION NO. : 17/680647
DATED : September 12, 2023
INVENTOR(S) : Michael Lee Nuccio, Michael Andreas Kock and Joshua L. Price It is certified that error appears in the above-identified patent and that said Letters Patent is hereby corrected as shown below:

On the Title Page

Item (54) TITLE and in the Specification, Column 1, Lines 1-2, SHOULD READ: INIR6 TRANSGENIC MAIZE DNA WITH SELECTABLE MARKER AND JUNCTION DELETION

Item (60) DELETE:
"." after Feb. 3, 2021 on the last line of the Related U.S. Application Data
INSERT:
--, provisional application No. 63/059,963, filed on July 31, 2020, provisional application No. 63/059,916, filed on July 31, 2020, provisional application No. 63/059,860, filed July 31, 2020, provisional application No. 63/059,813, filed July 31, 2020.--

Signed and Sealed this
Twentieth Day of February, 2024

Katherine Kelly Vidal
*Director of the United States Patent and Trademark Office*